United States Patent
Akitaya et al.

(10) Patent No.: US 6,300,058 B1
(45) Date of Patent: Oct. 9, 2001

(54) METHOD FOR MEASURING MESSENGER RNA

(75) Inventors: Tatsuo Akitaya, Takasuzu (JP); Masato Mitsuhashi, Irvine, CA (US); Allan Cooper, Bellview, WA (US)

(73) Assignees: Hitachi Chemical Research Center, Inc., Irvine, CA (US); Hitachi Chemical Company, Ltd., Tokyo (JP)

( * ) Notice: Subject to any disclaimer, the term of this patent is extended or adjusted under 35 U.S.C. 154(b) by 0 days.

(21) Appl. No.: 07/974,409

(22) Filed: Nov. 12, 1992

Related U.S. Application Data

(63) Continuation-in-part of application No. 07/857,059, filed on Mar. 24, 1992, now abandoned, which is a continuation-in-part of application No. 07/827,208, filed on Jan. 29, 1992, now abandoned, and a continuation-in-part of application No. 07/827,975, filed on Jan. 29, 1992, now abandoned.

(51) Int. Cl.[7] ..................... C12Q 1/68
(52) U.S. Cl. ............ 435/6; 435/7.9; 435/7.92; 536/23.1; 536/24.3; 536/24.31; 536/24.32; 702/19; 702/20
(58) Field of Search .............. 435/6, 7.9, 7.92; 536/23.1, 24.3, 24.31, 24.32

(56) References Cited

U.S. PATENT DOCUMENTS

| | | | |
|---|---|---|---|
| 4,675,285 | 6/1987 | Clark et al. ............................... | 435/6 |
| 4,729,950 | 3/1988 | Kricka et al. ........................... | 435/28 |
| 4,734,363 | 3/1988 | Dattagupta et al. ................. | 435/91.5 |
| 4,751,177 | 6/1988 | Stabinsky ................................ | 435/6 |
| 4,797,355 | 1/1989 | Stabinsky ................................ | 435/6 |
| 4,851,330 | 7/1989 | Kohne ...................................... | 435/6 |
| 4,894,325 | 1/1990 | Englehardt et al. ..................... | 435/6 |
| 4,978,724 | 12/1990 | Clark ..................................... | 525/350 |
| 5,081,584 | 1/1992 | Omichinski et al. ................. | 364/497 |
| 5,082,935 | 1/1992 | Cruickshak ....................... | 536/24.32 |
| 5,084,565 | 1/1992 | Parodos et al. ........................... | 435/6 |

FOREIGN PATENT DOCUMENTS

| | | |
|---|---|---|
| 0130515 | 1/1985 | (EP) . |
| 0152886 | 8/1985 | (EP) . |
| 0369775 | 5/1990 | (EP) . |
| 0370694 | 5/1990 | (EP) . |
| 9006042 | 6/1990 | (EP) . |
| 9006045 | 6/1990 | (EP) . |
| 0422872 | 4/1991 | (EP) . |
| 0469610 | 2/1992 | (EP) . |
| 2187283 | 9/1987 | (GB) . |
| 3168085 | 7/1991 | (JP) . |
| 8603782 | 7/1986 | (WO) . |
| 8801302 | 2/1988 | (WO) . |
| 9006044 | 6/1990 | (WO) . |
| 9006045 | 6/1990 | (WO) . |
| 9102092 | 2/1991 | (WO) . |

OTHER PUBLICATIONS

Dunn et al., "Mapping Viral, RNA by Sandwich Hybridization" *Methods in Enzymology*, vol. 65, pt. 1, 1980, pp. 468–479.*

L. J. Emorine et al., "Structure of the gene for human $\beta_2$–adrenergic receptor: Expression and promoter characterization", Proceedings of the National Academy of Science, USA, vol. 84, Oct. 1987, pp. 6995–6999.

C. B. Harley, "Hybridization of Oligo(dT) to RNA on Nitrocellulose", Gene Analysis Techniques, vol. 4, 1987. pp. 17–22.

A. Palva et al., "Laboratory Methods: Quantification of α–Amylase mRNA in *Bacillus subtilis* by Nucleic Acid Sandwich Hybridization", DNA, vol. 7, No. 2, 1988, pp. 135–142.

R. Nussinov, "Efficient algorithms for searching for exact repetition of nucleotid sequences.", Journal of Molecular Evolution, vol. 19, Nos. 3–4, pp. 283–285.

W. W. Ralph et al., "A modified Chou and Fasman protein structure algorithm,", Computer Application in the Biosciences, vol. 8, No. 3, Sep. 1987, pp. 211–216.

C. Hough et al., "Differential down–regulation of $\beta_1$–and $\beta_2$–adrenergic receptor mRNA in $C_6$ glioma cells", Biochemical and Biophysical Research Communications, vol. 170, No. 1, 1990, pp. 46–52.

A. Ballagi–Pordany et al., "Quantitive determination of mRNA phenotypes by the polymerase chain reation", Analytical Biochemistry, vol. 196, 1991, pp. 89–94.

B. Feve et al., "Differential regulation of $\beta_1$–and $\beta_2$–adrenergic receptor protein and mRNA levels by glucocorticoids during 3T3–F442A adipose differentiation", Journal of Biological Chemistry, vol. 265, No. 27, Sep. 25, 1990, pp. 16343–16349.

(List continued on next page.)

*Primary Examiner*—David Guzo
(74) *Attorney, Agent, or Firm*—Knobbe, Martens, Olsen & Bear, LLP

(57) ABSTRACT

The present invention provides a method for detecting and quantifying mRNA in a sample. The mRNA that can be detected has a unique sequence. The method includes immobilizing a first polynucleotide to an insoluble support. The first polynucleotide has a first sequence that hybridizes to the unique sequence on the mRNA. After immobilization of the first polynucleotide, the sample is applied to the insoluble support under conditions that allow the unique sequence on the mRNA to hybridize with the first polynucleotide. Thereafter, a second polynucleotide is applied to the insoluble support. This second polynucleotide has a second sequence thereon that hybridizes to a portion of the mRNA other than the unique sequence. The application of the second polynucleotide is performed under conditions that allow the second polynucleotide to hybridize with mRNA immobilized on said support, if present. Finally, the amount of the second polynucleotide immobilized on the support is measured to provide an indication of the amount of mRNA present in the sample. Polynucleotide immobilized supports and sequences useful in the method are also provided.

21 Claims, 68 Drawing Sheets

OTHER PUBLICATIONS

P. Muzzin et al., "An adipose tissue–specific β–adrenergic receptor", Journal of Biological Chemistry, vol. 266, No. 35, Dec. 15, 1991, pp. 24053–24058.

C. Albretsen et al., "Optimal conditions for hybridization with oligonucleotides: a study with myc–oncogene DNA probes", Analytical Biochemistry, vol. 170, 1988, pp. 193–202.

M. S. Waterman et al., "Phase transitions in sequence matches and nucleic acid structure", Proceedings of the National Academy of Science USA, vol. 84, Mar. 1987, pp. 1239–1243.

M. S. Waterman et al., "A new algorithm for best subsequence alignments with application to tRNA–rRNA comparisons", Journal of Molecular Biology, vol. 197, 1987, pp. 723–728.

R. J. Cano et al., "DNA hybridization assay using ATTOPHOS™, a fluorescent substrate for alkaline phosphatase", Biotechniques, vol. 12, No. 2, Feb. 1992, pp. 264–269.

N. P. Gerard, "Human substance P receptor (NK–1):Organization of the gene, chromosome localization, and functional expression of cDNA clones", Biochemistry, vol. 30, 1991, pp. 10640–10646.

S. –I. Hirai et al., "Characterization of junD: a new member of the jun protooncogene family", The EMBO Journal, vol. 8, No. 5, 1989, pp. 1433–1439.

D. T. Jones et al., "Molecular cloning of five GTP–binding protein cDNA species from rat olfactory neuroepithelium", Journal of Biological Chemistry, vol. 262, No. 29, Oct. 15, 1987, pp. 14241–14249.

L. Li et al., "Different members of the jun protooncogene family exhibit distinct patterns of expression in response to type β transforming growth factor", Journal of Biological Chemistry, vol. 265, No. 3, Jan. 25, 1990, pp. 1556–1562.

Y. Yokota et al., "Molecular characterization of a functional cDNA for rat substance P receptor", Journal of Biological Chemistry, vol. 264, No. 30, Oct. 25, 1989, pp. 17649–17652.

J. Codina et al., "$\alpha_i$–3 cDNA encodes the α subunit of $G_k$, the stimulatory G protein of receptor–regulated $K^+$ channels", Journal of Biological Chemistry, vol. 263, No. 14, May 15, 1988, pp. 6746–6750.

H. Itoh et al., "Presence of three distinct molecular species of $G_i$ protein α subunit", Journal of Biological Chemistry, vol. 263, No. 14, May 15, 1988, pp. 6656–6664.

K. Hattori et al., "Structure and chromosomal localization of the functional intronless human JUN protooncogene", Proceedings of the National Academy of Science USA, vol. 85, Dec. 1988, pp. 9148–9152.

P. Bray et al., "Human cDNA clones for an α subunit of $G_i$ signal–transduction proteins", Proceedings of the National Academy of Science USA, vol. 84, Aug. 1987, pp. 5115–5119.

C. R. Beals et al., "A small multigene family encodes $G_i$ signal–transduction proteins", Proceedings of the National Academy of Science USA, vol. 84, Nov. 1987, pp. 7886–7890.

B. A. Harris, "Complete cDNA sequence of a human stimulatory GTP–binding protein alpha subunit", Nucleic Acids Research, vol. 16, No. 8, 1988, p. 3585.

R. Mattera et al., "Identification by molecular cloning of two Forms of the α–subunit of the human liver stimulatory ($G_s$) regulatory component of adenylyl cyclase", FEBS Letters, vol. 206, No. 1, Sep. 1986, pp. 36–42.

J. R. Didsbury et al., "Molecular cloning of a new human G protein", FEBS Letters, vol. 219, No. 1, Jul. 1987, pp. 259–263.

A. Swaroop et al., "Differential expression of novel $G_{s\alpha}$ signal transduction protein cDNA species", Nucleic Acids Research, vol. 19, No. 17, 1991, pp. 4725–4729.

Polsky–Cynkin et al., "Use of DNA Immobilized on Plastic and Agarose Supports to Detect DNA by Sandwich Hybridization", Clinical Chemsitry, vol. 31, No. 9, 1985, pp. 1438–1443.

Kitabayashi et al., "Nucleotide Sequence of Rat c–jun Protooncogene", Nucleic Acids Research, vol. 18, No. 11, 1990, EMBL Accession No. X17215.

Hershey et al., "Molecular Characterization of a Functional cDNA Encoding the Rat Substance P Receptor", Science, vol. 247, Feb. 23, 1990, pp. 958–961.

Chung et al., "Cloning and Sequence Analysis of the Human Brain B–adrenergic Receptor", FEBS Letters, vol. 211, No. 2, pp. 200–206.

Saiki et al., "Primer–Directed Enzymatic Amplification of DNA with a Thermostable DNA Polymerase", Science, vol. 239, Jan. 29, 1988, pp. 487–491.

I. Raineri et al., "Improved Efficiency for Single–Sided PCR by Creating a Reusable Pool of First–Strand cDNA Coupled to a Solid Phase", Nucleic Acids Research, vol. 19, No. 14, 1991, p. 4010.

S. Inouye et al., "Microplate Hybridization of Amplified Viral DNA Segment", Journal of Clinical Microbiology, vol. 28, No. 6, Jun. 1990, pp. 1469–1472.

R. Bischoff et al., "Introduction of 5'–Terminal Functional Groups into Synthetic Oligonucletides for Selective Immobilization", Analytical Biochemistry, vol. 164, No. 2, Aug. 1, 1987, pp. 336–344.

J. Rey–Campos et al., "Synthesis of Thymosin $\alpha_1$ Precursor cDNA and Purification of Active mRNA by Affinity Chromatography", International Journal of Biochemistry, vol. 15, 1983, pp. 155–157.

T. Atkinson et al., "A convenient procedure for the synthesis of oligodeoxyribonucleotide affinity columns for the isolation of mRNA", Nucleic Acids Research, vol. 16, No. 13, 1988, p. 6232.

J. A. Arias et al., "Promoter–dependent Transcription by RNA Polymerase II Using Immobilized Enzyme Complexes", Journal of Biological Chemistry, vol. 264, No. 6, 1989, pp. 3223–3229.

Y. Masu et al., "cDNA cloning of bovine substance–K receptor through oocyte expression system", Nature, vol. 329, No. 29, 1987, pp. 836–838.

C. R. Thrash et al., "Synthesis of RNA from Cellulose–bound Complementary DNA", Journal of Biological Chemistry, vol. 252, No. 16, 1977, pp. 5615–5618.

S. L. Griffiths et al., "Diabetes–induced changes in guanine–nucleotide–regulatory–protein mRNA detected using synthetic oligonucleotide probes", European Journal of Biochemistry, vol. 193, No. 2, 1990, pp. 367–374.

Y. Wataya et al., "Kagaku Ryoho no Ryoiki", vol. 8, No. 3, 1992, pp. 487–496.

M. S. Urdea et al., "A comparison of non–radiosotopic hybridization assay methods using fluoroscent chemiluminescent and enzyme labeled synthetic oligodeoxyribonucleotide probes", Nucleic Acids Research, vol. 16, No. 11, 1988, pp. 4937–1956.

Bethesda Research Laboratories Life Technologies, Inc. Product: Vanadyl Ribonucleoxide Complex.

Biofeedback; "A Procedure for Productive Coupling of Synthetic Oligonucleotides to Polystyrene Microtier Wells for Hybridization Capture"; Biotechniques; vol. 8, p. 278–279, 1990.

Pal Venetianer, et al., Pro Nat. Acad. Sci. USA, Vl. 71, No. 10,pp. 3892–3895, Oct. 1974; "Enzymatic Synthesis of Solid Phase–Bound DNA Sequences Corresponding to Specific Mammalian Gene".

P.T. Gilham, Journal of the American Chemical Society, vol. 86, pp. 4982–4985; "The Synthesis of Polynucleotide–Celluloses and Their use in the Fractionation of Polynucleotides".

M.R. Ven Murthy, et al., Nucleic Acids Research, vol. 14, No. 17, Jul. 24, 1986; "Preparation and Biochemical Manipulation of mRNAs and CDNAs on small Oligo(dt)–cellulose discs".

Jane A. Matthews, et al., Analytical Biochemistry 169, pp. 1–25 (1988); "Analytical Strategies for the Use of DNA Probes".

Stefan Stamm, et al., Nucleic Acids Research, vol. 19, No. 16, pp. 1350; "Sanchored PCR: PCR with cDNA Coupled to a Solid Phase".

R. Julian S. Duncan, et al., Analytical Biochemistry 132, pp. 68–73 (1983); "A New Regent Which May Be Used to Introduce Sulfhydryl Groups into Proteins, and Its Us in the Preparation Conjugates for Immunoassay".

Seiichi Hashida, et al., Journal of Applied Biochemistry 6, pp. 56–63 (1984) ; "More Useful Maleimide Compounds for the Conjugation of Fab' to Horseradish Peroxidase through Thiol Groups in the Hinge".

Hidenori Yamada, et al., Biochemistry 1981, 20 pp. 4836–4842; "Selective Modification of Aspartic Acid–101 in Lysozyme by Carbodiimide Reaction".

James V. Staros, et al., Analytical Biochemistry 156, pp. 220–222(1986); "Enhancement by N–Hydroxsuccinimide of Water–Soluble Carbodiimide–Mediated Coupling reactions".

Norman Arnheim, et al., C&EN, Oct. 1, 1990, pp. 36–46; "Polymerase Chain Reaction".

* cited by examiner

SATA: Succinimidyl-S-acetylthioacetate
Sulfo-SMCC: Sulfosuccinimidyl-4-(N-maleimidomethyl) cyclohexane-1-carboxylate EDC: 1-ethyl-3-(3-dimethylaminopropyl) carbodiimode hydrochloride
Sulfo-NHS: N-hydroxysulfosuccinimide

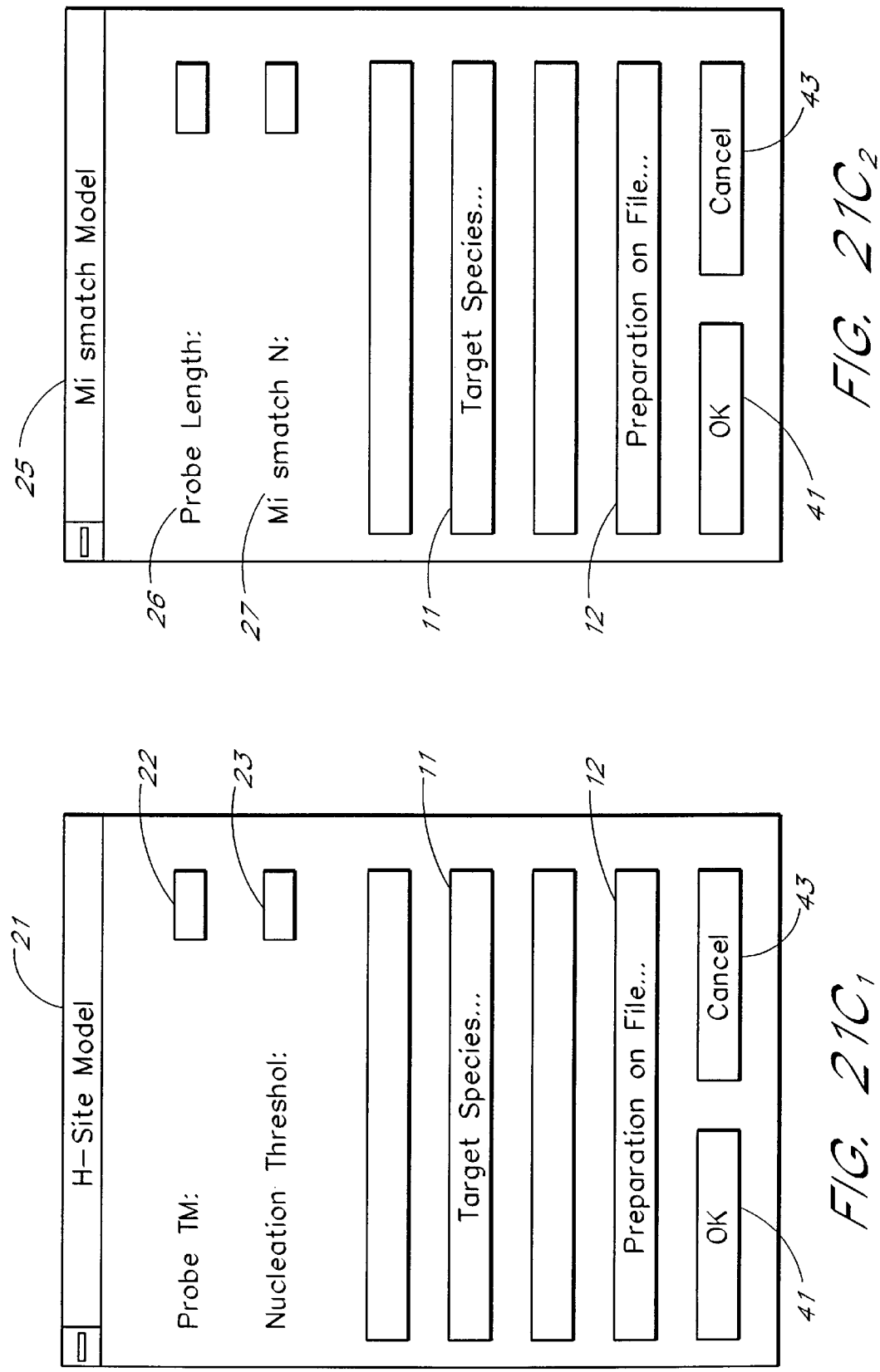

```
┌─────────────────────────────────────────────────────┐
│ ▭  Probes Selected — JUNMIX.prb         ╱―156       │
├─────────────────────────────────────────────────────┤
│   File                                              │
├─────────────────────────────────────────────────────┤
│                                                   ▲ │
│  ┌ PROBE:       C:\HITACHI\JUNMIX.PRP               │
│  │ HYBRIDIZATION:  C:\HITACHI\HUMBJU                │
│  │ Length = 374    Hairpin = 3 5                    │
│  │ Locus       Pos     Tm                           │
│  │ humbjunx    374    61.47    ─────────────        │
│155│ musbjunx   365    61.47    ─────────────        │
│  │ humdjunx    41    34.82    t────────g─g─        │
│  │ humbjunx   182    31.12    a──────────gt gg      │
│  └ humdjunx   602    31.12    c────────x c─gg       │
│    PROBE:       C:\HITACHI\JUNMIX.PRP               │
│    HYBRIDIZATION:  C:\HITACHI\HUMBJU                │
│    Length = 467    Hairpin = 2 13                   │
│    Locus       Pos     Tm                           │
│    humbjunx   467    61.7     ─────────────         │
│    musbjunx   458    51.6     ───────────c─         │
│    humdjunx    32    29.35    t gagcgg──────        │
│    humdjunx    32    29.35    t gagcgg──────        │
│                                                   ▼ │
├─────────────────────────────────────────────────────┤
│ ←  │                                         │  →  │
└─────────────────────────────────────────────────────┘
```

FIG. 25

```
PROBE:         C:\HITACHI\JUNMIX.PRP
HYBRIDIZATION: C:\HITACHI\HUMBJUNX.CDS
Length = 374  Hairpin = 3 5
Locus      Pos   Tm
humbjunx   374   61.47  --------------------
musbjunx   365   61.47  --------------------
humdjunx   41    34.82  t---------g-g--agt
humbjunx   182   31.12  a---------gtgg--gc
humdjunx   602   31.12  c---------c-ggg-gc
humdjunx   602   31.12  c---------c-ggg-gc PROBE:         C:\HITACHI\JUNMIX.PRP
HYBRIDIZATION: C:\HITACHI\HUMBJUNX.CDS
Length = 377  Hairpin = 2 14
Locus      Pos   Tm
humbjunx   377   61.55  --------------------
musbjunx   368   61.55  --------------------
humdjunx   383   28.12  tg-cg-c--g---------
musdjunx   383   28.12  tg-ca-c--g---------
musdjunx   383   28.12  tg-ca-c--g---------

PROBE:         C:\HITACHI\JUNMIX.PRP
HYBRIDIZATION: C:\HITACHI\HUMBJUNX.CDS
Length = 389  Hairpin = 3 3
Locus      Pos   Tm
humbjunx   389   61.7   --------------------
muscjunx   314   56.65  -c------------------
musbjunx   380   50.85  ----------------t--g
humcjunx   314   49.35  -t-----------g------
humdjunx   395   33.85  -----------tt-gc--ag
musdjunx   395   33.85  -----------tt-gc--ag
humcjunx   326   32.35  g-ttcgcc-----------tg
humdjunx   404   32.35  --ttcgcc-----------t-
muscjunx   326   32.35  gcttcgcc-----------tg
musdjunx   253   30.85  gacg-gct-ct---------
humbjunx   953   30.65  g---------t--c-cagct-
musdjunx   83    27.3   cc-gcggt-gt--------g PROBE:         C:\HITACHI\JUNMIX.PRP
HYBRIDIZATION: C:\HITACHI\HUMBJUNX.CDS
Length = 397  Hairpin = 4 1
Locus      Pos   Tm
humbjunx   397   61.55  --------------------
muscjunx   322   53.44  ----------------g---
humcjunx   322   45.33  -----g---------g---
musbjunx   388   41.38  ---------t--g-----t
humdjunx   214   36.83  cccctgc-----------
humdjunx   99    36.16  cg-----gc-c--------
musdjunx   261   34.55  -ct-----------gatct
humdjunx   400   33.27  c---ag---------g---
musdjunx   400   33.27  c---ag---------a---
humcjunx   334   32.28  -----------tgcg--c-
humdjunx   412   32.28  -----------t-a-g-c-
muscjunx   334   32.28  -----------tgcg--c-
humbjunx   658   30.17  cc-cc---------gt---
humdjunx   241   28.95  -c--cacc-c---------
humdjunx   342   28.95  c-cca-ca---------ag
musbjunx   606   28.95  ---ct-a-ac---------
musdjunx   229   28.95  -c-ctgcg-c---------
musdjunx   91    26.67  -gt---------gcc-ccg
```

FIG. 26A

```
PROBE:         C:\HITACHI\JUNMIX.PRP
HYBRIDIZATION: C:\HITACHI\HUMBJUNX.CDS
Length = 417  Hairpin = 2 15
Locus       Pos    Tm
humbjunx    417    60.08   ----------------------
musbjunx    408    55.52   ------------------c----
humdjunx    420    37.3    c------g---------g---t-a-
musbjunx    61     29.0    g---gg---------ca-cctgt-
muscjunx    672    26.27   gc-gc---------a-g--aga--

PROBE:         C:\HITACHI\JUNMIX.PRP
HYBRIDIZATION: C:\HITACHI\HUMBJUNX.CDS
Length = 461  Hairpin = 4 9
Locus       Pos    Tm
humbjunx    461    61.3    --------------------
musbjunx    452    61.3    --------------------
musbjunx    452    61.3    --------------------

PROBE:         C:\HITACHI\JUNMIX.PRP
HYBRIDIZATION: C:\HITACHI\HUMBJUNX.CDS
Length = 467  Hairpin = 2 13
Locus       Pos    Tm
humbjunx    467    61.7    ---------------------
musbjunx    458    51.6    -----------------c-g-
humdjunx    32     29.35   tgagcgg---------gcgg-
humdjunx    32     29.35   tgagcgg---------gcgg- PROBE:         C:\HITACHI\JUNMIX.PRP
HYBRIDIZATION: C:\HITACHI\HUMBJUNX.CDS
Length = 477  Hairpin = 2 4
Locus       Pos    Tm
humbjunx    477    61.37   -----------------
humdjunx    489    34.93   c-c---cg---------
humdjunx    489    34.93   c-c---cg---------

PROBE:         C:\HITACHI\JUNMIX.PRP
HYBRIDIZATION: C:\HITACHI\HUMBJUNX.CDS
Length = 487  Hairpin = 3 3
Locus       Pos    Tm
humbjunx    487    61.14   ---------------
musdjunx    74     51.0    ct-------------
humdjunx    499    45.64   ---------t---g
humdjunx    527    30.72   cc-c-c---------
musdjunx    97     30.72   ttc-c---------g
musdjunx    580    30.72   -cc---------t-g
musdjunx    637    30.72   cc-cc---------g
musdjunx    637    30.72   cc-cc---------g PROBE:         C:\HITACHI\JUNMIX.PRP
HYBRIDIZATION: C:\HITACHI\HUMBJUNX.CDS
Length = 498  Hairpin = 3 2
Locus       Pos    Tm
humbjunx    498    61.26   ----------------
humbjunx    498    61.26   ----------------
```

FIG. 26B

```
PROBE:    C:\HITACHI\JUNMIX.PRP
HYBRIDIZATION:  C:\HITACHI\HUMBJUNX.CDS
Length = 504  Hairpin = 3 2
Locus      Pos   Tm
humbjunx   504   61.47  ------------------
musbjunx   495   40.35  c--a------------t-
humdjunx   609   35.29  cg---------cgggg-
humdjunx   609   35.29  cg---------cgggg-
```

FIG. 26C

OligoProbe DesignStation

Probes:   C:\HITACHI\HUMBJUNX.CDS
Database: C:\HITACHI\JUNMIX.SEQ

Mismatch Model, l = 21, k = 4

| Position | length | \multicolumn{5}{c}{Mismatches} | | | | | screensN | Probe |
|---|---|---|---|---|---|---|---|---|---|---|---|
| | | 0 | 1 | 2 | 3 | 4 | 5 | 6 | 7 | 8 | |
| 1 | 21 | 1 | 1 | 1 | 1 | 1 | | | | | ATGTGCACTAAAATGGAACAG |
| 2 | 21 | 1 | 1 | 1 | 1 | 1 | | | | | TGTGCACTAAAATGGAACAGC |
| 3 | 21 | 1 | 1 | 1 | 1 | 1 | | | | | GTGCACTAAAATGGAACAGCC |
| 4 | 21 | 1 | 1 | 1 | 1 | 1 | | | | | TGCACTAAAATGGAACAGCCC |
| 5 | 21 | 1 | 1 | 1 | 1 | 1 | | | | | GCACTAAAATGGAACAGCCCT |
| 6 | 21 | 1 | 1 | 1 | 1 | 1 | | | | | CACTAAAATGGAACAGCCCTT |
| 7 | 21 | 1 | 1 | 1 | 1 | 1 | | | | | ACTAAAATGGAACAGCCCTTC |
| 8 | 21 | 1 | 1 | 1 | 1 | 1 | | | | | CTAAAATGGAACAGCCCTTCT |
| 9 | 21 | 1 | 1 | 1 | 1 | 1 | | | | | TAAAATGGAACAGCCCTTCTA |
| 10 | 21 | 1 | 1 | 1 | 1 | 1 | | | | | AAAATGGAACAGCCCTTCTAC |
| 11 | 21 | 1 | 1 | 1 | 1 | 1 | | | | | AAATGGAACAGCCCTTCTACC |
| 12 | 21 | 1 | 1 | 1 | 1 | 1 | | | | | AATGGAACAGCCCTTCTACCA |
| 13 | 21 | 1 | 1 | 1 | 1 | 1 | | | | | ATGGAACAGCCCTTCTACCAC |
| 14 | 21 | 1 | 1 | 1 | 1 | 1 | | | | | TGGAACAGCCCTTCTACCACG |
| 15 | 21 | 1 | 1 | 1 | 1 | 1 | | | | | GGAACAGCCCTTCTACCACGA |
| 16 | 21 | 1 | 1 | 1 | 1 | 1 | | | | | GAACAGCCCTTCTACCACGAC |
| 17 | 21 | 1 | 1 | 1 | 1 | 1 | | | | | AACAGCCCTTCTACCACGACG |
| 18 | 21 | 1 | 1 | 1 | 1 | 1 | | | | | ACAGCCCTTCTACCACGACGA |
| 19 | 21 | 1 | 1 | 1 | 1 | 1 | | | | | CAGCCCTTCTACCACGACGAC |
| 20 | 21 | 1 | 1 | 1 | 1 | 1 | | | | | AGCCCTTCTACCACGACGACT |
| 21 | 21 | 1 | 1 | 1 | 1 | 1 | | | | | GCCCTTCTACCACGACGACTC |
| 22 | 21 | 1 | 1 | 1 | 1 | 1 | | | | | CCCTTCTACCACGACGACTCA |
| 23 | 21 | 1 | 1 | 1 | 1 | 1 | | | | | CCTTCTACCACGACGACTCAT |
| 24 | 21 | 1 | 1 | 1 | 1 | 1 | | | | | CTTCTACCACGACGACTCATA |
| 25 | 21 | 1 | 1 | 1 | 1 | 1 | | | | | TTCTACCACGACGACTCATAC |
| 26 | 21 | 1 | 1 | 1 | 1 | 1 | | | | | TCTACCACGACGACTCATACA |
| 27 | 21 | 1 | 1 | 1 | 1 | 1 | | | | | CTACCACGACGACTCATACAC |
| 28 | 21 | 1 | 1 | 1 | 1 | 1 | | | | | TACCACGACGACTCATACACA |
| 29 | 21 | 1 | 1 | 1 | 1 | 1 | | | | | ACCACGACGACTCATACACAG |
| 30 | 21 | 1 | 1 | 1 | 1 | 1 | | | | | CCACGACGACTCATACACAGC |
| 31 | 21 | 1 | 1 | 1 | 1 | 1 | | | | | CACGACGACTCATACACAGCT |
| 32 | 21 | 1 | 1 | 1 | 1 | 1 | | | | | ACGACGACTCATACACAGCTA |
| 33 | 21 | 1 | 1 | 1 | 1 | 1 | | | | | CGACGACTCATACACAGCTAC |
| 34 | 21 | 1 | 1 | 1 | 1 | 1 | | | | | GACGACTCATACACAGCTACG |
| 35 | 21 | 1 | 1 | 1 | 1 | 1 | | | | | ACGACTCATACACAGCTACGG |
| 36 | 21 | 1 | 1 | 1 | 1 | 1 | | | | | CGACTCATACACAGCTACGGG |
| 37 | 21 | 1 | 1 | 1 | 1 | 1 | | | | | GACTCATACACAGCTACGGGA |
| 38 | 21 | 1 | 1 | 1 | 1 | 1 | | | | | ACTCATACACAGCTACGGGAT |
| 39 | 21 | 1 | 1 | 1 | 1 | 1 | | | | | CTCATACACAGCTACGGGATA |
| 40 | 21 | 1 | 1 | 1 | 1 | 1 | | | | | TCATACACAGCTACGGGATAC |
| 41 | 21 | 1 | 1 | 1 | 1 | 1 | | | | | CATACACAGCTACGGGATACG |
| 42 | 21 | 1 | 1 | 1 | 1 | 1 | | | | | ATACACAGCTACGGGATACGG |
| 43 | 21 | 1 | 1 | 1 | 1 | 1 | | | | | TACACAGCTACGGGATACGGC |
| 44 | 21 | 1 | 1 | 1 | 1 | 1 | | | | | ACACAGCTACGGGATACGGCC |
| 45 | 21 | 1 | 1 | 1 | 1 | 1 | | | | | CACAGCTACGGGATACGGCCG |
| 46 | 21 | 1 | 1 | 1 | 1 | 1 | | | | | ACAGCTACGGGATACGGCCGG |
| 47 | 21 | 1 | 1 | 1 | 1 | 1 | | | | | CAGCTACGGGATACGGCCGGG |
| 48 | 21 | 1 | 1 | 1 | 1 | 1 | | | | | AGCTACGGGATACGGCCGGGC |
| 49 | 21 | 1 | 1 | 1 | 1 | 1 | | | | | GCTACGGGATACGGCCGGGCC |
| 50 | 21 | 1 | 1 | 1 | 1 | 1 | | | | | CTACGGGATACGGCCGGGCCC |
| 51 | 21 | 1 | 1 | 1 | 1 | 1 | | | | | TACGGGATACGGCCGGGCCCC |
| 52 | 21 | 1 | 1 | 1 | 1 | 1 | | | | | ACGGGATACGGCCGGGCCCCT |
| 53 | 21 | 1 | 1 | 1 | 1 | 1 | | | | | CGGGATACGGCCGGGCCCCTG |

FIG. 40

OligoProbe DesignStation

Probes: C:\HITACHI\HUMBJUNX.CDS
Database: C:\HITACHI\JUNMIX.SEQ

Mismatch Model, l = 21, k = 4

| Position | Mismatches | | | | | | | | screensN | |
|---|---|---|---|---|---|---|---|---|---|---|
| length | 0 | 1 | 2 | 3 | 4 | 5 | 6 | 7 | 8 | Probe |
| 1  21 | 0 | 0 | 0 | 0 | 0 | | | | | ATGTGCACTAAAATGGAACAG |
| 2  21 | 0 | 0 | 0 | 0 | 0 | | | | | TGTGCACTAAAATGGAACAGC |
| 3  21 | 0 | 0 | 0 | 0 | 0 | | | | | GTGCACTAAAATGGAACAGCC |
| 4  21 | 0 | 0 | 0 | 0 | 0 | | | | | TGCACTAAAATGGAACAGCCC |
| 5  21 | 0 | 0 | 0 | 0 | 0 | | | | | GCACTAAAATGGAACAGCCCT |
| 6  21 | 0 | 0 | 0 | 0 | 0 | | | | | CACTAAAATGGAACAGCCCTT |
| 7  21 | 0 | 0 | 0 | 0 | 0 | | | | | ACTAAAATGGAACAGCCCTTC |
| 8  21 | 0 | 0 | 0 | 0 | 0 | | | | | CTAAAATGGAACAGCCCTTCT |
| 9  21 | 0 | 0 | 0 | 0 | 0 | | | | | TAAAATGGAACAGCCCTTCTA |
| 10  21 | 0 | 0 | 0 | 0 | 0 | | | | | AAAATGGAACAGCCCTTCTAC |
| 11  21 | 0 | 0 | 0 | 0 | 0 | | | | | AAATGGAACAGCCCTTCTACC |
| 12  21 | 0 | 0 | 0 | 0 | 0 | | | | | AATGGAACAGCCCTTCTACCA |
| 13  21 | 0 | 0 | 0 | 0 | 0 | | | | | ATGGAACAGCCCTTCTACCAC |
| 14  21 | 0 | 0 | 0 | 0 | 0 | | | | | TGGAACAGCCCTTCTACCACG |
| 15  21 | 0 | 0 | 0 | 0 | 0 | | | | | GGAACAGCCCTTCTACCACGA |
| 16  21 | 0 | 0 | 0 | 0 | 0 | | | | | GAACAGCCCTTCTACCACGAC |
| 17  21 | 0 | 0 | 0 | 0 | 0 | | | | | AACAGCCCTTCTACCACGACG |
| 18  21 | 0 | 0 | 0 | 0 | 0 | | | | | ACAGCCCTTCTACCACGACGA |
| 19  21 | 0 | 0 | 0 | 0 | 0 | | | | | CAGCCCTTCTACCACGACGAC |
| 20  21 | 0 | 0 | 0 | 0 | 0 | | | | | AGCCCTTCTACCACGACGACT |
| 21  21 | 0 | 0 | 0 | 0 | 0 | | | | | GCCCTTCTACCACGACGACTC |
| 22  21 | 0 | 0 | 0 | 0 | 0 | | | | | CCCTTCTACCACGACGACTCA |
| 23  21 | 0 | 0 | 0 | 0 | 0 | | | | | CCTTCTACCACGACGACTCAT |
| 24  21 | 0 | 0 | 0 | 0 | 0 | | | | | CTTCTACCACGACGACTCATA |
| 25  21 | 0 | 0 | 0 | 0 | 0 | | | | | TTCTACCACGACGACTCATAC |
| 26  21 | 0 | 0 | 0 | 0 | 0 | | | | | TCTACCACGACGACTCATACA |
| 27  21 | 0 | 0 | 0 | 0 | 0 | | | | | CTACCACGACGACTCATACAC |
| 28  21 | 0 | 0 | 0 | 0 | 0 | | | | | TACCACGACGACTCATACACA |
| 29  21 | 0 | 0 | 0 | 0 | 0 | | | | | ACCACGACGACTCATACACAG |
| 30  21 | 0 | 0 | 0 | 0 | 0 | | | | | CCACGACGACTCATACACAGC |
| 31  21 | 0 | 0 | 0 | 0 | 0 | | | | | CACGACGACTCATACACAGCT |
| 32  21 | 0 | 0 | 0 | 0 | 0 | | | | | ACGACGACTCATACACAGCTA |
| 33  21 | 0 | 0 | 0 | 0 | 0 | | | | | CGACGACTCATACACAGCTAC |
| 34  21 | 0 | 0 | 0 | 0 | 0 | | | | | GACGACTCATACACAGCTACG |
| 35  21 | 0 | 0 | 0 | 0 | 0 | | | | | ACGACTCATACACAGCTACGG |
| 36  21 | 0 | 0 | 0 | 0 | 0 | | | | | CGACTCATACACAGCTACGGG |
| 37  21 | 0 | 0 | 0 | 0 | 0 | | | | | GACTCATACACAGCTACGGGA |
| 38  21 | 0 | 0 | 0 | 0 | 0 | | | | | ACTCATACACAGCTACGGGAT |
| 39  21 | 0 | 0 | 0 | 0 | 0 | | | | | CTCATACACAGCTACGGGATA |
| 40  21 | 0 | 0 | 0 | 0 | 0 | | | | | TCATACACAGCTACGGGATAC |
| 41  21 | 0 | 0 | 0 | 0 | 0 | | | | | CATACACAGCTACGGGATACG |
| 42  21 | 0 | 0 | 0 | 0 | 0 | | | | | ATACACAGCTACGGGATACGG |
| 43  21 | 0 | 0 | 0 | 0 | 0 | | | | | TACACAGCTACGGGATACGGC |
| 44  21 | 0 | 0 | 0 | 0 | 0 | | | | | ACACAGCTACGGGATACGGCC |
| 45  21 | 0 | 0 | 0 | 0 | 0 | | | | | CACAGCTACGGGATACGGCCG |
| 46  21 | 0 | 0 | 0 | 0 | 0 | | | | | ACAGCTACGGGATACGGCCGG |
| 47  21 | 0 | 0 | 0 | 0 | 0 | | | | | CAGCTACGGGATACGGCCGGG |
| 48  21 | 0 | 0 | 0 | 0 | 0 | | | | | AGCTACGGGATACGGCCGGGC |
| 49  21 | 0 | 0 | 0 | 0 | 0 | | | | | GCTACGGGATACGGCCGGGCC |
| 50  21 | 0 | 0 | 0 | 0 | 0 | | | | | CTACGGGATACGGCCGGGCCC |
| 51  21 | 0 | 0 | 0 | 0 | 0 | | | | | TACGGGATACGGCCGGGCCCC |
| 52  21 | 0 | 0 | 0 | 0 | 0 | | | | | ACGGGATACGGCCGGGCCCCT |
| 53  21 | 0 | 0 | 0 | 0 | 0 | | | | | CGGGATACGGCCGGGCCCCTG |

FIG. 44A (Partial File -- 10 pages of 190 pages)

OligoProbe DesignStation

Probes:        C:\HITACHI\HUMBJUNX.CDS
Preparation:   C:\HITACHI\JUNMIX.PRP

| Locus | pos | Tm | Locus | pos | Tm | Locus | pos | Tm |
|---|---|---|---|---|---|---|---|---|
| atgtgcactaaaatggaacagcccttctac | | | | | | | | |
| 1   30 | 1 | | 1 | 1 | 2 | 2 | 2 | 2   2   3   4 |
| humbjunx | 1 | 60.76 | | | | | | |
| musbjunx | 1 | 50.03 | | | | | | |
| muscjunx | 1 | 30.07 | | | | | | |
| musdjunx | 721 | 27.84 | | | | | | |
| | | | | | | | | |
| tgtgcactaaaatggaacagcccttctac | | | | | | | | |
| 2   29 | 1 | | 1 | 1 | 2 | 2 | 2 | 2   2   3   4 |
| humbjunx | 65533 | 60.68 | | | | | | |
| musbjunx | 65533 | 49.58 | | | | | | |
| muscjunx | 1 | 29.97 | | | | | | |
| musdjunx | 721 | 27.66 | | | | | | |
| | | | | | | | | |
| gtgcactaaaatggaacagcccttctac | | | | | | | | |
| 3   28 | 1 | | 1 | 1 | 2 | 2 | 2 | 2   2   3   4 |
| humbjunx | 65533 | 60.60 | | | | | | |
| musbjunx | 65533 | 49.10 | | | | | | |
| muscjunx | 1 | 29.86 | | | | | | |
| musdjunx | 721 | 27.47 | | | | | | |
| | | | | | | | | |
| tgcactaaaatggaacagcccttctacc | | | | | | | | |
| 4   28 | 1 | | 1 | 1 | 2 | 2 | 2 | 2   2   3   4 |
| humbjunx | 65533 | 60.60 | | | | | | |
| musbjunx | 65533 | 46.57 | | | | | | |
| muscjunx | 1 | 29.86 | | | | | | |
| musdjunx | 729 | 27.47 | | | | | | |
| | | | | | | | | |
| gcactaaaatggaacagcccttctacc | | | | | | | | |
| 5   27 | 1 | | 1 | 1 | 2 | 2 | 2 | 2   2   3   4 |
| humbjunx | 5 | 60.51 | | | | | | |
| musbjunx | 5 | 45.96 | | | | | | |
| muscjunx | 1 | 29.75 | | | | | | |
| musdjunx | 729 | 27.26 | | | | | | |

FIG. 44B

```
LOCUS       HUMBJUNX     1044 bp     DNA             141 T           19-DEC-1991
BASE COUNT      195     A     368 C     340 G
ORIGIN
     1 ATGTGCACTA AAATGGAACA GCCCTTCTAC CACGACGACT CATACACAGC TACGGGATAC
    61 GGCCCGGGCCC CTGGTGGCCT CTCTCTACAC GACTACAAAC TCCTGAAACC GAGCCTGGCG
   121 GTCAACCTGG CCGACCCCTA CCGGAGTCTC AAAGCGCCTG GGGCTCGCGG ACCCGGCCCA
   181 GAGGGCGGCG GTGGCGGCAG CTACTTTCT GGTCAGGGCT CGGACACCGG CGGTCTCTC
   241 AAGCTCGCCT CTTCGGAGCT GGAACGCCTG ATTGTCCCCA ACAGCAACGG CGTGATCACG
   301 ACGACGCCTA CACCCCGGG ACAGTACTTT TACCCCGCGG GGGGTGGCAG CGGTGGAGGT
   361 GCAGGGGGCG CAGGGGGCGG CGTCACCGAG GAGCAGGAGG GCTTCGCCGA CGGCTTTGTC
   421 AAAGCCCTGG ACGATCTGCA CAAGATGAAC CACGTGACAC CCCCAACGT GTCCCTGGGC
   481 GCTACCGGGG GCCCCCCCGC TGGGCCCCGG GGCGTCTACG CCCTCCCCGA GCCACCTCCC
   541 GTTTACACCA ACCTCAGCAG CTACTCCCCA GCCTCTGCGT GCCTCGGAGG CGCCGGGGCT
   601 GCCGTCGGGA CCGGGAGCTC GTACCCGACG ACCACCATCA GCTACCTCCC ACACGCGCCG
   661 CCCTTCGCCG GTGCCACCC GGGCCAGCTG GGCTTGGGCC GGGGGCCTC CACCTTCAAG
   721 GAGGAACCGC AGACCGTGCC GGAGGGCGCG AGCCCGGACG CCACGCCGCC GGTGTCCCCC
   781 ATCAACATGG AAGACCAAGA GCGCATCAAA GTGGAGCGCA AGCGGCTGCG GAACCGGCTG
   841 GCGGCCACCA AGTGCCGGAA GCGGAAGCTG GAGCGCATCG CGCGGCTGGA GGACAAGGTG
   901 AAGACGCTCA AGGCCGAGAA CGCGGGGCTG CGCGGGGCTG CCGGCCTCCT CCGGGAGCAG
   961 GTGGCCCAGC TCAAACAGAA GGTCATGACC ACGTGTCAGCA ACGGCGTGCT GCTGCTGCTT
  1021 GGGGTCAAGG GACACGCCTT CTGA
```

FIG. 47

| LOCUS | HUMBJUNX | 1044 bp | DNA | 141 T | 19-DEC-1991 |
|---|---|---|---|---|---|
| BASE COUNT | 195 | A | 340 G | 368 C | |
| ORIGIN | | | | | |
| 1 | ATGTGCACTA | AAATGGAACA | GCCCTTCTAC | CACGACGACT | CATACACAGC | TACGGGATAC |
| 61 | GGCCGGGCCC | CTGGTGCCCT | CTCTCTACAC | GACTACAAAC | TCCTGAAACC | GAGCCTGCCG |
| 121 | GTCACCTGG | CCGACCCCTA | CCGGAGTCTC | AAAGCGCCTG | GGGCTCGCGG | ACCCGGCCA |
| 181 | GAGGGGCCG | GTGGCGGCAG | CTACTTTCT | GGTCAGGGCT | CGGACACCGG | CGCGTCTCTC |
| 241 | AAGCTCGCCT | CTTCGGAGCT | GGAACGCCTG | ACAGTACTTT | ACAGCAACGG | CGTGATCACG |
| 301 | ACGACGCCTA | CACCCCCGGG | ACAGTACTTT | TACCCCGCG | GGGGTGGCAG | CGGTGGAGGT |
| 361 | GCAGGGGCG | CAGGGGGCGG | CGTCACCGCG | GAGCAGGAGG | GCTTCGCCGA | CGGCTTTGTC |
| 421 | AAAGCCCTGG | ACGATCTGCA | CAAGATGAAC | CACGTGACAC | CCCCAACGT | GTCCCTGGGC |
| 481 | GCTACCGGG | GGCCCCCCGC | TGGGCCCCGGG | GGCGTCTACG | CCGGCCCCGGA | GCCACCTCCC |
| 541 | GTTTACACCA | ACCTCAGCAG | CTACTCCCCA | GCCTCTGCGT | CCTCGGGAGG | CGCCGGGGCT |
| 601 | GCCGTCGGGA | CCGGGAGCTC | GTACCCGACG | ACCACCATCA | GCTACCTCCC | ACACGCGCCG |
| 661 | CCCTTCGCCG | GTGGCCACCC | GGCGCAGCTG | GGCTTGGGCC | GCCGGCCTC | CACCTTCAAG |
| 721 | GAGGAACCGC | AGACCGTGCC | GGAGGCCGCC | AGCCGGGACG | GCCACGCCGCC | GTGTCCCCC |
| 781 | ATCAACATGG | AAGACCAAGA | GCGCATCAAA | GTGGAGCGCA | AGCGGCTGCG | GAACCGGCTG |
| 841 | GCGGCCACCA | AGTGCCGGAA | GCGGAAGCTG | GAGCGCATCG | CGCGGCTGCG | GGACAAGGTG |
| 901 | AAGACGCTCA | AGGCCCAGAA | GCGCATCAAA | TCGAGTACCG | CGGCCCTCCT | CGGGGAGCAG |
| 961 | GTGGCCCAGC | TCAAACAGAA | GGTCATGACC | CACGTCAGCA | ACGGCTGTCA | CGGGGAGCAG |
| 1021 | GGGGTCAAGG | GACACGCCTT | CTGA | | | |

FIG. 48A

```
LOCUS         HUMCJUNX     996 bp       DNA              19-DEC-1991
BASE COUNT     226    A   342 C    299 G   129 T
ORIGIN
   1 ATGACTGCAA AGATGGAAAC GACCTTCTAT GACGATGCCC TCAACGCCTC GTTCCTCCCG
  61 TCCGAGAGCG GACCTTATGG CTACAGTAAC CCCAAGATCC TGAAACAGAG CATGACCCTG
 121 AACCTGGCCG ACCCAGTGGG GAGCCTGAAG CCGCACCTCC GCGCCAAGAA CTCGGACCTC
 181 CTCACCTCGC CCGACGTGGG GCTGCTCAAG CTGGCGTCGC CCGAGCTGGA GCGCCTGATA
 241 ATCCAGTCCA GCAACGGGCA CATCACCACC ACGCCGACCC CCACCCAGTT CCTGTGCCCC
 301 AAGAACGTGA CAGATGAGCA GGAGGGGTTC GCCGAGGGCT TCGTGCGCGC CCTGGCCGAA
 361 CTGCACAGCC AGAACACGCT GCCCAGCGTC ACGTCGGCGG CGCAGCCGGT CAACGGGGCA
 421 GGCATGGTGG CTCCCGCGGT AGCCTCGGTG GCAGGGGGCA GCGGGAGCGG CGGCTTCAGC
 481 GCCAGCCTGC ACAGCGAGCC GCCCGTCTAC GCAAACCTCA GCAACTTCAA CCCAGGCGCG
 541 CTGAGCAGCG GCGGCGGGGC GCCCTCCTAC GGGGCGGGCG GCCTGGCCTT TCCCGCGCAA
 601 CCCCAGCAGC AGCAGCAGCC GCCGCACCAC CTGCCCCAGC AGATGCCCGT GCAGCACCCG
 661 CGGCTGCAGG CCCTGAAGGA GGAGCCTCAG ACAGTGCCCG AGATGCCCGG CGAGACACCG
 721 CCCCTGTCCC CCATCGACAT GGAGTCCCAG GAGCGGATCA AGGCGGAGAG GAAGCGCATG
 781 AGGAACCGCA TCGCTGCCCT CAAGTGCCGA AAAAGGAAGC TGGAGAGAAT CGCCCCGCTG
 841 GAGGAAAAAG TGAAAACCTT GAAAGCTCAG AACTCGGAGC TGGCGTCCAC GGCCAACATG
 901 CTCAGGGAAC AGGTGGCACA GCTTAAACAG AAAGTCATGA ACCACGTTAA CAGTGGGTGC
 961 CAACTCATGC TAACGCAGCA GTTGCAAACA TTTGA
```

FIG. 48B

```
LOCUS        HUMDJUNX        1044 bp  ss-mRNA           PRI      24-MAY-1991
DEFINITION   Human junD mRNA
ACCESSION    X56681
KEYWORDS     jun-D gene; oncogene.
SOURCE       Homo sapiens RNA.
  ORGANISM   Homo sapiens
             Eukaryota; Animalia; Metazoa; Chordata; Vertebrate; Mammalia;
             Theria; Eutheria; Primates; Haplorhini; Catarrhini; Hominidae REFERENCE    1  (bases 1 to 1891)
  AUTHORS    Shaul, Y.
  JOURNAL    Unpublished (1990)
  STANDARD   full automatic
REFERENCE    2  (sites)
  AUTHORS    Berger, I. and Shaul, Y.
  TITLES     Structure and function of human jun-D
  JOURNAL    Unpublished (1990)
  STANDARD   full staff_review
COMMENT      from EMBL 26  entry HSJUNDR;    dated 18-MAR-1991.
FEATURES               Location/Qualifiers
     mRNA              1...1891
                       /gene="junD"
                       /evidence=EXPERIMENTAL
     CDS               175...1218
                       /product="junD protien"
                       /gene="junD"
                       /codon_start=1
     polyA_site        1891..1891
```

FIG. 48C

| BASE COUNT | 162 | A | 405 | C | 360 | G | 117 | T | | |
|---|---|---|---|---|---|---|---|---|---|---|
| ORIGIN | | | | | | | | | | |
| 1 | ATGGAAACAC | CCTTCTACGG | CGATGAGGCG | CTGAGCGGCC | TGGGCGGCGG | CGCCAGTGGC |
| 61 | AGCGGCGGCA | CGTTCGCGTC | CCCGGGCCCG | TTGTTCCCCG | GGGCGCCCCC | GACGGCCGCG |
| 121 | GCCGGCAGCA | TGATGAAGAA | GGACGCGCTG | ACGCTGAGCC | TGAGTGAGCA | GGTGGCGGCA |
| 181 | GCGCTCAAGC | CTGCGCCCGC | GCCCGCCCTG | TACCCCCTG | CCGCCGACGG | CGCCCCCAGC |
| 241 | GGGCCACCCC | CCGACGGCCT | GCTCGCCTCT | CCCGACCTGG | GGCTGCTGAA | GCTGGCCTCC |
| 301 | CCCGAGCTCG | AGCGCCCTCAT | CATCCAGTCC | AACGGGCTGG | TCACCACCAC | GCCGACGAGC |
| 361 | TCACAGTTCC | TCTACCCCAA | GGTGGCGGCC | AGCGGAGAGC | AGGAGTTCGC | CGAGGGCTTC |
| 421 | GTCAAGGCCC | TGGAGGATTT | ACACAAGCAG | AACCAGCTCG | GCGGGGCCG | GGCCGCTGCC |
| 481 | GCCGCCGCCG | CCGCCGCCGG | GGGCCCCTCG | GCACGCGCCA | CGGGCTCCGC | GCCCCCGGC |
| 541 | GAGCTGGCCC | CGGCGGGCGC | CGCGCCTGTCT | GCGCCTGTCT | ACGCGAACCT | GAGCAGCTAC |
| 601 | GCGGGGGCCG | CCGGGGGGCG | GGGGGCGCC | GCGACGGTCG | CCTTCGCTGC | CGAACCTGTG |
| 661 | CCCTTCCCGC | CGCCGCCACC | CCCAGGGCGC | TTGGGCCCGC | CGCGCCTGGC | TGCGCTCAAG |
| 721 | GACGAGCCAC | AGACGGTGCC | CGACGTGCCC | AGCTTCGGCG | AGAGCCCGCC | GTTGTCGCCC |
| 781 | ATCGACATGG | ACACGCAGGA | GCGCATCAAG | GCGGAGCGCA | AGCGGGCTGCG | CAACCGCATC |
| 841 | GCCGCCTCCA | AGTGCCGCAA | GCGCAAGCTG | GAGCGCATCT | CGCGCCTGGA | AGAGAAAGTG |
| 901 | AAGACCCTCA | AGAGTCAGAA | CACGGAGCTG | GCGTCCACGG | CGAGCCTGCT | GCGCGAGCAG |
| 961 | GTGGCGCAGC | TCAAGCAGAA | AGTCCTCAGC | CACGTCAACA | GCGGCTGCCA | GCTGCTGCCC |
| 1021 | CAGCACCAGG | TCCCGGGGTA | CTGA | | | |

*FIG. 48D*

| LOCUS | MUSBJUNX | 1035 bp | DNA | 159 T | 19-DEC-1991 |
|---|---|---|---|---|---|
| BASE COUNT | 210 A | 333 C | 333 G | | |

ORIGIN

```
   1 ATGTGCACGA AAATGGAACA GCCTTTCTAT CACGACGACT CTTACGCAGC GGCGGGATAC
  61 GGTCGGAGCC CTGGCAGCCT GTCTCTACAC GACTACAAAC TCCTGAAACC CACCTTGGCG
 121 CTCAACCTGG CGGATCCCTA TCGGGGTCTC AAGGGTCCTG GGGCGCGGGG TCCAGGCCCG
 181 GAGGGCAGTG GGGCAGGCAG CTACTTTTCG GGTCAGGGAT CAGACACAGG CGCATCTCTG
 241 AAGCTAGCCT CCACGGAACT GGAGCGCTTG ATCGTCCCCA ACAGCAACGG CGTGATCACG
 301 ACGACGCCCA CGCCTCCGGG ACAGTACTTT TACCCCCGTG GGGGTGGCAG CGGTGGAGGT
 361 ACAGGGGGCG GCGTCACCGA GGAGCAGGAG GGCTTTGCGG ACGGTTTTGT CAAAGCCCTG
 421 GACGACCTGC ACAAGATGAA CCACGTGACG CCCCCCAACG TGTCCCTGGG CGCCAGCGGG
 481 GGTCCCCAGG CCGGCCCAGG GGGCGTCTAT GCTGGTCCGG AGCCGCCTCC CGTCTACACC
 541 AACCTCAGCA GTTACTCTCC AGCCTCTGCA CCCTCTGGAG GCTCCGGGAC CGCCCGTGGG
 601 ACTGGGAGCT CATACCCGAC GGCCACCATC AGCTACCTCC CACATGCACC ACCCTTTGCG
 661 GGCGGCCACC CGGAGGCACG GGGTTTGAGT CGTGGCGCTT CCGCCTTTAA AGAGGAACCG
 721 CAGACCGTAC CGGAGCCGAC CAGCCGCGAC GCCACGCCCG CTGTGTCCCC CATCAACATG
 781 GAAGACCAGG AGCGCATCAA AGTGGAGCGA AAGCGGGCTG GAACAGGCT GGCGGCCACC
 841 AAGTGCCGGA AGCGGAAGCT GGAGCGCATC GCCCGGGCCG AAGCGGAAGGT GAAGACACTC
 901 AAGGCTGAGA ACGCGGGGCT GTCGAGTGCT GCCGGTCTCC TAAGGGAGCA AGTGGCGCAG
 961 CTCAAGCAGA AGGTCATGAC CCATGTCAGC AACGGCTGCC AACGGCTGCC AGTTGCTGCT AGGGGTCAAG
1021 GGACACGCCT TCTGA
```

FIG. 48E

```
LOCUS        MUSCJUNX       1005 bp    DNA                      19-DEC-1991
BASE COUNT     223 A       334 C       300 G       148 T
ORIGIN
    1 ATGACTGCAA AGATGGAAAC GACCTTCTAC GACGATGCCC TCAACGCCTC GTTCCTCCAG
   61 TCCGAGAGCG GTGCCTACGG CTACAGTAAC CCTAAGATCC TAAAACAGAG CATGACCTTG
  121 ACCTGGCCG  ACCCGGTGGG CAGTCTGAAG CCGCACCTCC GCGCCAAGAA CTCGGACCTT
  181 CTCACGTCGC CCGACGTCGG GCTGCTCAAG CTGGCGTCGC CGGAGCTGGA GCGCCTGATC
  241 ATCCAGTCCA GCAATGGGCA CATCACCACT ACACCGACCC CCACCCAGTT CTTGTGCCCC
  301 AAGAACGTGA CCGACGAGCA GGAGGGCTTC GCCGAGGGCT TCGTGCCGCG CCTGGCTGAA
  361 CTGCATAGCC AGAACACGCT TCCCAGTGTC ACCTCCGCGG CACAGCCGGT CAGCGGGGCG
  421 GGCATGGTGG CTCCCGCGGT GGCCTCAGTA GCAGGCGCTG GCGGCGGTGG TGGCTACAGC
  481 GCCAGCCTGC ACAGTGAGCC TCCGGTCTAC GCCAACCTCA GCAACTTCAA CCCCGGTGCG
  541 CTGAGCAGCG GCGGTGGGGC GCCCTCCTAT GGGCCGGCCCG GGCTGGCCTT TCCCTCGCAG
  601 CCGCAGCAGC AGCAGCAGCC GCCGCATCCT TGCCCCAACA GATCCCGGTG
  661 CAGCACCCGC GGCTGCAAGC CCTGAAGGAA CCGTGCCGGA CCGTGCCGGA GATGCCGGGA
  721 GAGACGCCGC CCCTGTCCCC TATCGACATG AGCCGGATCA AAGGGAAGCT GGCAGAGAGG
  781 AAGCGCATGA GGAACCGCAT TGCCGCCTCC AAGTGCCGGA AAGGAAGCT  GGAGCGGATC
  841 GCTCGGCTAG AGGAAAAAGT GAAAACCTTG AAAGCGCAAA ACTCCGAGCT GGCATCCACG
  901 GCCAACATGC TCAGGGAACA GGTGGCACAG CTTAAGCAGA AAGTCATGAA CCACGTTAAC
  961 AGTGGGTGCC AACTCATGCT AACGCAGCAG TTGCAAACGT TTTGA
```

FIG. 48F

| LOCUS | MUSDJUNX | 1026 bp | DNA | | 19-DEC-1991 |
|---|---|---|---|---|---|
| BASE COUNT | 172 A | 382 C | 343 G | 129 T | |

ORIGIN

```
   1 ATGGAAACGC CCTTCTATGG CGAGGAGGCG CTGAGCGGCC TGGCTGCGGG TGCGTCGAGC
  61 GTCGCTGGTG CTACTGGGGC CCCCGGCGGT GGTGGCTTCG CGCCCCCGGG CCGGCGCTTC
 121 CCCGGGGCGC CCCCGACGAG CAGCATGCTG AAGAAAGACG CGCTGACGCT CAGCCTGGCG
 181 GAGCAGGGAG CGGCGGGATT GAAACCAGGG TCGGCCACTG CACCTTCTGC GCTGCGCCCC
 241 GACGGCGCCC CCGACGGGCT GCTGGCTTCG CCGGATCTTG GGCTGCTCAA ACTCGCGTCG
 301 CCGGAGCTGG AGAGGCTGAT CATCCAGTCC AACGGGCTGG TGACCACTAC CCCGACCAGT
 361 ACGCAGTTCC TCTACCCGAA GGTGGCAGCC AGCGAGGAGC AGGAGTTCGC CGAAGGCTTC
 421 GTCAAGGCGC TGGAGGACCT GCACAAGCAA AGCCAGTCGG GTGCGGCCAC CGGGGCCACC
 481 TCAGGGGCTC CCGGCCCTCC CGCGCCCGCC GACCTGGCCG CCACCCCCGG GGCCACGGAG
 541 ACCCCGGTCT ACGCCAACCT GAGCAGTTTC GCGGGGTGGC GCCGGGCCCC TGGGGGCGCG
 601 GCCACCGTGG CTTTCGCCGC GGAGCCAGTG CCCTTCCCGC CGCCCCCGGG CGCGCTGGGG
 661 CCGCCGCCAC CTCCGCATCC ACCGCGCCTG GCCGCGCTCA AGGACGAGCC GCAGACCGTG
 721 CCGGACGTGC CGAGCTTCGG CGAGCAGCCT CCGACAGCCC CCGCTGTCGC CCATCGACAT GGACACGCAA
 781 GAACGCATCA AGGCGGAGCG CAAGAGGCTG CGCAACCGCA TCGCCGCCTC CAAATGCCGC
 841 AAGCGCAAGC TGGAGCGTAT CTCGCGCCTG GAGGAGAAAG TCAAGACCCT CAAAAGCCAG
 901 AACACCGAGC TGGCGTCCAC CGCCAGCCTG CTGCGCGAGC AGGTGGCGCA GCTCAAACAG
 961 AAAGTCCTCA GCCACGTCAA CAGCGGGTGC CAGCTGCTGC CCCAGCACCA GGTCCCGGCG
1021 TACTGA
```

FIG. 48G

SEQUENCE LISTING (1) GENERAL INFORMATION:

(iii) NUMBER OF SEQUENCES: 457

(2) INFORMATION FOR SEQ ID NO:1:

(i) SEQUENCE CHARACTERISTICS:
        (A) LENGTH: 22 bases
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Gs mRNA NUCLEOTIDE PROBE (xi) SEQUENCE DESCRIPTION: SEQ ID NO:1:

TTCATCCTCC CACAGAGCCT TG                              22

(2) INFORMATION FOR SEQ ID NO:2:

(i) SEQUENCE CHARACTERISTICS:
        (A) LENGTH: 22 bases
        (B) TYPE: nucleic acid
        (C) STRANDEDNESS: single
        (D) TOPOLOGY: linear (ii) MOLECULE TYPE: cDNA to mRNA (iii) HYPOTHETICAL: NO

```
        (iv) ANTI-SENSE: NO (vi) ORIGINAL SOURCE:
             (A) ORGANISM: Gi-2 mRNA NUCLEOTIDE PROBE (xi) SEQUENCE DESCRIPTION: SEQ ID NO:2:

ATGGTCAGCC CAGAGCCTCC GG                                             22

(2) INFORMATION FOR SEQ ID NO:3:

(i) SEQUENCE CHARACTERISTICS:
            (A) LENGTH: 22 bases
            (B) TYPE: nucleic acid
            (C) STRANDEDNESS: single
            (D) TOPOLOGY: linear (ii) MOLECULE TYPE: cDNA to mRNA (iii) HYPOTHETICAL: NO (iv) ANTI-SENSE: NO (vi) ORIGINAL SOURCE:
            (A) ORGANISM: G PROTEIN SENSE PCR PRIMER (xi) SEQUENCE DESCRIPTION: SEQ ID NO:3:

AGCACCATTG TGAAGCAGAT GA                                             22

(2) INFORMATION FOR SEQ ID NO:4:

(i) SEQUENCE CHARACTERISTICS:
            (A) LENGTH: 22 bases
            (B) TYPE: nucleic acid
            (C) STRANDEDNESS: single
            (D) TOPOLOGY: linear (ii) MOLECULE TYPE: cDNA to mRNA (iii) HYPOTHETICAL: NO (iv) ANTI-SENSE: YES (vi) ORIGINAL SOURCE:
            (A) ORGANISM: G PROTEIN ANTISENSE PCR PRIMER (xi) SEQUENCE DESCRIPTION: SEQ ID NO:4:

CTCTGGCCTC CCACATCAAA CA                                             22

(2) INFORMATION FOR SEQ ID NO:5:

(i) SEQUENCE CHARACTERISTICS:
            (A) LENGTH: 22 bases
            (B) TYPE: nucleic acid
            (C) STRANDEDNESS: single
            (D) TOPOLOGY: linear (ii) MOLECULE TYPE: cDNA to mRNA (iii) HYPOTHETICAL: NO (iv) ANTI-SENSE: NO (vi) ORIGINAL SOURCE:
            (A) ORGANISM: SUBSTANCE P RECEPTOR mRNA PROBE (xi) SEQUENCE DESCRIPTION: SEQ ID NO:5:

GGACTTATGA GAAAGCGTAC CA                                             22

(2) INFORMATION FOR SEQ ID NO:6:

(i) SEQUENCE CHARACTERISTICS:
```

```
        (A) LENGTH: 22 bases
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
         (A) ORGANISM: HUMAN B2 RECEPTOR mRNA PROBE (xi) SEQUENCE DESCRIPTION: SEQ ID NO:6:

ATGCTGGCCG TGACGCACAG CA                                              22

(2) INFORMATION FOR SEQ ID NO:11:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:11:

CCCTGAAGGA AGAGCCGCAG AC                                              22

(2) INFORMATION FOR SEQ ID NO:12:

(i) SEQUENCE CHARACTERISTICS:
        (A) LENGTH: 28
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:12:

CGTGGGTCAT GACTTTCTGC TTGAGCTG                                        28

(2) INFORMATION FOR SEQ ID NO:13:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:13:

CCATGTCGAT GGGGGACAGC GG                                              22

(2) INFORMATION FOR SEQ ID NO:14:

(i) SEQUENCE CHARACTERISTICS:
```

(A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:14:

CTGTTTAAGC TGCGCCACCT G                                              21

(2) INFORMATION FOR SEQ ID NO:15:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:15:

GTCTGCGGCT CCTCCTTCAG GG                                             22

(2) INFORMATION FOR SEQ ID NO:16:

(i) SEQUENCE CHARACTERISTICS:
        (A) LENGTH: 28
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:16:

CGTGGGTCAA GACTTTCTGC TTGAGCTG                                       28

(2) INFORMATION FOR SEQ ID NO:17:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:17:

CACTTGGTGG CCGCCAG                                                   17

(2) INFORMATION FOR SEQ ID NO:18:

(i) SEQUENCE CHARACTERISTICS:
        (A) LENGTH: 17
        (B) TYPE: nucleic acid
        (C) STRANDEDNESS: double (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:18:

GAGCATGTTG GCCGTGG                                                          17

(2) INFORMATION FOR SEQ ID NO:19:

(i) SEQUENCE CHARACTERISTICS:
            (A) LENGTH: 17
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:19:

GATGCGCTCC TGCGTGT                                                          17

(2) INFORMATION FOR SEQ ID NO:20:

(i) SEQUENCE CHARACTERISTICS:
            (A) LENGTH: 21
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:20:

GCCTGTTCTG GCTTTTGAGG G                                                     21

(2) INFORMATION FOR SEQ ID NO:21:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:21:

CCGGTGTCCC CCATCAACAT GG                                                    22

(2) INFORMATION FOR SEQ ID NO:22:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:22:

CCCCTGTCCC CCATCGACAT GG                                                    22

(2) INFORMATION FOR SEQ ID NO:23:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:23:

CCGTTGTCGC CCATCGACAT GG                                                    22

(2) INFORMATION FOR SEQ ID NO:24:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:24:

CCTGTGTCCC CCATCAACAT GG                                                    22

(2) INFORMATION FOR SEQ ID NO:25:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:25:

CCCCTGTCCC CTATCGACAT GG                                                    22

(2) INFORMATION FOR SEQ ID NO:26:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:26:

CCCCTGTCCC CTATCGACAT GG                                              22

(2) INFORMATION FOR SEQ ID NO:27:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:27:

CCCCTGTCCC CTATCGACAT GG                                              22

(2) INFORMATION FOR SEQ ID NO:28:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:28:

CCGCTGTCGC CCATCGACAT GG                                              22

(2) INFORMATION FOR SEQ ID NO:29:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:29:

CCGCTGTCGC CCATCGACAT GG                                              22

(2) INFORMATION FOR SEQ ID NO:30:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:30:

CCGCTGTCGC CCATCGACAT GG                                           22

(2) INFORMATION FOR SEQ ID NO:31:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:31:

CCCTTGTCCC CCATCGACAT GG                                           22

(2) INFORMATION FOR SEQ ID NO:32:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:32:

CCCTTGTCCC CCATCGACAT GG                                           22

(2) INFORMATION FOR SEQ ID NO:33:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:33:

CCCCTGTCCC CTATTGACAT GG                                           22

(2) INFORMATION FOR SEQ ID NO:34:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:34:

CCCCTGTCCC CTATTGACAT GG                                           22

(2) INFORMATION FOR SEQ ID NO:35:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:35:

ACCGTTAATC CCATTGACAT GG                                      22

(2) INFORMATION FOR SEQ ID NO:36:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:36:

CCGCTGTCCA CAATCGACGA AT                                      22

(2) INFORMATION FOR SEQ ID NO:37:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:37:

GTGCTGTCCC CCATCGAGCT TG                                      22

(2) INFORMATION FOR SEQ ID NO:38:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:38:

CCGCTGTGCA CCATUCACAT GG                                      22

(2) INFORMATION FOR SEQ ID NO:39:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:39:

GTCCACCGGG TCGAGTTTGT C                                              21

(2) INFORMATION FOR SEQ ID NO:40:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:40:

GTCCACCGTG TCGAATTTGT C                                              21

(2) INFORMATION FOR SEQ ID NO:41:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:41:

GTCCACCGCG TCGAGTTCGT C                                              21

(2) INFORMATION FOR SEQ ID NO:42:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:42:

GTTCACCGCG TCGAGTTCGT C                                              21

(2) INFORMATION FOR SEQ ID NO:43:

(i) SEQUENCE CHARACTERISTICS:
        (A) LENGTH: 21
        (B) TYPE: nucleic acid

```
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:43:

GTCCACCGTG TCGAATTCGT C                                              21

(2) INFORMATION FOR SEQ ID NO:44:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:44:

GTCCACCGTG TCGAATTCGT C                                              21

(2) INFORMATION FOR SEQ ID NO:45:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:45:

GTCCACCGTG TCGAATTCGT C                                              21

(2) INFORMATION FOR SEQ ID NO:46:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:46:

GTCCACCGCG TGCAGTTTGT C                                              21

(2) INFORMATION FOR SEQ ID NO:47:

(i) SEQUENCE CHARACTERISTICS:
        (A) LENGTH: 21
        (B) TYPE: nucleic acid
        (C) STRANDEDNESS: double
        (D) TOPOLOGY: linear
```

(ii) MOLECULE TYPE: cDNA to mRNA (iii) HYPOTHETICAL: NO (iv) ANTI-SENSE: NO (xi) SEQUENCE DESCRIPTION: SEQ ID NO:47:

GTCCACCGCG TCGAGTTTGT C                                              21

(2) INFORMATION FOR SEQ ID NO:48:

(i) SEQUENCE CHARACTERISTICS:
           (A) LENGTH: 21
           (B) TYPE: nucleic acid
           (C) STRANDEDNESS: double
           (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:48:

GTCCACCGCG TCGAGTTTGT C                                              21

(2) INFORMATION FOR SEQ ID NO:49:

(i) SEQUENCE CHARACTERISTICS:
           (A) LENGTH: 21
           (B) TYPE: nucleic acid
           (C) STRANDEDNESS: double
           (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:49:

GTCCACCGTG TCGAATTTGT C                                              21

(2) INFORMATION FOR SEQ ID NO:50:

(i) SEQUENCE CHARACTERISTICS:
           (A) LENGTH: 21
           (B) TYPE: nucleic acid
           (C) STRANDEDNESS: double
           (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:50:

GTCCACCGTG TCGAATTTGT C                                              21

(2) INFORMATION FOR SEQ ID NO:51:

(i) SEQUENCE CHARACTERISTICS:
           (A) LENGTH: 21
           (B) TYPE: nucleic acid
           (C) STRANDEDNESS: double
           (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:51:

GTCCAACGTG TCGAATTCGT C         21

(2) INFORMATION FOR SEQ ID NO:52:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:52:

GTCCAACGTG TCGAATTCGT C         21

(2) INFORMATION FOR SEQ ID NO:53:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:53:

GTACACCGCG TGCACTTCGT C         21

(2) INFORMATION FOR SEQ ID NO:54:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:54:

CTCCACCGGG TCAACTTTGT C         21

(2) INFORMATION FOR SEQ ID NO:55:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:55:

AACCACCGCG TCGAATTACC A                                                21

(2) INFORMATION FOR SEQ ID NO:56:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:56:

AACCACCGCG TCGAATTACC A                                                21

(2) INFORMATION FOR SEQ ID NO:57:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:57:

GTCCACCGGG TCGAATGTCG A                                                21

(2) INFORMATION FOR SEQ ID NO:58:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:58:

GTCCACCGGG TCGAATGTCG A                                                21

(2) INFORMATION FOR SEQ ID NO:59:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:59:

GTCCACCGGG TCGAATGTCG A                                                21

(2) INFORMATION FOR SEQ ID NO:60:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:60:

GTCCACCGGG TCGAATGTCG A                                      21

(2) INFORMATION FOR SEQ ID NO:61:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:61:

GTCCACCGGG TCGAATGTCG A                                      21

(2) INFORMATION FOR SEQ ID NO:62:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:62:

CTGGCGGCCA CCAAGTG                                          17

(2) INFORMATION FOR SEQ ID NO:63:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:63:

ATCGCTGCCT CCAAGTG                                          17

(2) INFORMATION FOR SEQ ID NO:64:

(i) SEQUENCE CHARACTERISTICS:
    (A) LENGTH: 17
    (B) TYPE: nucleic acid
    (C) STRANDEDNESS: double
    (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:64:

ATGGCGGCCA CCTCCAA                                                17

(2) INFORMATION FOR SEQ ID NO:65:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:65:

CTGGCGGCCA CCAAGTG                                                17

(2) INFORMATION FOR SEQ ID NO:66:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:66:

ATTGCCGCCT CCAAGTG                                                17

(2) INFORMATION FOR SEQ ID NO:67:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:67:

ATTGCCGCCT CCAAGTG                                                17

(2) INFORMATION FOR SEQ ID NO:68:

(i) SEQUENCE CHARACTERISTICS:
        (A) LENGTH: 17

```
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:68:

ATTGCCGCCT CCAAGTG                                            17

(2) INFORMATION FOR SEQ ID NO:69:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:69:

CTGGCCGCCA CCCCCGG                                            17

(2) INFORMATION FOR SEQ ID NO:70:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:70:

CTGGCGTCCA CCGCCAG                                            17

(2) INFORMATION FOR SEQ ID NO:71:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:71:

CTGGCGTCCA CCGCCAG                                            17

(2) INFORMATION FOR SEQ ID NO:72:

(i) SEQUENCE CHARACTERISTICS:
        (A) LENGTH: 17
        (B) TYPE: nucleic acid
        (C) STRANDEDNESS: double
        (D) TOPOLOGY: linear
```

(ii) MOLECULE TYPE: cDNA to mRNA (iii) HYPOTHETICAL: NO (iv) ANTI-SENSE: NO (xi) SEQUENCE DESCRIPTION: SEQ ID NO:72:

CTGGCGTCCA CCGCCAA                                                17

(2) INFORMATION FOR SEQ ID NO:73:

(i) SEQUENCE CHARACTERISTICS:
            (A) LENGTH: 17
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:73:

ATCGCTGCCT CCAAGTG                                                17

(2) INFORMATION FOR SEQ ID NO:74:

(i) SEQUENCE CHARACTERISTICS:
            (A) LENGTH: 17
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:74:

CCGGCGGCGA CCAACCC                                                17

(2) INFORMATION FOR SEQ ID NO:75:

(i) SEQUENCE CHARACTERISTICS:
            (A) LENGTH: 17
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:75:

GGCGCGGCAG CCAATGG                                                17

(2) INFORMATION FOR SEQ ID NO:76:

(i) SEQUENCE CHARACTERISTICS:
            (A) LENGTH: 17
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:76:

GTGGCTGCAT CCAAGTG                                                              17

(2) INFORMATION FOR SEQ ID NO:77:

(i) SEQUENCE CHARACTERISTICS:
            (A) LENGTH: 17
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:77:

GTGGCGGCCA CCAAGTG                                                              17

(2) INFORMATION FOR SEQ ID NO:78:

(i) SEQUENCE CHARACTERISTICS:
            (A) LENGTH: 17
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:78:

CTGGCGGCAA CCAAGGC                                                              17

(2) INFORMATION FOR SEQ ID NO:79:

(i) SEQUENCE CHARACTERISTICS:
            (A) LENGTH: 17
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:79:

CTGGCGGCCA CCATGAA                                                              17

(2) INFORMATION FOR SEQ ID NO:80:

(i) SEQUENCE CHARACTERISTICS:
            (A) LENGTH: 17
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:80:

CTGGCGGCCA CCATGAA                                                          17

(2) INFORMATION FOR SEQ ID NO:81:

(i) SEQUENCE CHARACTERISTICS:
          (A) LENGTH: 17
          (B) TYPE: nucleic acid
          (C) STRANDEDNESS: double
          (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:81:

CTGGCGGCCA CCATGAA                                                          17

(2) INFORMATION FOR SEQ ID NO:82:

(i) SEQUENCE CHARACTERISTICS:
          (A) LENGTH: 17
          (B) TYPE: nucleic acid
          (C) STRANDEDNESS: double
          (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:82:

CGACGACCAC CATCAGC                                                          17

(2) INFORMATION FOR SEQ ID NO:83:

(i) SEQUENCE CHARACTERISTICS:
          (A) LENGTH: 17
          (B) TYPE: nucleic acid
          (C) STRANDEDNESS: double
          (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:83:

CCACGGCCAA CATGCTC                                                          17

(2) INFORMATION FOR SEQ ID NO:84:

(i) SEQUENCE CHARACTERISTICS:
          (A) LENGTH: 17
          (B) TYPE: nucleic acid
          (C) STRANDEDNESS: double
          (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:84:

CCACGGCGAG CCTGCTG                                                   17

(2) INFORMATION FOR SEQ ID NO:85:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:85:

CGACGGCCAC CATCAGC                                                   17

(2) INFORMATION FOR SEQ ID NO:86:

(i) SEQUENCE CHARACTERISTICS:
        (A) LENGTH: 27
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:86:

CGTGGGTCAA GACTTCTGCT TGAGCTG                                        27

(2) INFORMATION FOR SEQ ID NO:87:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:87:

CCACGGCCAA CATGCTC                                                   17

(2) INFORMATION FOR SEQ ID NO:88:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:88:

CCACGGCCAA CATGCTC                                                   17

(2) INFORMATION FOR SEQ ID NO:89:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:89:

CCACGGCCAA CATGCTC                                              17

(2) INFORMATION FOR SEQ ID NO:90:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:90:

CCACCGCCAG CCTGCTG                                              17

(2) INFORMATION FOR SEQ ID NO:91:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:91:

CCACCGCCAG CCTGCTG                                              17

(2) INFORMATION FOR SEQ ID NO:92:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:92:

CCACCGCCAG CCTGCTG                                              17

(2) INFORMATION FOR SEQ ID NO:93:

(i) SEQUENCE CHARACTERISTICS:

```
            (A) LENGTH: 17
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:93:

CCACGGCCAA CATGCTC                                                  17

(2) INFORMATION FOR SEQ ID NO:94:

(i) SEQUENCE CHARACTERISTICS:
            (A) LENGTH: 17
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:94:

CCACCGCCAA CATGCTC                                                  17

(2) INFORMATION FOR SEQ ID NO:95:

(i) SEQUENCE CHARACTERISTICS:
            (A) LENGTH: 17
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:95:

CCACGGCCAA CATGCTC                                                  17

(2) INFORMATION FOR SEQ ID NO:96:

(i) SEQUENCE CHARACTERISTICS:
            (A) LENGTH: 17
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:96:

CCACTGCCAA CATGCTC                                                  17

(2) INFORMATION FOR SEQ ID NO:97:

(i) SEQUENCE CHARACTERISTICS:
            (A) LENGTH: 17
            (B) TYPE: nucleic acid
            (C) STRANDEDNESS: double
```

(D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:97:

CCTACACCAA CATGACC                                                17

(2) INFORMATION FOR SEQ ID NO:98:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:98:

CCACGGCCAA CATCGTC                                                17

(2) INFORMATION FOR SEQ ID NO:99:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:99:

CCACGGCCAA CATCGTC                                                17

(2) INFORMATION FOR SEQ ID NO:100:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:100:

GGAAGCTGGA GCGCATC                                                17

(2) INFORMATION FOR SEQ ID NO:101:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:101:

AGTCCCAGGA GCGGATC                                                17

(2) INFORMATION FOR SEQ ID NO:102:

(i) SEQUENCE CHARACTERISTICS:
           (A) LENGTH: 17
           (B) TYPE: nucleic acid
           (C) STRANDEDNESS: double
           (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:102:

ACACGCAGGA GCGCATC                                                17

(2) INFORMATION FOR SEQ ID NO:103:

(i) SEQUENCE CHARACTERISTICS:
           (A) LENGTH: 17
           (B) TYPE: nucleic acid
           (C) STRANDEDNESS: double
           (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:103:

AAGACCAGGA GCGCATC                                                17

(2) INFORMATION FOR SEQ ID NO:104:

(i) SEQUENCE CHARACTERISTICS:
           (A) LENGTH: 17
           (B) TYPE: nucleic acid
           (C) STRANDEDNESS: double
           (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:104:

AGTCTCAGGA GCGGATC                                                17

(2) INFORMATION FOR SEQ ID NO:105:

(i) SEQUENCE CHARACTERISTICS:
           (A) LENGTH: 17
           (B) TYPE: nucleic acid
           (C) STRANDEDNESS: double
           (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:105:

AGTCTCAGGA GCGGATC                                                                    17

(2) INFORMATION FOR SEQ ID NO:106:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:106:

AGTCTCAGGA GCGGATC                                                                    17

(2) INFORMATION FOR SEQ ID NO:107:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:107:

ACACGCAAGA ACGCATC                                                                    17

(2) INFORMATION FOR SEQ ID NO:108:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:108:

ACACGCAAGA ACGCATC                                                                    17

(2) INFORMATION FOR SEQ ID NO:109:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:109:

ACACGCAAGA ACGCATC                                                   17

(2) INFORMATION FOR SEQ ID NO:110:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:110:

AGTCTCAGGA GCGGATC                                                   17

(2) INFORMATION FOR SEQ ID NO:111:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:111:

AGTCTCAGGA GCGGATC                                                   17

(2) INFORMATION FOR SEQ ID NO:112:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:112:

AGTCGCAGGA GAGAATC                                                   17

(2) INFORMATION FOR SEQ ID NO:113:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:113:

AGTCGCAGGA GAGAATC                                                   17

(2) INFORMATION FOR SEQ ID NO:114:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:114:

GCAAGCTGGA GCGCATC                                                   17

(2) INFORMATION FOR SEQ ID NO:115:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:115:

ACACGCAGGA GCGAAAA                                                   17

(2) INFORMATION FOR SEQ ID NO:116:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:116:

AACAGCAGGA GCGCATC                                                   17

(2) INFORMATION FOR SEQ ID NO:117:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:117:

CCACGCAGGA GCGCTGC                                                   17

(2) INFORMATION FOR SEQ ID NO:118:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:118:

GCACGCAGGA GCGCTGC                                                          17

(2) INFORMATION FOR SEQ ID NO:119:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:119:

ACACGCTGGA GCGCGTG                                                          17

(2) INFORMATION FOR SEQ ID NO:120:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:120:

CGCTCAAGGC CGAGAACGCG G                                                     21

(2) INFORMATION FOR SEQ ID NO:121:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:121:

AACTGCACAG CCAGAACACG C                                                     21

(2) INFORMATION FOR SEQ ID NO:122:

(i) SEQUENCE CHARACTERISTICS:
        (A) LENGTH: 21
        (B) TYPE: nucleic acid (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:122:

CCCTCAAGAG TCAGAACACG G                                              21

(2) INFORMATION FOR SEQ ID NO:123:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:123:

TACTCTCCAG CCTCTGCACC C                                              21

(2) INFORMATION FOR SEQ ID NO:124:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:124:

AACTGCATAG CCAGAACACG C                                              21

(2) INFORMATION FOR SEQ ID NO:125:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:125:

AACTGCATAG CCAGAACACG C                                              21

(2) INFORMATION FOR SEQ ID NO:126:

(i) SEQUENCE CHARACTERISTICS:
        (A) LENGTH: 21
        (B) TYPE: nucleic acid
        (C) STRANDEDNESS: double
        (D) TOPOLOGY: linear

```
        (ii) MOLECULE TYPE: cDNA to mRNA (iii) HYPOTHETICAL: NO (iv) ANTI-SENSE: NO (xi) SEQUENCE DESCRIPTION: SEQ ID NO:126:

AACTGCATAG CCAGAACACG C                                              21

(2) INFORMATION FOR SEQ ID NO:127:

(i) SEQUENCE CHARACTERISTICS:
            (A) LENGTH: 21
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:127:

CCCTCAAAAG CCAGAACACC G                                              21

(2) INFORMATION FOR SEQ ID NO:128:

(i) SEQUENCE CHARACTERISTICS:
            (A) LENGTH: 21
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:128:

CCCTCAAAAG CCAGAACACC G                                              21

(2) INFORMATION FOR SEQ ID NO:129:

(i) SEQUENCE CHARACTERISTICS:
            (A) LENGTH: 21
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:129:

CCCTCAAAAG CCAGAACACC G                                              21

(2) INFORMATION FOR SEQ ID NO:130:

(i) SEQUENCE CHARACTERISTICS:
            (A) LENGTH: 21
            (B) TYPE: nucleic acid
            (C) STRANDEDNESS: double
            (D) TOPOLOGY: linear (ii) MOLECULE TYPE: cDNA to mRNA (iii) HYPOTHETICAL: NO
```

(iv) ANTI-SENSE: NO (xi) SEQUENCE DESCRIPTION: SEQ ID NO:130:

GCCTCAGCCG CCGCACCACT T                                              21

(2) INFORMATION FOR SEQ ID NO:131:

(i) SEQUENCE CHARACTERISTICS:
              (A) LENGTH: 21
              (B) TYPE: nucleic acid
              (C) STRANDEDNESS: double
              (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:131:

GCCTCAGCCG CCGCACCACT T                                              21

(2) INFORMATION FOR SEQ ID NO:132:

(i) SEQUENCE CHARACTERISTICS:
              (A) LENGTH: 21
              (B) TYPE: nucleic acid
              (C) STRANDEDNESS: double
              (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:132:

ACCTGAGGAA CAAGAACGCC G                                              21

(2) INFORMATION FOR SEQ ID NO:133:

(i) SEQUENCE CHARACTERISTICS:
              (A) LENGTH: 21
              (B) TYPE: nucleic acid
              (C) STRANDEDNESS: double
              (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:133:

CCCCCAGATG CCAGTGCAGC A                                              21

(2) INFORMATION FOR SEQ ID NO:134:

(i) SEQUENCE CHARACTERISTICS:
              (A) LENGTH: 21
              (B) TYPE: nucleic acid
              (C) STRANDEDNESS: double
              (D) TOPOLOGY: linear (ii) MOLECULE TYPE: cDNA to mRNA (iii) HYPOTHETICAL: NO (iv) ANTI-SENSE: NO -continued (xi) SEQUENCE DESCRIPTION: SEQ ID NO:134:

ACCTCAAGGA CCATGTGGCG C                                    21

(2) INFORMATION FOR SEQ ID NO:135:

(i) SEQUENCE CHARACTERISTICS:
      (A) LENGTH: 21
      (B) TYPE: nucleic acid
      (C) STRANDEDNESS: double
      (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:135:

TGCTCAAAAT CCTGAACACC G                                    21

(2) INFORMATION FOR SEQ ID NO:136:

(i) SEQUENCE CHARACTERISTICS:
      (A) LENGTH: 21
      (B) TYPE: nucleic acid
      (C) STRANDEDNESS: double
      (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:136:

GCCTCAAGAA CCTGAACACC G                                    21

(2) INFORMATION FOR SEQ ID NO:137:

(i) SEQUENCE CHARACTERISTICS:
      (A) LENGTH: 21
      (B) TYPE: nucleic acid
      (C) STRANDEDNESS: double
      (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:137:

GCCTCAAGAA GCTGAACACC G                                    21

(2) INFORMATION FOR SEQ ID NO:138:

(i) SEQUENCE CHARACTERISTICS:
      (A) LENGTH: 21
      (B) TYPE: nucleic acid
      (C) STRANDEDNESS: double
      (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:138:

ACCCCAAAAG CCAGAACAGT T                                    21

(2) INFORMATION FOR SEQ ID NO:139:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:139:

CTCTGGCCTC CCACATCAAA CA        22

(2) INFORMATION FOR SEQ ID NO:140:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:140:

TCATCTGCTT CACAATGGTG CT        22

(2) INFORMATION FOR SEQ ID NO:141:

(i) SEQUENCE CHARACTERISTICS:
        (A) LENGTH: 26
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:141:

GTTTTCACTC TAGTTCTGAG AACATC        26

(2) INFORMATION FOR SEQ ID NO:142:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:142:

CAAAGTCGAT CTGCAGGTTG C        21

(2) INFORMATION FOR SEQ ID NO:143:

(i) SEQUENCE CHARACTERISTICS:
       (A) LENGTH: 22
       (B) TYPE: nucleic acid
       (C) STRANDEDNESS: double
       (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:143:

ATGGTCAGCC CAGAGCCTCC GG                                              22

(2) INFORMATION FOR SEQ ID NO:144:

(i) SEQUENCE CHARACTERISTICS:
       (A) LENGTH: 21
       (B) TYPE: nucleic acid
       (C) STRANDEDNESS: double
       (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:144:

GTCTTCACTC TCGTCCGAAG A                                               21

(2) INFORMATION FOR SEQ ID NO:145:

(i) SEQUENCE CHARACTERISTICS:
       (A) LENGTH: 22
       (B) TYPE: nucleic acid
       (C) STRANDEDNESS: double
       (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:145:

GCCTTGGCAT GCTCATAGAA TT                                              22

(2) INFORMATION FOR SEQ ID NO:146:

(i) SEQUENCE CHARACTERISTICS:
       (A) LENGTH: 22
       (B) TYPE: nucleic acid
       (C) STRANDEDNESS: double
       (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:146:

TTCATCCTCC CACAGAGCCT TG                                              22

(2) INFORMATION FOR SEQ ID NO:147:

(i) SEQUENCE CHARACTERISTICS:
       (A) LENGTH: 20

(B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:147:

CGCATCATGG CAGAAAGCAG                                                    20

(2) INFORMATION FOR SEQ ID NO:148:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:148:

AGTACAATTG TGAAGCAGAT GA                                                 22

(2) INFORMATION FOR SEQ ID NO:149:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:149:

AGCACCATCG TCAAGCAGAT GA                                                 22

(2) INFORMATION FOR SEQ ID NO:150:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:150:

AGCACCATTG TGAAACAGAT GA                                                 22

(2) INFORMATION FOR SEQ ID NO:151:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:151:

AGCACCATTG TGAAGCAGAT GA                                                        22

(2) INFORMATION FOR SEQ ID NO:152:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:152:

AGCACCATTG TGAAGCAGAT GA                                                        22

(2) INFORMATION FOR SEQ ID NO:153:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:153:

AGCACAATTG TGAAGCAGAT GA                                                        22

(2) INFORMATION FOR SEQ ID NO:154:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:154:

AGCACCATCG TCAAGCAGAT GA                                                        22

(2) INFORMATION FOR SEQ ID NO:155:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:155:

AGTACTATTG TGAAACAGAT GA                                              22

(2) INFORMATION FOR SEQ ID NO:156:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:156:

AGCACCATTG TGAAGCAGAT GA                                              22

(2) INFORMATION FOR SEQ ID NO:157:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:157:

AGCACCATTG TGAAGCAGAT GA                                              22

(2) INFORMATION FOR SEQ ID NO:158:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:158:

AGCACCATCG TCAAGCAGAT GA                                              22

(2) INFORMATION FOR SEQ ID NO:159:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:159:

AGCACCATTG TGAAGCAGAT GA                                        22

(2) INFORMATION FOR SEQ ID NO:160:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:160:

GCCACCATGG TGAAGAAGAT GA                                        22

(2) INFORMATION FOR SEQ ID NO:161:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:161:

CTCACCATTG TGAAGCACCT AC                                        22

(2) INFORMATION FOR SEQ ID NO:162:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:162:

TGTTTGATGT GGGAGGTCAG AG                                        22

(2) INFORMATION FOR SEQ ID NO:163:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:163:

TGTTTGATGT GGGTGGTCAG CG                22

(2) INFORMATION FOR SEQ ID NO:164:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:164:

TGTTTGATGT AGGTGGCCAA AG                22

(2) INFORMATION FOR SEQ ID NO:165:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:165:

TGTTTGACGT GGGTGGCCAG CG                22

(2) INFORMATION FOR SEQ ID NO:166:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:166:

TGTTTGACGT CGGAGGCCAG CG                22

(2) INFORMATION FOR SEQ ID NO:167:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:167:

TGTTTGACGT GGGAGGCCAG AG                22

```
(2) INFORMATION FOR SEQ ID NO:168:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:168:

TGTTTGATGT GGGTGGTCAG CG                                              22

(2) INFORMATION FOR SEQ ID NO:169:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:169:

TGTTTGATGT AGGTGGCCAA AG                                              22

(2) INFORMATION FOR SEQ ID NO:170:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:170:

TGTTCGATGT GGGCGGCCAG CG                                              22

(2) INFORMATION FOR SEQ ID NO:171:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:171:

TGTTTGACGT TGGGGGCCAG CG                                              22

(2) INFORMATION FOR SEQ ID NO:172:

(i) SEQUENCE CHARACTERISTICS:
```

(A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:172:

TGGTGGATGT GGGAGGGCAG AG                                           22

(2) INFORMATION FOR SEQ ID NO:173:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:173:

CTGATGATGT GGGAGGCCTA CT                                           22

(2) INFORMATION FOR SEQ ID NO:174:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:174:

GAGTGGATGT GGTAGACCAG AG                                           22

(2) INFORMATION FOR SEQ ID NO:175:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:175:

AGTTTGATAT GGGGGGCCAG AG                                           22

(2) INFORMATION FOR SEQ ID NO:176:

(i) SEQUENCE CHARACTERISTICS:
            (A) LENGTH: 26
            (B) TYPE: nucleic acid
            (C) STRANDEDNESS: double (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:176:

GATGTTCTCA GAACTAGAGT GAAAAC                26

(2) INFORMATION FOR SEQ ID NO:177:

(i) SEQUENCE CHARACTERISTICS:
            (A) LENGTH: 26
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:177:

TTTGTTCTCA GCTCCCCCTG TCCCCT                26

(2) INFORMATION FOR SEQ ID NO:178:

(i) SEQUENCE CHARACTERISTICS:
            (A) LENGTH: 26
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:178:

GATGTTCTTC GGACGAGAGT GAAGAC                26

(2) INFORMATION FOR SEQ ID NO:179:

(i) SEQUENCE CHARACTERISTICS:
            (A) LENGTH: 26
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:179:

ACTGTGCCCA GTACTTCCTG GACAAG                26

(2) INFORMATION FOR SEQ ID NO:180:

(i) SEQUENCE CHARACTERISTICS:
            (A) LENGTH: 26
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:180:

GACATCCTCC GAACCAGGGT CAAAAC                                              26

(2) INFORMATION FOR SEQ ID NO:181:

(i) SEQUENCE CHARACTERISTICS:
        (A) LENGTH: 26
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:181:

GATGTTCTCA GAACTAGAGT GAAAAC                                              26

(2) INFORMATION FOR SEQ ID NO:182:

(i) SEQUENCE CHARACTERISTICS:
        (A) LENGTH: 26
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:182:

GATGTGCTGC GGACCCGTGT GAAGAC                                              26

(2) INFORMATION FOR SEQ ID NO:183:

(i) SEQUENCE CHARACTERISTICS:
        (A) LENGTH: 26
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:183:

GATGTTCTTC GGACGAGAGT GAAGAC                                              26

(2) INFORMATION FOR SEQ ID NO:184:

(i) SEQUENCE CHARACTERISTICS:
        (A) LENGTH: 26
        (B) TYPE: nucleic acid
        (C) STRANDEDNESS: double
        (D) TOPOLOGY: linear (ii) MOLECULE TYPE: cDNA to mRNA (iii) HYPOTHETICAL: NO

```
    (iv) ANTI-SENSE: NO (xi) SEQUENCE DESCRIPTION: SEQ ID NO:184:

AAGCACAATT AATTAAGAGT GAAACG                                        26

(2) INFORMATION FOR SEQ ID NO:185:

(i) SEQUENCE CHARACTERISTICS:
        (A) LENGTH: 26
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:185:

GACATCCTCC GAACCAGGGT CAAAAC                                        26

(2) INFORMATION FOR SEQ ID NO:186:

(i) SEQUENCE CHARACTERISTICS:
        (A) LENGTH: 26
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:186:

TCAGTTCGAG GACCTAAACC GAAACA                                        26

(2) INFORMATION FOR SEQ ID NO:187:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:187:

GGAGGTTGAA GATAGACTTT G                                             21

(2) INFORMATION FOR SEQ ID NO:188:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:188:
```

GCAACCTGCA GATCGACTTT G                                    21

(2) INFORMATION FOR SEQ ID NO:189:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:189:

GACGGCTAAA GATTGACTTT G                                    21

(2) INFORMATION FOR SEQ ID NO:190:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:190:

AGTACCAGCT GATTGACTGT G                                    21

(2) INFORMATION FOR SEQ ID NO:191:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:191:

CTTCTCTGCA GAGCTGCTTT C                                    21

(2) INFORMATION FOR SEQ ID NO:192:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:192:

GGAGATTGAA AATCGACTTT G                                    21

-continued (2) INFORMATION FOR SEQ ID NO:193:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:193:

GCAACCTGCA GATCGACTTT G                                      21

(2) INFORMATION FOR SEQ ID NO:194:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:194:

AAAACGTGCA GTTTGTTTTT G                                      21

(2) INFORMATION FOR SEQ ID NO:195:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:195:

AGTACCAGCT GATCGACTGT G                                      21

(2) INFORMATION FOR SEQ ID NO:196:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:196:

ATTCTCTGCA GAACTGCTTT C                                      21

(2) INFORMATION FOR SEQ ID NO:197:

```
    (i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:197:

GTAACATCCA GTTTGTCTTC G                                           21

(2) INFORMATION FOR SEQ ID NO:198:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:198:

TCTCAGAACT AGAGTGAAAA C                                           21

(2) INFORMATION FOR SEQ ID NO:199:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:199:

GCTACGGACC CGCGTAAAGA C                                           21

(2) INFORMATION FOR SEQ ID NO:200:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:200:

TCTTCGGACG AGAGTGAAGA C                                           21

(2) INFORMATION FOR SEQ ID NO:201:

(i) SEQUENCE CHARACTERISTICS:
        (A) LENGTH: 21
        (B) TYPE: nucleic acid
```

(C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:201:

GGGAAATCGA AGATTGAGGA C                                              21

(2) INFORMATION FOR SEQ ID NO:202:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:202:

TCTCCGGAGA AGACGTGAAA C                                              21

(2) INFORMATION FOR SEQ ID NO:203:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:203:

TCTCAGAACT AGAGTGAAAA C                                              21

(2) INFORMATION FOR SEQ ID NO:204:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:204:

GCTGCGGACC CGTGTGAAGA C                                              21

(2) INFORMATION FOR SEQ ID NO:205:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:205:

TCTTCGGACG AGAGTGAAGA C                                      21

(2) INFORMATION FOR SEQ ID NO:206:

(i) SEQUENCE CHARACTERISTICS:
      (A) LENGTH: 21
      (B) TYPE: nucleic acid
      (C) STRANDEDNESS: double
      (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:206:

TTCCTGGACA AGATTGATGT G                                      21

(2) INFORMATION FOR SEQ ID NO:207:

(i) SEQUENCE CHARACTERISTICS:
      (A) LENGTH: 21
      (B) TYPE: nucleic acid
      (C) STRANDEDNESS: double
      (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:207:

CGCATGGAGG ACACTGAACC A                                      21

(2) INFORMATION FOR SEQ ID NO:208:

(i) SEQUENCE CHARACTERISTICS:
      (A) LENGTH: 21
      (B) TYPE: nucleic acid
      (C) STRANDEDNESS: double
      (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:208:

AACTCGGGCA AGAGCACCAT C                                      21

(2) INFORMATION FOR SEQ ID NO:209:

(i) SEQUENCE CHARACTERISTICS:
      (A) LENGTH: 22
      (B) TYPE: nucleic acid
      (C) STRANDEDNESS: double
      (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:209:

GGGCGGATGA TCATCCCAAG CT                                                        22

(2) INFORMATION FOR SEQ ID NO:210:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:210:

AATATGATGA GGCAGCCAGC TA                                                        22

(2) INFORMATION FOR SEQ ID NO:211:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:211:

CAGTCTAACT ACATTCCAAC TC                                                        22

(2) INFORMATION FOR SEQ ID NO:212:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:212:

AATTCTATGA GCATGCCAAG GC                                                        22

(2) INFORMATION FOR SEQ ID NO:213:

(i) SEQUENCE CHARACTERISTICS:
            (A) LENGTH: 20
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:213:

GACCTTTCTT AAATGTGACA                                            20

(2) INFORMATION FOR SEQ ID NO:214:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:214:

CTGTGATCTC CAAGGCTGCG                                            20

(2) INFORMATION FOR SEQ ID NO:215:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:215:

CTGCATTCTA GAACTTCACA                                            20

(2) INFORMATION FOR SEQ ID NO:216:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:216:

TCAACGACTG CCGTGACATC                                            20

(2) INFORMATION FOR SEQ ID NO:217:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:217:

CTGCTTTCTG CCATGATGCG                                            20

(2) INFORMATION FOR SEQ ID NO:218:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:218:

CTGATTTCCC ACGTTATGTT                                                  20

(2) INFORMATION FOR SEQ ID NO:219:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:219:

TTGCTGACCC CCAGCGTGCG                                                  20

(2) INFORMATION FOR SEQ ID NO:220:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:220:

CTGCTTGCTG TCATTGTCAC                                                  20

(2) INFORMATION FOR SEQ ID NO:221:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:221:

CTGCTTGCTG AGAAGGTCCT                                                  20

(2) INFORMATION FOR SEQ ID NO:222:

(i) SEQUENCE CHARACTERISTICS:
    (A) LENGTH: 20
    (B) TYPE: nucleic acid
    (C) STRANDEDNESS: double
    (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:222:

CTGCTTTCTG CCATGATGCG                                                   20

(2) INFORMATION FOR SEQ ID NO:223:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:223:

CAGCTCTTTG CCCTGACTGG                                                   20

(2) INFORMATION FOR SEQ ID NO:224:

(i) SEQUENCE CHARACTERISTICS:
        (A) LENGTH: 26
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:224:

AAGCACAATT AATTAAGAGT GAAACG                                            26

(2) INFORMATION FOR SEQ ID NO:225:

(i) SEQUENCE CHARACTERISTICS:
        (A) LENGTH: 26
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:225:

AACAGAAATA AGAAATAAA TGAAAT                                             26

(2) INFORMATION FOR SEQ ID NO:226:

(i) SEQUENCE CHARACTERISTICS:
        (A) LENGTH: 26

```
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:226:

GATGTTCTCA GAACTAGAGT GAAAAC                                          26

(2) INFORMATION FOR SEQ ID NO:227:

(i) SEQUENCE CHARACTERISTICS:
        (A) LENGTH: 26
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:227:

TGTCAGTTTG AAGACCTCAA TAAAAG                                          26

(2) INFORMATION FOR SEQ ID NO:228:

(i) SEQUENCE CHARACTERISTICS:
        (A) LENGTH: 26
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:228:

GATGTGCTGC GGACCCGTGT GAAGAC                                          26

(2) INFORMATION FOR SEQ ID NO:229:

(i) SEQUENCE CHARACTERISTICS:
        (A) LENGTH: 26
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:229:

AGCAAGTTTG AGGACCTGAA TAAACG                                          26

(2) INFORMATION FOR SEQ ID NO:230:

(i) SEQUENCE CHARACTERISTICS:
        (A) LENGTH: 26
        (B) TYPE: nucleic acid
        (C) STRANDEDNESS: double
        (D) TOPOLOGY: linear
```

```
      (ii) MOLECULE TYPE: cDNA to mRNA (iii) HYPOTHETICAL: NO (iv) ANTI-SENSE: NO (xi) SEQUENCE DESCRIPTION: SEQ ID NO:230:

GATGTTCTTC GGACGAGAGT GAAGAC                                              26

(2) INFORMATION FOR SEQ ID NO:231:

(i) SEQUENCE CHARACTERISTICS:
          (A) LENGTH: 26
          (B) TYPE: nucleic acid
          (C) STRANDEDNESS: double
          (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:231:

TGCCAGTTTG AAGATCTGAA CCGAAG                                              26

(2) INFORMATION FOR SEQ ID NO:232:

(i) SEQUENCE CHARACTERISTICS:
          (A) LENGTH: 26
          (B) TYPE: nucleic acid
          (C) STRANDEDNESS: double
          (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:232:

GACATCCTCC GAACCAGGGT CAAAAC                                              26

(2) INFORMATION FOR SEQ ID NO:233:

(i) SEQUENCE CHARACTERISTICS:
          (A) LENGTH: 26
          (B) TYPE: nucleic acid
          (C) STRANDEDNESS: double
          (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:233:

ACACAGTTTG AAAGCAAAAA CCGCTC                                              26

(2) INFORMATION FOR SEQ ID NO:234:

(i) SEQUENCE CHARACTERISTICS:
          (A) LENGTH: 26
          (B) TYPE: nucleic acid
          (C) STRANDEDNESS: double
          (D) TOPOLOGY: linear (ii) MOLECULE TYPE: cDNA to mRNA
```

(iii) HYPOTHETICAL: NO (iv) ANTI-SENSE: NO (xi) SEQUENCE DESCRIPTION: SEQ ID NO:234:

GATGTTCTCA GAACTAGAGT GAAAAC                          26

(2) INFORMATION FOR SEQ ID NO:235:

(i) SEQUENCE CHARACTERISTICS:
           (A) LENGTH: 26
           (B) TYPE: nucleic acid
           (C) STRANDEDNESS: double
           (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:235:

TGTCAGTTTG AAGACCTCAA TAAAAG                          26

(2) INFORMATION FOR SEQ ID NO:236:

(i) SEQUENCE CHARACTERISTICS:
           (A) LENGTH: 26
           (B) TYPE: nucleic acid
           (C) STRANDEDNESS: double
           (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:236:

CATGCTCTGA GCACTGGAGA GAAAAG                          26

(2) INFORMATION FOR SEQ ID NO:237:

(i) SEQUENCE CHARACTERISTICS:
           (A) LENGTH: 26
           (B) TYPE: nucleic acid
           (C) STRANDEDNESS: double
           (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:237:

AGCCAGCCTG TAGCCCTCAA TAAAAG                          26

(2) INFORMATION FOR SEQ ID NO:238:

(i) SEQUENCE CHARACTERISTICS:
           (A) LENGTH: 22
           (B) TYPE: nucleic acid
           (C) STRANDEDNESS: double
           (D) TOPOLOGY: linear (ii) MOLECULE TYPE: cDNA to mRNA (iii) HYPOTHETICAL: NO (iv) ANTI-SENSE: NO

```
        (xi) SEQUENCE DESCRIPTION: SEQ ID NO:238:

GACAAGATTG ATGTGATCAA GC                                           22

(2) INFORMATION FOR SEQ ID NO:239:

(i) SEQUENCE CHARACTERISTICS:
          (A) LENGTH: 22
          (B) TYPE: nucleic acid
          (C) STRANDEDNESS: double
          (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:239:

AAGCAGGTCT ACCGGGCCAC GC                                           22

(2) INFORMATION FOR SEQ ID NO:240:

(i) SEQUENCE CHARACTERISTICS:
          (A) LENGTH: 22
          (B) TYPE: nucleic acid
          (C) STRANDEDNESS: double
          (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:240:

AAAATGTTTG ACGTGGGAGG CC                                           22

(2) INFORMATION FOR SEQ ID NO:241:

(i) SEQUENCE CHARACTERISTICS:
          (A) LENGTH: 22
          (B) TYPE: nucleic acid
          (C) STRANDEDNESS: double
          (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:241:

AAGGAAATTT ACACCCACTT CA                                           22

(2) INFORMATION FOR SEQ ID NO:242:

(i) SEQUENCE CHARACTERISTICS:
          (A) LENGTH: 22
          (B) TYPE: nucleic acid
          (C) STRANDEDNESS: double
          (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:242:
```

```
AAGATGTTTG ATGTGGGTGG TC                                               22

(2) INFORMATION FOR SEQ ID NO:243:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:243:

AAGGAGATCT ACACGCACTT CA                                               22

(2) INFORMATION FOR SEQ ID NO:244:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:244:

AAAATGTTTG ATGTAGGTGG CC                                               22

(2) INFORMATION FOR SEQ ID NO:245:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:245:

AAGGAGGTCT ACACTCACTT TA                                               22

(2) INFORMATION FOR SEQ ID NO:246:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:246:

AGGCTGTTTG ACGTTGGGGG CC                                               22
```

(2) INFORMATION FOR SEQ ID NO:247:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:247:

CTAGAGATCT GCACCCCTCA CC                                              22

(2) INFORMATION FOR SEQ ID NO:248:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:248:

AAGATGTTTG ATGTGGGTGG TC                                              22

(2) INFORMATION FOR SEQ ID NO:249:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:249:

AAGGAGATCT ACACGCACTT CA                                              22

(2) INFORMATION FOR SEQ ID NO:250:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:250:

AAGATGTTTG ATGTGGGTGG TC                                              22

(2) INFORMATION FOR SEQ ID NO:251:

(i) SEQUENCE CHARACTERISTICS:

(A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:251:

AAGGAGATCT ACACGCACTT CA                                              22

(2) INFORMATION FOR SEQ ID NO:252:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:252:

AAGATGTTTG CTGTGGGTGT GG                                              22

(2) INFORMATION FOR SEQ ID NO:253:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:253:

AAGGAGAACT ACAAGAAGTT CT                                              22

(2) INFORMATION FOR SEQ ID NO:254:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:254:

CCGCAAGTGG ATCCAGTGCT TC                                              22

(2) INFORMATION FOR SEQ ID NO:255:

(i) SEQUENCE CHARACTERISTICS:
        (A) LENGTH: 22
        (B) TYPE: nucleic acid
        (C) STRANDEDNESS: double (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:255:

AATGATGTGA CTGCCATCAT CT                                                    22

(2) INFORMATION FOR SEQ ID NO:256:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:256:

ATGTTGAAGC TGGGGCTCTA GT                                                    22

(2) INFORMATION FOR SEQ ID NO:257:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:257:

GAAGGCGTGA CTGCCATCAT CT                                                    22

(2) INFORMATION FOR SEQ ID NO:258:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:258:

CCTACACAGC AGGATGTGCT GC                                                    22

(2) INFORMATION FOR SEQ ID NO:259:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:259:

GAGGGTGTCA CGGCCATCAT CT                                              22

(2) INFORMATION FOR SEQ ID NO:260:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:260:

TTGTTTTAGC TGGCAGTGCT GA                                              22

(2) INFORMATION FOR SEQ ID NO:261:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:261:

GAGGGAGTGA CAGCAATTAT CT                                              22

(2) INFORMATION FOR SEQ ID NO:262:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:262:

CGGTTTTAGT TGAGTCTTTA CA                                              22

(2) INFORMATION FOR SEQ ID NO:263:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:263:

TCGGGAGTAT CAGCTCAACG AC                                              22

(2) INFORMATION FOR SEQ ID NO:264:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:264:

TTGTTTTAGC TGGCAGTGCT GA                                              22

(2) INFORMATION FOR SEQ ID NO:265:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:265:

GAGGGAGTGA CAGCAATTAT CT                                              22

(2) INFORMATION FOR SEQ ID NO:266:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:266:

GTGTTTCAGA TGGCATTGCT GC                                              22

(2) INFORMATION FOR SEQ ID NO:267:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:267:

```
CAGGGAGTGG CAGACATTTT CT                                                    22

(2) INFORMATION FOR SEQ ID NO:268:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:268:

GCCAACAAAA AGATCGAGAA GC                                                    22

(2) INFORMATION FOR SEQ ID NO:269:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:269:

GGACAAAGTC AACTTCCACA TG                                                    22

(2) INFORMATION FOR SEQ ID NO:270:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:270:

CGCAGCAAGA TGATCGACCG CA                                                    22

(2) INFORMATION FOR SEQ ID NO:271:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:271:

GGACAAGGCG GCCGTGGAGC GC                                                    22
```

(2) INFORMATION FOR SEQ ID NO:272:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:272:

CAAAGGAAAA AGCACAAGAA GC                                              22

(2) INFORMATION FOR SEQ ID NO:273:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:273:

AGACAAAGCC CACCTGCTCA TT                                              22

(2) INFORMATION FOR SEQ ID NO:274:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:274:

TGAGGAAAAA ATAAAGAGAA GT                                              22

(2) INFORMATION FOR SEQ ID NO:275:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:275:

GTCAGGAGTA ATATTCCACA GC                                              22

(2) INFORMATION FOR SEQ ID NO:276:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:276:

TTTGGCGAGA AGATTAAGAA GT                                             22

(2) INFORMATION FOR SEQ ID NO:277:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:277:

CCGAGGAGCG GCGATGCACA TG                                             22

(2) INFORMATION FOR SEQ ID NO:278:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:278:

GCCAACAAAA AGATCGAGAA GC                                             22

(2) INFORMATION FOR SEQ ID NO:279:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:279:

GGACAAAGTC AACTTCCACA TG                                             22

(2) INFORMATION FOR SEQ ID NO:280:

(i) SEQUENCE CHARACTERISTICS:
        (A) LENGTH: 22
        (B) TYPE: nucleic acid

```
          (C) STRANDEDNESS: double
          (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:280:

GCCAACAAAA AGATCGAGAA GC                                              22

(2) INFORMATION FOR SEQ ID NO:281:

(i) SEQUENCE CHARACTERISTICS:
          (A) LENGTH: 22
          (B) TYPE: nucleic acid
          (C) STRANDEDNESS: double
          (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:281:

GGACAAAGTC AACTTCCACA TG                                              22

(2) INFORMATION FOR SEQ ID NO:282:

(i) SEQUENCE CHARACTERISTICS:
          (A) LENGTH: 22
          (B) TYPE: nucleic acid
          (C) STRANDEDNESS: double
          (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:282:

GCCAACAAAA AGATCGAGAA GC                                              22

(2) INFORMATION FOR SEQ ID NO:283:

(i) SEQUENCE CHARACTERISTICS:
          (A) LENGTH: 22
          (B) TYPE: nucleic acid
          (C) STRANDEDNESS: double
          (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:283:

GGACAAAGTC AACTTCCACA TG                                              22

(2) INFORMATION FOR SEQ ID NO:284:

(i) SEQUENCE CHARACTERISTICS:
          (A) LENGTH: 22
          (B) TYPE: nucleic acid
          (C) STRANDEDNESS: double
          (D) TOPOLOGY: linear
```

(ii) MOLECULE TYPE: cDNA to mRNA (iii) HYPOTHETICAL: NO (iv) ANTI-SENSE: NO (xi) SEQUENCE DESCRIPTION: SEQ ID NO:284:

GCCAACAAAA AGATCGAGAA GC                    22

(2) INFORMATION FOR SEQ ID NO:285:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:285:

GGACAAAGTC AACTTCCACA TG                    22

(2) INFORMATION FOR SEQ ID NO:286:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:286:

ACCAAAAACA AGATCAAGAA GC                    22

(2) INFORMATION FOR SEQ ID NO:287:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:287:

AGACAAATTC ATCTTCCACA AG                    22

(2) INFORMATION FOR SEQ ID NO:288:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:288:

AGGACATCAA AAACAACCT                                                19

(2) INFORMATION FOR SEQ ID NO:289:

(i) SEQUENCE CHARACTERISTICS:
             (A) LENGTH: 19
             (B) TYPE: nucleic acid
             (C) STRANDEDNESS: double
             (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:289:

AGTGACCAGG ACCTGCTTC                                                19

(2) INFORMATION FOR SEQ ID NO:290:

(i) SEQUENCE CHARACTERISTICS:
             (A) LENGTH: 19
             (B) TYPE: nucleic acid
             (C) STRANDEDNESS: double
             (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:290:

GGGGCCGCCT CCGGGCCAG                                                19

(2) INFORMATION FOR SEQ ID NO:291:

(i) SEQUENCE CHARACTERISTICS:
             (A) LENGTH: 19
             (B) TYPE: nucleic acid
             (C) STRANDEDNESS: double
             (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:291:

TATGACCTGG TTCTTGCTG                                                19

(2) INFORMATION FOR SEQ ID NO:292:

(i) SEQUENCE CHARACTERISTICS:
             (A) LENGTH: 19
             (B) TYPE: nucleic acid
             (C) STRANDEDNESS: double
             (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:292:

CCATCATCCT CTTCCTCAA 19

(2) INFORMATION FOR SEQ ID NO:293:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:293:

TTCTGTTAGG TGCTGGAGA 19

(2) INFORMATION FOR SEQ ID NO:294:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:294:

GGCCAAAGAT CCGAACGGA 19

(2) INFORMATION FOR SEQ ID NO:295:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:295:

AATGACCAGT AGTTAATTT 19

(2) INFORMATION FOR SEQ ID NO:296:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:296:

AGGACATCCT CCGAACCAG 19

(2) INFORMATION FOR SEQ ID NO:297:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:297:

TATGACCAGG TGCTCCACG                                              19

(2) INFORMATION FOR SEQ ID NO:298:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:298:

AGGACATCCT CCGAACCAG                                              19

(2) INFORMATION FOR SEQ ID NO:299:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:299:

TATGACCAGG TGCTCCACG                                              19

(2) INFORMATION FOR SEQ ID NO:300:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:300:

AGGACATCCT CCGAACCAG                                              19

(2) INFORMATION FOR SEQ ID NO:301:

(i) SEQUENCE CHARACTERISTICS:
    (A) LENGTH: 19
    (B) TYPE: nucleic acid
    (C) STRANDEDNESS: double
    (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:301:

TATGACCAGG TGCTCCACG                                                    19

(2) INFORMATION FOR SEQ ID NO:302:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:302:

AGGACATCCT CCGAACCAG                                                    19

(2) INFORMATION FOR SEQ ID NO:303:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:303:

TATGACCAGG TGCTCCACG                                                    19

(2) INFORMATION FOR SEQ ID NO:304:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:304:

AGGACATCCT CCGAACCAG                                                    19

(2) INFORMATION FOR SEQ ID NO:305:

(i) SEQUENCE CHARACTERISTICS:
        (A) LENGTH: 19

(B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:305:

TATGACCAGG TGCTCCACG                                                    19

(2) INFORMATION FOR SEQ ID NO:306:

(i) SEQUENCE CHARACTERISTICS:
            (A) LENGTH: 19
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:306:

AGGACATCCT CCGAACCAG                                                    19

(2) INFORMATION FOR SEQ ID NO:307:

(i) SEQUENCE CHARACTERISTICS:
            (A) LENGTH: 19
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:307:

TATGACCAGG TGCTCCACG                                                    19

(2) INFORMATION FOR SEQ ID NO:308:

(i) SEQUENCE CHARACTERISTICS:
            (A) LENGTH: 19
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:308:

GGGACATCTT CTCAACCAG                                                    19

(2) INFORMATION FOR SEQ ID NO:309:

(i) SEQUENCE CHARACTERISTICS:
            (A) LENGTH: 19
            (B) TYPE: nucleic acid
            (C) STRANDEDNESS: double
            (D) TOPOLOGY: linear

```
        (ii) MOLECULE TYPE: cDNA to mRNA (iii) HYPOTHETICAL: NO (iv) ANTI-SENSE: NO (xi) SEQUENCE DESCRIPTION: SEQ ID NO:309:

TATGACCAGG TGCTCAAGT                                                   19

(2) INFORMATION FOR SEQ ID NO:310:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:310:

CCCTGAAGGA GGAGCCGCAG AC                                               22

(2) INFORMATION FOR SEQ ID NO:311:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:311:

CCTTTAAAGA GGAGCCGCAG AC                                               22

(2) INFORMATION FOR SEQ ID NO:312:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:312:

CCCTGAAGGA AGAGCCGCAG AC                                               22

(2) INFORMATION FOR SEQ ID NO:313:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA
```

(iii) HYPOTHETICAL: NO (iv) ANTI-SENSE: NO (xi) SEQUENCE DESCRIPTION: SEQ ID NO:313:

CCTTCAAGGA GGAACCGCAG AC                                                                22

(2) INFORMATION FOR SEQ ID NO:314:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:314:

CCCTGAAGGA GGAGCCTCAG AC                                                                22

(2) INFORMATION FOR SEQ ID NO:315:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:315:

GTCGAGTTCG TCTTTCAGAA CT                                                                22

(2) INFORMATION FOR SEQ ID NO:316:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:316:

GTCGAGTTCG TCCTTCAGAA AT                                                                22

(2) INFORMATION FOR SEQ ID NO:317:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:317:

GTCGAGTTCG TCTTTCATAA CT                                                22

(2) INFORMATION FOR SEQ ID NO:318:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:318:

GTCGTGTTCG TCGTGCCGAA CT                                                22

(2) INFORMATION FOR SEQ ID NO:319:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:319:

GTCGTGTTCC TCTTTCAGAA CT                                                22

(2) INFORMATION FOR SEQ ID NO:320:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:320:

GTCGTGTTCG TCTTTCAGAA CT                                                22

(2) INFORMATION FOR SEQ ID NO:321:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:321:

```
GGACAGTACT TTTACCCCCG                                                    20

(2) INFORMATION FOR SEQ ID NO:322:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:322:

ACCCAGTTCT TGTGCCCCAA                                                    20

(2) INFORMATION FOR SEQ ID NO:323:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:323:

ACGCAGTTCC TCTACCCGAA                                                    20

(2) INFORMATION FOR SEQ ID NO:324:

(i) SEQUENCE CHARACTERISTICS:
        (A) LENGTH: 26
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:324:

CGTGGGTCAA GACTCTGCTT GAGCTG                                             26

(2) INFORMATION FOR SEQ ID NO:325:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:325:

GGACAGTACT TTTACCCCCG                                                    20
```

(2) INFORMATION FOR SEQ ID NO:326:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:326:

GGAAAGCAGC GGTACCCCAC                                               20

(2) INFORMATION FOR SEQ ID NO:327:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:327:

TCACAGTTCC TCTACCCCAA                                               20

(2) INFORMATION FOR SEQ ID NO:328:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:328:

GGACAGCACT TTTAATCCCA                                               20

(2) INFORMATION FOR SEQ ID NO:329:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:329:

GCCAGTTGCT GCTAGGGGTC                                               20

(2) INFORMATION FOR SEQ ID NO:330:

(i) SEQUENCE CHARACTERISTICS:

```
         (A) LENGTH: 20
         (B) TYPE: nucleic acid
         (C) STRANDEDNESS: double
         (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:330:

GCCAACTCAT GCTAACGCAG                                                20

(2) INFORMATION FOR SEQ ID NO:331:

(i) SEQUENCE CHARACTERISTICS:
         (A) LENGTH: 20
         (B) TYPE: nucleic acid
         (C) STRANDEDNESS: double
         (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:331:

TCCAAATGCC GCAAGCGCAA                                                20

(2) INFORMATION FOR SEQ ID NO:332:

(i) SEQUENCE CHARACTERISTICS:
         (A) LENGTH: 20
         (B) TYPE: nucleic acid
         (C) STRANDEDNESS: double
         (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:332:

GCCAGCCCCC GAGAACGCGC                                                20

(2) INFORMATION FOR SEQ ID NO:333:

(i) SEQUENCE CHARACTERISTICS:
         (A) LENGTH: 20
         (B) TYPE: nucleic acid
         (C) STRANDEDNESS: double
         (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:333:

GCCAACTCAT GCTAACGCAG                                                20

(2) INFORMATION FOR SEQ ID NO:334:

(i) SEQUENCE CHARACTERISTICS:
         (A) LENGTH: 20
         (B) TYPE: nucleic acid
         (C) STRANDEDNESS: double
```

(D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:334:

TCCAAGTGCC GCAAGCGCAA                                           20

(2) INFORMATION FOR SEQ ID NO:335:

(i) SEQUENCE CHARACTERISTICS:
            (A) LENGTH: 20
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:335:

CCCAACTCAT GCTGACGGGC                                           20

(2) INFORMATION FOR SEQ ID NO:336:

(i) SEQUENCE CHARACTERISTICS:
            (A) LENGTH: 21
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:336:

AAGGTCATGA CCCATGTCAG C                                         21

(2) INFORMATION FOR SEQ ID NO:337:

(i) SEQUENCE CHARACTERISTICS:
            (A) LENGTH: 21
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:337:

AAAGTCATGA ACCACGTTAA C                                         21

(2) INFORMATION FOR SEQ ID NO:338:

(i) SEQUENCE CHARACTERISTICS:
            (A) LENGTH: 21
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:338:

AAAGTCCTCA GCCACGTCAA C                                              21

(2) INFORMATION FOR SEQ ID NO:339:

(i) SEQUENCE CHARACTERISTICS:
            (A) LENGTH: 21
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:339:

AAGGTCATGA CCCACGTCAG C                                              21

(2) INFORMATION FOR SEQ ID NO:340:

(i) SEQUENCE CHARACTERISTICS:
            (A) LENGTH: 21
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:340:

AAAGTCATGA ACCACGTTAA C                                              21

(2) INFORMATION FOR SEQ ID NO:341:

(i) SEQUENCE CHARACTERISTICS:
            (A) LENGTH: 21
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:341:

AAAGTCCTCA GCCACGTCAA C                                              21

(2) INFORMATION FOR SEQ ID NO:342:

(i) SEQUENCE CHARACTERISTICS:
            (A) LENGTH: 21
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:342:

AAAATCCTCA GCCACATCCT G                                              21

(2) INFORMATION FOR SEQ ID NO:343:

(i) SEQUENCE CHARACTERISTICS:
            (A) LENGTH: 21
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:343:

AGGGCTTCGC CGACGGCTTT G                                              21

(2) INFORMATION FOR SEQ ID NO:344:

(i) SEQUENCE CHARACTERISTICS:
            (A) LENGTH: 21
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:344:

AGGGCTTCGC CGAGGGCTTC G                                              21

(2) INFORMATION FOR SEQ ID NO:345:

(i) SEQUENCE CHARACTERISTICS:
            (A) LENGTH: 21
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:345:

AGGGGTTCGC CGAGGGCTTC G                                              21

(2) INFORMATION FOR SEQ ID NO:346:

(i) SEQUENCE CHARACTERISTICS:
            (A) LENGTH: 21
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:346:

CCCCTGCCGC CGACGGCGCC C                                            21

(2) INFORMATION FOR SEQ ID NO:347:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:347:

AGGAGTTCGC CGAGGGCTTC G                                            21

(2) INFORMATION FOR SEQ ID NO:348:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:348:

AGGAGTTCGC CGAAGGCTTC G                                            21

(2) INFORMATION FOR SEQ ID NO:349:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:349:

GGGGCGCCCC CGACGGCCGC G                                            21

(2) INFORMATION FOR SEQ ID NO:350:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:350:

CTGGCTTCGC CGGATCTTGG G                                            21

-continued (2) INFORMATION FOR SEQ ID NO:351:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:351:

CGCCCTTCGC CGGTGGCCAC C                                      21

(2) INFORMATION FOR SEQ ID NO:352:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:352:

CGGCACCCCC CGACGGCCTG C                                      21

(2) INFORMATION FOR SEQ ID NO:353:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:353:

ACCACCACGC CGACGAGCTC A                                      21

(2) INFORMATION FOR SEQ ID NO:354:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:354:

AGCTCATACC CGACGGCCAC C                                      21

(2) INFORMATION FOR SEQ ID NO:355:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:355:

CGCTGCGCCC CGACGGCGCC C                                             21

(2) INFORMATION FOR SEQ ID NO:356:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:356:

AGGGCTTCGT GCGCGCCCTG G                                             21

(2) INFORMATION FOR SEQ ID NO:357:

(i) SEQUENCE CHARACTERISTICS:
        (A) LENGTH: 13
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:357:

NNNNNNNNNN NNN                                                      13

(2) INFORMATION FOR SEQ ID NO:358:

(i) SEQUENCE CHARACTERISTICS:
        (A) LENGTH: 13
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:358:

TNNNNNNNNG NGN                                                      13

(2) INFORMATION FOR SEQ ID NO:359:

(i) SEQUENCE CHARACTERISTICS:
        (A) LENGTH: 13
        (B) TYPE: nucleic acid

```
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:359:

ANNNNNNNNG TGG                                                          13

(2) INFORMATION FOR SEQ ID NO:360:

(i) SEQUENCE CHARACTERISTICS:
        (A) LENGTH: 13
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:360:

CNNNNNNNNC NGG                                                          13

(2) INFORMATION FOR SEQ ID NO:361:

(i) SEQUENCE CHARACTERISTICS:
        (A) LENGTH: 13
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:361:

NNNNNNNNNN NNN                                                          13

(2) INFORMATION FOR SEQ ID NO:362:

(i) SEQUENCE CHARACTERISTICS:
        (A) LENGTH: 13
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:362:

NNNNNNNNNN NCN                                                          13

(2) INFORMATION FOR SEQ ID NO:363:

(i) SEQUENCE CHARACTERISTICS:
        (A) LENGTH: 13
        (B) TYPE: nucleic acid
        (C) STRANDEDNESS: double
        (D) TOPOLOGY: linear
```

-continued (ii) MOLECULE TYPE: cDNA to mRNA (iii) HYPOTHETICAL: NO (iv) ANTI-SENSE: NO (xi) SEQUENCE DESCRIPTION: SEQ ID NO:363:

TGAGCGGNNN NNN                                                13

(2) INFORMATION FOR SEQ ID NO:364:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:364:

ATGTGCACTA AAATGGAACA G                                       21

(2) INFORMATION FOR SEQ ID NO:365:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:365:

TGTGCACTAA AATGGAACAG C                                       21

(2) INFORMATION FOR SEQ ID NO:366:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:366:

GTGCACTAAA ATGGAACAGC C                                       21

(2) INFORMATION FOR SEQ ID NO:367:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:367:

TGCACTAAAA TGGAACAGCC C                                       21

(2) INFORMATION FOR SEQ ID NO:368:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:368:

GCACTAAAAT GGAACAGCCC T                                       21

(2) INFORMATION FOR SEQ ID NO:369:

(i) SEQUENCE CHARACTERISTICS:

(A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:369:

CACTAAAATG GAACAGCCCT T                                              21

(2) INFORMATION FOR SEQ ID NO:370:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:370:

ACTAAAATGG AACAGCCCTT C                                              21

(2) INFORMATION FOR SEQ ID NO:371:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:371:

CTAAAATGGA ACAGCCCTTC T                                              21

(2) INFORMATION FOR SEQ ID NO:372:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:372:

TAAAATGGAA CAGCCCTTCT A                                              21

(2) INFORMATION FOR SEQ ID NO:373:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:373:

AAAATGGAAC AGCCCTTCTA C                                              21

(2) INFORMATION FOR SEQ ID NO:374:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:374:

AAATGGAACA GCCCTTCTAC C                                              21

(2) INFORMATION FOR SEQ ID NO:375:

(i) SEQUENCE CHARACTERISTICS:
        (A) LENGTH: 21 base pairs (B) TYPE: nucleic acid
        (C) STRANDEDNESS: single
        (D) TOPOLOGY: linear (xi) SEQUENCE DESCRIPTION: SEQ ID NO:375:

AATGGAACAG CCCTTCTACC A                                           21

(2) INFORMATION FOR SEQ ID NO:376:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:376:

ATGGAACAGC CCTTCTACCA C                                           21

(2) INFORMATION FOR SEQ ID NO:377:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:377:

TGGAACAGCC CTTCTACCAC G                                           21

(2) INFORMATION FOR SEQ ID NO:378:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:378:

GGAACAGCCC TTCTACCACG A                                           21

(2) INFORMATION FOR SEQ ID NO:379:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:379:

GAACAGCCCT TCTACCACGA C                                           21

(2) INFORMATION FOR SEQ ID NO:380:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:380:

AACAGCCCTT CTACCACGAC G                                           21

(2) INFORMATION FOR SEQ ID NO:381:

(i) SEQUENCE CHARACTERISTICS:
        (A) LENGTH: 21 base pairs
        (B) TYPE: nucleic acid

```
        (C) STRANDEDNESS: single
        (D) TOPOLOGY: linear (xi) SEQUENCE DESCRIPTION: SEQ ID NO:381:

ACAGCCCTTC TACCACGACG A                                              21

(2) INFORMATION FOR SEQ ID NO:382:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:382:

CAGCCCTTCT ACCACGACGA C                                              21

(2) INFORMATION FOR SEQ ID NO:383:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:383:

AGCCCTTCTA CCACGACGAC T                                              21

(2) INFORMATION FOR SEQ ID NO:384:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:384:

GCCCTTCTAC CACGACGACT C                                              21

(2) INFORMATION FOR SEQ ID NO:385:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:385:

CCCTTCTACC ACGACGACTC A                                              21

(2) INFORMATION FOR SEQ ID NO:386:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:386:

CCTTCTACCA CGACGACTCA T                                              21

(2) INFORMATION FOR SEQ ID NO:387:

(i) SEQUENCE CHARACTERISTICS:
        (A) LENGTH: 21 base pairs
        (B) TYPE: nucleic acid
        (C) STRANDEDNESS: single
```

```
        (D) TOPOLOGY: linear (xi) SEQUENCE DESCRIPTION: SEQ ID NO:387:

CTTCTACCAC GACGACTCAT A                                              21

(2) INFORMATION FOR SEQ ID NO:388:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:388:

TTCTACCACG ACGACTCATA C                                              21

(2) INFORMATION FOR SEQ ID NO:389:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:389:

TCTACCACGA CGACTCATAC A                                              21

(2) INFORMATION FOR SEQ ID NO:390:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:390:

CTACCACGAC GACTCATACA C                                              21

(2) INFORMATION FOR SEQ ID NO:391:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:391:

TACCACGACG ACTCATACAC A                                              21

(2) INFORMATION FOR SEQ ID NO:392:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:392:

ACCACGACGA CTCATACACA G                                              21

(2) INFORMATION FOR SEQ ID NO:393:

(i) SEQUENCE CHARACTERISTICS:
        (A) LENGTH: 21 base pairs
        (B) TYPE: nucleic acid
        (C) STRANDEDNESS: single
        (D) TOPOLOGY: linear
```

(xi) SEQUENCE DESCRIPTION: SEQ ID NO:393:

CCACGACGAC TCATACACAG C                                              21

(2) INFORMATION FOR SEQ ID NO:394:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:394:

CACGACGACT CATACACAGC T                                              21

(2) INFORMATION FOR SEQ ID NO:395:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:395:

ACGACGACTC ATACACAGCT A                                              21

(2) INFORMATION FOR SEQ ID NO:396:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:396:

CGACGACTCA TACACAGCTA C                                              21

(2) INFORMATION FOR SEQ ID NO:397:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:397:

GACGACTCAT ACACAGCTAC G                                              21

(2) INFORMATION FOR SEQ ID NO:398:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:398:

ACGACTCATA CACAGCTACG G                                              21

(2) INFORMATION FOR SEQ ID NO:399:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:399:

CGACTCATAC ACAGCTACGG G                                              21

(2) INFORMATION FOR SEQ ID NO:400:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:400:

GACTCATACA CAGCTACGGG A                                              21

(2) INFORMATION FOR SEQ ID NO:401:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:401:

ACTCATACAC AGCTACGGGA T                                              21

(2) INFORMATION FOR SEQ ID NO:402:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:402:

CTCATACACA GCTACGGGAT A                                              21

(2) INFORMATION FOR SEQ ID NO:403:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:403:

TCATACACAG CTACGGGATA C                                              21

(2) INFORMATION FOR SEQ ID NO:404:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:404:

CATACACAGC TACGGGATAC G                                              21

(2) INFORMATION FOR SEQ ID NO:405:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:405:

ATACACAGCT ACGGGATACG G                               21

(2) INFORMATION FOR SEQ ID NO:406:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:406:

TACACAGCTA CGGGATACGG C                               21

(2) INFORMATION FOR SEQ ID NO:407:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:407:

ACACAGCTAC GGGATACGGC C                               21

(2) INFORMATION FOR SEQ ID NO:408:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:408:

CACAGCTACG GGATACGGCC G                               21

(2) INFORMATION FOR SEQ ID NO:409:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:409:

ACAGCTACGG GATACGGCCG G                               21

(2) INFORMATION FOR SEQ ID NO:410:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:410:

CAGCTACGGG ATACGGCCGG G                               21

(2) INFORMATION FOR SEQ ID NO:411:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:411:

AGCTACGGGA TACGGCCGGG C                                              21

(2) INFORMATION FOR SEQ ID NO:412:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:412:

GCTACGGGAT ACGGCCGGGC C                                              21

(2) INFORMATION FOR SEQ ID NO:413:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:413:

CTACGGGATA CGGCCGGGCC C                                              21

(2) INFORMATION FOR SEQ ID NO:414:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:414:

TACGGGATAC GGCCGGGCCC C                                              21

(2) INFORMATION FOR SEQ ID NO:415:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:415:

ACGGGATACG GCCGGGCCCC T                                              21

(2) INFORMATION FOR SEQ ID NO:416:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:416:

CGGGATACGG CCGGGCCCCT G                                              21

(2) INFORMATION FOR SEQ ID NO:417:

(i) SEQUENCE CHARACTERISTICS:
        (A) LENGTH: 30
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:417:

ATGTGCACTA AAATGGAACA GCCCTTCTAC                                            30

(2) INFORMATION FOR SEQ ID NO:418:

(i) SEQUENCE CHARACTERISTICS:
         (A) LENGTH: 29
         (B) TYPE: nucleic acid
         (C) STRANDEDNESS: double
         (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:418:

TGTGCACTAA AATGGAACAG CCCTTCTAC                                             29

(2) INFORMATION FOR SEQ ID NO:419:

(i) SEQUENCE CHARACTERISTICS:
         (A) LENGTH: 28
         (B) TYPE: nucleic acid
         (C) STRANDEDNESS: double
         (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:419:

GTGCACTAAA ATGGAACAGC CCTTCTAC                                              28

(2) INFORMATION FOR SEQ ID NO:420:

(i) SEQUENCE CHARACTERISTICS:
         (A) LENGTH: 28
         (B) TYPE: nucleic acid
         (C) STRANDEDNESS: double
         (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:420:

TGCACTAAAA TGGAACAGCC CTTCTACC                                              28

(2) INFORMATION FOR SEQ ID NO:421:

(i) SEQUENCE CHARACTERISTICS:
         (A) LENGTH: 27
         (B) TYPE: nucleic acid
         (C) STRANDEDNESS: double
         (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:421:

| | |
|---|---|
| GCACTAAAAT GGAACAGCCC TTCTACC | 27 |

(2) INFORMATION FOR SEQ ID NO:422:

(i) SEQUENCE CHARACTERISTICS:
        (A) LENGTH: 1044 base pairs
        (B) TYPE: nucleic acid
        (C) STRANDEDNESS: single
        (D) TOPOLOGY: linear (xi) SEQUENCE DESCRIPTION: SEQ ID NO:422:

| | |
|---|---|
| ATGTGCACTA AAATGGAACA GCCCTTCTAC CACGACGACT CATACACAGC TACGGGATAC | 60 |
| GGCCGGGCCC CTGGTGGCCT CTCTCTACAC GACTACAAAC TCCTGAAACC GAGCCTGGCG | 120 |
| GTCAACCTGG CCGACCCCTA CCGGAGTCTC AAAGCGCCTG GGCTCGCGG ACCCGGCCCA | 180 |
| GAGGGCGGCG GTGGCGGCAG CTACTTTTCT GGTCAGGGCT CGGACACCGG CGCGTCTCTC | 240 |
| AAGCTCGCCT CTTCGGAGCT GGAACGCCTG ATTGTCCCCA ACAGCAACGG CGTGATCACG | 300 |
| ACGACGCCTA CACCCCCGGG ACAGTACTTT TACCCCCGCG GGGGTGGCAG CGGTGGAGGT | 360 |
| GCAGGGGGCG CAGGGGGCGG CGTCACCGAG GAGCAGGAGG GCTTCGCCGA CGGCTTTGTC | 420 |
| AAAGCCCTGG ACGATCTGCA CAAGATGAAC CACGTGACAC CCCCCAACGT GTCCCTGGGC | 480 |
| GCTACCGGGG GGCCCCCGGC TGGGCCCGGG GGCGTCTACG CCGGCCCGGA GCCACCTCCC | 540 |
| GTTTACACCA ACCTCAGCAG CTACTCCCCA GCCTCTGCGT CCTCGGGAGG CGCCGGGGCT | 600 |
| GCCGTCGGGA CCGGGAGCTC GTACCCGACG ACCACCATCA GCTACCTCCC ACACGCGCCG | 660 |
| CCCTTCGCCG GTGGCCACCC GGCGCAGCTG GGCTTGGGCC GCGGCGCCTC CACCTTCAAG | 720 |
| GAGGAACCGC AGACCGTGCC GGAGGCGCGC AGCCGGGACG CCACGCCGCC GGTGTCCCCC | 780 |
| ATCAACATGG AAGACCAAGA GCGCATCAAA GTGGAGCGCA AGCGGCTGCG GAACCGGCTG | 840 |
| GCGGCCACCA AGTGCCGGAA GCGGAAGCTG GAGCGCATCG CGCGCCTGGA GGACAAGGTG | 900 |
| AAGACGCTCA AGGCCGAGAA CGCGGGGCTG TCGAGTACCG CCGGCCTCCT CCGGGAGCAG | 960 |
| GTGGCCCAGC TCAAACAGAA GGTCATGACC CACGTCAGCA ACGGCTGTCA GCTGCTGCTT | 1020 |
| GGGGTCAAGG GACACGCCTT CTGA | 1044 |

(2) INFORMATION FOR SEQ ID NO:423:

(i) SEQUENCE CHARACTERISTICS:
        (A) LENGTH: 1044 base pairs
        (B) TYPE: nucleic acid
        (C) STRANDEDNESS: single
        (D) TOPOLOGY: linear (xi) SEQUENCE DESCRIPTION: SEQ ID NO:423:

| | |
|---|---|
| ATGTGCACTA AAATGGAACA GCCCTTCTAC CACGACGACT CATACACAGC TACGGGATAC | 60 |
| GGCCGGGCCC CTGGTGGCCT CTCTCTACAC GACTACAAAC TCCTGAAACC GAGCCTGGCG | 120 |
| GTCAACCTGG CCGACCCCTA CCGGAGTCTC AAAGCGCCTG GGCTCGCGG ACCCGGCCCA | 180 |
| GAGGGCGGCG GTGGCGGCAG CTACTTTTCT GGTCAGGGCT CGGACACCGG CGCGTCTCTC | 240 |
| AAGCTCGCCT CTTCGGAGCT GGAACGCCTG ATTGTCCCCA ACAGCAACGG CGTGATCACG | 300 |
| ACGACGCCTA CACCCCCGGG ACAGTACTTT TACCCCCGCG GGGGTGGCAG CGGTGGAGGT | 360 |
| GCAGGGGGCG CAGGGGGCGG CGTCACCGAG GAGCAGGAGG GCTTCGCCGA CGGCTTTGTC | 420 |
| AAAGCCCTGG ACGATCTGCA CAAGATGAAC CACGTGACAC CCCCCAACGT GTCCCTGGGC | 480 |
| GCTACCGGGG GGCCCCCGGC TGGGCCCGGG GGCGTCTACG CCGGCCCGGA GCCACCTCCC | 540 |

```
GTTTACACCA ACCTCAGCAG CTACTCCCCA GCCTCTGCGT CCTCGGGAGG CGCCGGGGCT      600

GCCGTCGGGA CCGGGAGCTC GTACCCGACG ACCACCATCA GCTACCTCCC ACACGCGCCG      660

CCCTTCGCCG GTGGCCACCC GGCGCAGCTG GGCTTGGGCC GCGGCGCCTC CACCTTCAAG      720

GAGGAACCGC AGACCGTGCC GGAGGCGCGC AGCCGGACG CCACGCCGCC GGTGTCCCCC      780

ATCAACATGG AAGACCAAGA GCGCATCAAA GTGGAGCGCA AGCGGCTGCG GAACCGGCTG      840

GCGGCCACCA AGTGCCGGAA GCGGAAGCTG GAGCGCATCG CGCGCCTGGA GGACAAGGTG      900

AAGACGCTCA AGGCCGAGAA CGCGGGGCTG TCGAGTACCG CCGGCCTCCT CCGGGAGCAG      960

GTGGCCCAGC TCAAACAGAA GGTCATGACC CACGTCAGCA ACGGCTGTCA GCTGCTGCTT     1020

GGGGTCAAGG GACACGCCTT CTGA                                           1044
```

(2) INFORMATION FOR SEQ ID NO:424:

(i) SEQUENCE CHARACTERISTICS:
    (A) LENGTH: 996 base pairs
    (B) TYPE: nucleic acid
    (C) STRANDEDNESS: single
    (D) TOPOLOGY: linear (xi) SEQUENCE DESCRIPTION: SEQ ID NO:424:

```
ATGACTGCAA AGATGGAAAC GACCTTCTAT GACGATGCCC TCAACGCCTC GTTCCTCCCG       60

TCCGAGAGCG GACCTTATGG CTACAGTAAC CCCAAGATCC TGAAACAGAG CATGACCCTG      120

AACCTGGCCG ACCCAGTGGG GAGCCTGAAG CCGCACCTCC GCGCCAAGAA CTCGGACCTC      180

CTCACCTCGC CCGACGTGGG GCTGCTCAAG CTGGCGTCGC CCGAGCTGGA GCGCCTGATA      240

ATCCAGTCCA GCAACGGGCA CATCACCACC ACGCCGACCC CCACCCAGTT CCTGTGCCCC      300

AAGAACGTGA CAGATGAGCA GGAGGGGTTC GCCGAGGGCT TCGTGCGCGC CCTGGCCGAA      360

CTGCACAGCC AGAACACGCT GCCCAGCGTC ACGTCGGCGG CGCAGCCGGT CAACGGGGCA      420

GGCATGGTGG CTCCCGCGGT AGCCTCGGTG GCAGGGGGCA GCGGCAGCGG CGGCTTCAGC      480

GCCAGCCTGC ACAGCGAGCC GCCGGTCTAC GCAAACCTCA GCAACTTCAA CCCAGGCGCG      540

CTGAGCAGCG GCGGCGGGGC GCCCTCCTAC GGCGCGGCCG GCCTGGCCTT TCCCGCGCAA      600

CCCCAGCAGC AGCAGCAGCC GCCGCACCAC CTGCCCCAGC AGATGCCCGT GCAGCACCCG      660

CGGCTGCAGG CCCTGAAGGA GGAGCCTCAG ACAGTGCCCG AGATGCCCGG CGAGACACCG      720

CCCCTGTCCC CCATCGACAT GGAGTCCCAG GAGCGGATCA AGGCGGAGAG GAAGCGCATG      780

AGGAACCGCA TCGCTGCCTC CAAGTGCCGA AAAAGGAAGC TGGAGAGAAT CGCCCGGCTG      840

GAGGAAAAAG TGAAAACCTT GAAAGCTCAG AACTCGGAGC TGGCGTCCAC GGCCAACATG      900

CTCAGGGAAC AGGTGGCACA GCTTAAACAG AAAGTCATGA ACCACGTTAA CAGTGGGTGC      960

CAACTCATGC TAACGCAGCA GTTGCAAACA TTTTGA                               996
```

(2) INFORMATION FOR SEQ ID NO:425:

(i) SEQUENCE CHARACTERISTICS:
    (A) LENGTH: 1044 base pairs
    (B) TYPE: nucleic acid
    (C) STRANDEDNESS: single
    (D) TOPOLOGY: linear (xi) SEQUENCE DESCRIPTION: SEQ ID NO:425:

```
ATGGAAACAC CCTTCTACGG CGATGAGGCG CTGAGCGGCC TGGGCGGCGG CGCCAGTGGC       60

AGCGGCGGCA CGTTCGCGTC CCCGGGCCGC TTGTTCCCCG GGGCGCCCCC GACGGCCGCG      120
```

-continued

| | |
|---|---|
| GCCGGCAGCA TGATGAAGAA GGACGCGCTG ACGCTGAGCC TGAGTGAGCA GGTGGCGGCA | 180 |
| GCGCTCAAGC CTGCGCCCGC GCCCGCCTCC TACCCCCCTG CCGCCGACGG CGCCCCCAGC | 240 |
| GCGGCACCCC CCGACGGCCT GCTCGCCTCT CCCGACCTGG GGCTGCTGAA GCTGGCCTCC | 300 |
| CCCGAGCTCG AGCGCCTCAT CATCCAGTCC AACGGGCTGG TCACCACCAC GCCGACGAGC | 360 |
| TCACAGTTCC TCTACCCCAA GGTGGCGGCC AGCGAGGAGC AGGAGTTCGC CGAGGGCTTC | 420 |
| GTCAAGGCCC TGGAGGATTT ACACAAGCAG AACCAGCTCG GCGCGGGCCG GGCCGCTGCC | 480 |
| GCCGCCGCCG CCGCCGCCGG GGGGCCCTCG GGCACGGCCA CGGGCTCCGC GCCCCCCGGC | 540 |
| GAGCTGGCCC CGGCGGCGGC CGCGCCCGAA GCGCCTGTCT ACGCGAACCT GAGCAGCTAC | 600 |
| GCGGGCGGCG CCGGGGGCGC GGGGGGCGCC GCGACGGTCG CCTTCGCTGC CGAACCTGTG | 660 |
| CCCTTCCCGC CGCCGCCACC CCCAGGCGCG TTGGGGCCGC CGCGCCTGGC TGCGCTCAAG | 720 |
| GACGAGCCAC AGACGGTGCC CGACGTGCCG AGCTTCGGCG AGAGCCCGCC GTTGTCGCCC | 780 |
| ATCGACATGG ACACGCAGGA GCGCATCAAG GCGGAGCGCA AGCGGCTGCG CAACCGCATC | 840 |
| GCCGCCTCCA AGTGCCGCAA GCGCAAGCTG GAGCGCATCT CGCGCCTGGA AGAGAAAGTG | 900 |
| AAGACCCTCA AGAGTCAGAA CACGGAGCTG GCGTCCACGG CGAGCCTGCT GCGCGAGCAG | 960 |
| GTGGCGCAGC TCAAGCAGAA AGTCCTCAGC CACGTCAACA GCGGCTGCCA GCTGCTGCCC | 1020 |
| CAGCACCAGG TCCCGGCGTA CTGA | 1044 |

(2) INFORMATION FOR SEQ ID NO:426:

(i) SEQUENCE CHARACTERISTICS:
        (A) LENGTH: 1035 base pairs
        (B) TYPE: nucleic acid
        (C) STRANDEDNESS: single
        (D) TOPOLOGY: linear (xi) SEQUENCE DESCRIPTION: SEQ ID NO:426:

| | |
|---|---|
| ATGTGCACGA AAATGGAACA GCCTTTCTAT CACGACGACT CTTACGCAGC GGCGGGATAC | 60 |
| GGTCGGAGCC CTGGCAGCCT GTCTCTACAC GACTACAAAC TCCTGAAACC CACCTTGGCG | 120 |
| CTCAACCTGG CGGATCCCTA TCGGGGTCTC AAGGGTCCTG GGCGCGGGG TCCAGGCCCG | 180 |
| GAGGGCAGTG GGGCAGGCAG CTACTTTTCG GGTCAGGGAT CAGACACAGG CGCATCTCTG | 240 |
| AAGCTAGCCT CCACGGAACT GGAGCGCTTG ATCGTCCCCA ACAGCAACGG CGTGATCACG | 300 |
| ACGACGCCCA CGCCTCCGGG ACAGTACTTT TACCCCCGTG GGGGTGGCAG CGGTGGAGGT | 360 |
| ACAGGGGGCG GCGTCACCGA GGAGCAGGAG GGCTTTGCGG ACGGTTTTGT CAAAGCCCTG | 420 |
| GACGACCTGC ACAAGATGAA CCACGTGACG CCCCCCAACG TGTCCCTGGG CGCCAGCGGG | 480 |
| GGTCCCCAGG CCGGCCCAGG GGGCGTCTAT GCTGGTCCGG AGCCGCCTCC CGTCTACACC | 540 |
| AACCTCAGCA GTTACTCTCC AGCCTCTGCA CCCTCTGGAG GCTCCGGGAC CGCCGTCGGG | 600 |
| ACTGGGAGCT CATACCCGAC GGCCACCATC AGCTACCTCC CACATGCACC ACCCTTTGCG | 660 |
| GGCGGCCACC CGGCACAGCT GGGTTTGAGT CGTGGCGCTT CCGCCTTTAA AGAGGAACCG | 720 |
| CAGACCGTAC CGGAGGCACG CAGCCGCGAC GCCACGCCGC CTGTGTCCCC CATCAACATG | 780 |
| GAAGACCAGG AGCGCATCAA AGTGGAGCGA AAGCGGCTGC GGAACAGGCT GGCGGCCACC | 840 |
| AAGTGCCGGA AGCGGAAGCT GGAGCGCATC GCGCGCCTGG AGGACAAGGT GAAGACACTC | 900 |
| AAGGCTGAGA ACGCGGGGCT GTCGAGTGCT GCCGGTCTCC TAAGGGAGCG AGTGGCGCAG | 960 |
| CTCAAGCAGA AGGTCATGAC CCATGTCAGC AACGGCTGCC AGTTGCTGCT AGGGGTCAAG | 1020 |
| GGACACGCCT TCTGA | 1035 |

(2) INFORMATION FOR SEQ ID NO:427:

(i) SEQUENCE CHARACTERISTICS:
        (A) LENGTH: 1005 base pairs
        (B) TYPE: nucleic acid
        (C) STRANDEDNESS: single
        (D) TOPOLOGY: linear (xi) SEQUENCE DESCRIPTION: SEQ ID NO:427:

```
ATGACTGCAA AGATGGAAAC GACCTTCTAC GACGATGCCC TCAACGCCTC GTTCCTCCAG      60
TCCGAGAGCG GTGCCTACGG CTACAGTAAC CCTAAGATCC TAAAACAGAG CATGACCTTG     120
AACCTGGCCG ACCCGGTGGG CAGTCTGAAG CCGCACCTCC GCGCCAAGAA CTCGGACCTT     180
CTCACGTCGC CCGACGTCGG GCTGCTCAAG CTGGCGTCGC CGGAGCTGGA GCGCCTGATC     240
ATCCAGTCCA GCAATGGGCA CATCACCACT ACACCGACCC CCACCCAGTT CTTGTGCCCC     300
AAGAACGTGA CCGACGAGCA GGAGGGCTTC GCCGAGGGCT TCGTGCGCGC CCTGGCTGAA     360
CTGCATAGCC AGAACACGCT TCCCAGTGTC ACCTCCGCGG CACAGCCGGT CAGCGGGGCG     420
GGCATGGTGG CTCCCGCGGT GGCCTCAGTA GCAGGCGCTG GCGGCGGTGG TGGCTACAGC     480
GCCAGCCTGC ACAGTGAGCC TCCGGTCTAC GCCAACCTCA GCAACTTCAA CCCGGGTGCG     540
CTGAGCAGCG GCGGTGGGGC GCCCTCCTAT GGCGCGGCCG GGCTGGCCTT TCCCTCGCAG     600
CCGCAGCAGC AGCAGCAGCC GCCTCAGCCG CCGCACCACT TGCCCCAACA GATCCCGGTG     660
CAGCACCCGC GGCTGCAAGC CCTGAAGGAA GAGCCGCAGA CCGTGCCGGA GATGCCGGGA     720
GAGACGCCGC CCCTGTCCCC TATCGACATG GAGTCTCAGG AGCGGATCAA GGCAGAGAGG     780
AAGCGCATGA GGAACCGCAT TGCCGCCTCC AAGTGCCGGA AAAGGAAGCT GGAGCGGATC     840
GCTCGGCTAG AGGAAAAAGT GAAAACCTTG AAAGCGCAAA ACTCCGAGCT GGCATCCACG     900
GCCAACATGC TCAGGGAACA GGTGGCACAG CTTAAGCAGA AAGTCATGAA CCACGTTAAC     960
AGTGGGTGCC AACTCATGCT AACGCAGCAG TTGCAAACGT TTTGA                   1005
```

(2) INFORMATION FOR SEQ ID NO:428:

(i) SEQUENCE CHARACTERISTICS:
        (A) LENGTH: 1026 base pairs
        (B) TYPE: nucleic acid
        (C) STRANDEDNESS: single
        (D) TOPOLOGY: linear (xi) SEQUENCE DESCRIPTION: SEQ ID NO:428:

```
ATGGAAACGC CCTTCTATGG CGAGGAGGCG CTGAGCGGCC TGGCTGCGGG TGCGTCGAGC      60
GTCGCTGGTG CTACTGGGGC CCCCGGCGGT GGTGGCTTCG CGCCCCCGGG CCGCGCTTTC     120
CCCGGGGCGC CCCCGACGAC CAGCATGCTG AAGAAAGACG CGCTGACGCT CAGCCTGGCG     180
GAGCAGGGAG CGGCGGGATT GAAACCAGGG TCGGCCACTG CACCTTCTGC GCTGCGCCCC     240
GACGGCGCCC CCGACGGGCT GCTGGCTTCG CCGGATCTTG GGCTGCTCAA ACTCGCGTCG     300
CCGGAGCTGG AGAGGCTGAT CATCCAGTCC AACGGGCTGG TGACCACTAC CCCGACCAGT     360
ACGCAGTTCC TCTACCCGAA GGTGGCAGCC AGCGAGGAGC AGGAGTTCGC CGAAGGCTTC     420
GTCAAGGCGC TGGAGGACCT GCACAAGCAA AGCCAGCTGG GTGCGGCCAC CGCGGCCACC     480
TCAGGGGCTC CCGCGCCTCC CGCGCCCGCC GACCTGGCCG CCACCCCCGG GGCCACGGAG     540
ACCCCGGTCT ACGCCAACCT GAGCAGTTTC GCGGGTGGCG CCGGGCCCCC TGGGGCGCG     600
GCCACCGTGG CTTTCGCCGC GGAGCCAGTG CCCTTCCCGC CGCCCCGGG CGCGCTGGGG     660
CCGCCGCCAC CTCCGCATCC ACCGCGCCTG GCCGCGCTCA AGGACGAGCC GCAGACCGTG     720
```

```
CCGGACGTGC CGAGCTTCGG CGACAGCCCT CCGCTGTCGC CCATCGACAT GGACACGCAA      780

GAACGCATCA AGGCGGAGCG CAAGAGGCTG CGCAACCGCA TCGCCGCCTC CAAATGCCGC      840

AAGCGCAAGC TGGAGCGTAT CTCGCGCCTG GAGGAGAAAG TCAAGACCCT CAAAAGCCAG      900

AACACCGAGC TGGCGTCCAC CGCCAGCCTG CTGCGCGAGC AGGTGGCGCA GCTCAAACAG      960

AAAGTCCTCA GCCACGTCAA CAGCGGCTGC CAGCTGCTGC CCCAGCACCA GGTCCCGGCG     1020

TACTGA                                                                1026
```

(2) INFORMATION FOR SEQ ID NO:600:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:600:

```
CACGACTACA AACTCCTGAA AC                                                22
```

(2) INFORMATION FOR SEQ ID NO:601:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:601:

```
AAATACAATA AACTATTGAA AA                                                22
```

(2) INFORMATION FOR SEQ ID NO:602:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:602:

```
TACGAGTCCA CATTCCTGTT CC                                                22
```

(2) INFORMATION FOR SEQ ID NO:603:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:603:

CACGACTACA AACTCCTGAA AC                                                    22

(2) INFORMATION FOR SEQ ID NO:604:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:604:

AGTAACCCCA AGATCCTGAA AC                                                    22

(2) INFORMATION FOR SEQ ID NO:605:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:605:

TACGAGTCCA CATTCCTGTT TG                                                    22

(2) INFORMATION FOR SEQ ID NO:606:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:606:

CACGACTTCA ACGTCCTGAG TA                                                    22

(2) INFORMATION FOR SEQ ID NO:614:

(i) SEQUENCE CHARACTERISTICS:
            (A) LENGTH: 26
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:614:

GAGGACAAGG TGAAGACACT CAAGGC                                             26

(2) INFORMATION FOR SEQ ID NO:615:

(i) SEQUENCE CHARACTERISTICS:
        (A) LENGTH: 26
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:615:

GAGGAAAAAG TGAAAACCTT GAAAGC                                             26

(2) INFORMATION FOR SEQ ID NO:616:

(i) SEQUENCE CHARACTERISTICS:
        (A) LENGTH: 26
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:616:

GAGGAGAAAG TCAAGACCCT CAAAAG                                             26

(2) INFORMATION FOR SEQ ID NO:617:

(i) SEQUENCE CHARACTERISTICS:
        (A) LENGTH: 26
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:617:

GAGGACAAGG TGAAGACGCT CAAGGC                                             26

(2) INFORMATION FOR SEQ ID NO:618:

(i) SEQUENCE CHARACTERISTICS:
        (A) LENGTH: 26
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:618:

GAGGAAAAAG TGAAAACCTT GAAAGC                                        26

(2) INFORMATION FOR SEQ ID NO:619:

(i) SEQUENCE CHARACTERISTICS:
            (A) LENGTH: 26
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:619:

GAAGAGAAAG TGAAGACCCT CAAGAG                                        26

(2) INFORMATION FOR SEQ ID NO:620:

(i) SEQUENCE CHARACTERISTICS:
            (A) LENGTH: 26
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:620:

AAAGAAAAAA AGAAAAACTT AAAAGC                                        26

(2) INFORMATION FOR SEQ ID NO:628:

(i) SEQUENCE CHARACTERISTICS:
            (A) LENGTH: 17
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:628:

CTGGGGCCGA GCACTGG                                                  17

(2) INFORMATION FOR SEQ ID NO:629:

(i) SEQUENCE CHARACTERISTICS:
            (A) LENGTH: 17
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:629:

TAAGTGCCAG GCTAGAC                                                  17

(2) INFORMATION FOR SEQ ID NO:630:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:630:

GACGTGCCGA GCTTCGG                                              17

(2) INFORMATION FOR SEQ ID NO:631:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:631:

CACGCGCCGC CCTTCGC                                              17

(2) INFORMATION FOR SEQ ID NO:632:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:632:

TAAGTGTTGA GCTCGGG                                              17

(2) INFORMATION FOR SEQ ID NO:633:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:633:

GACGTGCCGA GCTTCGG                                              17

(2) INFORMATION FOR SEQ ID NO:634:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:634:

GACGTGTGGA GCTTCGG                                                          17

(2) INFORMATION FOR SEQ ID NO:700:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:700:

AGCACCATTG TGAAGCAGAT GA                                                    22

(2) INFORMATION FOR SEQ ID NO:701:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:701:

TGTTTGATGT GGGAGGCCAG AG                                                    22

(2) INFORMATION FOR SEQ ID NO:702:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:702:

AGCACAATTG TGAAGCAGAT GA                                                    22

(2) INFORMATION FOR SEQ ID NO:703:

(i) SEQUENCE CHARACTERISTICS:
        (A) LENGTH: 22

(B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:703:

AGCACCATCG TCAAGCAGAT GA                                             22

(2) INFORMATION FOR SEQ ID NO:704:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:704:

AGTACTATTG TGAAACAGAT GA                                             22

(2) INFORMATION FOR SEQ ID NO:705:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:705:

AGCACCATTG TGAAGCAGAT GA                                             22

(2) INFORMATION FOR SEQ ID NO:706:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:706:

AGCACCATTG TGAAGCAGAT GA                                             22

(2) INFORMATION FOR SEQ ID NO:707:

(i) SEQUENCE CHARACTERISTICS:
        (A) LENGTH: 22
        (B) TYPE: nucleic acid
        (C) STRANDEDNESS: double
        (D) TOPOLOGY: linear

```
        (ii) MOLECULE TYPE: cDNA to mRNA (iii) HYPOTHETICAL: NO (iv) ANTI-SENSE: NO (xi) SEQUENCE DESCRIPTION: SEQ ID NO:707:

TGTTTGATGT AGGTGGCCAA AG                                                22

(2) INFORMATION FOR SEQ ID NO:708:

(i) SEQUENCE CHARACTERISTICS:
             (A) LENGTH: 22
             (B) TYPE: nucleic acid
             (C) STRANDEDNESS: double
             (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:708:

TGTTCGATGT GGGCGGCCAG CG                                                22

(2) INFORMATION FOR SEQ ID NO:709:

(i) SEQUENCE CHARACTERISTICS:
             (A) LENGTH: 22
             (B) TYPE: nucleic acid
             (C) STRANDEDNESS: double
             (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:709:

TGTTTGACGT TGGGGGCCAG CG                                                22

(2) INFORMATION FOR SEQ ID NO:805:

(i) SEQUENCE CHARACTERISTICS:
             (A) LENGTH: 22
             (B) TYPE: nucleic acid
             (C) STRANDEDNESS: double
             (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:805:

TGTTTGACGT GGGAGGCCAG AG                                                22

(2) INFORMATION FOR SEQ ID NO:806:

(i) SEQUENCE CHARACTERISTICS:
             (A) LENGTH: 22
             (B) TYPE: nucleic acid
             (C) STRANDEDNESS: double
             (D) TOPOLOGY: linear (ii) MOLECULE TYPE: cDNA to mRNA
```

-continued (iii) HYPOTHETICAL: NO (iv) ANTI-SENSE: NO (xi) SEQUENCE DESCRIPTION: SEQ ID NO:806:

TGTTTGATGT GGGTGGTCAG CG  22

METHOD FOR MEASURING MESSENGER RNA

RELATED APPLICATIONS

The present application is a continuation-in-part of application Ser. No. 07/857,059, filed Mar. 24, 1992, now abandoned, which is a continuation-in-part of Ser. No. 07/827,208,filed Jan. 29, 1992, now abandoned. The present application is also a continuation-in-part of application Ser. No. 07/827,975, filed Jan. 29, 1992, now abandoned. The disclosures of all of these previous applications are hereby incorporated herein in their entirety by this reference thereto.

BACKGROUND OF THE INVENTION

1. Field of the Invention

This invention is related to a method for measuring messenger RNA (mRNA) and polynucleotide-immobilized supports useful in this method. Specifically, this invention is related to measuring methods and reagents in which various types of mRNA can be measured at the same time. In one embodiment of this invention, the mRNA need not be purified from the cell, and the mRNA can be rapidly quantified with high sensitivity.

2. Description of Previous Techniques

Previously well-known techniques for measuring mRNA levels include the Northern Blot Method (See, e.g., J. Sambrook, et al., Molecular Cloning, 2nd ed., Cold spring Harbor Laboratory Press, 1989 hereafter referred to as "Molecular Cloning"), the Dot Blot Method (See, e.g., Molecular Cloning), Ribonuclease Protection Assay (See, e.g., Molecular Cloning), and the Reverse PCR Method (H. A. Erlich (ed.), PCR Technology-Principles and Applications for DNA Amplification, Stockton Press, New York, N.Y., 1989). The disclosures of all of these previous references are hereby incorporated by reference.

The Northern Blot Method detects mRNA which is separated by molecular weight using electrophoresis. The separated molecules are immobilized on a membrane and mRNA levels are determined by hybridization of marker DNA probes. With this method, the molecular weight of the subject mRNA must generally be known. By using this method a complex between a labeled probe, mRNA and an insoluble membrane is formed. The amount of label in the complex at the appropriate site on the membrane is then measured colorimetrically or by radioactive emissions.

The Dot Blot Method detects mRNA by hybridization with a labeled probe after purified mRNA is immobilized as a spot on a membrane. This method can be used to rapidly examine many samples at one time. However, both the Dot Blot and the Northern Blot methods require the use of a specific labeled probe for each mRNA which is desired to be detected.

The Ribonuclease Protection Assay method is used to detect mRNA after it is initially purified. The purified mRNA is hybridized with a labeled RNA probe, and then treated with a ribonuclease that specifically digests single stranded RNA. The labeled RNA probe will form a duplex in the solution and be protected from digestion. This is then immobilized on a membrane after separation of the double-stranded RNA/probe complex.

The reverse PCR method is used where cDNA is synthesized using reverse transcriptase and purified mRNA. This cDNA can be immobilized to a membrane. The synthesized cDNA is then amplified using standard PCR (Polymerase Chain Reaction) methods. After separating cDNA according to its molecular weight by electrophoresis, it becomes a single band. The DNA is then immobilized on a membrane, and detected by hybridization with a labeled DNA probe. However, after PCR, no quantitative information remains due to the amplification of the original message.

All of the foregoing methods take extended periods of time to perform since the mRNA used must be in at least a partially purified form. Also, electrophoresis of the samples and immobilization to a membrane is necessary. Both of these steps reduce the reliability of quantification of the mRNA.

Thus, there remains a need to resolve the above problems, and to provide a method of measuring for rapidly determining messenger RNA levels and a measuring reagent useful in such a method.

SUMMARY OF THE INVENTION

In the mRNA assay methods of the present invention, a first and a second polynucleotide probe can be used. The inventors have discovered that immobilization of probes (a first polynucleotide) rather than samples, on a water-insoluble support can provide a basis for the rapid quantification of multiple unpurified samples containing mRNA. Applicants have provided an efficient method of identifying appropriate specific probes for this purpose. In preferred forms of the present invention, the first polynucleotide probe has a nucleotide sequence complementary to a region which is unique in the sample to the mRNA and does not bind other portions in the target mRNA. The inventors also discovered that a single kind of second polynucleotide probe can be used for simultaneous quantification of various mRNAs. However, any of a variety of probes that bind to a different region of the mRNA than the first probe can be used for this purpose. In this regard, the inventors have found that a second polynucleotide probe containing sequences complementary to a polyadenylic acid tail of mRNA can be used in such a simultaneous assay method. Based on these and other discoveries, the inventors established the present invention.

One embodiment of the present invention is a highly sensitive, quantitative and rapid method for detecting and quantifying mRNA in a sample without the need to purify mRNA from cells. In this embodiment of the invention, the method comprises the following steps:

(a) identifying a polynucleotide sequence that is unique to the mRNA;

(b) immobilizing a first polynucleotide to an insoluble support, the first polynucleotide having a first sequence complementary to the sequence unique to the mRNA;

(c) incubating the sample with the insoluble support under conditions wherein the unique sequence will hybridize with the first polynucleotide, thereby immobilizing mRNA present in the sample to the insoluble support;

(d) washing non-immobilized components of the sample from the insoluble support;

(e) labeling mRNA on the support in a manner that label is incorporated onto the support related to the amount of mRNA on the support; and (f) measuring the amount of label immobilized on the support.

In a preferred embodiment, the above step of labeling mRNA on the support involves incubating a labeled probe, most preferably poly-d(T), with the insoluble support under conditions wherein the labeled probe will hybridize with mRNA on the support, and the labeled probe bears a label and is complementary to a part of the mRNA other than a part of the mRNA complementary to the first probe, thereby immobilizing to the insoluble support the label on the labeled probe which has hybridized with the mRNA; and thereafter washing any non-immobilized labeled probe from the insoluble support.

In addition, the above method of labeling nucleic acids in step (e) can preferably involve labeling the oligonucleotides with a nucleic acid stain, most preferably from the group consisting of ethidium bromide, yoyo-1 and toto-1.

In a further preferred embodiment, the above method can utilize a label, wherein the label comprises a radionuclide, or alternatively biotin. In the method using biotin, the incubation can preferably be with enzyme-conjugated streptavidin; followed by measurement of the amount of enzyme bound to the insoluble support. In this embodiment step (f) can additionally comprise adding streptavidin bound to alkaline phosphatase to the insoluble support.

In still another embodiment of the preferred method, the mRNA can code for a β receptor, and wherein the first polynucleotide comprises the sequence of SEQ ID NO:6. An alternative embodiment of the above method includes mRNA coding for the α subunit of Gs protein, wherein the first polynucleotide comprises a sequence complementary to a sequence selected from the group consisting of SEQ ID NO:1, 145–146, 209–212, 268–287, 705 and 708.

Yet another alternative mRNA sequence that can be used with the present invention method codes for the Gi-2 protein, wherein the first polynucleotide comprises a sequence complementary to a sequence selected from the group consisting of SEQ ID NO:703, 706, 142, 143, 187–197 and 238–253. The present method can also preferably involve the use mRNA coding for substance P receptor, wherein the first polynucleotide comprises the sequence of SEQ ID NO:5.

mRNA encoding Gi-3 protein can also be used in the present method, wherein the first polynucleotide comprises a sequence complementary to a sequence selected from the group consisting of SEQ ID NO:704, 707, 144, 198–208 and 254–267. Still another embodiment of the above method can involve the mRNA coding for the Gi-1 protein, wherein the first polynucleotide comprises a sequence complementary to a sequence selected from the group consisting of SEQ ID NO:702, 705, 141, and 224–237. An even further preferred embodiment includes mRNA coding for G protein, wherein the first polynucleotide comprises a sequence complementary to a sequence selected from the group consisting of SEQ ID NO:700, 701, 139, 140, 148–159, 162–172, 176–186 and 3–4.

Most preferably, the first sequence hybridizes to a unique sequence of the mRNA and not to other polynucleotides present in the sample, and even more preferably, the sample comprises a cell lysate.

In an alternative preferred embodiment, the label in the above method can be measured by light emitted therefrom, and step (f) of the method comprises measuring the amount of light emitted by the label. The method of measuring the light can preferably involve; recording the amount of light on film; and measuring the exposure of this film using a densitometer. In addition, the light measurement can alternatively comprise adding ATTOPHOS and measuring fluorescence emitted using a fluorimeter.

The present invention method in step (a) above can advantageously include a computer program, with the computer program preferably involving use of an H-site model.

The H-site model of step (a) is preferably used to identify the first polynucleotide probe of the method by the steps of:
specifying a minimum melting temperature for the first nucleotide probe and the nucleotide sequence specific to the organism;
specifying a nucleation threshold that places a minimum value on the number of base pairs at any nucleation site;
determining the melting temperatures ($T_m$) of the first nucleotide probe and the sequence specific to the organism at every possible hybridization point; and
selecting the nucleotide probe having the highest $T_m$ value.

The computerized method of identifying the first polynucleotide probe can preferably have the melting temperature determined by the formula;
$T_m$=81.5−16.6(log[Na])−0.63% (formamide)+0.41(%(G+C))−600/N, wherein Log[Na] is the log function of the sodium concentration, 0.063%(formamide) is the concentration of formamide, %(G+C) is the percentage of matched GC base pairs, and N is the probe length.

Additionally the method of step (a) can be used to identify the second polynucleotide probe using the H-site computerized model by the steps of:
specifying a minimum melting temperature for the second nucleotide probe and the nucleotide sequence specific to the organism;
specifying a nucleation threshold that places a minimum value on the number of base pairs at any nucleation site;
determining the melting temperatures ($T_m$) of the first nucleotide probe and the sequence specific to the organism at every possible hybridization point; and
selecting the nucleotide probe of the proper length having the lowest $T_m$ value.

A method of identifying the second nucleotide probe can involve determining the melting temperature by the formula:
$T_m$=81.5−16.6(log[Na])−0.63%(formamide)+0.41(%(G+C))−600/N, wherein Log[Na] is the log function of the sodium concentration, 0.063%(formamide) is the concentration of formamide, %(G+C) is the percentage of matched GC base pairs, and N is the probe length.

A different embodiment of the present invention is a method of inhibiting RNase activity in a sample containing RNA in a buffer system containing SDS and EDTA, comprising adding vanadyl ribonucleoside complex to the sample. Preferably, there is at least a five-fold molar excess of EDTA over RNA in the sample and most preferably, the vanadyl ribonucleoside complex is added in combination with proteinase K. In an alternative preferred embodiment, the vanadyl ribonucleoside complex is added in combination with RNasin.

Yet another different embodiment of the present invention is a polynucleotide-immobilized support that is useful in detecting and quantifying the amount of β receptor mRNA in a sample, comprising:
an insoluble support;
a first polynucleotide bound to the support, the first polynucleotide comprising a sequence that is complimentary to a sequence unique to β receptor mRNA.
More preferably, the sequence unique to β receptor mRNA comprises a sequence selected from the group consisting of SEQ ID NO:6.

Still another preferred embodiment of the present invention is a polynucleotide-immobilized support that is useful in detecting and quantifying the amount of jun oncogene mRNA in a sample, comprising:
an insoluble support;
a first polynucleotide bound to the support, the first polynucleotide comprising a sequence that is complementary to a sequence unique to jun oncogene mRNA.
Preferably, the sequence unique to the jun oncogene mRNA comprises a sequence selected from the group consisting of SEQ ID NO:11–35, 39–53, 62–138, 310–342, 600–606, 614–620, and 628–634.

Another embodiment of the present invention is a polynucleotide-immobilized support that is useful in detecting and quantifying the amount of G protein mRNA in a sample, comprising:

an insoluble support;

a first polynucleotide bound to the support, the first polynucleotide comprising a sequence that is complementary to a sequence unique to G protein mRNA.

Preferably, the sequence unique to G protein mRNA comprises a sequence selected from the group consisting of 1, 2, 700–709, 139–159, 162–172 and 176–309.

Another preferred embodiment of the present invention is a polynucleotide-immobilized support that is useful in detecting and quantifying the amount of Substance P receptor mRNA in a sample, comprising:

an insoluble support;

a first polynucleotide bound to the support, the first polynucleotide comprising a sequence that is complementary to a sequence unique to Substance P receptor mRNA.

Preferably the sequence unique to Substance P receptor mRNA comprises the sequence of SEQ ID NO:5.

BRIEF DESCRIPTION OF THE FIGURES

FIGS. 21A–21C show display screen representations of the main oligoprobe design station dialog windows of this invention;

FIG. 25 is a display screen representation of the probesedit window, wherein SEQ ID NOs:357, 357, 358, 359, 360, 361, 362, 363, and 363 are assigned to the first nucleotide sequence to the last nucleotide sequence (from the top to the bottom), respectively;

FIG. 26 is a printout of the probesedit output file;

FIG. 40 is the first page of a printcut of a sample file containing the output of the Mismatch Model program of this invention, wherein SEQ ID NOs:364 to 416 are assigned to the first nucleotide sequence (Position Length No. 1) to the last nucleotide sequence (Position Length No. 53), respectively;

FIG. 44A is the first page of a printout of a sample file containing output of Mismatch Model program, wherein SEQ ID NOs:364 to 416 are assigned to the first nucleotide sequence (Position Length No. 1) to the last nucleotide sequence (Position Length No. 53), respectively;

FIG. 44B is the first page of a printout of a sample file containing output of H-Site Model program, wherein SEQ ID NOs:417 to 421 are assigned to the first nucleotide sequence to the last nucleotide sequence (from the top to bottom), respectively;

FIG. 47 is a printout of a sample target species file, wherein SEQ ID NOs:422 is assigned to the nucleotide sequence;

FIG. 48 is a printout of a sample preparation file, wherein SEQ ID NOs:423 and 424 are assigned to the first and second nucleotide sequences on page 48, SEQ ID NOs:425 and 426 are assigned to the first and second nucleotide sequences on page 48(2), and SEQ ID NOs:427 and 428 are assigned to the first and second nucleotide sequences on page 48(3).

DETAILED DESCRIPTION OF THE INVENTION

Target mRNA

Figure 1:
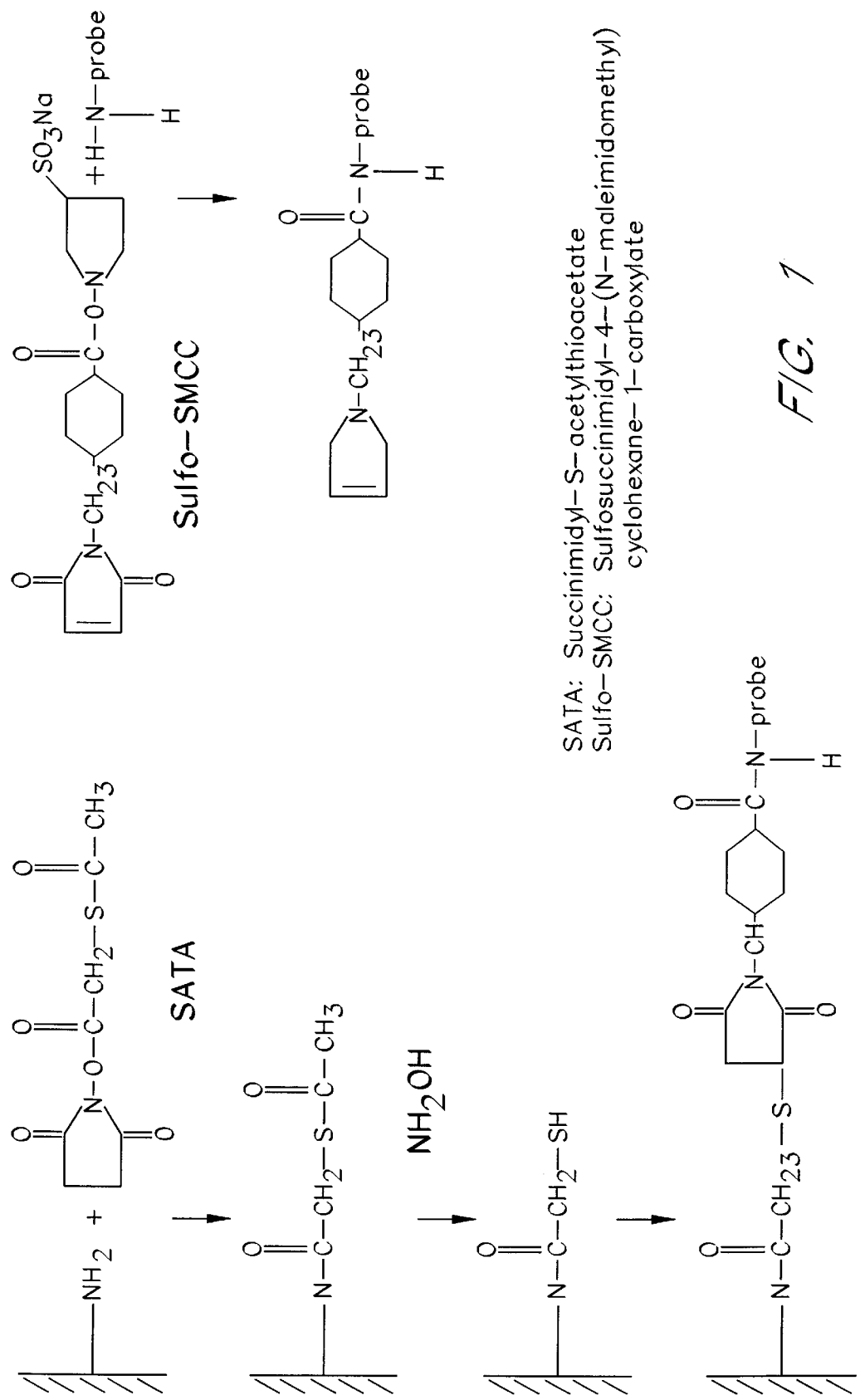
FIG. 1 illustrates an immobilization procedure of a first polynucleotide probe onto an insoluble support by the maleimide method.

Previously, in order to genetically diagnose an infectious disease, procedures utilizing DNA were generally performed. Although, with DNA diagnosis, the existence of an external gene can be confirmed, it cannot be determined if the known gene is in an unexpressed carrier state or expressed in the diseased state.

In living organisms, once a gene is activated, the DNA coding for that gene is transcribed into mRNA, and the mRNA is subsequently translated into protein. Thus, the activation of the external gene can be determined by measuring the levels of mRNA.

Currently, to genetically diagnose a protein deficiency state, most experimenters have limited themselves to analysis at the DNA level. However, this method cannot be used to determine abnormalities of transcription or translation. If mRNA levels could be measured easily, the diseased state might be more precisely recognized. In a diseased state where mRNA cannot be detected, it can be said that there is a defect in transcription, while if normal levels of mRNA are detected, there is probably an abnormality in translation.

In addition, the amount of mRNA produced in the cell reflects the amount of expression of a gene, so it would be useful in the course of an abnormal condition, such as an illness or drug reaction, to examine mRNA levels. As discussed in greater detail below, measuring any of a large number of mRNAs can provide clinically useful information. Particular examples include mRNA for the β receptor, substance P, G protein and oncogenes, such as jun.

For the aforementioned reasons, the ability to measure mRNA would be useful for diagnosing and recognizing the pathophysiology of various disease states. This method would be especially useful for diagnosis of hereditary diseases, cancer, and infectious diseases.

A preferred target of this invention is mRNA of eukaryote cells which contain polyadenylic acid tail on their 3'-terminal end. Once the specific nucleotide sequence of the mRNA is known, virtually any mRNA can be measured using the methods of the present invention. Examples of such mRNAs are human G protein, human $β_2$ receptor, substance P, lymphocyte surface antigen, immunoglobulin, collagen, and adrenaline receptor.

Test Samples

Test samples containing target mRNA can be obtained from a variety of sources. Preferred sources include living samples or cell solutions which have been treated to inactivate ribonuclease (RNase) activity. Purification of mRNA for standard samples can be conducted according to the methods usually associated with Northern Blot procedures or Dot Blot procedures method. Kits for the purification of mRNA are commercially available.

A test sample can be prepared from a living sample by treatment with 10 mM of ethylenediaminetetraacetic acid (EDTA) (pH 8.0), 0.2 M NaCl, 0.5% of sodium dodecyl sulfate (SDS), 500 Unit/ml of RNase inhibitor, 10 mM of Vanadyl Ribonucleoside Complex and 200 μg/l of Proteinase K (hereafter called Lysis buffer) to lyse the cells and inhibit RNase activity. After lysis of the cells, NaCl concentration is adjusted to 0.5M.

In the methods of the present invention that involve probing samples containing RNA, or in any procedure in which it is desired to prevent the degradation of RNA, it is advantageous to inhibit the activity of any ribonucleases (RNases) which may be present. One Rnase inhibitor which can be used is Vanadyl Ribonucleoside Complex (VRC) (Bethesda Research Laboratories, Gaithersburg, Md.). VRC has been reported to be useful during cell fractionation and in the preparation of RNA, and has been shown not to interfere with the phenol extraction or ethanol precipitation of RNA. In addition, VRC does not affect other cytoplasmic components of cells. Therefore, VRC is an ideal inhibitor of RNase in many experimental procedures.

However, prior art procedures for inhibiting RNases with VRC taught that VRC should not be used in buffer systems containing EDTA or SDS, which are commonly used in the field of molecular biology. The reason for this prohibition was that it was believed that the Complex would dissociate in the presence of these buffers, leading to a loss of RNase inhibiting activity. In fact, the BRL insert accompanying the VRC product recommends that a five- to ten-fold molar excess of EDTA be added to an RNA solution containing VRC in order "destroy" the VRC prior to ethanol extraction of the RNA from the solution. The apparent inability to use VRC together with common buffers that include EDTA and SDS thus presented a major impediment to the exploitation of VRC as an RNase inhibitor.

We have discovered, however, that VRC is in fact an effective RNase inhibitor even in the presence of SDS and/or EDTA. Thus, VRC can be used in assays which use buffers including SDS or EDTA, where heretofore it was believed that VRC would not be effective in such systems. VRC is an effective RNase inhibitor at the concentrations of EDTA and SDS that are normally used when manipulating RNA or when performing a variety of other molecular biology techniques. For example, we have found that VRC effectively inhibits RNase in a buffer solution comprising approximately 1 mM EDTA. We also found VRC to be effective in 0.5% SDS solutions, and is believed to be effective in solutions ranging up to 2% SDS, more preferably up to 1% SDS. VRC can, of course, also be used in other solutions including EDTA and SDS.

Figure 10:
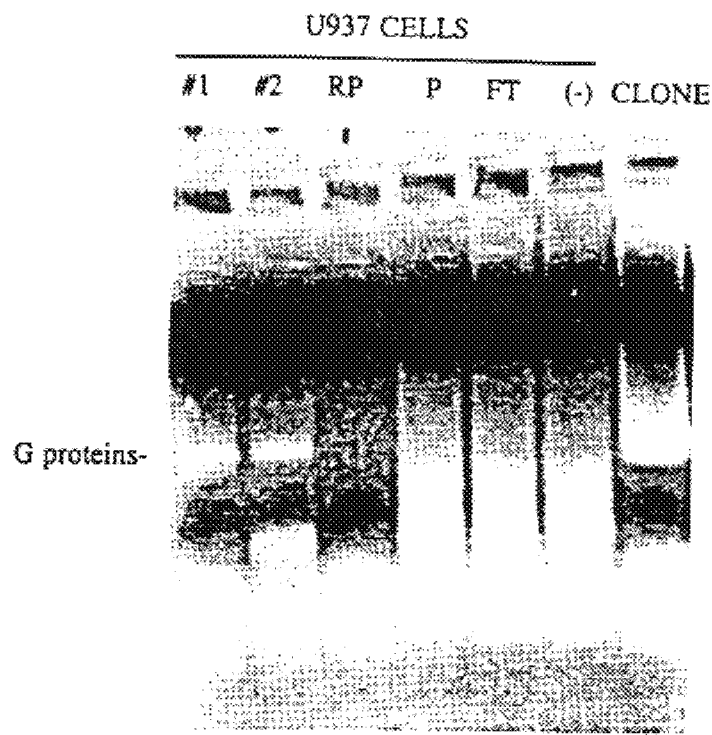
FIG. 10 shows a gel showing the effect of various RNase inhibitors on mRNA preparations containing SDS and EDTA.
Figure 11:
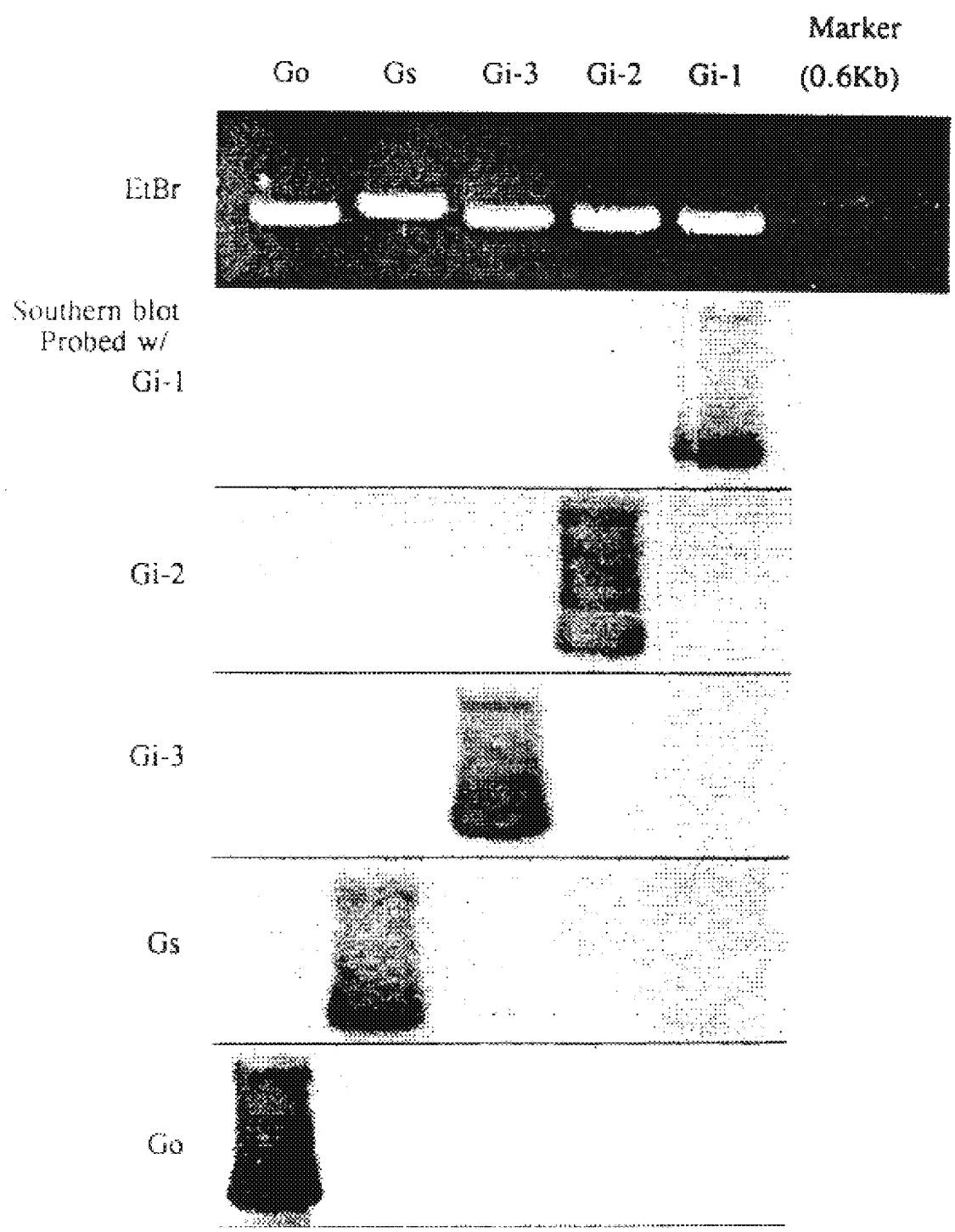
FIG. 11 shows a gel of five different G protein oligonucleotides amplified with the $G_2$ and $G_4$ PCR primers and also provides Southern blots using each of the five G protein sequences as a probe.
Figure 12:
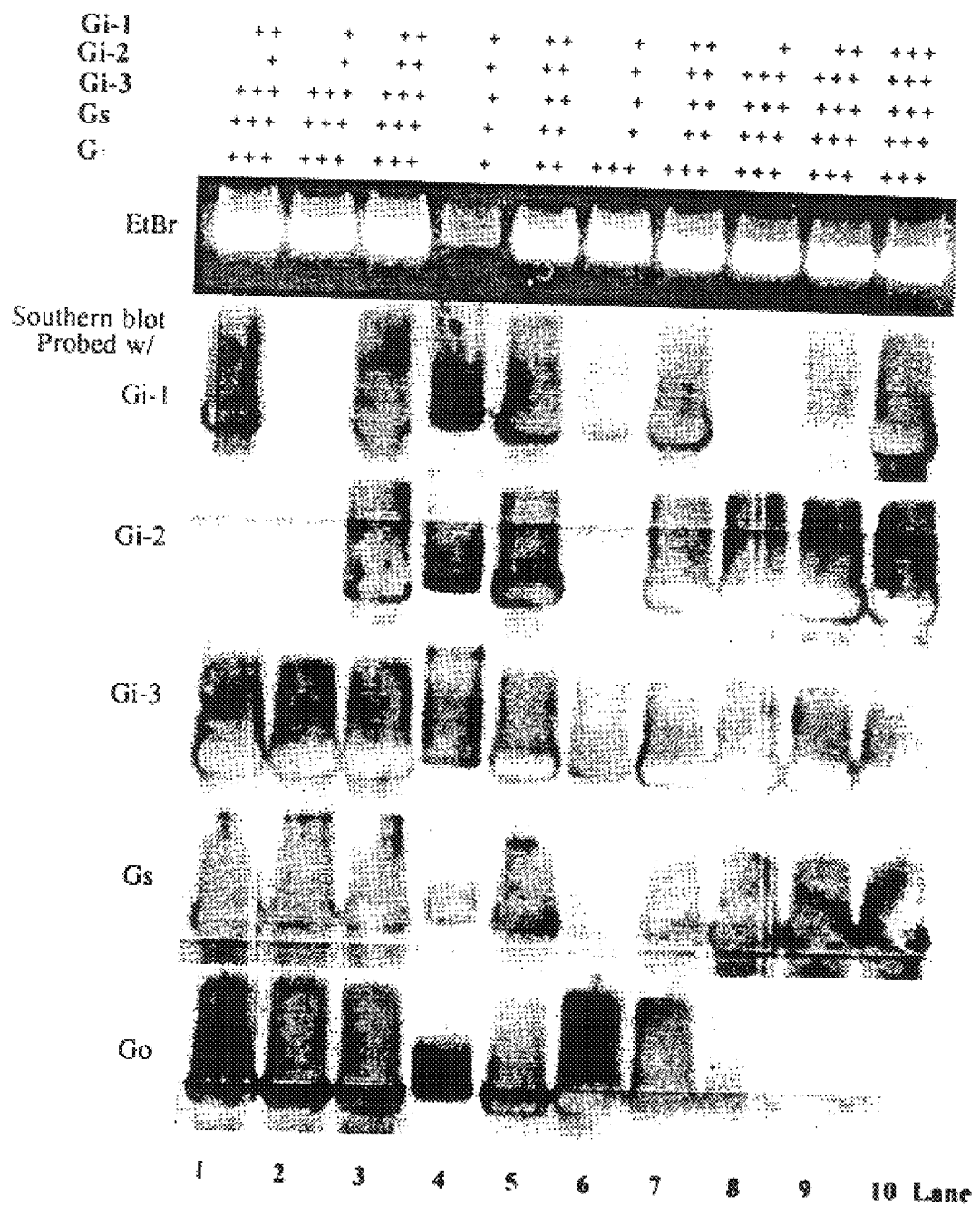
FIG. 12 shows a gel of samples containing varying amounts of each of five different G protein oligonucleotides (as indicated by number of "+" symbols) amplified with the $G_2$ and $G_4$ PCR primers and also provides Southern blots using each of the five G protein sequences as a probe.

We have found that VRC is a particularly potent inhibitor of RNases when used in combination with Proteinase K. Proteinase K is also available from BRL. As shown in the gel in FIG. 10, mRNA prepared from U937 cells (human macrophage cell line) was protected from RNase degradation by a combination of VRC and Proteinase K. Lane 1 of the gel shows the mRNA from a cell preparation which included VRC, Proteinase K, and RNasin, while lane 2 represents the mRNA from a cell preparation that included VRC and Proteinase K. RNasin is available from Promega of Madison, Wis. The distinct band 10 in lanes 1 and 2 matches the band seen in lane 7, which contains pure clonal cDNA from an RNase-free preparation of U937 cells, thus showing that the mRNA in the preparations of lanes 1 and 2 did not experience substantial mRNA degradation.

A comparison of lanes 1 and 2 with lanes 3–6 shows that VRC in combination with Proteinase K inhibits RNase activity in the above-mentioned mRNA preparation from U937 cells to a far greater extent than either Protein K alone (lane 4), Proteinase K in combination with RNasin (lane 3), or a commercial RNase-inhibiting preparation sold under the name "FastTrack" (available from In Vitrogen of San Diego, Calif.) (lane 5). None of lanes 3–5 exhibit the distinct band 10 representing undegraded mRNA. On the contrary, lane 4 (Proteinase K alone) and lane 5 (FastTrack) have the same smear of degraded mRNA as band 20 in lane 6 (no inhibitors). The gel shown in FIG. 10 also shows the effectiveness of VRC in a buffer solution of 1 mM EDTA and 0.5% SDS, which is the buffer used in the U937 cell preparations tested, since lane 2 (VRC and Proteinase K) shows less mRNA degradation than lane 4 (Proteinase K alone) or lane 3 (Proteinase K and RNasin).

First Polynucleotide Probe

In the practice of the present invention, a first polynucleotide probe is bound to an insoluble support. This first polynucleotide is used to trap the target mRNA to a solid support. Thus, the first polynucleotide probe comprises a nucleotide sequences which can hybridize with a sequence of the mRNA that does not occur in other RNA in the sample. Such a sequence is referred to herein as a unique region of the mRNA. Preferably, the first polynucleotide probe does not bind to portions of the target mRNA other than the unique region.

A unique region can be identified by any of several methods. These include: (1) comparing the nucleotide sequence between several potential mRNAs and their target mRNAs; (2) getting a candidate sequence which can be compared with other nucleotide sequences; and (3) computer searching for nucleotide sequences which do not pair with the target mRNA. Information on various known mRNA sequences can be obtained from several genetic information databases.

The first polynucleotide probe is preferably an oligodeoxyribonucleotide (DNA) rather than an oligoribonucleotide (RNA) since DNA is more stable than RNA. The number of nucleotides is not restricted; however, if an oligodeoxyonucleotide is used as the first probe, a preferred length is 17–40 nucleotides. If a cDNA of target RNA is available, a part or the entire cDNA can be used as the first nucleotide probe. The first nucleotide probe can also be easily manufactured by using a DNA synthesizer or by a commercial manufacturer.

In this invention, the first nucleotide probe used is immobilized to an insoluble support. It may be chemically modified for immobilization, such as by adding an amino group onto the 5'-terminal or 3'-terminal of the polynucleotide.

Insoluble Support

In the practice of the present invention, the first nucleotide probe is immobilized to an insoluble support. The insoluble support can be any of a variety of insoluble materials, such as a plastic plate, membrane filter, microtiter plate or any other insoluble material to which polynucleotides can be attached. The insoluble support is preferably made of a material which can immobilize the first nucleotide probe by covalent bonds. For example, a plastic plate, such as polystyrene, which has a carboxyl group or amino group on the surface thereof can be used. Such plates are available commercially. However, procedures for introducing these residues are also well known in the art. One commercially available plastic plate which has carboxyl group, on its surface is Sumilon microtiter plate MS-3796F made by Sumitomo Bakelite. A plastic plate having an amino group on the surface is the Sumilon microtiter plate MS-3696F.

Immobilization of First Polynucleotide

In the practice of the present invention, the first polynucleotide probe is immobilized onto the insoluble support. Various methods of immobilizing polynucleotides to the insoluble support are available, including covalent binding, ionic binding, and the physical absorbance method. However, the covalent binding method is preferred. Thus, in certain embodiments of the present invention, the polynucleotides are immobilized to microtiter plates which exhibit functional groups, such as carboxyl residues, amine residues, or hydroxyl residues on the surface thereof.

In a preferred procedure for immobilization of the polynucleotide to an insoluble support exhibiting a functional group, the 5'-terminal end of the polynucleotide is covalently linked to the functional group. Any of a variety of methods for covalent binding of polynucleotides to these functional groups can be used. Examples of preferred well-known methods include the maleimide method and carbodiimide method.

The maleimide method, illustrated in. FIG. 1, involves the reaction between a substance containing a maleimide group and another material containing a sulfhydryl residue (SH). In order to attach the 5' end of a polynucleotide to an immobilized support using the maleimide method, the 5' end of the polynucleotide is reacted with a maleimide compound. A suitable maleimide compound is sulfosuccinimidyl-4-(N-maleimidomethyl) cyclohexane-1-carboxylate (sulfo-SMCC).

The SH residue is provided on the support by a reaction between a support having an amino group and succinimidyl-S-acetylthioacetate (SATA), followed by deacetylation using hydroxylamine ($NH_2OH$). (Sulfo-SMCC and SATA are readily available from a variety of commercial sources, including the Pierce Company.) The resulting SH group on the support can then react with the maleimide group on the 5' end of the polynucleotide to form a polynucleotide-immobilized support. One problem we have experienced in the use of the maleimide method is that the SH group on the plate can react not only with an amino group at the 5' end of the polynucleotide, but can also react with primary amino groups on the purine bases, adenine and guanine. In order to assure that the polynucleotides are immobilized at their 5' ends, the amino groups on the purine bases can be protected by pairing the polynucleotide to a complementary polynucleotide prior to immobilization. After immobilization, the complementary polynucleotide can be removed through denaturation, such as through heating.

Figure 2:
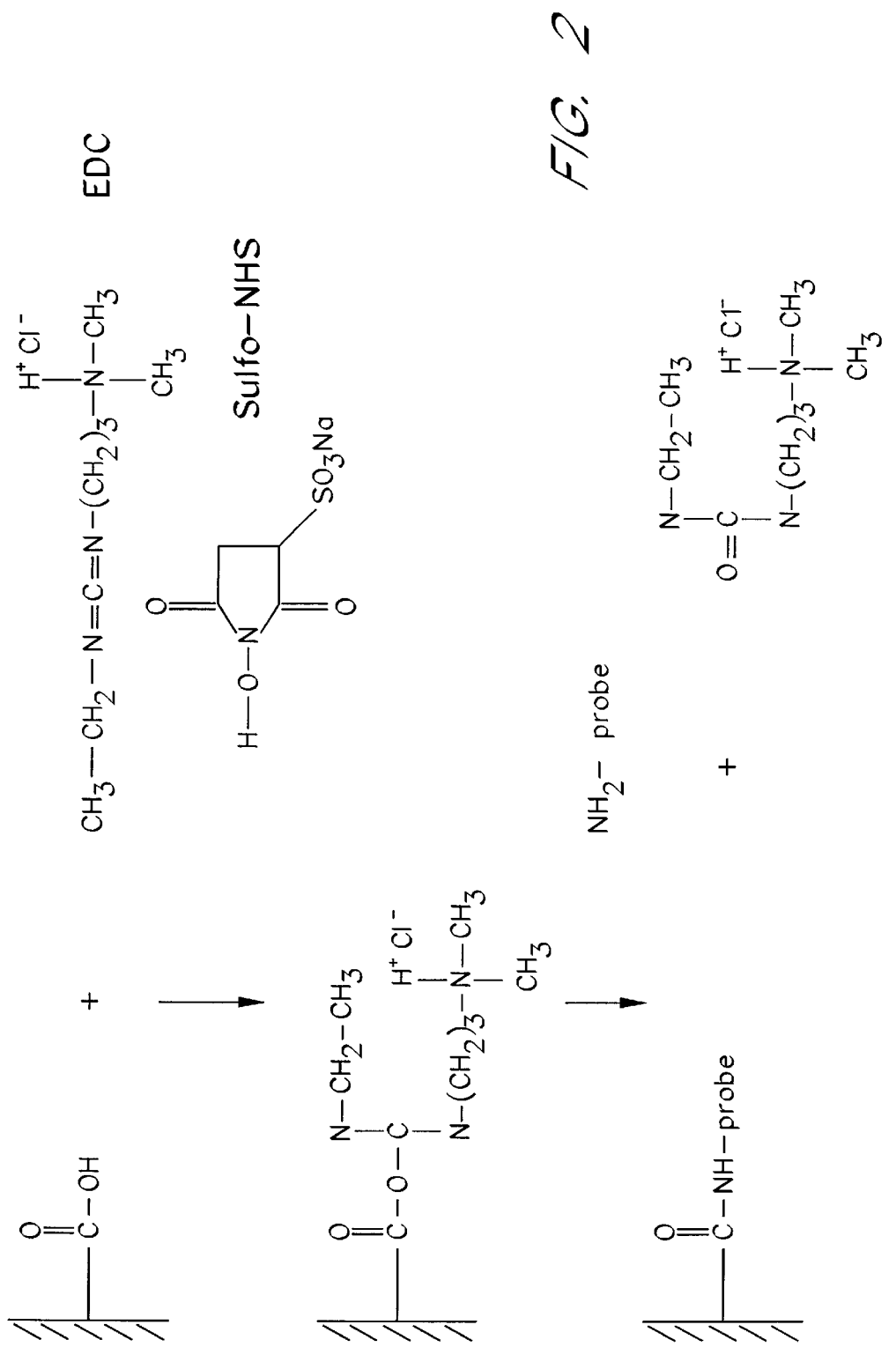
FIG. 2 illustrates an immobilization procedure of a first nucleotide probe onto an insoluble support by the carbodiimide method.

The carbodiimide method is illustrated in FIG. 2. This method involves a reaction between an amino group and a material containing a carboxyl residue using a carbodiimide compound. An example of a carbodiimide compound is 1-ethyl-3-(3-dimethylaminopropyl) carbodiimide hydrochloride (hereafter called EDC). This reaction can be enhanced with N-hydroxysulfosuccinimide (hereafter called Sulfo-NHS). Both EDC and Sulfo-NHS are available from well known commercial sources, including the Pierce Company.

In the practice of a preferred carbodiimide method for attaching polynucleotides to a support, a support having a carboxyl residue attached is used. EDC is activated by reaction with Sulfo-NHS. This activated EDC is reacted with support containing surface-bound carboxyl residues. This can then be reacted with polynucleotides having an amino group at their 5'-terminal ends, resulting in a polynucleotide-immobilized support.

In order to assure that the polynucleotides are immobilized at their 5' end, primary amino groups on adenyl, guanyl and cytosyl groups can be protected by hybridizing the nucleotide to a complementary polynucleotide prior to immobilization. After immobilization, the complementary polynucleotide can be removed through denaturation, such as through heating.

We have found that non-specific binding of activated amino or carboxyl residues on insoluble supports can be effectively reduced or eliminated by treating the plates to which polynucleotides have been immobilized with a primary amine compound, preferably glycine.

Second Polynucleotide Probe

The second nucleotide probe contains sequences which can also hybridize to target mRNA that is trapped by the first bound nucleotide sequence. Preferably, the second polynucleotide probe hybridizes to a different portion of the target mRNA than does the first polynucleotide probe. In an especially preferred embodiment, the second nucleotide probe consists of nucleotides which are complementary to the polyadenylic acid tail of the target mRNA. The second nucleotide probe is also preferably DNA rather than RNA due to the higher stability of DNA. The number of nucleotides is not limited; however, a polynucleotide of 15–40 nucleotides is preferable. Thus a poly (dT) sequence of 15–40 nucleotides is a preferred second polynucleotide probe. Such a second polynucleotide probe would serve as a universal second probe for virtually any target mRNA from eukaryotic cells. However, if a cDNA to the target RNA is available, a part or all of this cDNA can also function as a second polynucleotide probe. The second nucleotide probe can also be easily manufactured by a DNA synthesizer or commercial manufacturer.

The second polynucleotide probe is preferably labeled in order to easily detect its presence. A variety of chemical substances are available which can label the target substance. For example, a variety of radionuclides can be used, such as the radioisotopes $^{32}P$, $^{35}S$, $^{3}H$, and $^{125}I$. Enzymes can also be used to label the second polynucleotide probes. Suitable enzymes include alkaline phosphatase, luciferase, and peroxidase. Other labels might be chemical compounds such as biotin, avidin, streptavidin, and digoxigenin. Labels which provide a colorimetric indication or a radionuclide are preferred. In a preferred embodiment, biotin is attached to the nucleotide probe, followed by an avidin, such as streptavidin, conjugated to an enzyme such as alkaline phosphatase. The presence of the enzyme can be detected by various substrates, such as ATTOPHOS which provides a flourescent marker that can be detected through fluorimetry.

In certain embodiments, part or all of the labeling compound is substituted with part or all of the second nucleotide probe. Techniques for substituting portions of polynucleotides are well known for a variety of labels and kits are commercially available for many of these. For example, one can use a DNA 3'-end Labeling Kit or oligo-deoxythymidylic acid to label the probe.

Nucleic acid can also be "labeled" by staining with a nucleic acid stain. Thus, where a relatively large amount of nucleic acid is present, ethidium bromid (EtBr) can be used to identify the presence of nucleic acid. This is useful within the context of the present invention, for example, if mRNA has hybridized to a short immobilized anti-sense probe then substantially more nucleic acid will be immobilized than if no mRNa had hybridized. However, more sensitive stains are more preferable. Such more sensitive stains include the various cyanine nucleic acid stains, such as POPO, BOBO, YOYO and TOTO available from Moecular Probes (California). These stains are described, e.g., in *Science*, 257:885 (1992). Particularly preferred stains for use in the context of the present invention include the shorter wavelength forms, TOTO-1 and YOYO-1, still more preferably YOYO-1. As little as four picograms of stained DNA can be detected by visible fluorescence upon stimulation with a transilluminator or hand-held UV lamp. Thus, these stains provide a particularly easy and sensitive method of identifying the presence of nucleic acids.

Figure 15:
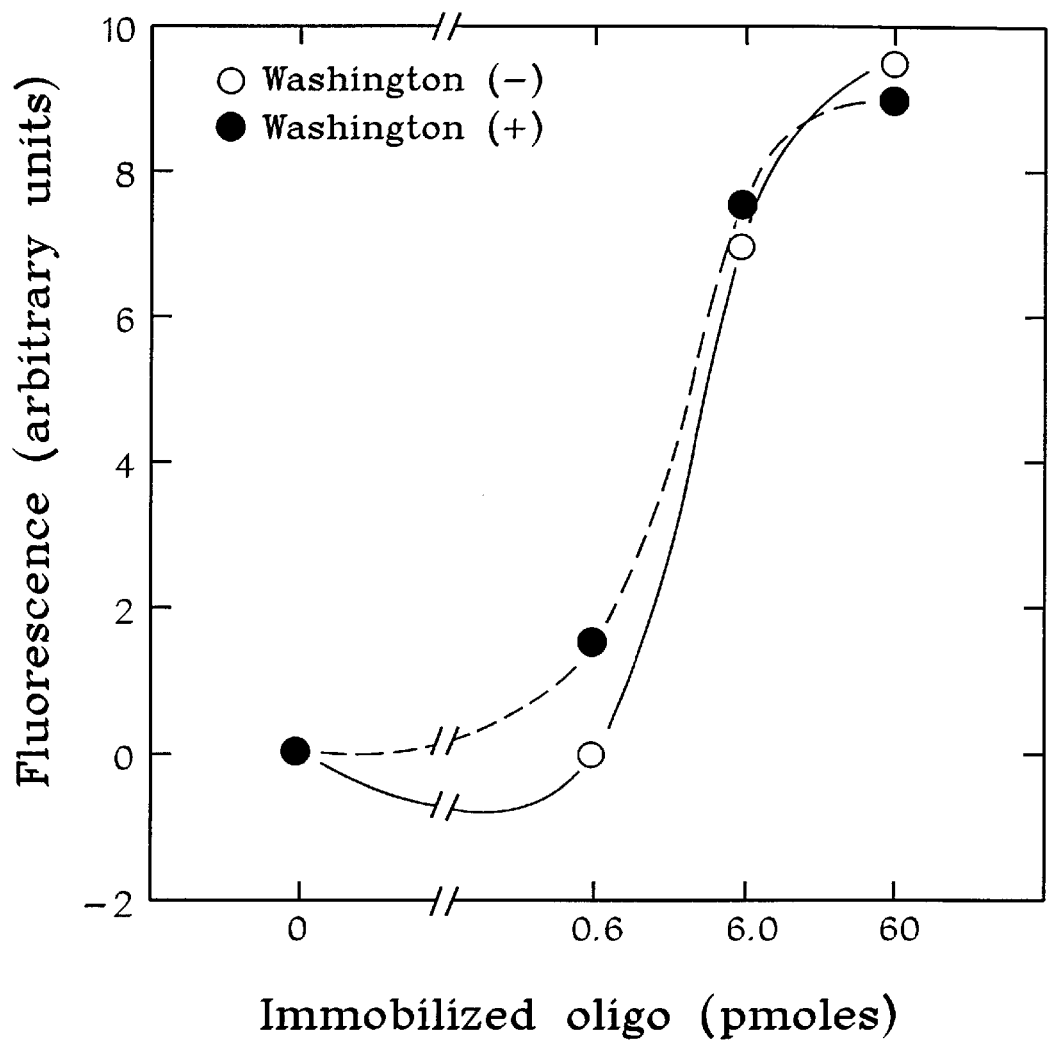
FIG. 15 is a graph showing the relationship between YOYO-1 fluorescense and amount of immobilized oligonucleotide.

We tested the ability of YOYO-1 to stain oligonucleotides immobilized to wells as discussed herein. We first immobilized various known amounts of oligonucleotides to wells and washed to remove non-immobilized oligonucleotides. We then added 1:1000 dilution of YOYO-1 in water. We then used a fluorimeter directly without washing. The relation between pmoles of oligonucleotide is shown in FIG. 15 with open circles. We also incubated the TOTO-1 stained immobilized oligonucleotides for ten minutes, washed and added water, followed by use of the fluorimeter. The washed results are shown in dark circles in FIG. 15. It can be seen that washing does not signicantly effect the amount of staining and that the amount of staining is related to the amount of oligonucleotide.

We also tested the time course of YOYO-1 staining over the course of one hour. We included a control in which no oligonucleotide was immobilized to the plate. The oligonucleotide-immobilized plate is shown iri open circles in FIG. 16 and the control in dark circles in that Figure. It can be seen from FIG. 16 that after an initial spike, relatively constant staining is found.

Figure 17:
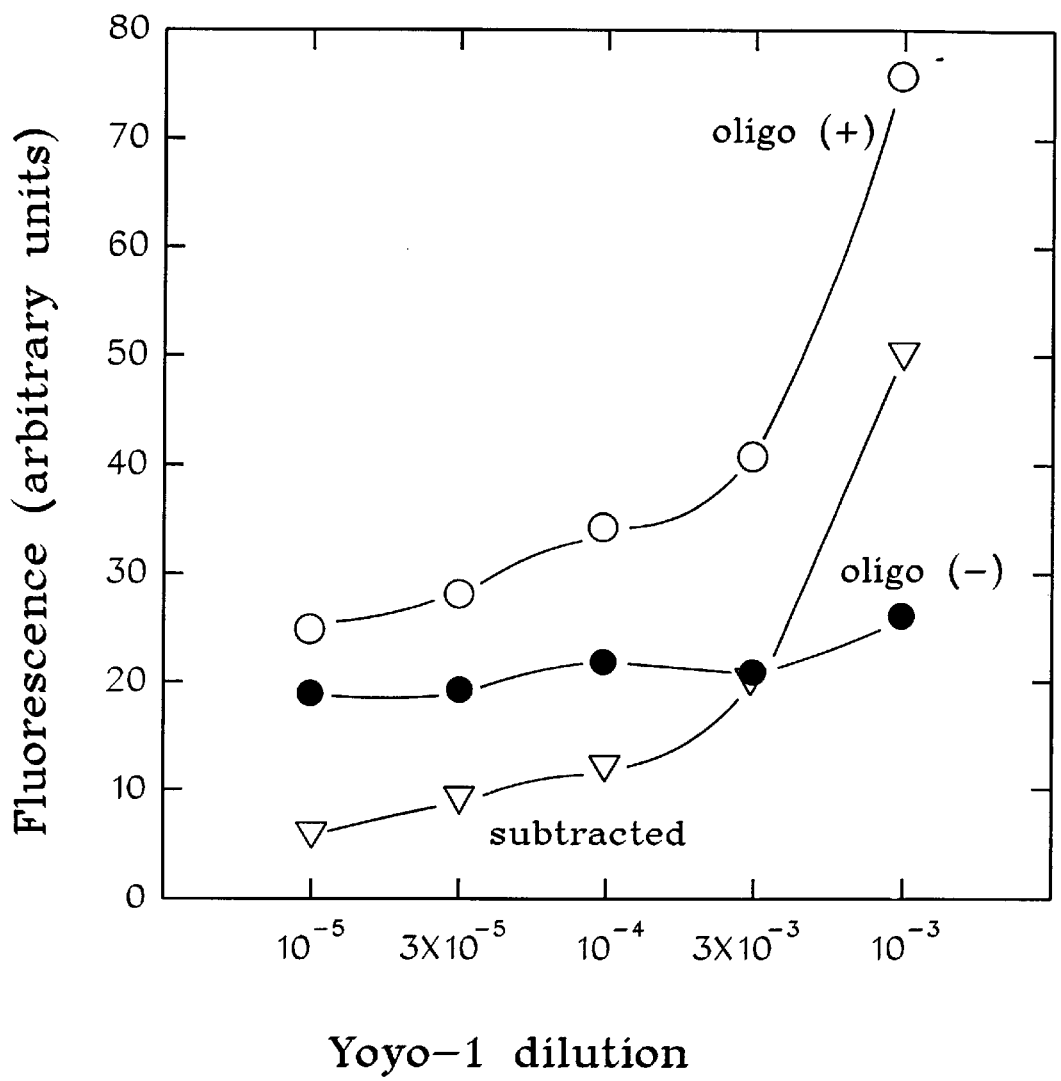
FIG. 17 is a graph showing the dose response of YOYO-1 concentration.

We further tested the dose response of constant amounts of oligonucleotides with oligonucleotides immobilized in wells (open circles in FIG. 17) and control wells with no oligonucleotide (closed circles in FIG. 17). The difference between the immobilized and non-immobilized is shown in FIG. 17 as triangles. It can be seen that a sharp increase in fluorescence occurs between $10^{-4}$ and $10^{-3}$ dilution.

Figure 18:
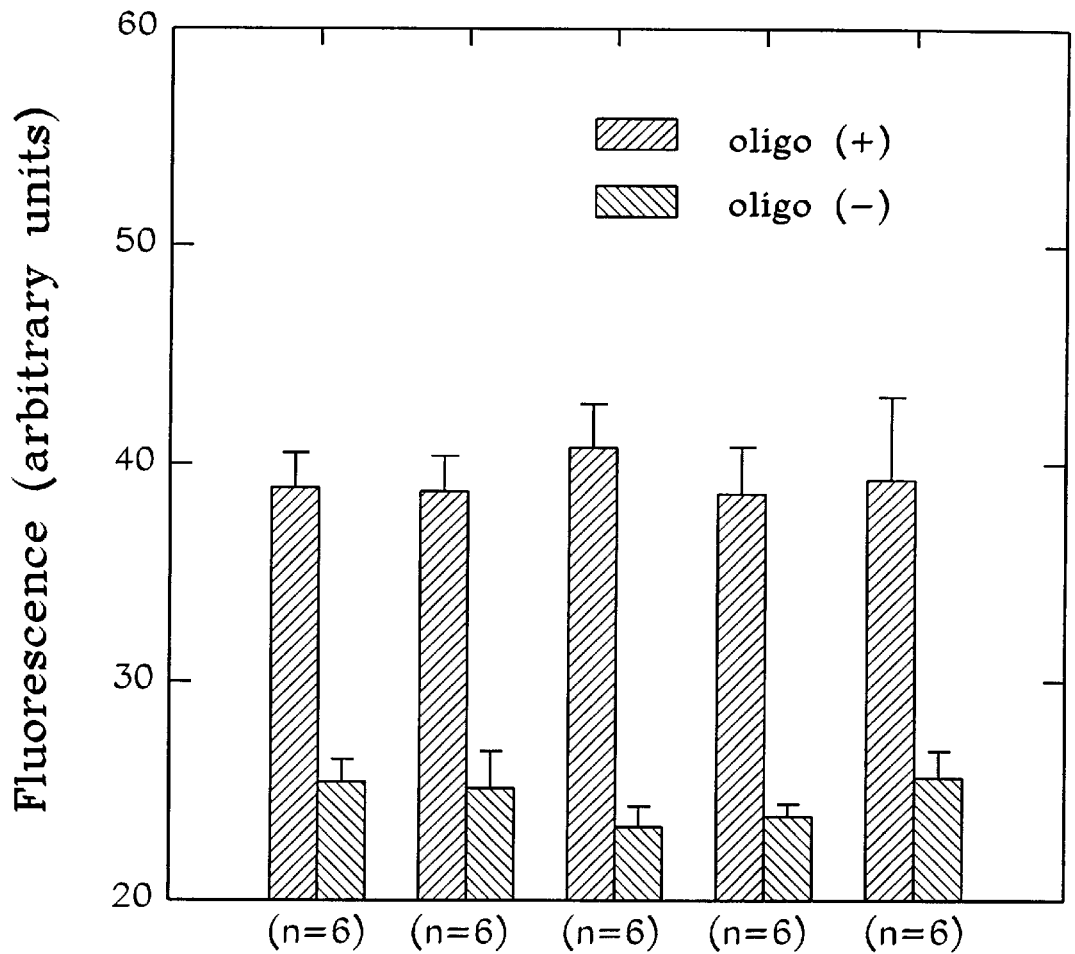
FIG. 18 is a bar graph showing the reproducibility of YOYO-1 staining based on quantitation of immobilized oligonucleotides.
Figure 19:
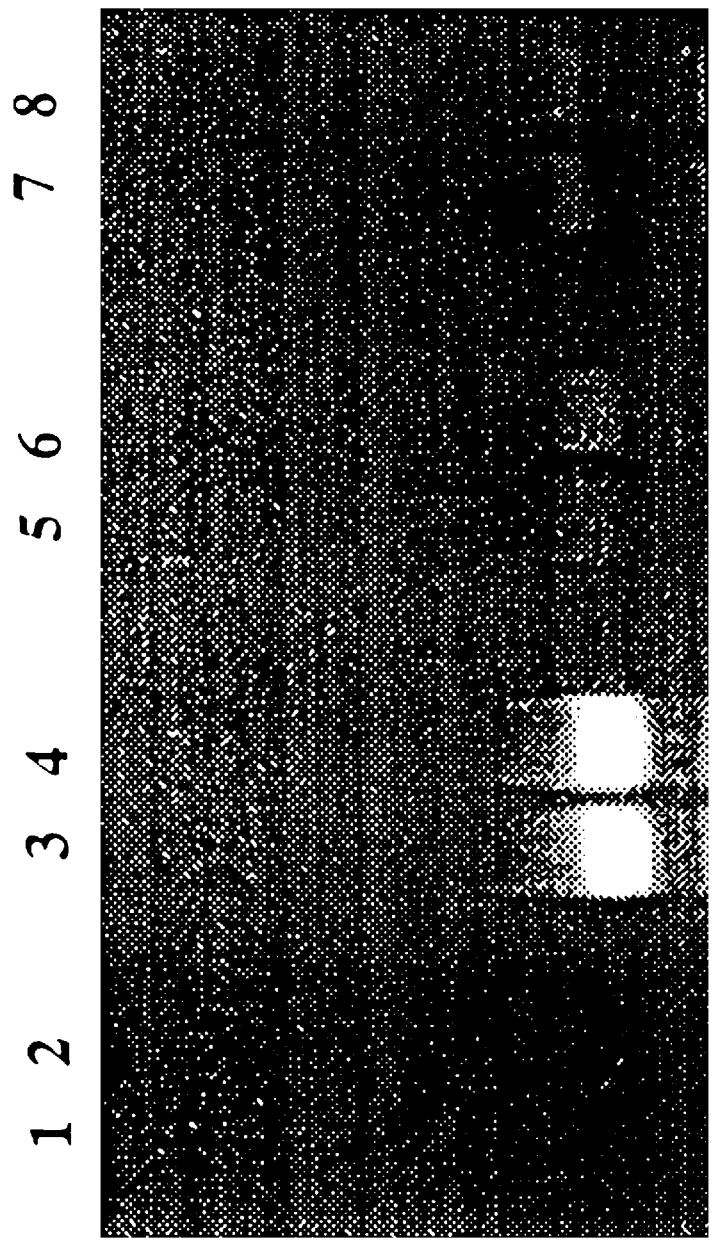
FIG. 19 exhibits a Polaroid picture of agarose gel electrophoresis of the PCR amplified ds-cDNA of jun oncogene from human peripheral blood leukocytes.

We also tested the reproducability of staining of both oligonucleotide-immobilized wells and non-immobilized wells. We repeated the experiment five times and graphically depicted the data for both oligonucleotide immobilized (+) and non-immobilized (−) wells in FIG. 18. It can be seen that the data was substantially similar for each experiment.

Thus, the data depicted in FIGS. 15–18 shows that use of YOYO-1 as a staining agent provides a reliable indication of the amount of oligonucleotide present.

Application or Sample

In the preferred methods of the present invention, a sample containing mRNA is applied to the insoluble support to which the first polynucleotide probe has been bound. Any target mRNA found in the sample is allowed to hybridize with the first polynucleotide probe. This can be accomplished by incubation at temperature dependent on a variety of factors, as is well known to those with ordinary skill in the art. These factors include the length of complementary nucleotide sequences, the ratio of Guanine or Cytosine (GC contents) within the entire base content in the complementary nucleotide sequences, NaCl concentration in buffer, the number of bases which mismatch in the complementary nucleotide sequence, and the type of nucleotide. In a preferred form of this invention, the following equation can be used to calculate the preferred incubation temperature:

$$T_{inc.}=16.6 \times \log (M)+0.41 (GC)+81.5-675/n-15 \text{ (° C.)}.$$

In the equation shown above, M is the NaCl concentration (M) in solution, GC represents GC contents (%), n represents the length of nucleotide sequences (the number of nucleotides).

The incubation time can also be determined according to methods described in the Molecular Cloning manual.

The time for incubation is preferably from 1 hour to overnight, and the sample should preferably be gently swung during incubation. Incubation is preferably performed in an appropriate buffer solution. The same buffer used to hybridize RNA and DNA in the Northern Blot or the Dot Blot Methods can be used. The buffer is preferably prepared in a way so as not to contaminate it with RNase. If any RNase contamination is present, the activation thereof should be controlled to be as low as possible. RNase-free buffers are commercially available, such as within mRNA purification kits or lysis buffer as shown before.

In order to eliminate RNase activity from water used in the methods of this invention, the water is preferably treated with Diethylpyrocarbonate (DEPC). The preferred DEPC treatment involves addition of 0.1% DEPC to the water, followed by storage overnight at 37° C. and sterilization in an autoclave.

Washing Procedures

Preferably, after incubation, unbound components of the sample are washed from the insoluble support. Appropriate solutions for washing include the lysis buffer as shown before or the buffer included in the mRNA purification kit.

Application of Second Polynucleotide Probe

The second polynucleotide probe is applied to the insoluble support after any washing of unbound components of the sample, under conditions as described above in connection with the hybridization of mRNA in the sample with the first nucleotide probe. This is preferably followed by washing, as described above.

Quantitation

The amount of mRNA in the sample is quantitated by measuring the amount of second polynucleotide probe bound to the insoluble support after application thereto in accordance with the present invention. In this regard, a physical or chemical quantity or activity of the label on the second polynucleotide can be measured by several techniques, including optical density, emitted-light intensity, or radiation. The label itself can provide this indication or can require other compounds which bind thereto or catalyze the label. Other mechanisms for detecting label include the use of compounds that can chemically react against the label, detection of colored label, detection of light emission, detection of radiation or of catalytic ability.

In a preferred measurement technique, the label on the second polynucleotide is biotin. The presence of this label can be detected by reaction with the enzymes Peroxidase or Alkaline phosphatase. These enzymes can be specifically directed to biotin by conjugation with avidin or streptavidin. The presence of the enzymes is then detected by addition of an appropriate substrate to provide a detectable color-developing or light-emitting reaction. The alkaline phosphatase labeled streptavidin can be readily obtained from the commercial market. A preferred substrate for alkaline phosphatase is adamantyl-1,2-dioxetane phosphate (AMPPD). Upon reaction with the alkaline phosphatase, AMPPD will emit light at a wavelength of 447 nm. This light can be detected in accordance with techniques known in the art.

In the reaction between alkaline phosphatase and AMPPD, an enhancer such as 5-N-tetradecanoyl-amino-fluorescein can be added. 5-N-tetradecanoyl-amino-fluorescein has the ability to convert light of 477 nm wavelength to 530 nm wavelength which is more readily detectable.

Other preferred labels include an antigen, such as digoxigenin or an antibody. An antigen can be detected by its ability to bind to an antibody directed thereto. Such antibodies, or an antibody directly used to label the second polynucleotide probe, can be detected by their ability to bind protein A. The antibody itself can be labeled directly with a radionuclide, such as $^{125}I$, or can be labeled by binding thereto of protein A labeled with the radionuclide. The radionuclide can then be detected in accordance with techniques well known in the art.

Well-known techniques for the detection of label include the detection of label which appears by a color-developing reaction by a spectrophotometer. Other such techniques include the detection of a light emitting reaction using X-ray film or an instant camera, and the detection of radiation using a radiation counter.

The emission reactions are recorded by X-ray film or instant camera film in the dark room. The X-ray film which is exposed by emission reactions are recorded as a blot, so this shading of the blot can be measured by a densitometer. If one uses an instant camera such as a Polaroid, the picture is read by a scanner to decide the location of the blot on the computer, measuring the shading of the blot using graphic analysis software.

To measure the amount of target mRNA in an unknown sample solution, an arithmetic plot for showing the relationship between a standard solution of target mRNA and relative concentration in a blot can be used. The standard solution for target mRNA need not be purified target mRNA. Thus, the standards can also be a mixture in which the amount of target mRNA is known.

Schematic Example

Figure 3:
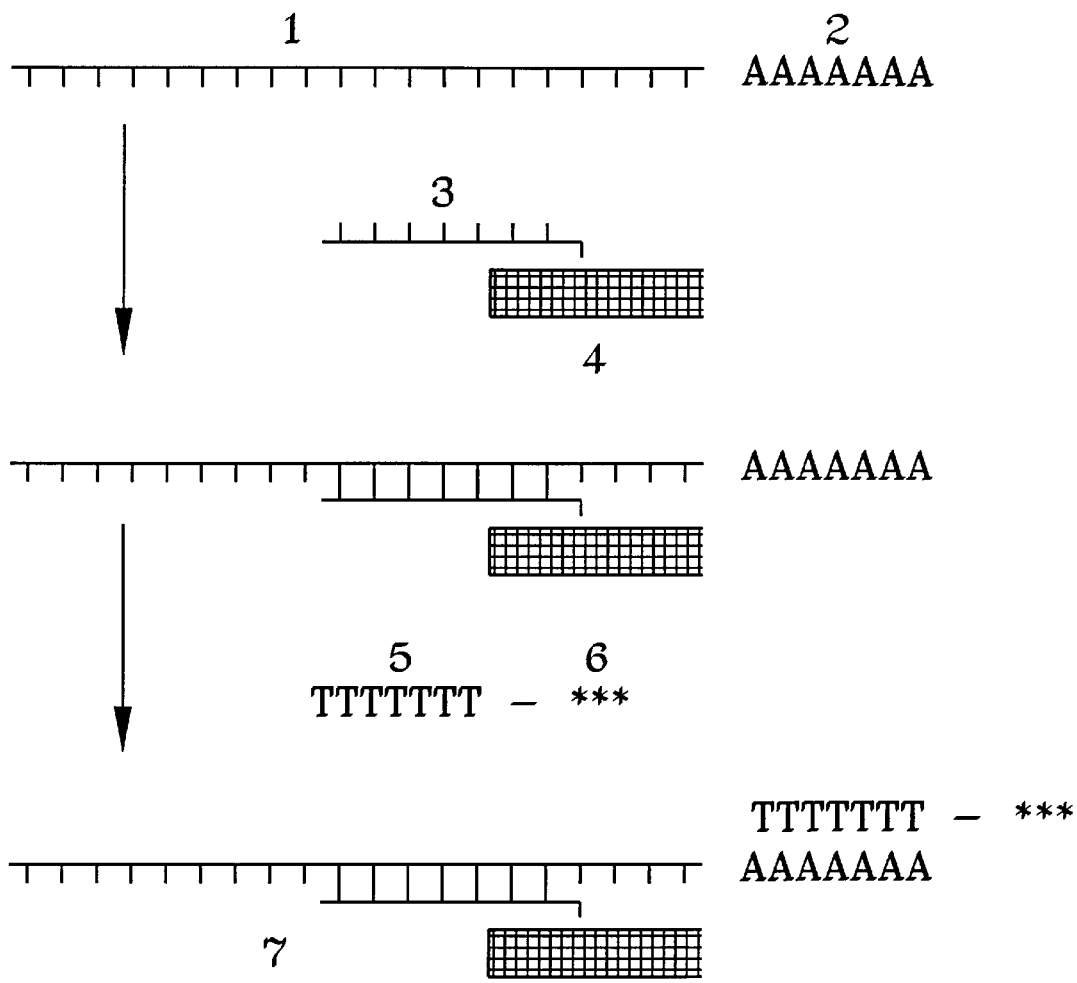
FIG. 3 schematically shows the principle of an mRNA quantification method in accordance with the present invention.

A schematic representation of an exemplary method in accordance with the present invention is shown in FIG. 3. The target mRNA 1 is shown having a polyadenylic acid tail 2. The first nucleotide probe 3 is immobilized to an insoluble support 4, then mixed the target mRNA 1. The target mRNA 1 hybridizes with the first nucleotide probe 3, thereby immobilizing the target mRNA to the insoluble support. Then, a second nucleotide probe 5 which bears a label 6 hybridizes with a portion of the target mRNA other than the portion hybridized with the first nucleotide probe. As shown, the second nucleotide probe 5 comprises poly (dT) and hybridizes with the polyadenylic acid tail 2 of the target mRNA 1. The resulting complex 7 can then be identified by detecting the presence of the label 6.

Time-Savings of Invention

Advantageously, the present invention provides a method of measuring mRNA which can be performed in far less time than previously known methods. Table 1 hereinbelow compares the time needed to measure DNA using the method of this invention and a Northern blot method.

TABLE 1

Comparison For Measurement Of mRNA

| Present Invention | Time (hours) | Northern Blot Method | Time (hours) |
|---|---|---|---|
| Lysis of Cell | 1 | Purification of mRNA | 48 |
| Hybridization of the first nucleotide probe to mRNA | 1 | Separation of mRNA by electrophoresis with Agarose Gel | 1 |
| | | denaturing of mRNA | 1 |
| | | moving the mRNA to membrane | |
| | | immobilization of mRNA to membrane | 2 |
| hybridization of the second nucleotide probe to mRNA | 1 | hybridization of the mRNA and probe | 12 |
| | 1 | | |
| washing and blocking | 0.2 | washing and blocking | 4 |
| detection | 1 | detection | 1 |
| Total | about 5 hours | | about 70 hours |

As shown in Table 1, the methods of this invention generally take 5 hours or less to complete, while the Northern blot method generally requires about 70 hours. These times do not include the labeling time (about 12 hours) of the nucleotide probes nor the time for immobilization of the first nucleolide probe because these constructs can be prepared prior to the measurement.

Particular examples of target mRNi that can be measured to obtain clinically useful information are provided below. The examples included herein are intended to illustrate certain preferred embodiments of the present invention. These examples are not intended to limit the invention in any manner.

β Receptor

A potential target for using mRNA measurement to determine a diseased state utilizes the mRNA for the β receptor. The β receptor is a protein located in human nerve tissue. In particular, abnormalities in the $β_2$ receptor has been found to be closely correlated with asthma. Thus, measuring the mRNA for $β_2$ receptor can be used to determine the pathophysiology of asthma patients, and could also be used to assess the effectiveness of anti-asthma agents.

EXAMPLE 1

Measurement of Human $β_2$ Receptor mRNA (Preparation of Calibration Line)

(1) Preparation of the First Nucleotide Probe

An oligodeoxyribonucleotide probe containing the nucleotide sequence shown below with an amino group attached to its 5' end was synthesized by Genosys, Inc. (TX). In this sequence, A, C, G and T indicate adenine, cytosine, guanine, and thymine, respectively. Based on computer analysis (DNASIS, Hitachi Software Engineering America, Ltd., CA), this sequence was determined to be homologous to the human $β_2$ adrenergic receptor mRNA.

5'-NH$_2$-ATG CTG GCC GTG ACG CAC AGC A-3'
(Seq ID NO: 6)

(2) Immobilization of the First Nucleotide Probe Onto Insoluble Supports

Both EDC and sulfo-NHS (Pierce, IL) were dissolved in DEPC-treated water at concentrations of 20 mM and 10 mM, respectively. EDC/Sulfo-NHS solution was then prepared by mixing equal volumes of both EDC and sulfo-NHS. The first nucleotide probe was dissolved in DEPC-treated water at a concentration of 1 µg/µl and then mixed with the EDC/Sulfo-NHS solution in the ration 1:25 (Vol:Vol).

50 µl of this probe solution was added to each well of a microtiter plate (MS-3796F, Sumitomo Bakelite, JAPAN), which were known to express carboxyl groups on their surface. After incubation at room temperature overnight, the reaction solution was removed by aspiration.

(3) Preparation of mRNA

DNA plasmid pUC18 containing the human $\beta_2$ adrenergic receptor cDNA (pTF, American Type Culture Collection) was digested with PstI and EcoRI, and mixed with the pBC phagemid (Stratagene, CA) which had been predigested with the same restriction enzymes. The resultant plasmid was linearized by PstI, extracted once with phenolchloroform, precipitated in ethanol, and used to transcribe the human $\beta_2$ receptor mRNA using the Riboprobe system and T7 RNA polymerase (Promega, WI). The transcribed human $\beta_2$ receptor mRNA was treated with RNase-free DNase to digest the remaining template cDNA, then purified with one cycle of phenol extraction and ethanol precipitation. The resultant mRNA showed up as a single band on agarose (FMC bioproducts, ME) gel electrophoresis. Messenger RNA concentration was measured by a spectrophotometer at 260 and 280 nm against standard mRNA solutions prepared at concentrations of 25 pg, 250 pg, 2.5 ng, 25 ng and 250 ng, respectively.

(4) Hybridization of the First Nucleotidle Probe to mRNA

In order to remove RNase from the well, the first nucleotide probe-immobilized wells were treated with 250 µl of lysis buffer containing 0.5 M NaCl at 45° C. for one hour. The buffer was removed from individual wells by aspiration, and 50 µl of lysis buffer containing varying concentrations of standard human $\beta_2$ receptor mRNA was added into each well. These solutions were incubated at 59° C. for one hour to allow hybridization.

(5) Preparation of the Second Nucleotide Probe

The second nucleotide probe was a 15-mer oligo(dT) labeled with biotin at the 5' end.

(6) Hybridization of the Labeled Second Nucleotide Probe to the Poly(A) Tail of mRNA After hybridization of the first nuclectide probe and mRNA described in step (4), the hybridization solution was removed by aspiration and the individual wells were washed with 250 µl of lysis buffer. Fifty µl of lysis buffer containing 0.5 M NaCl and 1 µl of the biotinylated second probe solution (35 pmol/µl) was added into each well, and incubated at room temperature for an additional one hour.

(7) Measurement of Chemical Activities of the Labeled Second Nucleotide Probe

Following the hybridization described in step (6), the hybridization solution was removed by aspiration and wells were washed once with 250 µl of lysis buffer. A blocking buffer consisting of (0.05%(w/v) Tween 20, 500 mM NaCl, 100 mM Tris-HCl, pH 7.5) was added into each well and incubated at room temperature for five minutes to reduced nonspecific binding. Reaction solutions were then removed by aspiration, 50 µl of blocking solution containing 1/5000 vol. of alkaline phosphatase-conjugated streptavidin solution (Clontech, CA) was added into each well, and incubated at room temperature for 30 minutes. Each well was then washed with 250 µl of washing buffer containing 500 mM NaCl, 100 mM Tris-HCl, pH 7.5, and 50 µl of Lumiphos 530 solution (Boehringer-Mannheim, IN) whole plates were placed on X-ray film (XAR5, Kodak, NY) in specific holders (MYC, Kodak, NY). X-ray film was exposed to a generated chemiluminescent light at room temperature for one hour, and then developed using a film processor (QX-400, Konica, Japan). Relative intensities of individual wells on X-ray films were quantified by densitometry (model 620, Bio-Rad, CA).

(8) Results

Figure 4:
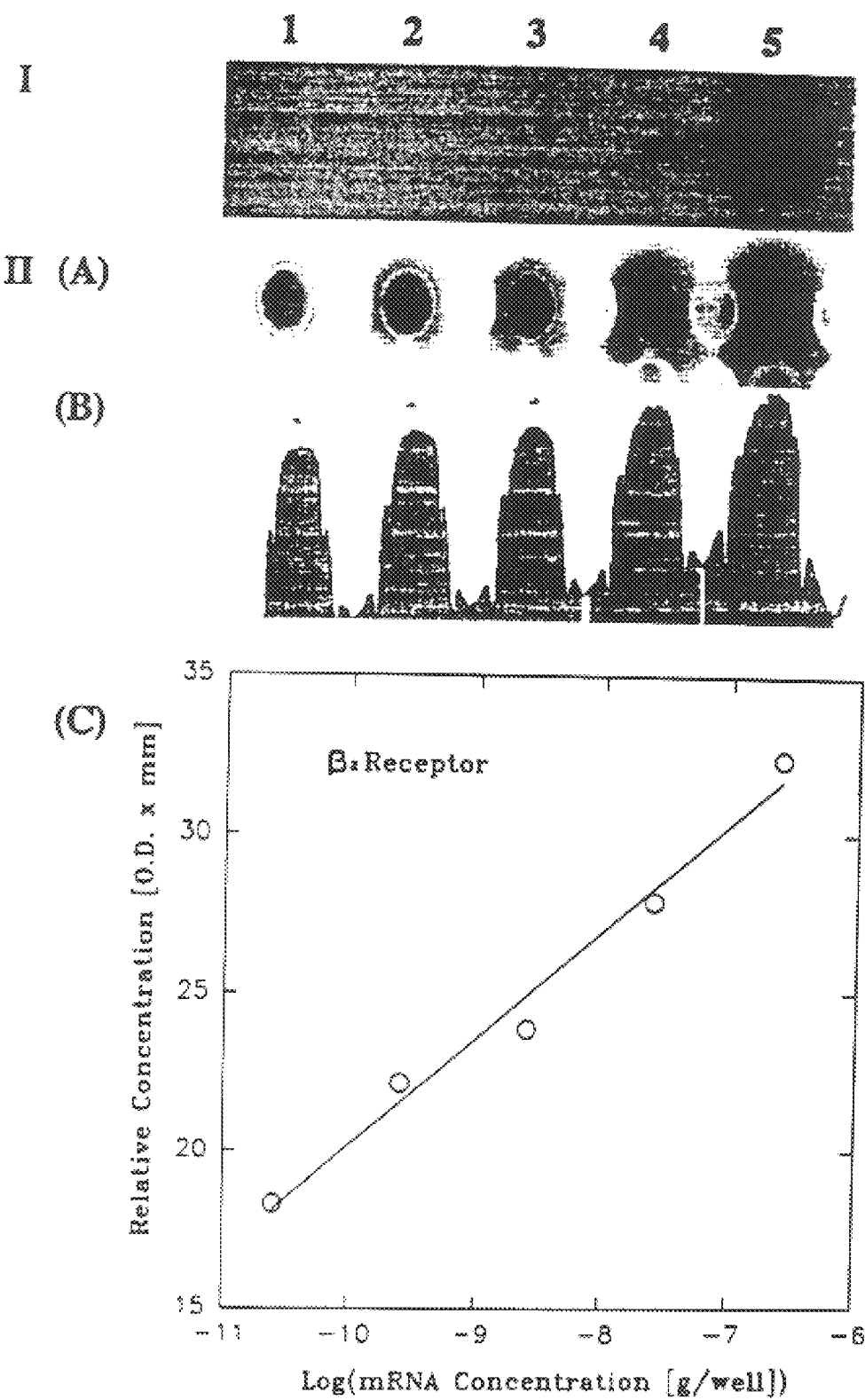
FIG. 4(I) shows a photographic image of an X-ray film exposed to chemiluminescent light derived from the human $\beta_2$ adrenergic receptor cDNA probe on a Northern membrane, in which various concentrations of the human $\beta_2$ adrenergic receptor mRNA were immobilized. (II.A) shows a photographic image of an X-ray film exposed to chemiluminescent light derived from the oligo-(dT) probe in accordance with the present invention in which various concentrations of the human $\beta_2$ adrenergic receptor mRNA were trapped onto the first oligonucleotide-immobilized plastic plate. (II.B) shows a densitogram of the image shown in (II.A.). (II.C) graphically depicts the relationship between relative intensity of chemiluminescent signals and concentrations of mRNA of the image shown in (II.A).

The results of Example 1 are shown in FIG. 4. The inset (A) shows results of an X-ray film exposed to chemiluminescent light during the detection of mRNAs by the invented method; (B) shows a densitographic representation of the same image as in (A): (C) exemplifies a calibration line of the mRNA in which the X-axis represents concentrations of mRNA and the Y-axis represents the relative intensity of chemiluminescence in an individual well. Wells 1, 2, 3, 4 and 5 of FIG. 4 correspond to the amounts of tested mRNA at 25 pg, 250 pg, 2.5 ng, 25 ng and 250 ng, respectively. As shown in (A), mRNAs were detected in amounts over 25 pg by the invented method. The calibration line shown in (C) shows the high linearity of signal when increasing concentrations from 25 pg to 250 ng of mRNA.

COMPARISON 1

Quantification of mRNA by Northern Blot (1) Agarose Gel Electrophoresis of mRNA

Ten mM of sodium phosphate buffer, pH 7.0 containing 0.1% DEPC was heated to 37° C. overnight and autoclaved. A 1% agarose solution was prepared using this 10 mM DEPC-treated phosphate buffer. The solution was chilled to ca. 50° C., and iodine acetate was added to 0.2% (W/V). A gel slab was formed (6.5 cm×10 cm) with combs and placed at room temperature for one hour to allow hardening. Five µl of DEPC-treated water containing 250 ng, 25 ng, 2.5 ng, 250 pg or 25 pg of mRNA described in example 1.(3), were mixed with 7 µl of loading buffer (125 µl DMSO, 42 µl 40% glyoxal, 3 µl 1 M sodium phosphate buffer, pH 7.0), and incubated at 50° C. for one hour. Samples were applied to the gel, and electrophoresed in a solution of DEPC-treated 10 mM phosphate buffer at constant 6V/cm for 15 minutes without circulation. An additional one hour of electrophoresis was performed with circulation.

Following electrophoresis, gels were immersed in 50 mM sodium hydroxide containing 0.5 µg/ml ethidium bromide (Sigma, MO.) for 20 minutes, and 0.1 M Tris-HCl buffer, pH 7.5 for 40 minutes. Gels were then transferred into fresh 0.1 M Tris-HCl buffer and photographed under UV light.

(2) Northern Transfer of mRNA Onto Membranes

Filter paper (3 MM Chr, Whatman, N.J.) and a nylon membrane (Magnagraph, Micron Separations, MA) were immersed in sterile water for 20 minutes and then placed in 10×SSPE (1.5 M NaCl, 115 mM sodium phosphate, 11.5 mM EDTA in water, pH 7.4 adjusted with 10 N NaOH). A blotting sponge (Stratagen, CA) was also immersed in 10×SSPE. The 3 MM filter, nylon membrane, agarose gel, and sponge were assembled from the bottom in a Posi-blot Pressure blotter (Staratagen, CA), to cause the mRNA to transferred onto the nylon membrane by positive pressure (835 mmHg for 45 minutes). The nylon membrane was dried, and the mRNA was permanently immobilized onto the nylon membrane by UV light cross linkage at 120 mjoules (Stratalinker 1800, Stratagen, CA).

(3) Preparation of Biotinylated cDNA Probe

DNA probes were prepared from $\beta_2$ receptor cDNA by using a DNA labeling kit resultant plasmid and cDNA were separated by agarose gel electrophoresis. A band of $\beta_2$ receptor cDNA was cut out and removed from the gel using the Gene clean kit (Bio 101, CA). 0.1 µg of above cDNA dissolyed in 5 µl of water was incubated at 95° C. for 10 minutes, and then incubated with 2 µl of hexanucleotide mixture, 2 µl of dNTP and 1 µl of Klenow enzyme (DNA labeling kit, Boehringer-Mannheim, IN) at 37° C. for one hour. Following incubation, the reaction was terminated by addition of 2 µl of 0.2 M EDTA, pH 8.0, 2.5 µl of 4.0 M LiCl and 75 µl of 100% ethanol, and cooled at –70° C. for 30 minutes to precipitate cDNA. After centrifugation, the pellet was washed once with 70% ethanol and then dissolved in 50 µl of water.

(4) Hybridization of Biotinylated cDNA Probe to mRNA

The mRNA containing membranes were incubated in hybridization buffer containing 0.5 M NaCl (ECL, Amersham, IL.) at 45° C. for one hour. Biotinylated cDNA probe described above were first heat denatured at 95° C. for 10 minutes, immediately cooled on ice, and then added to the hybridization buffer. Hybridization was continued at 40° C. overnight.

(5) Chemical Activity Measurements of Labeled cDNA Probe

After hybridization, membranes were washed twice in 0.5×SSPE solution containing 36% (W/V) urea, 0.4% (W/V) SDS and 0.5 M NaCl at 65° C. for 15 minutes each, followed by washing twice in 2×SSPE with 0.5 M NaCl at room temperature for five minutes each. Membranes were then incubated with 100 mM Tris-HCl buffer, pH 7.0, containing 2% blocking reagent (Boehringer-Mannheim, IN) and 150 mM NaCl at room temperature for three hours. 1/5000 vol. of alkaline phosphatase-conjugated streptavidin (Clontech, CA) was added to the above solution and incubated at room temperature 30 minutes. Membranes were washed twice with 100 mM Tris-HCl pH 7.0, containing 150 mM NaCl at room temperature for 30 minutes each followed by one washing with alkaline phosphate buffer (100 mM NaCl, 5 mM $MgCl_2$ in Tris-HCl buffer, pH 9.5) at room temperature for 2 minutes. Membranes were then soaked in Lumi-Phos 530 (Boehringer-Mannheim, IN), and quickly placed between two sheets of transparent plastic film. Chemiluminescent membrane signals were exposed to X-ray film (XAR5, Kodak, NY) in specific holders (MYC, Kodak, NY) at room temperature for one hour.

(6) Results

The Northern blot results of Comparison 1 are shown in FIG. 4(I), in which the chemiluminescent signals of mRNA were exposed to an X-ray film. Lanes 1, 2, 3, 4, and 5 of FIG. 4(I) correspond to 25 pg, 250 pg, 2.5 ng, 25 ng and 250 ng of applied mRNA, respectively. Because this cDNA probe is approximately 100 fold larger than the oligonucleotide probe used in Example 1, the amount of incorporated biotin is also 100 fold more than the oligonucleotide. This result indicates that the cDNA probes used in Comparison 1 are approximately 100 fold more sensitive than the oligonucleotide probe. However, as seen in FIG. 4(I), a conventional Northern blot can only detect samples containing greater than 25 ng of mRNA. This is far less sensitive than the invented method as exemplified by FIG. 4(I). Also, the invention as described by FIG. 8(I) used less sensitive oligonucleotide probes when compared to the cDNA probes used on the Northern Blot.

EXAMPLE 2

Detection of Human $\beta_2$ Receptor mRNA from Unknown Samples and Evaluation of Reproducibility (1) Preparation of the First Nucleotide Probe and its Immobilization onto the Insoluble Support The first nucleotide probe was prepared and immobilized onto an insoluble support as described in Example 1.

(2) Preparation of Standard mRNA mRNA was prepared as described in Example 1.

(3) Preparation of Cell Lysates

Human HL60 promyelocytic leukemia cells were collected by centrifugation, washed with PBS (8 g NaCl, 0.2 g KCl, 1.44 g $Na_2HP_4$ and 0.24 g $KH_2PO_4$ in 1 liter of water, pH 7.4). Cells were then resuspended in lysis buffer at a concentration of $1 \times 10^7$ cells/ml. The solution was repeatedly passed through a sterile plastic syringe fitted with a 21 gauge needle and incubated in a slow-shaking waterbath at 45° C. for one hour.

(4) Hybridization and Chemiluminescerit Detection

As described in Example 1, hybridization of the first nucleotide probe, preparation of the second nucleotide probe, hybridization of the labeled second nucleotide probe to the poly(A) tail of mRNA, and chemical activity measurement of the labeled second nucleotide probe was carried out.

(5) Preparation of Calibration Line

Figure 5:
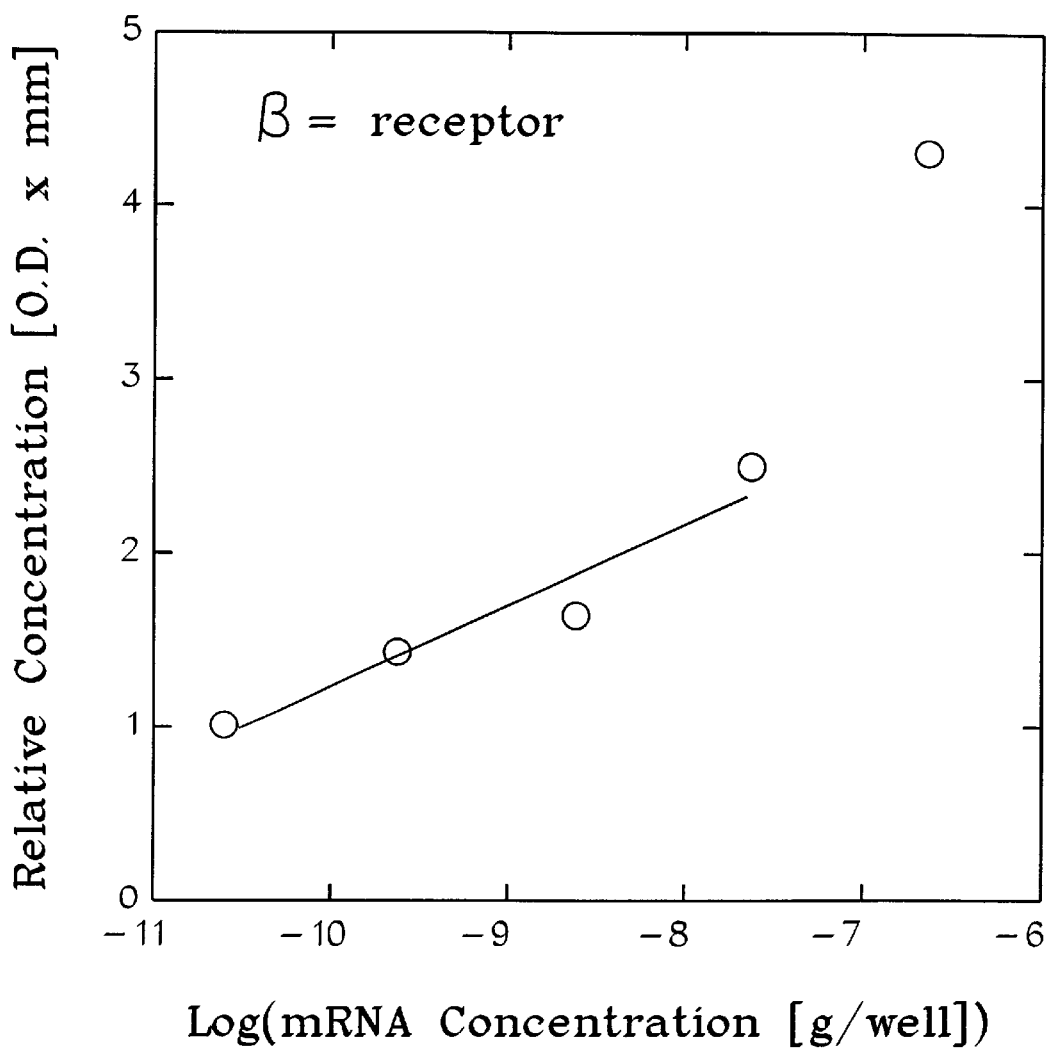
FIG. 5 graphically depicts the linear relationship between relative intensity of chemiluminescent signals and concentrations of mRNA in a separate experiment from that shown in FIG. 4.II.

As described in Example 1, a calibration line of known $\beta_2$ receptor mRNA concentrations was created (FIG. 5). The calibration line expresses a linear co-relationship between mRNA concentrations mapped to a logarithmic scale and the relative chemiluminescent intensity read from X-ray film.

(6) Evaluation of Reproducibility

Concentrations of $\beta_2$ receptor specific mRNA from HL60 cell lysates were determined three times. In Table 2, each concentration of $\beta_2$ receptor specific mRNA was determined from the calibration line described in section (5) above. The mean and standard error (S.E.) of data were calculated. Cell numbers were counted by a phase hemacytometer (American Scientific Products, IL). As shown in Table 2, three separate assays exhibited similar mRNA values at a range of 0.96 to 1.12 fg/cell. This suggests that the invented method provides reproducible method of quantifying specific mRNA levels.

TABLE 2

Concentrations of $\beta_2$ Receptor-Specific mRNA in HL60 Cells

| No. of assay | mRNA Concentration [fg/cell] |
| --- | --- |
| 1 | 1.01 |
| 2 | 0.96 |
| 3 | 1.12 |
| mean ± S.E. | 1.03 ± 0.04 |

G Proteins

Cell surface receptors for hormones and neurotransmitters are known to be coupled to intracellular heterotrimeric GTP-binding proteins (G proteins) composed of α, β and τ subunits. Once receptors are activated by specific ligands, receptor-coupled G proteins transduce signals to intracellular secondary effector systems, such as adenylyl cyclase, phospholipase C, and ion channels.

Recently, the molecular mechanisms of the interaction between receptors and G proteins have become less clear, because extensive molecular cloning has identified more subclasses of G protein α subunits than there are known cellular functions of G proteins. Furthermore, it has been found that a single receptor is also capable of coupling to multiple G proteins. For example, histamine $H_2$ receptors in human HL-60 cells were coupled to two different G proteins, which activated adenylyl cyclase and phospholipase C, respectively. It has also been reported that GABA-B receptors were capable of coupling to $G_o$, $G_o^*$ and $G_{i-1}$ proteins, but riot $G_{i-3}$ proteins. Moreover, CHO cells have been shown to express multiple G proteins, which activate the same phospholipase C pathways but are coupled selectively to different receptors. Some receptors may alter their G-protein subclass association depending on the state of differentiation of the cell or on the particular phase of the cell cycle. One example would be the mRNA coding for G protein. G protein binds to and controls the function of various receptors in the cell membrane. It catalyzes the intracellular reactions of cAMP and calcium ion free reaction systems. These molecules are used in various cellular transmitter systems.

G proteins are believed to be involved in causing various disease states. For example, a genetic deficiency of $G_s$ proteins is the molecular basis of hereditary osteodystrophy. Pituitary tumors in acromegalic patients have been shown to contain mutant Gs proteins. G proteins are also involved in invasive and metastatic melanoma cells. Rat models of streptozotocin-induced experimental diabetes suggest that the levels of mRNA for various subclasses of $G\alpha$ proteins are significantly altered from normal control rats. Furthermore, cellular functions of pertussis toxin-sensitive G proteins were shown to be significantly impaired in atherosclerotic porcine coronary arteries, while G protein function in leukocytes of patients with mania was hyperfunctional. Thus, those diseases which are known to be related to a malfunction of the G protein include atherosclerosis, bipolar disorder, diabetes mellitus, melanoma, and pituitary tumors.

Currently available immunological detection methods (Western blots) and mRNA detection methods (Northern blots) are not sensitive and require a lot of cellular material, making it difficult to study the role of G proteins in disease. It is not easy to ascertain the quantity of expressed G protein. If the mRNA for the G protein was measured, it could be used to recognize the pathophysiology of patients having one of the foregoing ailments. The effects of agents designed to arrest or control these conditions could also be measured using this technique. G protein consists of $\alpha$, $\beta$ and $\gamma$ subunits. The $\alpha$ subunit is known to have several allelic variations. Thus, by measuring each variation of G protein mRNA, the amount of expressed protein for each variation can be estimated.

EXAMPLE 3

Quantification of Human G Protein α Subunit-Specific mRNA (1) First Nucleotide Probe Preparation The first nucleotide probes used against Gs protein-specific mRNA and Gi-2 protein-specific mRNA were oligodeoxyribonucleotides. These nucleotide sequences, shown below, contain an amino group on their 5' end and were synthesized by Genosys (Texas).

The probe sequence used for quantifying Gs mRNA is shown below (Seq ID No. 1):

5'-NH$_2$-TTC ATC CTC CCA CAG AGC CTT G-3'

The sequence of probe used for quantifying Gi-2 mRNA is shown below (Seq ID No. 2):

5'-NH$_2$-ATG GTC AGC CCA GAG CCT CCG G-3'

(2) Immobilization of the Second Nucleotide Probe Onto Insoluble Supports

The first nucleotide probes were dissolved in DEPC-treated water at 1 μg/μl. Probes were then mixed with the EDC/Sulfo-NHS solution described in Example 1 Paragraph (2) in a ratio of 1:25 (Vol:Vol). A 50 μl sample was added to each well of a Sumilon microtiter plate (MS-3796F, Sumitomo BAkelite, JAPAN) and incubated overnight at room temperature. Following incubation, the reaction solution was removed with an aspirator.

(3) Preparation of Standard mRNA

A plasmid vector pGEM2 containing rat Gs protein cDNA (provided by Dr. R. R. Reed, Johns Hopkins University, U.S.A.) was linearized by digestion with NheI (Promega, WI). Gs protein-specific mRNA was prepared by the method described in Example 1 Paragraph (3) using T7 RNA polymerase (Promega, WI). The resultant mRNA concentrations were determined by spectrophotometry and subsequently diluted with DEPC-treated water as described in Example 1 Paragraph (3).

(4) Preparation of Cell Lysates

Human B lymphocyte-derived IM9 cells were centrifuged, washed with PBS, and resuspended in lysis buffer at $1 \times 10^7$ cells/ml as described in Example 2. Cells were then lysed by repeated passage through a sterile plastic syringe fitted with a 21 gauge needle, and then incubated in a slow-shaking waterbath at 45° C. for one hour.

(5) Hybridization of the First Nucleotide Probe to mRNA

In order to remove RNase contamination in the microtiter well, 250 μl of lysis buffer was added to each well at 45° C. for one hour as described in Example 1. The buffer was aspirated, and 50 μl of lysis buffer containing 0.5 M NaCl and various concentrations of human Gs protein mRNA was added into each well. Each sample was incubated at 51° C. for one hour to allow hybridization as described in Example 1.

(6) Hybridization of the Labeled Second Nucleotide Probe to a Poly(A) Tail of mRNA, and Measurement of Chemical Activities of the Labeled Second Nucleotide Probe After hybridization of the first nucleotide probe, the hybridization solution was aspirated off and individual wells were washed once with 250 μl of lysis buffer. Fifty μl of lysis buffer containing 0.5 M NaCl and 1 μl of the biotinylated second nucleotide probe solution (35 pmol/μl) was added into each well, and incubated at room temperature for one hour to allow hybridization.

Chemical activities of the labeled second nucleotide probe was measured as described in Example 1.

(7) Preparation of Calibration Line

Figure 6:
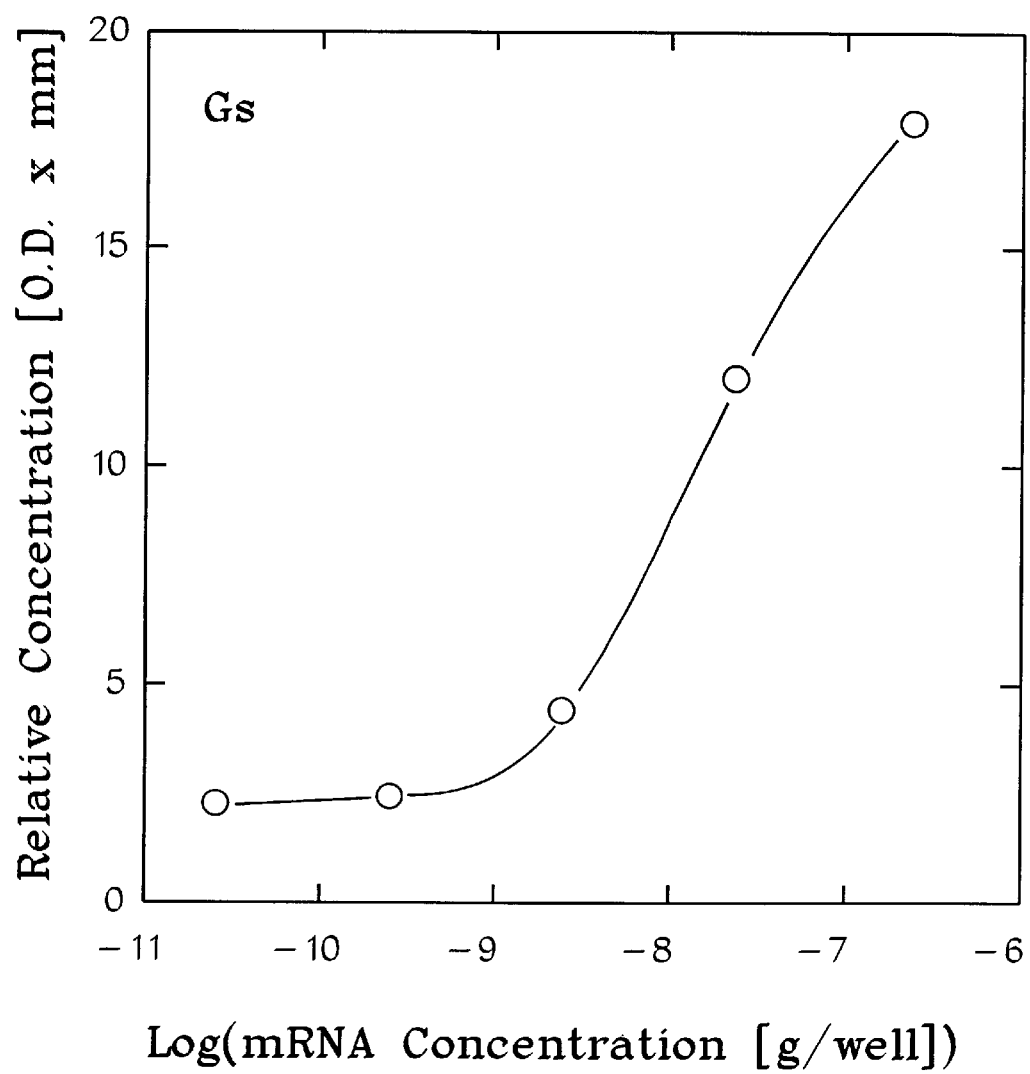
FIG. 6 graphically depicts a calibration line for the rat Gs protein mRNA of the invented method.

The calibration line of standard Gs protein-specific mRNA is shown in FIG. 6. The calibration line expresses a relationship between the common logarithm of mRNA concentrations and the relative intensity of ch emiluminescent signals exposed to X-ray film.

(8) Evaluation of Reproducibility

Concentrations of Gs protein and Gi-2 protein specific mRNAs from IM9 cell lysates were measured six times to test reproducibility of the present invention. The methods used for Gi-2 were similar to that described above for Gs, with the incubation temperature used for hybridization of Gi-2 mRNA being 59° C. Table 3 lists the mRNA concentrations as obtained from the calibration line, and, the mean, and the standard error. Cell numbers from each sample were counted with a phase hemacytometer (American Scientific Products, IL). As listed in Table 3, all six assays reported similar mRNA concentrations for both Gs and Gi-2 mRNA. This suggests that the current invention provides a reliable, reproducible means of measuring specific mRNA concentrations.

TABLE 3

| No. of Assay | mRNA Concentration [fg/cell] | |
| --- | --- | --- |
| | Gs | Gi-2 |
| 1 | 24.8 | 4.6 |
| 2 | 10.6 | 8.8 |
| 3 | 18.8 | 7.2 |
| 4 | 35.5 | 6.8 |
| 5 | 13.6 | 11.5 |
| 6 | 33.0 | 13.7 |
| mean ± S.E. | 22.7 ± 3.8 | 8.77 ± 1.24 |

EXAMPLE 4

Simultaneous Quantification of Various mRNAs Derived from Cell Lines by the Invented Method in Conjunction with Reverse PCR Method (1) Simultaneous Detection of Gs and Gi-2 Protein-Specific mRNAs in Various Cell Lysates by the Invented Method Using the method described in Example 3, specific mRNAs for both Gs and Gi-2 protein from various cell lysates, such as Juirkat human T-cells, IM9 human B cell, U937 human monocytes and HL60 human granulocytic cells were analyzed. Chemical activities of the labeled second probe were exposed to Polaroid film (667, Polaroid, MA) in a specific holder (model 901, Tropix, CA) at room temperature for 5 seconds, instead of exposing to X-ray films as described in Example 3.

(2) Simultaneous Detection of Gs and Gi-2 Protein-Specific mRNAs by the Conventional Reverse PCR Method (a) cDNA Preparation and Amplification by PCR mRNA was purified using the FastTrack kit (Invitrogen, CA) directly from various cell lysates as described in Example 3 Paragraph (4). Samples were dissolved in 10 μl DEPC-treated water, and cDNA was synthesized using the Superscript kit (Gibco/BRL Life Technologies, MD). Resultant cDNA was extracted once with phenol, precipitated in ethanol, and dissolved in 10 μl of DEPC-treated water.

One μl of solution containing cDNA was mixed with 1 μl each of 10 mM dATP, dCTP, dGTP and dTTP (Pharmacia LKB Biotechnology, NJ), 1 μl of 25 mM $MgCl_2$, 1 μl each of G protein-specific PCR primers, 0.5 μl of Taq polymarese (Promega, WI), and 5 μl of PCR buffer (Promega) to a final volume of 50 μl. Sense and antisense G protein-specific PCR primers are exibited below AGCACCATTGTGAAGCAGATGA (sense) (Seq ID No. 3)

CTCTGGCCTCCCACATCAAACA (5' to 3' antisense) (Seq ID No. 4)

These sequences are known to be highly conserved among various G proteins, with this pair of primers being known to amplify Gs, Gi-1, Gi-2, Gi-3 and Go protein specific cDNA from data gathered in preliminary experiments. Followed by pre-denaturation at 95° C. for 10 minutes, PCR was carried out in a DNA thermal cycler (Perkin-Elmer Cetus, CT) with 30 cycles of annealing at 55° C. for 1.5 minutes, extension at 72° C. for 4 minutes, and denaturation at 95° C. for 1.5 minutes, respectively.

(b) Agarose gel Electrophoresis of Amplified cDNA

A 1.2% agarose gel containing 0.00005% ethidium bromide, 0.001 M EDTA and Tris-acetate, pH 8.0 was prepared. Ten μl of each test solution was mixed with 2 μl of gel-loading buffer (0.25% bromophenol blue, 0.25% xylene cyanol and 15% Ficoll (Type 400, Pharmacia LKB Biotechnology, NJ; in water) and heated at 65° C. for five minutes prior to loading. Electrophoresis was performed al. 6 V/cm for one hour. After electrophoresis, the cDNA bands were examined under UV light illumination.

The gel was then immersed in 0.25 M HCl for 30 minutes (depurination), 0.5 M NaOH containing 1.5 M NaCl for one hour (denaturation), followed by 1 M Tris-HCl, pH 7.5 containing 1.5 M NaCl for one hour (neutralization).

(c) Transfer of Amplified cDNAs onto Membranes (Southern Blot)

Amplified cDNAs were transferred onto nylon membranes and immobilized by UV light as described in Comparison 1(2).

(d) Preparation of Biotin-Labeled cDNA Probes

Ten ng each of Gs and Gi-2 cDNA clones were amplified by PCR as described in (2)(a) above, with the modification that 20% of dTTP was replaced with biotin-labeled dUTP (Clontech). In preliminary Southern blot analysis, these biotin-labeled PCR products have been shown to specifically hybridize to Gs and Gi-2, respectively.

(e) Hybridization of Labeled cDNA Probes to Southern Membranes

As shown in Comparison Example 1 Paragraph 4, biotin-labeled PCR products were heat-denatured at 95° C. for 10 minutes, then hybridized to Southern membranes, on which PCR-amplified cDNAs from cell lysates were immobilized.

(f) Chemical Activity Measurement of Labeled cDNA Probes

Chemical activity of labeled cDNA probes was measured as described in Comparison 1 Paragraph (5).

(3) Results

Figure 7:
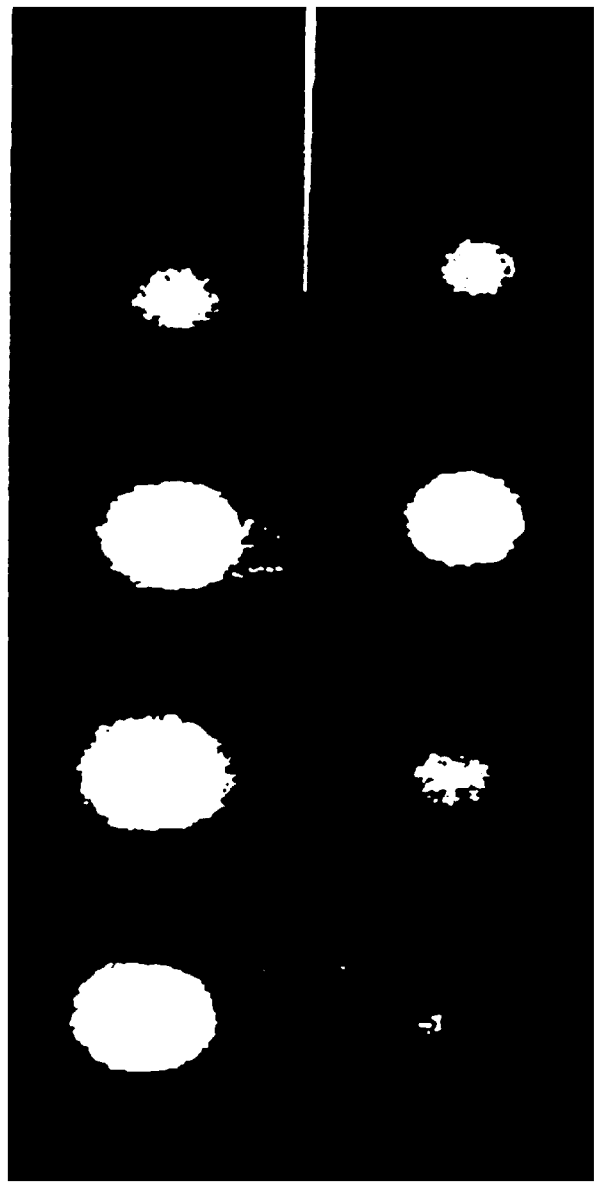
FIG. 7 shows a photographic image of a polaroid film exposed to chemiluminescent light derived from oligo-(dT) probe by the invented method, in which Gi-2 and GS protein mRNA in various cells were trapped onto the first polynucleotide-immobilized plastic plate.

The results of Example 4(1) are shown in FIG. 7. Polaroid film was exposed to chemiluminescent light derived from an oligo-(dT) probe by the invented method, in which Gi-2 and Gs protein mRNA from various cells were trapped onto the first oligonucleotide-immobilized plastic plate. Phosphate-buffered saline (PBS) was used as a control. As shown in FIG. 7, mRNA was detected from all cell lines.

Figure 8:
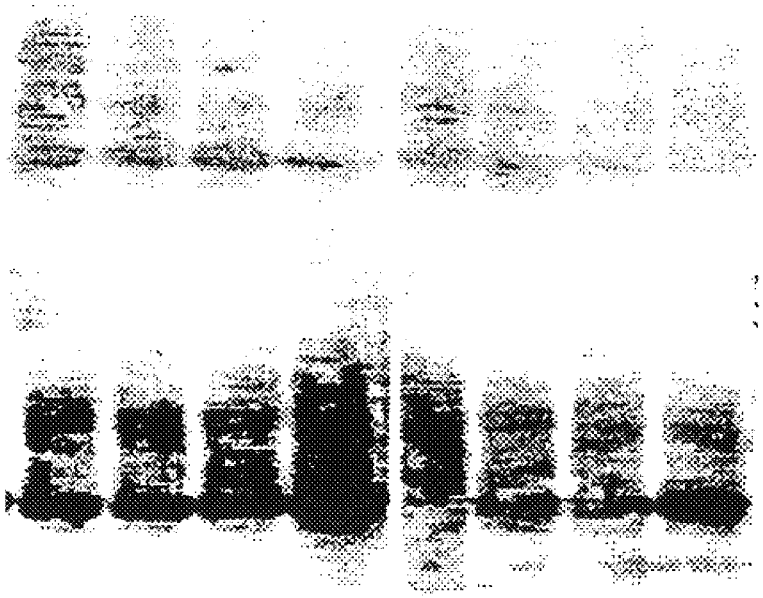
FIG. 8 shows a photographic image of an X-ray film exposed to chemiluminescent light derived from the Gi-2 and Gs protein cDNA probes on the Southern membrane, in which PCR-amplified G protein specific DNA from 4 different cell lines was immobilized.

The results of Example 4(2) are shown in FIG. 8, in which Gi-2 and Gs cDNA probes were used on a Southern Blot. PCR-amplified G protein specific DNA from four different cell lines were immobilized onto a membrane. FIG. 8 is a copy of the X-ray film detailing the chemiluminescent results of this probe. As shown in FIG. 8, mRNAs are detected in all cell lines. Therefore, the invented method provides a high enough reliability to be used for quantification of mRNA.

EXAMPLE 5

Methods for Amplifying G Proteins with PCR Primers (1) Materials

The cDNAs of rat G protein α subunits ($G_{i-1}$, $G_{i-2}$, $G_{i-3}$, $G_s$ and $G_o$) were provided by Dr. R. R. Reed (Johns Hopkins Univ., MD). λZAP libraries of rat pituitary and intestine were provided by Dr. D. G. Payan (Univ. Calif. San Francisco). Kirsten murine sarcoma virus transformed rat kidney cells (KNRK), human IM9 B-lymphocytes and human Jurkat T-lymphocytes were obtained from American Type Tissue Culture Collection, Rockville, Md.). Cell culture media, Superscript (Gibco/BRL, Gaithersburg, Md.), reagents for PCR (Promega, Madison, Wis.), ECL (Amersham, Arlington Height, Ill.), Genius, Lumi-Phos 530 (Boehringer-Mannheirn, Indianapolis, Ind.), FastTrack (Invitrogen San Diego, Calif.), λ gt10 library of human HL-60 cells, biotin-dUTP, alkaline phosphatase-conjugated streptavidine (Clontech, Palo Alto, Calif.), dNTP (Pharmacia, Piscataway, N.J.) were obtained from the designated suppliers. Other chemicals were purchased from Sigma (St. Louis, Mo.).

(2) Cell Culture

KRNK cells were grown in Dulbecco's modified Eagles medium containing 10% fetal calf serum, 100 U/ml penicillin and 100 μg/ml streptomycin at 37° C. in 5% $CO_2$/95% air. Cells were fed every other day and passaged at 70–90% confluency with 0.1% trypsin in $CA^{2+}$-$Mg^{2+}$-free saline containing 0.02% EDTA. IM9 and Jurkat cells was grown in RPMI 1640 containing 10% fetal calf serum, 100 U/ml penicillin and 100 μg/ml streptomycin at 37° C. in 5% $CO_2$/95%. Cell viability was more than 90% as assessed by the exclusion of trypan blue.

(3) Primer Design

Rat clones of Gα proteins ($G_{i-1}$ (RATBPGTPB), $G_{i-2}$ (RATBPGTPA), $G_{i-3}$ (RATBPGTP), $G_s$ (RATBPGTPD), and $G_o$ (RATBPGTPC) were retrieved from GenBank release 65.0 (HIBIIO, Hitachi America, Brisbane, Calif.). The nucleotide sequence similarity among these clones were then analyzed by the multiple alignment program (DNASIS, Hitachi). We have initially identified 7 highly conserved areas among them. These conserved nucleotide sequences were then analyzed against all mammalian sequences in GenBank in order to identify other similar sequences. The designed oligonucleotides (Seq. ID No. *) were synthesized by Genosys Biotechnologies (Woodlands, Tex.), and suspended in water at 100 pg/ml.

(4) PCR

One μl of the template DNA was mixed with 1 mM each of DATP, dGTP, dCTP and dTIP, 1 μl of each PCR primers, 1 μl of 25 mM $MgCl_2$, 5 μl PCR buffer, and 0.5 μl of Taq polymerase (18). PCR was then carried out in a DNA thermal cycler (model 480, Perkin-Elmer Cetus, Norwalk, Conn.) with 30 cycles of annealing temperature at ranging from 37° C. to 65° C. for 1.5 min, 72° C. extension for 4 min followed by 95° C. denature for 1.5 min. In separate experiments, 35% of dTTP was replaced with biotin-dUTP in order to prepare biotin-labeled probes.

(5) Southern Blot

PCR products were separated by electrophoresis in 1.2% agarose, and stained with ethidium bromide (19). Gels were then depurinated in 0.25 N HCl for 30 minutes and denatured in 0.5 N NaOH containing 1.5 M NaCl for 30 minutes. The gels were then neutralized with 1.0 M Tris, pH 7.6 containing 1.5 M NaCl for 30 minutes. Gels were then placed onto nylon membranes (MagnaGraph, MSI, Westboro, Mass.) prewetted in 10×SSPE for 10 min, and DNA was transferred onto membranes by positive pressure at 75 mmHg for 60 minutes (Posiblot, Stratagene, La Jolla, Calif.). The DNA from the gel was then cross-linked to the membranes with ultraviolet light at 120 mjoules (Stratalinker, Stratagene), and the membranes were incubated with hybridization buffer (ECL) containing 5% blocking reagent (ECL) and 0.5 M NaCl at 40° C. for more than 1 hour. Heat denatured biotin-labeled PCR probes were then added, and hybridization was continued overnight. The membranes were washed four times for 15 minutes each time with primary wash buffer (0.5×SSPE, 36 w/v % urea, 0.4 w/v % SDS) at 45–65° C., then washed twice for 5 minutes with secondary wash buffer (2×SSPE) at room temperature, and were incubated with the blocking buffer (Genius) for at least 3 hours at room temperature. Alkaline phosphatase-conjugated streptavidine (1:5,000 dilution) was then added, and incubation was continued for an additional 30–60 minutes at room temperature. The membranes were washed four times for 15 minutes with buffer A (100 mM Tris, pH 7.5, 150 mM NaCl) at room temperature, were washed for 2 minutes once with buffer C (100 mM Tris, pH 9.5, 100 mM NaCl, 50 mM $MgCl_2$), and soaked in Lumi-Phos 530 for approximately 1–2 minutes. The membranes were then wrapped with transparency films, and chemiluminescent signals were allowed to expose X-ray films (XAR-5, Kodak, Rochester, N.Y.) for between 10 minutes and 1 hour.

(6) mRNA Preparation and cDNA Synthesis

The cells were washed with phosphate buffered saline three times, homogenized in lysis buffer (FastTrack), and then incubated at 45° C. for 1 hour to eliminate any RNase activity. NaCl concentrations were adjusted at 0.5 M, and an oligo (dT) cellulose tablet was added to lysis buffer. Incubation was then continued at room temperature for an additional 40 minutes. After oligo (dT) cellulose was washed with binding buffer (FastTrack) four times, bound mRNA was eluted with DEPC-treated water. Concentrations of mRNA were determined in a spectrophotometer (Hitachi, U-2000, Irvine, Calif.) at $OD_{260}$. The first strand cDNA was synthesized from a template mRNA in the presence of 50 mM Tris, pH 8.3, 75 mM KCl, 3 mM $MgCl_2$, 10 mM DTT, 0.5 mM each of dATP, dCTP, dGTP, and dTTP, poly (dT) as a primer, and reverse transcriptase (Superscript) at 37° C. for 1 hour. Second strand cDNA was then synthesized in the same tube, containing 25 mM Tris, pH 7.5, 100 mM KCl, 5 mM $MgCl_2$, 10 mM $(NH_4)_2SO_4$, 0.15 mM β-NAD$^+$, 250 μM each of dATP, dGTP, dCTP and dTTP, 1.2 mM DTT, 65 U/ml DNA ligase, 250 U/ml DNA polymerase, and 13 U/ml RNase H (Superscript) for 2 hours at 16° C. Synthesized cDNAs were then extracted once with an equal volume of phenol:chloroform:isoamyl alcohol (25:24:1), precipitated with ethanol, and resuspended in $H_2O$.

(7) Graphic Presentation

Data on Polaroid films and X-ray films was scanned by Stratascan (Stratagene) with optimization of signal-to-noise ratio, then edited with desk top publishing software (PageMaker, Aldus, Seattle, Wash.).

EXAMPLE 6

Characterization of Cellular Components of G Protein α Subunits using PCR (1) Introduction Using the methods of Example 5, we have now identified and characterized two highly conserved oligonucleotide sequences among five different a subunits of G proteins, SEQ ID NO:7 and SEQ ID NO:8, which can used as PCR primers. We have found that the sequences of all the subclasses of G proteins can be amplified under the same PCR conditions using these two oligonucleotides as PCR primers, including both G protein sequences obtained from a mixture of rat Gα protein clones and cDNAs derived from various human tissues.

Although G proteins have been analyzed extensively from a biochemical and immunological point of view using various antibodies, antibody production without any cross-reactivity among various subclasses or with high species specificity has been quite difficult to obtain. Therefore, recent experiments have focused on Northern blot analyses to identify G protein-specific mRNA from various tissues or cells in different species. However, Northern blots require experienced handling and protection from RNase contamination, in addition to a large amount of starting cellular materials.

Figure 13:
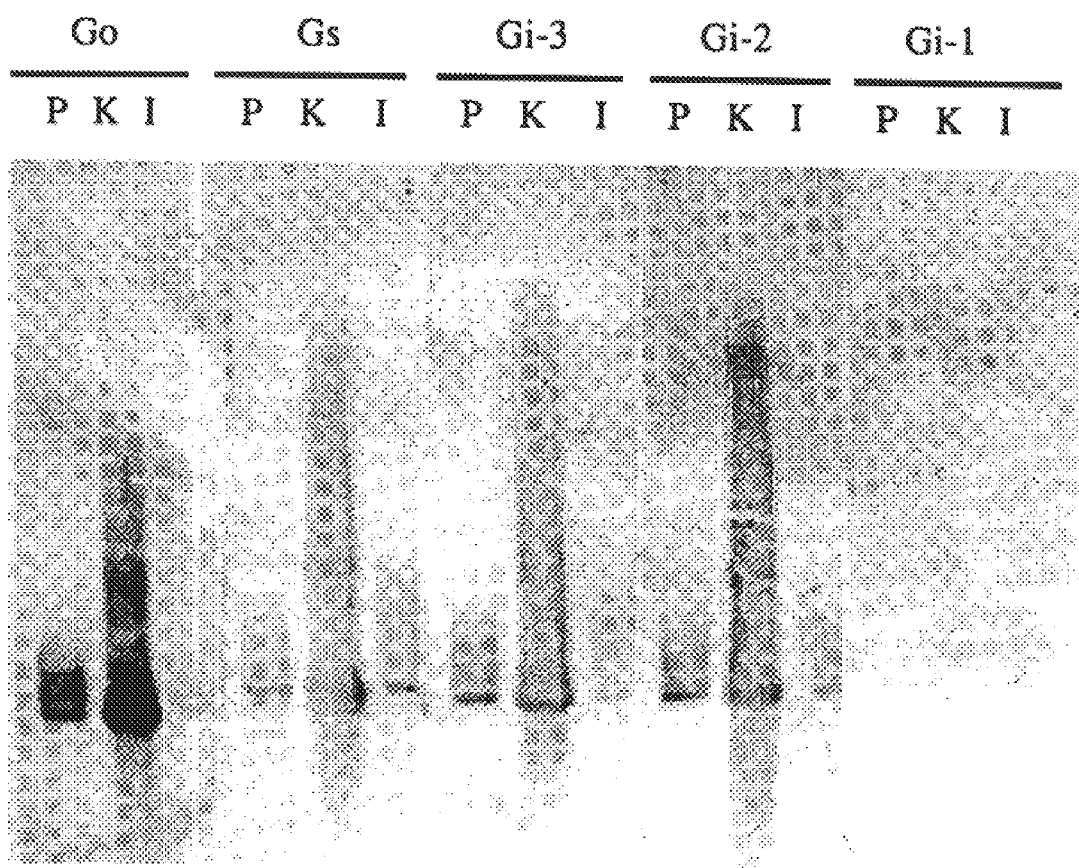
FIG. 13 shows a gel of λZAP EDNA libraries from rate pituitary (P), kidney (K) and intestinatal (I) amplified with each of five different G protein primers, as indicated.

In contrast to these conventional methods, PCR technology is more convenient and practically useful, because it requires less material than a Northern blot analysis and has great sensitivity. However, it is difficult for PCR to quantify the amount of DNA or mRNA in starting materials. Interestingly, the final PCR products obtained using the novel G-protein PCR primers of the present invention reflect the relative composition of each of the subclasses of Gα proteins present: in the starting materials. This is probably because the five different Gα proteins cDNAs are amplified at a similar rate with a single set of PCR primers under the same PCR conditions. If known mixtures of each of the subclasses of Gα protein clones are assayed together with unknown test samples, as shown in FIG. 13, the relative composition of Gα proteins can be determined fairly precisely. Therefore, the present method is ideal for the characterization of Gα proteins in various tissues and cells.

Performing PCR with the primers of the present invention is also useful in clinical and diagnostic assays in the detection of disease. Since G protein abnormalities have been associated with hereditary diseases, cancer, forms of diabetes, and other diseases, the present PCR primers for detecting and quantifying G proteins can be used to detect these diseases and assess their severity.

In the present study, we have identified $G_{i-1}$, $G_{i-2}$, $G_{i-3}$, $G_s$ and $G_o$ using the PCR primers of the present invention. Although recent cloning has identified more subclasses of G proteins, all of these newly identified G protein cDNAs showed high degree of homology to other known G proteins. Therefore, it is expected that the primers of the present invention will amplify these subclasses as well, and that the present PCR the present PCR technique can also be applied to these new G proteins. Moreover, this PCR method can be utilized to clone unique G protein genes as well.

(2) Primers We have designed two 22-mer oligonucleotides ($G_2$ and $G_4$—SEQ ID NOS:700 and 701) as PCR primers. As shown in Table 4 below, these oligonucleotides contain sequences which are highly conserved among five different Gα protein cDNAs, having only 0–4 base mismatches per sequence. No mismatch was found in the 4 bases at the 3' end of the $G_2$-sense and $G_4$-antisense sequences. Furthermore, $G_2$ and $G_4$ have no self-complementary sequences more than 3 base pairs in a row (data not shown). In order to analyze whether $G_2$ and $G_4$ are common to all the Gα proteins, but not to other unrelated sequences, a homology search (DNASIS) of $G_2$ and $G_4$ sequences was carried out against all mammalian sequences in GenBank. As a result, $G_2$ and $G_4$ were found to be common to all the types of Gα proteins and rhodopsins of various species, but less homologous to other unrelated sequences (data not shown).

TABLE 5

Nucleotide sequence similarity of PCR products among 5 different Gα protein clones.

|  | Gi-1 | Gi-2 | Gi-3 | Gs | G0 |
|---|---|---|---|---|---|
| Gi-1 | — | 73.4 | 76.8 | 50.2 | 64.0 |
| Gi-2 | 73.4 | — | 67.8 | 52.3 | 65.9 |
| Gi-3 | 76.8 | 67.8 | — | 47.6 | 62.6 |
| Gs | 50.2 | 52.3 | 47.6 | — | 55.6 |
| Go | 64.0 | 65.9 | 62.6 | 55.6 | — |

(3) PCR of Rat Cloned Gα Protein cDNAs

The cloned rat $G_{i-1}$, $G_{i-2}$, $G_{i-3}$, $G_s$ and $G_o$ cDNAs were diluted at 10 ng/μl, and 1 μl of DNA was mixed with 1 mM each of dATP, dGTP, DCTP and dTTP, 1 μl of each PCR primers, 1 μl of 25 mM $MgCl_2$, 5 μl PCR buffer, and 0.5 μl of Taq polymerase as described in the Materials and Methods. PCR was then carried out with 30 cycles of annealing temperature at 45° C. for 1.5 min, 72° extension for 4 min followed by 95° C. denaturation for 1.5 min, 72° C. extension for 4 min followed by 95° C. denaturation for 1.5 min. PCR products were then separated in 1.2% agarose gel, and stained with ethidium bromide (upper panel). Marker indicates a 0.6 Kb fragment of HindIII digested λ DNA. DNAs were then transferred onto nylon membranes, hybridized with subclass specific biotin-labeled probes as described in the Materials and Methods. The membranes were washed with primary wash buffer (0.5×SSPE, 36 w/v % urea, 0.4 w/v % SDS) at 65° C., incubated with the blocking buffer for at least 3 hours at room temperature, then alkaline phosphatase-conjugated streptoavidine (1:5,000 dilution) was added, and incubation was continued for an additional 30 min at room temperature. After extensive washing, membranes were soaked in Lumi-Phos 530 for approximately 1–2 min, then chemiluminescent signals were exposed to X-ray film for 10 min to 1 hr (lower 5 panels).

PCR was first carried out at different annealing temperatures ranging from 37° C. to 65° C. using the λ gt10 library of human HL-60 cells. As a result, PCR products were seen only at 45° C. and 55° C. with a size of approximately 500 bp (data not shown), which was similar to theoretical values (576 to 524 bp) (see Table 4 above). Therefore, all the PCR was then carried out at an annealing temperature of 45° C.

Figure 14:
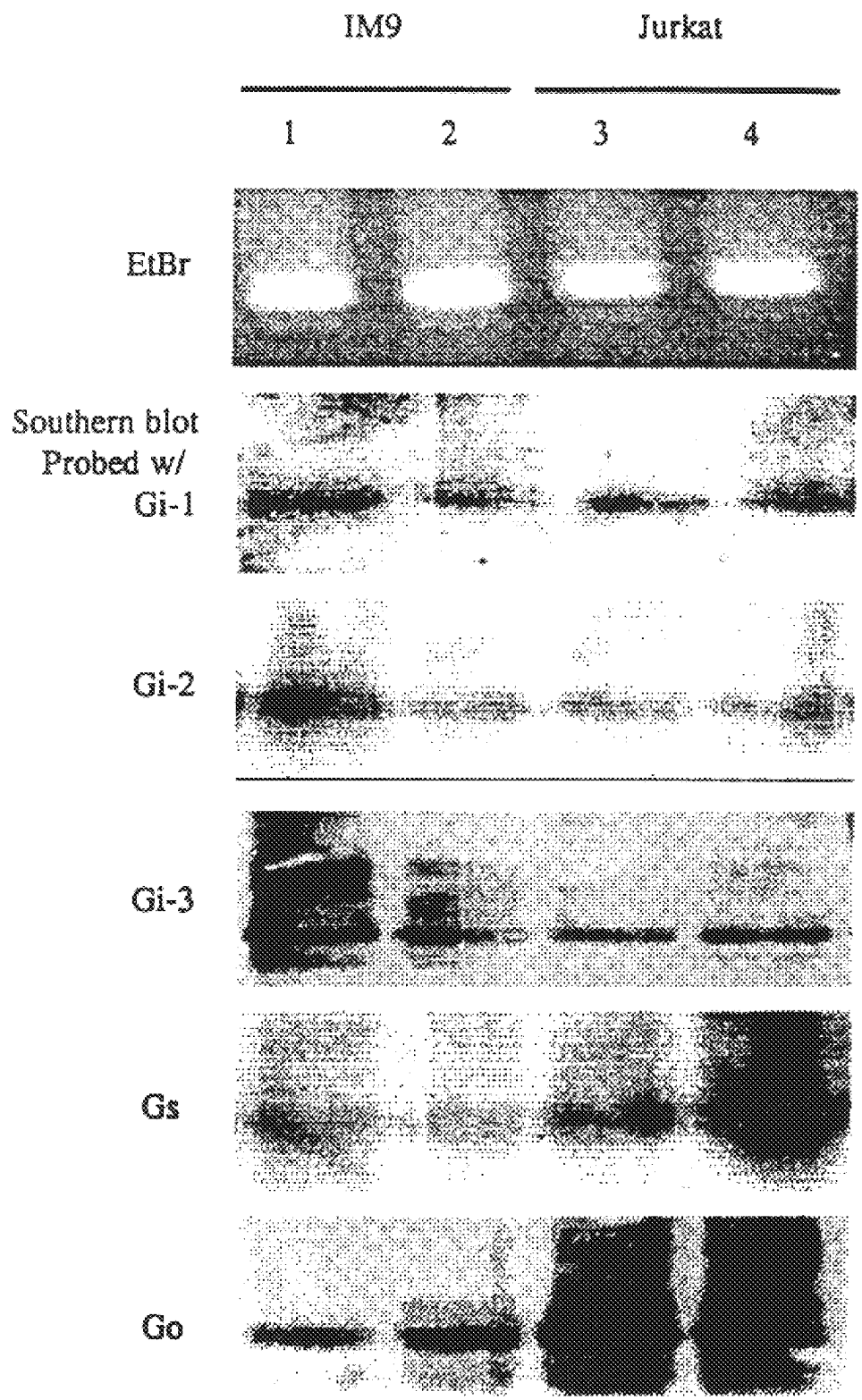
FIG. 14 shows a gel of 500 bp DNA from cDNAs of human IM9 and Jurkat cells amplified with $G_2$ and $G_4$ PCR primers.

As shown in FIG. 14, cloned rat Gα protein cDNAs ($G_{i-1}$, $G_{i-2}$, $G_{i-3}$, $G_s$, $G_o$) were successfully amplified using the same set of PCR primers ($G_2$ and $G_4$) with a size of

TABLE 4 consensus oligonucleotides (G2 and G4) among five different cDNAs of G protein α subunits
Consensus sequence (# of mismatch) [SEQ ID NO:]

| | G2 | | | G4 |
|---|---|---|---|---|
| | AGCACCATTGTGAAGCAGATGA [700] | Length (bp) | | TGTTTGATGTGGGAGGCCAGAG [701] |
| Gi-1 | AGCACaATTGTGAAGCAGATGA (1) [702] | 476 | | TGTTTGACGTGGGAGGCCAGAG (1) [805] |
| Gi-2 | AGCACCATcGTcAAGCAGATGA (2) [703] | 479 | | TGTTTGATGTGGGtGGtCAGcG (3) [806] |
| Gi-3 | AGtACtATTGTGAAaCAGATGA (3) [704] | 476 | | TGTTTGATGTaGGtGGCCAaAG (3) [707] |
| Gs | AGCACCATTGTGAAGCAGATGA (0) [704] | 524 | | TGTTcGATGTGGGcGGCCAGcG (3) [708] |
| G0 | AGCACCATTGTGAAGCAGATGA (0) [706] | 479 | | TGTTTGAcGTtGGgGGCCAGcG (4) [709] | approximately 500 bp in 1.2% agarose gels stained with ethidium bromide. According to the computer analysis (DNASIS), the nucleotide sequences of the amplified PCR products were less homologous among five Gα proteins with the percentage of similarity ranging from 76.8% to 47.6%.

This indicates that after PCR amplification, each of the components of Gα proteins can be identified by Southern blot analysis, even though the sizes of the PCR products generated are very similar among the five Gα proteins. Therefore, another PCR was carried out in which 35% of the dTTP was replaced with biotin-conjugated dUTP in order to prepare subclass-specific, biotin-labeled probes. Southern membranes were then probed with these biotin-PCR products. As shown in FIG. 14, these biotin-PCR probes were highly specific to each Gα protein subclass with washing temperature at 65° C. At low stringent washing, these probes cross-hybridized with other subclasses of Gα proteins (data not shown).

(4) PCR of a Mixture of Rat Cloned Gα Protein cDNAs $G_{1-1}$, $G_{i-2}$, $G_{i-3}$, $G_s$ and $G_o$ cDNA were diluted at 10 ng/μl (+++), 100 pg/μl (++) and 1 pg/μl (+), and various combinations of these diluted cDNA were used as a PCR templates (upper panel). Then, PCR and Southern blot were carried out as described in part (3) of this Example.

By using the $G_2$ and $G_4$ sequences, all the subclasses of Gα protein cDNA were amplified with PCR when an equal amount of $G_{i-1}$, $G_{i-2}$, $G_{i-3}$ and $G_o$ were present in test samples FIG. 13, lane 4, 5, 10). However, if all the concentrations of Gα protein cDNA are abundant, $G_o$ is less amplified (FIG. 13, lane 10), probably because the number of mismatches between $G_o$ and $G_4$ is higher than others between $G_4$ and the $G_2$ sequences. If 1 or 2 of the 5 Gα protein cDNAs were present in smaller quantities than the others, the amounts of amplified cDNA were relatively correlated with the starting concentrations of cDNAs (FIG. 13, lane 1, 2, 3, 8, 9). Furthermore, if 1 of 5 of the Gα proteins' cDNA is more abundant than that of the others, this G protein gene was amplified more than others (FIG. 13, lane 6, 7).

(5) PCR of Rat cDNAs from Various Tissues

Rat λZAP cDNA libraries of pituitary (P) and intestine (I), and cDNA from the mRNA of rat kidney cells (KNRK) were used as PCR templates. Then, PCR and Southern blot were carried out as described in part (3) of this Example.

Using this PCR method, Gα protein genes were amplified not only from cloned cDNAs, but also from various rat cDNAs (FIG. 15). In λZAP cDNA libraries from rat pituitary glands and cDNA from rat kidney KNRK cells, $G_o$ was more abundant than $G_s$, $G_{i-2}$ and $G_{i-3}$, and $G_{i-1}$ was undetectable (FIG. 15, lane 1, 2). λZAP cDNA library of rat intestine contained more $G_{i-2}$, $G_{i-3}$, and $G_s$ and $G_o$ (FIG. 15, lane 3).

(6) PCR of Human cDNAs cDNAs from the mRNA of human IM9 B-lymphocytes and Jurkat T-lymphocytes were used as PCR templates. Then, PCR was carried out with annealing temperature at 45° C. (1, 3) or 55° C. (2, 4). Southern blot were then performed as described in part (3) of this Example.

Figure 16:
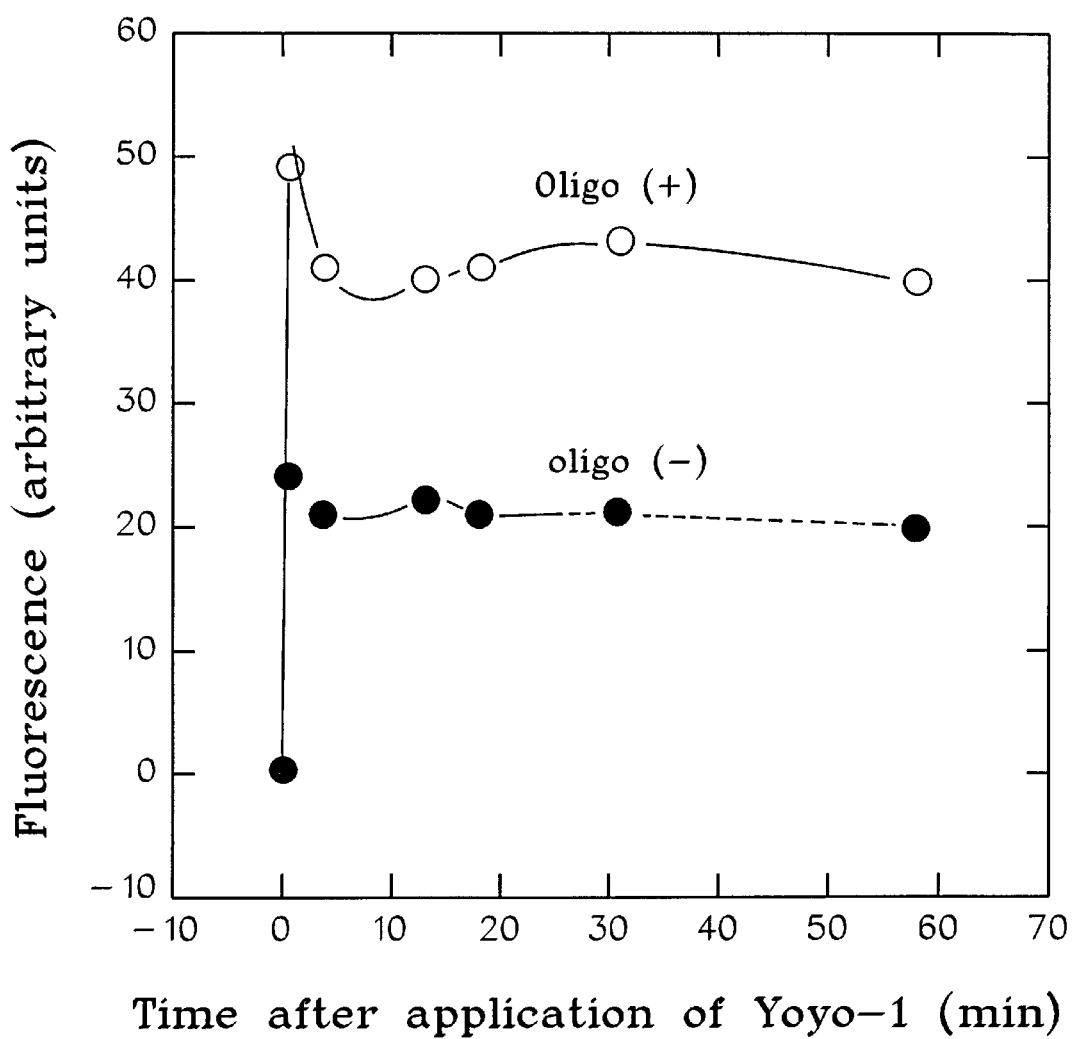
FIG. 16 is a graph showing the time course of YOYO-1 analysis.

According to sequence analyses, the PCR products of rat $G_{i-1}$, $G_{i-2}$, $G_{i-3}$, $G_s$ and $G_o$ sequence amplification exhibited a high degree of homology to human G protein cDNAs, see Table 6 below). Furthermore, as shown in FIG. 16, PCR with a pair of $G_2$ and $G_4$ primers could amplify 500 bp DNA from cDNAs of human IM9 and Jurkat cells. Unlike rat cDNAs (FIG. 15), both IM9 and Jurkat cells contained all the subclasses of Gα proteins (FIG. 16). However, $G_{i-3}$ is relatively more abundant in IM9 cells, while $G_s$ and $G_o$ were more in Jurkat cells than IM9 cells (FIG. 16).

TABLE 6

Nucleotide sequence similarity of PCR products between rat and human G proteins

|      | Length (bp) Rat | No. of Human | mismatch | % Similarity |
|------|-----------------|--------------|----------|--------------|
| Gi-1 | 476             | 476          | 62       | 87.0%        |
| Gi-2 | 479             | 479          | 44       | 90.8%        |
| Gi-3 | 476             | 476          | 40       | 91.6%        |
| Gs   | 524             | 482          | 52       | 89.2%        |
| Go   | 479             | 479          | 39       | 91.9%        |

It will be evident to one having ordinary skill in the art that a variety of sequences could serve as sense or antisense primers for PCR methods or as probes for the detection of mRNA as described herein. A method for identification of such sequences that are either common to a variety of G proteins or specific to a particular species is provided hereinbelow. In the preferred embodiment of this method of identification, a computer program is used to identify the sequences. Through use of such a program, we have identified a large number of both common and specific primers and probes. Provided as Tables 7 through 13 are various sense sequences identified through the use of such a program that are useful as G protein probes and primers.

All of the sequences listed in these tables are useful within the context of the PCR methods of the present invention. The complementary antisense sequences are also useful in certain aspects of the invention. As will be known having ordinary skill in the art, for common probes that are similar, but not identical to target sequences, stringency conditions can be varied (e.g. by changes in temperature and salinity) so that such probes will hybridize or fail to hybridize with a particular target sequence. Thus, also included within the present invention are sequences thar are capable of hybridizing with the same sequences as either the sense sequences listed or their anti-sense counterparts. Additional probes for G protein also include the following:

Common G Protein Probes

5'-CTCTGGCCTCCCACATCAAACA-3' (SEQ ID NO: 139)

5'-TCATCTGCTTCACAATGGTGCT-3' (SEQ ID NO: 140)

| Specific probes (Human & Rat common) | |
|---|---|
| | (SEQ ID NO: 141) |
| Gi-1 | 5'-GTTTTCACTCTAGTTCTGAGAACATC-3' |
| | (SEQ ID NO: 142) |
| Gi-2 | 5'-CAAAGTCGATCTGCAGGTTGC-3' |
| | (SEQ ID NO: 143) |
| | 5'-ATGGTCAGCCCAGAGCCTCCGG-3' |
| | (SEQ ID NO: 144) |
| Gi-3 | 5'-GTCTTCACTCTCGTCCGAAGA-3' |
| | (SEQ ID NO: 145) |
| Gs | 5'-GCCTTGGCATGCTCATAGAATT-3' |
| | (SEQ ID NO: 146) |
| | 5'-TTCATCCTCCCACAGAGCCTTG-3' |
| | (SEQ ID NO: 147) |
| Go | 5'-CGCATCATGGCAGAAAGCAG-3' |

TABLE 7

G protein common primer (G2-S)

| | | SEQ ID NO: | G2-S AGCACCATTGTGAAGCAGATGA |
|---|---|---|---|
| Human | | | |
| Gi-1 | HUMGNBPAI | 148 | ::T::A:::::::::::::::: |
| Gi-2 | HUMGIAA | 149 | ::::::::C::C:::::::::: |
| Gi-3 | HUMGIAB | 150 | ::::::::::::A:::::::: |
| Gs | HUMGNPAS | 151 | :::::::::::::::::::::: |
| Go | HUMGOAQ01 | 152 | :::::::::::::::::::::: |
| Rat | | | |
| Gi-1 | RATBPGTPB | 153 | :::::A:::::::::::::::: |
| Gi-2 | RATBPGTPA | 154 | ::::::::C::C:::::::::: |
| Gi-3 | RATBPGTP | 155 | ::T::T:::::::A:::::::: |
| Gs | RATBPGTPD | 156 | :::::::::::::::::::::: |
| Go | RATBPGTPC | 157 | :::::::::::::::::::::: |
| Gx | RATGXA | 158 | ::::::::C::C:::::::::: |
| Highest matched sequences in GenBank | | | |
| HUMADECYC adenyl cyclase | | 159 | :::::::::::::::::::::: |
| RATACOA1aCyl-coA oxidase | | 160 | GC::::::G:::::A::::::: |
| HUMTGASEtransglutaminase | | 161 | CT:::::::::::::::CC:AC |

TABLE 8

G protein common primer (G4-AS)

| | | | G4-AS SEQUENCE ID NO: TGTTTGATGTGGGAGGCCAGAG |
|---|---|---|---|
| Human | | | |
| Gi-1 | HUMGNBPA | 162 | ::::::::::::::::::T::::: |
| Gi-2 | HUMGIAA | 163 | ::::::::::::T::T:::C: |
| Gi-3 | HUMGIAB | 164 | :::::::::A::T:::::A:: |
| Gs | HUMGNPAS | 165 | :::::::C:::::T:::::::C: |
| Go | HUMGOAQ01 | 166 | :::::::C::C:::::::::C: |
| Rat | | | |
| Gi-1 | RATBPGTPB | 167 | :::::::C::::::::::::: |
| Gi-2 | RATBPGTPA | 168 | ::::::::::::T::T:::C: |
| Gi-3 | RATBPGTP | 169 | :::::::::A::T:::::A:: |
| Gs | RATBPGTPD | 170 | ::::C:::::::::C:::::C: |
| Go | RATBPGTPC | 171 | :::::::C::T::G:::::C: |
| Gx | RATGXA | 172 | ::G:G:::::::::::G::::: |
| Highest matched sequences in GenBank | | | |
| HUMLDLRRL LDL-receptor | | 173 | CTGA:::::::::::::TACT |
| MUSHEPGFA hepatocyte growth | | 174 | GAG:G:::::::T::A::::: |
| HUMKEREP epidermal keratin | | 175 | AG::::::AT:::GG::::::: |

TABLE 9

Gi-1 protein specific, human-rat common primer (Gi-1)

| | | SEQUENCE ID NO: | Gi-1 GATGTTCTCAGAACTAGAGTGAAAAC |
|---|---|---|---|
| Human | | | |
| Gi-1 | HUMGNBPAI | 176 | ::::::::::::::::::::::::: |
| Gi-2 | HUMGIAA | 177 | TT:::::::::CT:CCCCTGTCCCCT |
| Gi-3 | HUMGIAB | 178 | ::::::::TG:G::G:::::::G:: |
| Gs | HUMGNPAS | 179 | AC:::G:C:::T:::TCCTG::C::G |
| Go | HUMGOAQ01 | 180 | ::CA:C:::C::C::G::C::::: |

TABLE 9-continued

Gi-1 protein specific, human-rat common primer (Gi-1)

| | | SEQUENCE ID NO: | Gi-1 GATGTTCTCAGAACTAGAGTGAAAAC |
|---|---|---|---|
| Rat | | | |
| Gi-1 | RATBPGTPB | 181 | ::::::::::::::::::::::::: |
| Gi-2 | RATBPGTPA | 182 | :::::G::GC:G::CC:T:::::G:: |
| Gi-3 | RATBPGTP | 183 | ::::::::TC:G::G:::::::G:: |
| Gs | RATBPGTPD | 184 | A:GCACAATTA:TTA:::::::::CG |
| Go | RATBPGTPC | 185 | ::CA:C:::C::::C::G::C::::: |
| Gx | RATGXA | 186 | TCA::::GAG::C:::A:CC:::::CA |

TABLE 9A

Human-rodent common Gi-1 specific probes.

| Name in GenBank | Gi1-735 (5'-3')<br>GATGTTCTCAGAACTAGAGTGAAAAC | Gi1-1131 (5'-3')<br>TGTCAGTTTGAAGACCTCAATAAAAG | SEQ ID NOS:<br>(respectively) |
|---|---|---|---|
| Rat | | | |
| Gs    RATBPGTPD | A-GCACAATTA-TTA--------CG | AACAGAAA-A----AA-A----G---T | 224, 225 |
| Gi-1  RATBPGTPB | ------------------------- | -------------------------- | 226, 227 |
| Gi-2  RATBPGTPA | -----G--GC-G---CC-T-----G-- | A-CA--------G------G------C- | 228, 229 |
| Gi-3  RATBPGTP  | --------TC-G---G--------G-- | --C-----------T--G--CCG--- | 230, 231 |
| Go    RATBPGTPC | --CA-C---C----C--G--C----- | ACA---------AG-AAA--CCGCTC | 232, 233 |
| Human | | | |
| Gi-1  HUMGNBPA  | ------------------------- | -------------------------- | 234, 235 |
| GenBank\*\* | | | |
| HUMCPH192 | C---C---G--C---G---A-----G | | 236 |
| MUSGBPA   | | A-C---CC--T--C------------ | 237 |

\*: Size of PCR products using Gi1-735 and Gi1-1131 as primers.
\*\*: The highest matched sequences in GenBank (release 68.0) next to the G protein DNAs.

TABLE 10

Gi-2 protein specific; human-rat common primer (Gi-2)

| | SEQUENCE ID NO: | Gi-2<br>GCAACCTGCAGATCGACTTTG |
|---|---|---|
| Human | | |
| Gi-1 | HUMGNBPAI 187 | :G:GG-<br>T::A::::A::::::: |
| Gi-2 | HUMGIAA   188 | :::::::::::::::::::: |
| Gi-3 | HUMGIAB   189 | :ACGG::AA::::T::::::: |
| Gs   | HUMGNPAS  190 | AGT:::A::T::::T::::G:: |
| Go   | HUMGOAQ01 191 | CTTCT:::::::G:TG::::C |
| Rat | | |
| Gi-1 | RATBPGTPB 192 | :G:GAT::A:A::::::::: |
| Gi-2 | RATBPGTPA 193 | :::::::::::::::::::: |
| Gi-3 | RATBPGTP  194 | AA:::G:::::T:T:TT:::: |
| Gs   | RATBPGTPD 195 | AGT:::A::T:::::::G:: |
| Go   | RATBPGTPC 196 | ATTCT:::::::A:TG::::C |
| Gx   | RATGXA    197 | :T:::A:C:::T:T:T:::C: |

TABLE 10A

Human-rodent common Gi-2 specific probes.

| Name in GenBank | Gi2-742 (5'-3')<br>AAGATGTTTGATGTGGGTGGTC | Gi2-1102 (5'-3')<br>AAGGAGATCTACACGCACTTCA | SEQ ID NOS:<br>(respectively) |
|---|---|---|---|
| Rat | | | |
| Gs    RATBPGTPD | G-C-A-A--------ATCAAG- | ---C--G-----CG-GC-ACGC | 238, 239 |
| Gi-1  RATBPGTPB | --A--------C-----A--C- | -----A--T-----C------- | 240, 241 |
| Gi-2  RATBPGTPA | ---------------------- | ---------------------- | 242, 243 |

TABLE 10A-continued

Human-rodent common Gi-2 specific probes.

| Name in GenBank | Gi2-742 (5'-3')<br>AAGATGTTTGATGTGGGTGGTC | Gi2-1102 (5'-3')<br>AAGGAGATCTACACGCACTTCA | SEQ ID NOS:<br>(respectively) |
|---|---|---|---|
| Gi-3 RATBPGTP | --A-----------A-----C- | ------G-------T-----T- | 244, 245 |
| Go  RATBPGTPC | -G-C-------C--T--G--C- | CTA-------G---C-CTCA-C | 246, 247 |
| Mouse | | | |
| Gi-2 MUSGI | ---------------------- | ---------------------- | 248, 249 |
| Human | | | |
| Gi-2 HUMGIR | ---------------------- | ---------------------- | 250, 251 |
| GenBank | | | |
| HUMCMPF | ----------C---------TGG | | 252 |
| MUSHSP84A | | -------A-----A-A-G---T | 253 |

\*: Size of PCR products using Gi2-742 and Gi2-1102 as primers.
\*\*: The highest matched seqences in GenBank (release 68.0) next to the G protein DNAs.

TABLE 11

Gi-3 protein specific, human-rat common primer (Gi-3)

| | Gi-3<br>SEQUENCE<br>ID<br>NO: | TCTTCGGACGAGAGTGAAGAC |
|---|---|---|
| Human | | |
| Gi-1 | HUMGNBPAI | 198 :::CA:A::T:::::::::A:: |
| Gi-2 | HUMGIAA | 199 G::A:::::CC:C::A::::: |
| Gi-3 | HUMGIAB | 200 ::::::::::::::::::::: |
| Gs | HUMGNPAS | 201 GGGAAATCGA:::T:::G::: |
| Go | HUMGOAQ01 | 202 :::C:::::GA:::CGTG:A:: |
| Rat | | |
| Gi-1 | RATBPGTPB | 203 :::CA:A::T:::::::::A:: |
| Gi-2 | RATBPGTPA | 204 G::G:::::CC::T::::::: |
| Gi-3 | RATBPGTP | 205 ::::::::::::::::::::: |
| Gs | RATBPGTPD | 206 TTCCT::::A:::T:::T:TG |
| Go | RATBPGTPC | 207 CGCAT:::G::C:C::::CCA |
| Gx | RATGXA | 208 AAC::::G:A::::CACCAT: |

TABLE 11A

Human-rodent common Gi-3 specific probes.

| Name in GenBank | Gi3-407 (5'-3')<br>TTGTTTTAGCTGGCAGTGCTGA | Gi3-730 (5'-3')<br>GAGGGAGTGACAGCAATTATCT | SEQ ID NOS:<br>(respectively) |
|---|---|---|---|
| Rat | | | |
| Gs  RATBPGTPD | CC-CAAGT-GATC-------TC | A-T-AT-----T--C--C---- | 254, 255 |
| Gi-1 RATBPGTPB | A----GA------GGC-CTA-T | --A--C-----T--C--C---- | 256, 257 |
| Gi-2 RATBPGTPA | CCTACAC---A--AT------C | -----T--C--G--C--C---- | 258, 259 |
| Gi-3 RATBPGTP | ---------------------- | ---------------------- | 260, 261 |
| Go  RATBPGTPC | CG-------T--AGTC-TTAC- | TC------AT----TCAACGAC | 262, 263 |
| Human | | | |
| Gi-3 HUMGTPBP | ---------------------- | ---------------------- | 264, 265 |

TABLE 11A-continued

Human-rodent common Gi-3 specific probes.

| Name in GenBank | Gi3-407 (5'-3') TTGTTTTAGCTGGCAGTGCTGA | Gi3-730 (5'-3') GAGGGAGTGACAGCAATTATCT | SEQ ID NOS: (respectively) |
|---|---|---|---|
| GenBank** | | | |
| HUMAPOB | G-----C--A-----T-----C | | 266 |
| HUMINSR02 | | C--------G---AC---T--- | 267 |

*: Size of PCR products using Gi3-407 and Gi3-730 as primers.
**: The highest matched sequences in GenBank (reLease 68.0) next to the G protein DNAs.

TABLE 12

GS Protein specific, human-rat common primer (Gs)

| | | | Gs |
|---|---|---|---|
| | SEQUENCE ID NO: | | AATTCTATGAGCATGCCAAGGC |

| Human | | | |
|---|---|---|---|
| Gi-1 | HUMGNBPAI | 209 | GGGCGG::::T::::C:::::CT |
| Gi-2 | HUMGIAA | 210 | :::ATG:::::GCA::::GCTA |
| Gi-3 | HUMGIAB | 211 | C:G::::ACTA:::T::::CTC |
| Gs | HUMGNPAS | 212 | :::::::::::::::::::::: |

TABLE 12A

Human-rodent common Gs specific probes.

| Name in GenBank | Gs-246 (5'-3') GCCAACAAAAAGATCGAGAAGC | Gs-824 (5'-3') GGACAAAGTCAACTTCCACATG | SEQ ID NOS: (respectively) |
|---|---|---|---|
| Rat | | | |
| Gs RATBPGTPD | ---------------------- | ---------------------- | 268, 269 |
| Gi-1 RATBPGTPB | CG--G---G-T------CCGCA | ------G-CGGC-G-GG-GCGC | 270, 271 |
| Gi-2 RATBPGTPA | CAA-GG-------CA-A------ | A--------C-C--C-G-T---T | 272, 273 |
| Gi-3 RATBPGTP | TGAGGA------T-AA------T | -TCAGG---A-TA-------GC | 274, 275 |
| Go RATBPGTPC | TTTGG-G-G-----TA-----T | CCGAGG--CGGCGA-G------ | 276, 277 |
| Mouse | | | |
| Gs-1 MUSGS | ---------------------- | ---------------------- | 278, 279 |
| Gs-2 MUSGTPAMU | ---------------------- | ---------------------- | 280, 281 |
| Human | | | |
| Gs-1 HUMGSA1R | ---------------------- | ---------------------- | 282, 283 |
| Gs-2 HUMGSA2R | ---------------------- | ---------------------- | 284, 285 |
| GenBank** | | | |
| HUMMBP2 | A----A--C------A------ | | 286 |
| RATAFPM | | A------T---T--------A- | 287 |

*: Size of PCR products using Gs-246 and Gs-824 as primers.
**: The highest matched sequences in GenBank (release 68.0) next to the Gs protein DNAs.

TABLE 13

Go Protein specific, human-rat common primer (Go)

| | SEQUENCE ID NO: | Go<br>CTGCTTTCTGCCATGATGCG |
|---|---|---|
| Human | | |
| Gi-1 | HUMGNBPAI | 213 | GAC::::::TAA:::TGACA |
| Gi-2 | HUMGIAA | 214 | :::TGA:::C:A:G:C:::: |
| Gi-3 | HUMGIAB | 215 | ::::A::::AGA:CTTCACA |
| Gs | HUMGNPAS | 216 | TCAACGA:::::G:::CATC |
| Go | HUMGOAQ11 | 217 | :::::::::::::::::::: |
| Rat | | |
| Gi-1 | RATBPGTPB | 218 | :::A:::::CCA:G:T:::TT |
| Gi-2 | RATBPGTPA | 219 | T::::GA:CC:::GCG:::: |
| Gi-3 | RATBPGTP | 220 | ::::::G:::T:::TG:CAC |
| Gs | RATBPGTPD | 221 | ::::::G:::AG:A:G:C:T |
| Go | RATBPGTPC | 222 | :::::::::::::::::::: |
| Gx | RATGXA | 223 | :A::::C:T:::::C:::CTG: |

TABLE 13A

Human-rodent common Go specific probes.

| Name<br>in GenBank | | Go-1224 (5'-3')<br>AGGACATCCTCCGAACCAG | Go-1397 (5'-3')<br>TATGACCAGGTGCTCCACG | SEQ ID NOS:<br>(respectively) |
|---|---|---|---|---|
| Rat | | | | |
| Gs | RATBPGTPD | --------AAAAAC-A-CT | AG--------AC--G-TTC | 288, 289 |
| Gi-1 | RATBPGTPB | G--G-CG------GG---- | -------T---T--TGCT- | 290, 291 |
| Gi-2 | RATBPGTPA | CCAT-------TTCCT--A | -TCTGTT-------GG-GA | 292, 293 |
| Gi-3 | RATBPGTP | G-CCA-AGA-------GGA | A---------TA-T-AATTT | 294, 295 |
| Go | RATBPGTPC | -------------------- | -------------------- | 296, 297 |
| Mouse | | | | |
| Go-A | MUSGCASA | -------------------- | -------------------- | 298, 299 |
| Go-B | MUSGOASB | -------------------- | -------------------- | 300, 301 |
| Hamster | | | | |
| Go-1 | HAMHITA01 | -------------------- | -------------------- | 302, 303 |
| Go-2 | HAMHITA02 | -------------------- | -------------------- | 304, 305 |
| Human | | | | |
| Go | HUMGOA1(2) | -------------------- | -------------------- | 305, 307 |
| GenBank\*\* | | | | |
| | MUSPC3AA | G------T--TC------1 | | 308 |
| | RATACACA | | --------------A-GT | 309 |

\*: Size of PCR products using Go-1224 and Go-1397 as primers.
\*\*: The highest matched sequences in GenBank (release 68.0) next to the G protein DNAs.

Substance P

Another example of clinically useful measurement of mRNA would be for the mRNA of substance P. Substance P is a neurotransmitter. Because the nerves expressing substance P are involved in pain receptor pathways, the ability to measure the mRNA of substance P would be useful in the development of analgesics.

EXAMPLE 6

Detection of Human Substance P Receptor mRNA from Substance P Receptor cDNA-Transferred Cells, Vector-Transfected Cells, and Evaluation of their Reliability (1) Preparation of the First Nucleotide Probe The first nucleotide probe used for quantification of substance P receptor-specific mRNA was an oligodeoxyribonucleotides containing a 5' amino group. This probe was manufactured using a DNA synthesizer (model 380B, Applied Biosystems, CA) and is shown below:

5'-NH$_2$-GGA CTT ATG AGA AAG CGT ACC A-3' (Seq ID NO:5).

(2) Immobilization of the Second Nucleotide Probe onto Insoluble Supports

The first nucleotide probe were dissolved in DEPC-treated water at a concentration of 1 µg/µl, then mixed with the EDC/Sulfo-NHS solution described in Example 1 Paragraph (2) in a ratio of 1:25 (Vol:Vol). 50 µl of the above mixed solution was added to each well of a Sumilon microtiter plate (MS-3796F, Sumitomo Bakelite, JAPAN) and the plates were incubated overnight at room temperature. Following incubation, the reaction solution was removed with an aspirator.

(3) Preparation of Standard mRNA

A plasmid vector pKR2 containing human substance P receptor cDNA (provided by Dr. S. Nakanishi, Kyoto University, Japan) was linearized by SmaI (Promega, WI) digestion. Substance P receptor-specific mRNA was prepared by the method described in Example 1 Paragraph (3) using T7 RNA polymerase (Promega, WI). Concentrations of the resultant mRNA were determined by spectrophotometry and then diluted with DEPC-treated water to prepare standard mRNA solutions as described in Example 1 Paragraph (3).

(4) Preparation of Cell Lysates

One line of human T lymphocyte-derived Jurkat cells which had been transfected with substance P receptor cDNA was examined for transcription of substance P receptor mRNA (hereafter called JSP, provided by Dr D. G. Payan, University of California, San Francisco, Calif.). Another line of Jurkat cells which had been transfected with a vector that didn't express substance P receptor (hereafter called JVec, a kind gift of Dr. D. G. Payan, ibid) was used as a negative control. Cells were collected by centrifugation, washed with PBS, and resuspended in lysis buffer at 1×10$^7$ cells/ml as described in Example 2. The cells were sheared by repeated passage through a 21 gauge needle, then incubated in a slow-shaking waterbath at 45° C. for 1 hour.

(5) Hybridization of the First Nucleotide Probe to mRNA

In order to remove possible RNase contamination in the microtiter wells containing the bound first nucleotide probe, 250 µl of lysis buffer was added and incubated at 45° C. for 1 hour as described in Example 1. The buffer aspirated off, and 50 µl of lysis buffer containing 0.5 M NaCl and various concentrations of standard human substance P receptor-specific mRNA was added into each well, and incubated at 50° C. for 1 hour to allow hybridization as described in Example 1.

(6) Hybridization of the Labeled Second Nucleotide Probe to a Poly(A) Tail of mRNA, and Measurement of Chemical Activities of the Labeled Second Nucleotide Probe After hybridization of the first nucleotide probe to bound mRNA as described in Paragraph (5) above, the hybridization solution was removed by aspiration and individual wells were washed once with 250 µl of lysis buffer. Five µl of lysis buffer containing 0.5 M NaCl and 1 µl of the biotinylated second nucleotide probe solution (35 pmol/µl) was added into each well and incubated at room temperature for an additional 1 hour to allow the second hybridization as described in Example 1.

Chemical activities of the labeled second nucleotide probe was also measured as described in Example 1.

(7) Preparation of Calibration Line

Figure 9:
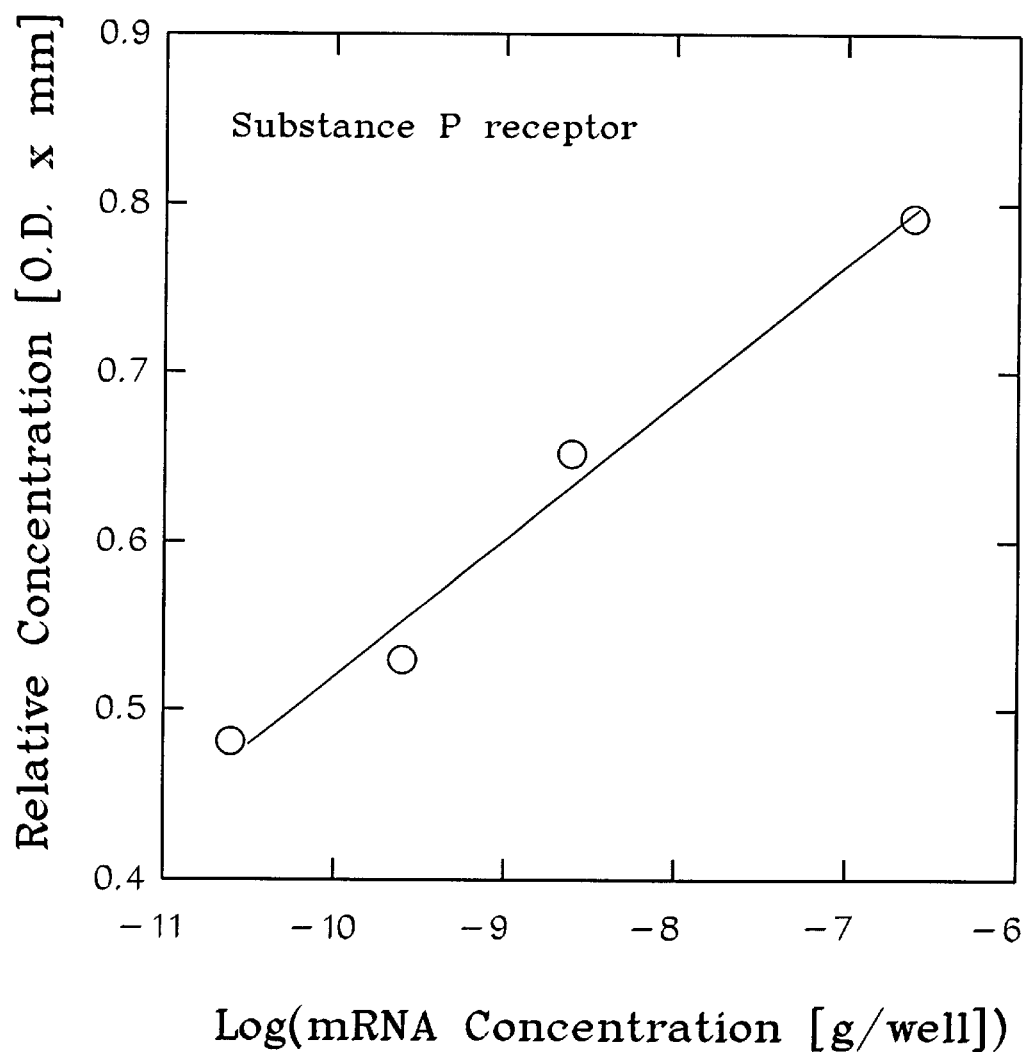
FIG. 9 graphically depicts a calibration line for the human substance P receptor mRNA of the invented method.

The calibration line of standard substance P receptor-specific mRNA is shown in FIG. 9.

(8) Evaluation of Reproducibility

Concentrations of substance P receptor-specific mRNA in JSP and JVec cell lysates were measured twice. Table 7 shows concentrations of mRNA obtained from the calibration line as described in Paragraph (7). Cell numbers from each sample were counted by a phase hemacytometer (American Scientific Products, IL). As shown in Table 14, substance P receptor-specific mRNA concentrations were found in JSP cells that had been transfected with substance P receptor cDNA, but were not detected from JVec cells transfected with only a control vector. This shows that the invented method provides good quantification of a specific mRNA with high reliability. quantification of a specific mRNA with high reliability.

TABLE 14

Concentrations of Substance P Receptor-Specific mRNA in Jurkat Cells Transfected with Substance P Receptor cDNA or Only a Control Vector.

| | mRNA Concentration | |
|---|---|---|
| No. of Assay | JSP [pg/cell] (Transfected) | JVec [fg/cell] (Control) |
| 1 | 135 | <0.1 |
| 2 | 62.4 | <0.1 |

Oligonucleotide Primers and Probes for the Detection of Jun Oncogenes

One aspect of the present invention relates to DNA primers and probes for the detection of jun oncogenes, such as by PCR. Expression of the jun gene can serve as a marker for cell growth.

It is well known that certain oncogenes, such as jun or fos are most rapidly expressed when cells are stimulated with outside stimuli to proliferate. Therefore, detection or quantification of levels of expression of jun or fos oncogenes will be a good marker for cellular mitogenic activity.

Jun oncogenes are one of oncogenes first reported by Maki, et al. (Proc. Natl. Acad. Sci. USA, 84:2848–2852, 1987), and current intensive molecular cloning identified at least three subtypes of jun oncogenes, such as jun-B, c-jun and jun-D. Based on nucleotide sequence comparison, three subtypes of jun oncogenes in both humans and mice are different (Ryder K, Nathans D, Proc. Natl. Acad. Sci. USA 85:8464–8467, 1988; Ryder K. et al., Proc. Natl. Acad. Sci., USA 85:1487–1491, 1988; Hattori K. et al., Proc. Natl. Acad. Sci. USA 85:9148–9152, 1988; Schuette J. et al., Cell, 59:987–997, 1989). However, because it is still unclear how these three different jun oncogenes are involved in cell growth, one has to analyze all of the three genes during cell growth.

Northern blot analysis is widely accepted in order to detect specific genes (Sambrook J. et al., Molecular cloning. A labcratory manual, 2nd eds. pp. 7.39–7.52), and some investigators have already adapted this method to detect jun oncogenes (Sherman, et al., Proc. Natl. Acad. Sci. USA, 87:5663–5666, 1990; Oursler M J et al., Proc. Natl. Acad. Sci. USA, 88:6613–6617, 1991). In this method, mRNA is first purified from tissues/cell of researchers' interest, separated on agarose gel electrophoresis. After electrophoresis, mRNA is transferred onto membranes, and hybridized with radioactive probes to identify positive band(s) on autoradiography. However, this method is not so sensitive that it is difficult to identify specific signals if materials have only small quantity of genes. Alternatively, because reverse PCR ("Molecular Cloning") is also used to detect a wide variety of genes from different tissues/cells, this technique is also applicable for the detection of jun oncogene. In this method, mRNA is first convert to cDNA by reverse transcriptase, then specific gene fragments are amplified by PCR by using one set of primers (sense and anti-sense primers). Amplified gene can be seen on agarose gel electrophoresis in the prepense of ethidium bromide. This method is much more sensitive than the conventional Northern blot analysis, but in order to detect three different subtypes of jun oncogenes, one has to prepare six primers. Also, because of different nucleotide sequences between humans and mice, one has to prepare human and mice primers separately.

One goal we accomplished with the present invention was the design of oligonucleotide sequences for both sense and anti-sense primers that could be readily used for detecting the minuscule amounts of the jun gene found in vivo. We also wanted these primers to be useful for detecting both human and murine jun sequences. Thus, we selected primers which fulfilled the below conditions:

(a) A common nucleotide sequence among three subtypes of jun oncogenes (jun-B, c-jun and jun-D), with maximum 4 base mismatches among them;

(b) A common nucleotide sequence among humans and mice, with maximum 4 base mismatches between them;

(c) At least 5 bases from 3' end are 100% identical without any mismatches among three subtypes and between humans and mice;

(d) A nucleotide sequence length in both sense primer and anti-sense primer from 17 to 50;

(e) A difference of $T_m$ between sense primer and anti-sense primer is within 2 degree C.;

(f) Lack of complementary structure with more than 4 bases long in either the sense or the anti-sense primer;

(g) Lack of complementary structure with more than 4 bases long between the sense and the anti-sense primer;

(h) Both the sense and the anti-sense primer exist in the area of coding sequence;

(i) The length of DNA to be amplified is greater than 200 bases; and (j) The nucleotide sequence homology of amplified genes among three subtypes of jun oncogenes is not greater than 80%, and after gene amplification by the PCR, one can characterize each subtype of jun ongenes by Southern Blot.

DNA fragments (both sense and anti-sense primers) which satisfy the conditions as shown above were investigated and the several candidate oligonucleotides were synthesized. The test results showed the sense primer 5'-CCCTGAAGGAGGAGCCGCAGAC-3' (SEQ ID NO:310) and anti-sense primer 5'-CGTGGGTCAAGACTCTGCTTGAGCTG-3' (SEQ ID NO:324) were desirable candidates.

Table 15 shows the nucleotide sequence homology between a preferred sense primer and three subtypes of jun oncogenes in both humans and mice.

TABLE 15

|  |  | Sense primer<br>5'-CCCTGAAGGAGGAGCCGCAGAC-3' | (SEQ ID NO:310) |
|---|---|---|---|
| Mouse | jun-B | --T-T---A-------------- | (SEQ ID NO:311) |
|  | c-jun | ----------A------------ | (SEQ ID NO:312) |
| Human | jun-B | --T-C--------A--------- | (SEQ ID NO:313) |
|  | c-jun | ----------------T----- | (SEQ ID NO:314) |

-: indicates identical base to the sense primer.

In addition, Table 16 shows the nucleotide sequence homology between the sense primers and three subtypes of jun oncogenes in both humans and mice.

TABLE 16

|  |  | Antisense primer<br>3'-GTCGAGTTCGTCTTTCAGAACTGGGTGC-5' | (SEQ ID NO:315) |
|---|---|---|---|
| Mouse | jun-B | ------------C-------A- | (SEQ ID NO:316) |
|  | c-jun | -----------------T---- | (SEQ ID NO:317) |
|  | jun-D | ----T--------G-G-C----- | (SEQ ID NO:318) |
| Human | jun-B | ----T----C------------ | (SEQ ID NO:319) |
|  | c-jun | ----T----------------- | (SEQ ID NO:320) |

-: indicates identical base to the sense primer.

Also, Table 17 shows nucleotide sequence homology of amplified genes between each of subtypes of jun oncogenes.

TABLE 17

| Subtypes | Homology (%) |
|---|---|
| jun-B & c-jun | 72.0 |
| jun-B & jun-D | 73.6 |
| c-jun & jun-D | 75.3 |

Table 18 shows the homology between human and mouse subtypes.

TABLE 18

| Subtypes | Homology between human & mouse (%) |
|---|---|
| jun-B | 93.0 |
| c-jun | 91.9 |

The primer sequences can be modified in a variety of ways. For example, a primary amine residue, nucleotide sequence recognized by a restriction enzyme, or RNA promoter sequences for further modification after PCR amplification, can be added to the 5' end of the primers. These modifications are represented herein by the designation "X". Thus, for example, a modified primer as shown in Table 16, can be represented as 5'-XCGTGGGTCAAGACTTCTGCTTGAGCTG-3' (SEQ ID NO:86) can also be used, in which X represents the primary amine residue, nucleotide sequence recognized by the restriction enzyme, or RNA promoter sequences for further modification after PCR amplification.

The attachment of a restriction site at the 5' end (X) is useful for cloning of amplified genes. The attachment of RNA promoter sequences at 5' end (X) is useful in RNA transcription and RNA transcription-based amplification. The attachment of primary amine at the 5' end is useful for coupling reaction to labeling compounds or solid supports, so that the amplified gene can be easily quantified.

For the above-mentioned nucleotide sequence (X) which undergoes cutting by a restriction enzyme, instead of those nucleotide sequences with higher frequency such as Eco RI or Bam HI, it is often desirable to use longer recognition sequences (e.g. 8 bases) which appear in lower frequency such as the nucleotide sequence, 5'-GCGGCCGC-3', which is recognized by NotI or the nucleotide sequence, 5'-TTAATTAA-3', which is recognized by PacI. The reason for this is the relatively common nucleotide sequences recognized by EcoRI or BamHI can result in false positive reaction during PCR amplification because of priming of primers to undesirable DNA sequences.

The above-mentioned nucleotide sequence (X) containing an RNA promoter can be any of a variety of such sequences, such as the T7, SP6 or T3 RNA promoter sequences.

The above-mentioned primary amine residues (X) can be added at the 5' end during oligonucleotide synthesis.

The DNA fragments for the sense primer and anti-sense primer in this invention can be easily synthesized in DNA synthesizer which are available in the market. These synthesized oligonucleotides can be purified by high pressure liquid chromatography or gel electrophoresis.

The test material to be analyzed is usially a total RNA or purified mRNA from cells or tissues. If desired, cells or tissues can be tested in their natural state without any pretreatment; however, in the case of drug testing, this can be accomplished by reacting the drug with cells or tissues in the test tube, or the drug can be administered (intravenous injection, subcutaneous injection, intramuscular injection, oral administration, intra-abdominal injection) to a laboratory animal, and after a set time period, cells or tissues can be removed for RNA/mRNA purification.

Methods of purification of total RNA or mRNA are well known in the art. Examples of such methods are the standard protocol described in Sambrook, et al., "Molecular Cloning, A Laboratory Manual, 2nd Ed.," Cold Spring Harbor Press, Cold Spring Harbor, N.Y. (1989), and a commercially available kit such as FastTrack from Invitrogen (San Diego, Calif.). In either case, in order to avoid introducing RNase, hands should preferably be protected with vinyl gloves, and the instruments used for experiments not be touched with bare hands. Also, any glass containers to be used in the experiments should be heated prior to use at approximately 250 degrees C for at least 4 hours. Furthermore, 0.1% diethyl pyrocarbonate (hereafter abbreviated DEPC) is added to the water which is to be used, and after incubation at 37 degrees C overnight, treated water is autoclaved. Other basic procedures are undertaken as outlined in the "Molecular Cloning," pp. 7.3–7.5. Vanadyl ribonucleoside complex can also be added to samples as described above.

The method of synthesis of cDNA from mRNA template using reverse transcriptase is described in the "Molecular Cloning," pp. 8.11–8.13.

For PCR amplification, synthesized cDNA is mixed with sense primer, antisense primer, 4 types of deoxynucleotides (dATP, dCTP, dGTP and dTTP), Taq polymerase, inorganic salts, and other necessary materials, and PCR reaction is undertaken in the Thermal cycler (Perkin-Elmar Cetus). A typical PCR method is described in "Molecular Cloning," pp. 14.2–14.33).

In order to analyze the amplified gene, it is appropriate to use electrophoresis. After the amplified gene undergoes electrophoresis in agarose gel, the DNA is stained with ethidium bromide. The amplified DNA band will be then visible under fluorescent light as described in "Molecular Cloning," pp. E.3–E.4. After taking photographs of the DNA band, it is also possible to quantify the intensity of each bands by scanning photographs and analysis of scanned picture by commercially available system, such as Stratascan (Stratagene, La Jolla).

Furthermore, after agarose gel electrophoresis, amplified genes can be transblotted onto membranes, and subtypes specific genes can be detected by hybridizing with labeled probes followed by exposing labeled signals, such as 32P or chemiluminescence to either Polaroid films or X-ray films (Southern blot).

EXAMPLE 7

Synthesis of Sense and Anti-Sense Primers and Amplification of Mouse Clones of Jun Oncogenes The sense primer SEQ ID NO:9 (s943-2) and the anti-sense oligonucleotide SEQ ID NO:10 (AS1132-2) were synthesized by a synthesizer 380 B type (Applied Biosystems Co.). After treatment with ammonium hydroxide at 55° C. overnight, synthesized oligonucleotides were dryed in a Speed-Vac (Savant Co.), and the concentration was adjusted at 1 microgram/ml with water, and was stored at −20 degrees C until use.

1 microliter of one of the three types of mouse jun clones (jun-B, c-jun, or jun-D, obtained from ATCC), 1 microliter of sense primer, 1 microliter of anti-sense primer, 5 microliters of 10×buffer for PCR (Promega), 1 microliter of 25 mM magnesium chloride, 4 microliters of 10 mM dNTP mix, and 0.5 microliters of Taq polymerase (Promega) were missed, and water was added up to a total volume of 50 microliters. After adding of two drops of mineral oil, PCR was undertaken using the thermal cycler, model 480. After reaction mixture was heated at 95 degree C for 10 min, PCR was carried out with the following cycles 30 times: annealing at 55 degrees C for 1.5 minutes, extension at 72 degrees C for 4 minutes, and denaturing at 95 degrees C for 1.5 minutes.

After PCR, 10 microliters of the sample were mixed with 1 microliter of 10×loading buffer (0.25% bromophenol blue, 0.25% xylenecyanol FF, and 15% Ficoll, Type 400), and electrophoresis was carried out in 1.5% agarose gel containing 5 microgram/ml ethidium bromide. After electrophoresis, the amplified DNA bands were visualized by an ultraviolet light.

As a result, it was found that in each of the cases where the clones jun-B, c-jun, and jun-D were used, a single band for the amplified DNa was observed at the position of approximately 270 bp. This indicates that the above-mentioned set of primers can recognize and amplify all three types of mouse jun oncogenes, such as jun-B, c-jun, jun-D.

(1) Alternative Synthesis of PCR Primers for Amplification of Jun Gene Specific mRNA Sense (jun-s) and antisense (jun-as) oligodeoxyribonucleotides specific for jun oncogenes were synthesized in a DNA synthesizer as described above. The nucleotide sequences were as follows:

jun-s 5'-CCCTGAAGGAAGAGCCGCAGAC-3' (Seq ID NO: 11)

jun-as 5'-CGTGGGTCATGACTTTCTGCTTGAGCTG-3' (Seq ID No: 12)

(2) PCR Amplification of cDNA

To 1 µl of ss-cDNA as described in paragraph (IV), 0.1 µg (1 µl) each of jun-s and jun-as oligonucleotides, 5 µl of 10×PCR buffer (Promega), 1 µl of 25 mM MgCl$_2$, 4 µl of 10 mM dNTIP mixture (Promega), 0.5 µl Taq polymerase (Promega), and 36.5 µl of DEPC-water were mixed. Two drops of mineral oil were overlayered onto the reaction mixture to prevent evaporation. The reaction mixture was first heated at 95° C. for 10 minutes, then PCR was carried out in a Thermal cycler (Model 480, Perkin-Elmer Cetus) with 30 cycles of annealing at 55° C. for 1.5 minutes, extension at 72° C. for 4 minutes and denaturing at 95° C. for 1.5 minutes as described above.

Ten µl of the resultant PCR products were then mixed with 1 µl of 10×loading buffer, and applied to a 1.5% agarose gel containing 5 µg/ml ethidium bromide. Electrophoresis was carried out in a 1×TBE buffer at 100 V/6.5 cm width for approximately 1 hour. After electrophoresis, fluorescent DNA bands were recorded onto Polaroid film. Lanes 1–8 of FIG. 17 indicate duplicate experiments of a 1:1000 dilution, full strength (equivalent to 1 ml of blood), 1:10, and 1:100 dilution respectively of a leukocyte lysate. As shown in FIG. 17, the jun oncogene was amplified from the 1:10 and 1:100 dilution displaying an estimated size of 370 base pairs. This size is similar to the 372 bp theoretical value.

EXAMPLE 8

The Effect of Pretreatment with EGF on Expression of Jun Oncogenes in Human Mononuclear Leukocytes (1) Pretreatment of Human Leukocytes with EGF 40 ml of phosphate buffered saline (PBS) is added to 20 ml of heparinized human blood and mixed. 10 ml each of this sample is overlayered onto 3 ml of IsoLymph, then centrifuged for 30 minutes at 400×g. After washing the pellet three times with PBS, the pellet is resuspended in 3 ml of PBS. 1 ml each of this sample is then placed in three tubes (No. 1 to No. 3). 1 ml of PBS is placed in the fourth tube as control. The total of four tubes are incubated for 10 minutes at 37 degrees C, then EGF (Epidermal Growth Factor) is placed in tube No. 1 at a final concentration of 30 ng/ml. After 15 minutes, EGF is placed in the same manner in tube No. 2, and incubated for another 5 minutes. After 5 min, RNA is extracted from all 4 tubes simultaneously. Thus, the time period of the pretreatment of human leukocytes by EGF is 20 minutes for tube No. 1, 5 minutes for tube No. 2, 0 minutes for tube No. 3.

(2) Extraction of RNA from Cells

The above four tubes are taken out and undergo centrifugation by microfuge for 10 seconds. Then, the supernatant is discarded and the below described lysis buffer is added to the pellet, and after thorough mixing, this is incubated for 30 minutes at 45 degrees C.

Contents of lysis buffer:

10 mM EDTA pH 8.0

0.5% SDS (bacteria removed by non-bacterial filter)

0.2 M NaCl

DEPC treated water

RNA inhibitor 500 unites/ml

Vanadyl Complex 10 mM

Proteinase K 200 microgram/ml (3) Purification of mRNA

After 5 M NaCl is added to the above cell lysates to obtain a final concentration of 0.5 M, oligo (dT) cellulose (Stratagene Co.) is added, and undergoes a reaction for 30 minutes at room temperature. Then, after washing the cellulose in 10 ml binding buffer (20 mM Tris-HCl, pH 7.6, 1 mM EDTA, 0.5 M NaCl) 5 times, 0.35 ml of DEPC treated water is added, and mRNA is eluted from the solid phase. Then, 53 microliters of 2 M sodium acetate and 2.5 times the volume of ethanol are added, and after cooling in a dry ice for 20 minutes, this undergoes centrifugation at 15,000 rpm for 20 minutes. After washing the pellet in 75% ethanol one time, this is dried, and then dissolyed in 10 microliters of DEPC treated water.

(4) Synthesis of cDNA 50 mM Tris-HCl (pH 8.3), 75 mM KCl, 3 mM magnesium chloride, 10 mM DTT, 0.5 mM dNTP (dATP, dCTP, dGTP, dTTP), 50 micrograms/ml oligo (dT) primer, and 10,000 units/ml reverse transcriptase are added to 10 microliters of mRNA obtained from above to a total volume of 20 microliters, and this undergoes a reaction for one hour at 37 degrees C. After the reaction, 20 microliters of a phenol:chloroform:isoamyl alcohol mixture is added, and cooled for 20 minutes in a dry ice to precipitate the cDNA. After centrifugation for 20 minutes at 10,000 rpm, the pellet is washed one time in 75% ethanol. Then, after drying, this is dissolyed in 20 microliters of autoclaved water, and stored at −20 degrees C.

(5) PCR 1 microliter each of sense primer and anti-sense primer (1 mg/ml) for jun gene amplification are added with 2 microliters of cDNA. After mixing this with 50 mM KCl, 10 mM Tris-HCl (pH 8.4), 2.0 mM magnesium chloride, 100 micrograms/ml gelatin, and 0.2 mM dNTP, 2.5 units of Taq polymerase are added (final volume is 50 ml). After reaction mixture was heated at 95 degree C for 10 minutes, PCR was carried out with the following cycles 30 times: annealing at 55 degrees C for 1.5 minutes, extension at 72 degrees C for 4 minutes, and denaturing at 95 degrees C for 1.5 minutes.

(6) Agarose Gel Electrophoresis

After completing PCR, 10 microliters of the reacted solution is taken and undergoes electrophoresis in the same method as described in Example 7. The results showed that in the leukocytes which did not undergo treatment with EGF (i.e., sample which underwent 0 treatment time in tube No. 3) was found to have a minimal band for the amplified DNA at the position of about 270 bp size. However, it was found that the band of amplified DNA was increased after 5 min, then returned to the basal levels within 20 min.

EXAMPLE 9

Effect of Pretreatment with PHA on Jun Gene Expression in Human Leukocytes

In the place of EGF, PHA (at a final concentration of 10 micrograms/ml) was utilized and the pretreatment times were set at 0 minutes, 5 minutes, 15 minutes, and 30 minutes. Other procedures were identical to those of Example 8. As a result, with the pretreatment with PHA done at 15 minutes, it was found that the band for the amplified DNA at the position of approximately 270 bp was maximized, but (the time periods) afterwards, this band decreased.

As with the other mRNAs that can be analyzed in accordance with the methods of the present invention, a variety of jun sequences could serve as sense or antisense primers for PCR methods or as probes for the detection of mRNA as described herein. A method for identification of such sequences that are either common to a variety of jun mRNAs or specific to a particular species is provided hereinbelow. In the preferred embodiment of this method of identification, a computer program is used to identify the sequences. Through use of such a program, we have identified a large number of both common and specific primers and probes.

Provided as Tables 19 through 24 are various sense sequences identified through the use of such a program that are useful as jun gene probes and primers.

All of the sequences listed in these tables are useful within the context of the PCR methods of the present invention. The complementary antisense sequences are also useful in certain aspects of the invention. As will be known by those having ordinary skill in the art, for common probes that are similar, but not identical to target sequences, stringency conditions can be varied (e.g. by changes in temperature and salinity) so that such probes will hybridize or fail to hybridize with a particular target sequence. Thus, also included within the present invention are sequences thar are capable of hybridizing with the same sequences as either the sense sequences listed or their anti-sense counterparts. Additional probes for jun genes include the following:

Common Jun Gene Probes

5'-CCATGTCGATGGGGGACAGCGG-3 (SEQ ID NO: 13)

5'-CTGTTTAAGCTGCGCCACCTG-3' (SEQ ID NO: 14)

5'-GTCTGCGGCTCCTCCTTCAGGG-3' (SEQ ID NO: 15)

5'-CGTGGGTCAAGACTTTCTGCTTGAGCTG-3' (SEQ ID NO: 16)

Specific Probes

B type: 5'-CACITGGTGGCCGCCAG-3' (SEQ ID NO: 17)

C type: 5'-GAGCATGTFGGCCGTGG-3' (SEQ ID NO: 18)

Human D type: 5'-GATGCGCTCCTGCGTGT-3' (SEQ ID NO: 19)

Mouse D type: 5'-GCCTGTTCTGGCTTTTGAGGG-3' (SEQ ID NO: 20)

TABLE 19

Jun-common sense primer (S943-2).

| Locus GenBank | Pos | | Sequences (5'-3') CCGCTGTCCCCCATCGACATGG |
|---|---|---|---|
| Human | | | |
| B: humjunca | 1189 | SEQ ID NO: 21 | ---G----------A------ |
| C: humjuna | 1981 | SEQ ID NO: 22 | --C------------------ |
| D: humjundr | 943 | SEQ ID NO: 23 | ---T----G------------ |
| Mouse | | | |
| B: musjunba | 1079 | SEQ ID NO: 24 | --TG----------A------ |
| C: musjunc | 1344 | SEQ ID NO: 25 | --C--------T--------- |
| C: muscjun | 1646 | SEQ ID NO: 26 | --C--------T--------- |
| C: musjun | 1084 | SEQ ID NO: 27 | --C--------T--------- |
| D: musjund | 927 | SEQ ID NO: 28 | --------G------------ |
| D: musjunda | 782 | SEQ ID NO: 29 | --------G------------ |
| D: musjundr | 793 | SEQ ID NO: 30 | --------G------------ |
| Rat | | | |
| C: atjunap1 | 1082 | SEQ ID NO: 31 | --CT----------------- |

TABLE 19-continued

Jun-common sense primer (S943-2).

| Locus GenBank | Pos | | Sequences (5'-3') CCGCTGTCCCCCATCGACATGG |
|---|---|---|---|
| C: ratrjg9 | 2984 | SEQ ID NO: 32 | --CT----------------- |
| Chicken | | | |
| C: chkjun | 1470 | SEQ ID NO: 33 | --C-------T--T------- |
| Quail | | | |
| C: quljun | 1186 | SEQ ID NO: 34 | --C-------T--T------- |
| Drosophila | | | |
| C: drojun | 1038 | SEQ ID NO: 35 | A-CG-TAAT-----T------ |
| Highest matched sequences in EMBL | | | |
| SDNAM2G Yeast NAM2 gene (SEQ ID NO:36) | | | --------A-A------GAAT |
| PRK2TRFB Plasmid PK2 trfB ope (SEQ ID NO:37) | | | GT--------------GC-T- |
| DMSYT D.metanogaster synap (SEQ ID NO: 38) | | | ------G-A----UC------ |

TABLE 20

Jun-common antisense primer (AS1132-2).

| Locus | Pos | Sequences (5'-3') GTCCACCGCGTCGAATTTGTC |
|---|---|---|
| Human | | |
| B: humjunca | 1378 (SEQ ID NO: 39) | -------G------G------ |
| C: humjuna | 2170 (SEQ ID NO: 40) | -------T------------- |
| D: humjundr | 1132 (SEQ ID NO: 41) | --------------G--C--- |
| Mouse | | |
| B: musjunba | 1268 (SEQ ID NO: 42) | --T-----------G--C--- |
| C: musjunc | 1835 (SEQ ID NO: 43) | --------T--------C--- |
| C: muscjun | 1273 (SEQ ID NO: 44) | --------T--------C--- |
| C: musjun | 1533 (SEQ ID NO: 45) | --------T--------C--- |
| D: musjund | 982 (SEQ ID NO: 46) | -----------GC-G------ |
| D: musjunda | 1116 (SEQ ID NO: 47) | --------------G------ |
| D: musjundr | 971 (SEQ ID NO: 48) | --------------G------ |
| Rat | | |
| C: atjunap1 | 1271 (SEQ ID NO: 49) | --------T------------ |
| C: ratrjg9 | 3173 (SEQ ID NO: 50) | --------T------------ |
| Chicken | | |
| C: chkjun | 1659 (SEQ ID NO: 51) | -----A--T--------C--- |
| Quail | | |
| C: quljun | 1375 (SEQ ID NO: 52) | -----A--T--------C--- |
| Drosophila | | |
| C: drojun | 1227 (SEQ ID NO: 53) | --A-------GC-C--C--- |

TABLE 20-continued

Jun-common antisense primer (AS1132-2).

| Locus | Sequences (5'-3') Pos | GTCCACCGCGTCGAATTTGTC |
|---|---|---|
| Highest matched sequences in EMBL | | |
| HSATFA | Human mRNA for ATF-a (SEQ ID NO: 54) | C-------G---A-C------- |
| ECDCM | E. coli dom gene (SEQ ID NO: 55) | AA---------------ACCA |
| ECDCMA | E. coli dom (SEQ ID NO: 56) | AA---------------ACCA |
| OCIGKCI | Rabbit Ig germkine (SEQ ID NO: 57) | k--------G--------G-CGA |
| OCIGO5 | Rabbit Ig k2 L chain (SEQ ID NO: 58) | ---------G--------G-CGA |
| OCK1B4 | Rabbit Ig kappa L (SEQ ID NO: 59) | --------G---------G-CGA |
| OCIGKCG | Rabbit Ig kappa2 J-C (SEQ ID NO: 60) | ---------G--------G-CGA |
| OCIGKCO2 | Rabbit Ig kappa1 J-C (SEQ ID NO: 61) | ---------G--------G-CGA |

TABLE 21

Jun-B specific probe (B-1258).

| B1258(5'-3') | GenBank CTGGCGGCCACCAAGTG | |
|---|---|---|
| Human | | |
| B: HUMJUNCA | ----------------- | (SEQ ID NO: 62) |
| C: HUMJUNA | A-C--T---T------- | (SEQ ID NO: 63) |
| D: HUMJUNDR | A-----------TCCAA | (SEQ ID NO: 64) |
| Mouse | | |
| B: MUSJUNBA | ----------------- | (SEQ ID NO: 65) |
| C: MUSJUNC | A-T--C---T------- | (SEQ ID NO: 66) |
| MUSCJUN | A-T--C---T------- | (SEQ ID NO: 67) |
| MUSJUN | A-T--C---T------- | (SEQ ID NO: 68) |
| D: MUSJUND | -----C------CCCG- | (SEQ ID NO: 69) |
| MUSJUNDA | ------T-----GCCA- | (SEQ ID NO: 70) |
| MUSJUNDR | ------T-----GCCA- | (SEQ ID NO: 71) |
| Rat | | |
| C: RATRJG9 | ------T-----GCCAA | (SEQ ID NO: 72) |
| RATJUNAP | A-C--T---T------- | (SEQ ID NO: 73) |
| Chicken | | |
| C: CHKJUN | -C-----G-------CCC | (SEQ ID NO: 74) |
| Quail | | |
| C: QULJUN | GGC-----AG----TG- | (SEQ ID NO: 75) |
| Drosophila | | |
| C: DROJUN | G----T--AT------- | (SEQ ID NO: 76) |
| Homologous sequences in GenBank | | |
| J04695 | FIG. 2. Nucleo.  G--------A------G | (SEQ ID NO: 77) |

TABLE 21-continued

Jun-B specific probe (B-1258).

| | GenBank | |
|---|---|---|
| B1258(5'-3') | | CTGGCGGCCACCAAGTG |
| M27884 | FIG. 2. Nucleo. | --------A------GC (SEQ ID NO: 78) |
| HUMCNPG2 | green cone photo. | --------------T-AA (SEQ ID NO: 79) |
| HUMCNPR2 | green cone photo. | --------------T-AA (SEQ ID NO: 80) |
| HUMPIGMF2 | colour-blind pho. | --------------T-AA (SEQ ID NO: 81) |

TABLE 22 c-jun specific probe (C2147).

| Subtype | GenBank name | C2147.DNA CCACGGCCAACATGCTC | |
|---|---|---|---|
| Human | | | |
| B: | HUMJUNCA | -G---A---C---CAGC | (SEQ ID NO: 82) |
| C: | HUMJUNA | ----------------- | (SEQ ID NO: 83) |
| D: | HUMJUNDR | -------G-G-C----G | (SEQ ID NO: 84) |
| Mouse | | | |
| B: | MUSJUNBA | -G-------C---CAGC | (SEQ ID NO: 85) |
| C: | MUSJUN | ----------------- | (SEQ ID NO: 87) |
| | MUSCJUN | ----------------- | (SEQ ID NO: 88) |
| | MUSJUNC | ----------------- | (SEQ ID NO: 89) |
| D: | MUSJUND | ----C----G-C----G | (SEQ ID NO: 90) |
| | MUSJUNDR | ----C----G-C----G | (SEQ ID NO: 91) |
| | MUSJUNDA | ----C----G-C----G | (SEQ ID NO: 92) |
| Rat | | | |
| C: | RATJUNAP | ----------------- | (SEQ ID NO: 93) |
| | RATRJG9 | ----C------------ | (SEQ ID NO: 94) |
| Chicken | | | |
| C: | CHKJUN | ----------------- | (SEQ ID NO: 95) |
| Quail | | | |
| C: | QULJUN | ----T------------ | (SEQ ID NO: 96) |
| Drosophila | | | |
| C: | DROJUN | CCTACA--------ACC | (SEQ ID NO: 97) |
| Homologous sequences in GenBank | | | |
| MXBPALPA | L.enzymogenes | --------------CG-- | (SEQ ID NO: 98) |
| MXBPALP | L.enzymogenes | --------------CG-- | (SEQ ID NO: 99) |

TABLE 23

Human jun-D specific probe (HUMD965)

| Subtype | GenBank name | HUMD965<br>ACACGCAGGAGCGCATC | |
|---|---|---|---|
| Human | | | |
| B: | HUMJUNCA | GG-A--T---------- | (SEQ ID NO: 100) |
| C: | HUMJUNA | -GT-C--------G--- | (SEQ ID NO: 101) |
| D: | HUMJUNDR | ----------------- | (SEQ ID NO: 102) |
| Mouse | | | |
| B: | MUSJUNBA | -AGAC------------ | (SEQ ID NO: 103) |
| C: | MUSJUNC | -GT-T--------G--- | (SEQ ID NO: 104) |
| | MUSCJUN | -GT-T--------G--- | (SEQ ID NO: 105) |
| | MUSJUN | -GT-T--------G--- | (SEQ ID NO: 106) |
| D: | MUSJUND | -------A--A------ | (SEQ ID NO: 107) |
| | MUSJUNDA | -------A--A------ | (SEQ ID NO: 108) |
| | MUSJUNDR | -------A--A------ | (SEQ ID NO: 109) |
| Rat | | | |
| C: | RATJUNAP | -GT-T--------G--- | (SEQ ID NO: 110) |
| | RATRJG9 | -GT-T--------G--- | (SEQ ID NO: 111) |
| Chicken | | | |
| C: | CHKJUN | -GT--------A-A--- | (SEQ ID NO: 112) |
| Quail | | | |
| C: | QULJUN | -GT--------A-A--- | (SEQ ID NO: 113) |
| Drosophila | | | |
| C: | DROJUN | G--A--T---------- | (SEQ ID NO: 114) |
| Homologous sequences in GenBank | | | |
| CELPOLII | C.elegans RNA | --------------A-AA | (SEQ ID NO: 115) |
| ECOPRIAY | E. coli primo. | -ACA-------------- | (SEQ ID NO: 116) |
| SINOCK82 | Ockelbo 82 g. | C------------TGC | (SEQ ID NO: 117) |
| TRPPROC | Treponema pa. | G------------TGC | (SEQ ID NO: 118) |
| ECOCYSJIHA | E. coli NADPH- | ------T-------G-G | (SEQ ID NO: 119) |

TABLE 24

Mouse jun-D specific probe (MUSD1063).

| Subtype | GenBank name | MUSD1063.DNA<br>CCCTCAAAAGCCAGAACACCG | |
|---|---|---|---|
| Human | | | |
| B: | HUMJUNCA | -G-----GGC-G-----G-G- | (SEQ ID NO: 120) |
| C: | HUMJUNA | AA--GC-C-----------GC | (SEQ ID NO: 121) |
| D: | HUMJUNDR | -------G--T---------G- | (SEQ ID NO: 122) |
| Mouse | | | |
| B: | MUSJUNBA | TA---TCC----TCTG----C | (SEQ ID NO: 123) |
| C: | MUSJUNC | AA--GC-T-----------GC | (SEQ ID NO: 124) |

TABLE 24-continued

Mouse jun-D specific probe (MUSD1063).

| Subtype | GenBank name | MUSD1063.DNA<br>CCCTCAAAAGCCAGAACACCG |
|---|---|---|
| | MUSJUN | AA--GC-T----------GC (SEQ ID NO: 125) |
| | MUSCJUN | AA--GC-T----------GC (SEQ ID NO: 126) |
| D: | MUSJUNDA | -------------------- (SEQ ID NO: 127) |
| | MUSJUNDR | -------------------- (SEQ ID NO: 128) |
| | MUSJUND | -------------------- (SEQ ID NO: 129) |

Rat

| C: | RATRJG9 | G-----GCC---GC-C---TT (SEQ ID NO: 130) |
|---|---|---|
| | RATJUNAP | G-----GCC---GC-C---TT (SEQ ID NO: 131) |

Chicken

| C: | CHKJUN | A---G-GG-A-A-----G--- (SEQ ID NO: 132) |
|---|---|---|

Quail

| C: | QULJUN | ---C--G-T-----TG--G-A (SEQ ID NO: 133) |
|---|---|---|

Drosophila

| C: | DROJUN | A------GGA---TGTGGCGC (SEQ ID NO: 134) |
|---|---|---|

Homologous sequences in GenBank.

| M27221 | | TG--------T--T------- (SEQ ID NO: 135) |
|---|---|---|
| DROAMY | D.erecta | G-------G-A--T------- (SEQ ID NO: 136) |
| DROAMYQ | D.erecta | G-------G-A--T------- (SEQ ID NO: 137) |
| HUMIGCMUDE | Immunoglob. | A--C-------------GTT (SEQ ID NO: 138) |

TABLE 25

Human-rodent common jun-B specific probes.

| | Name in<br>GenBank | B-504 (5'-3')<br>CACGACTACAAACTCCTGAAAC | Seq. ID No: | B-739 (5'-3')<br>GGACAGTACTTTTACCCCCG | Seq. ID No: | Size<br>(bp) |
|---|---|---|---|---|---|---|
| Mouse | | | | | | |
| jun-B | MUSJUNBA | --------------------- | 600 | -------------------- | 321 | 251 |
| c-JUN | MUSCJUN | A-AT--A-T-----AT-----A | 601 | ACC----T---G-G-----AA | 322 | |
| jun-D | MUSJUND | T----G-C--C-T-----TTCC | 602 | ACG----T-C-C-----GAA | 323 | |
| Human | | | | | | |
| jun-B | HUMJUNCA | --------------------- | 603 | -------------------- | 325 | 251 |
| C-jun | HUMJUNA | AGTA--CC---GA--------- | 604 | ---A--C-GCGG------AC | 326 | |
| jun-D | HUMJUNDR | T----G-C--C-T-----TTTG | 605 | TC-----T-C-C------AA | 327 | |
| GenBank | | | | | | |
| | MUSMETI | -------T---CG------GTA | 606 | | | |
| | RATMYHCD2 | | | ------C-------AT---A | 328 | |

*Size of PCR products using B-504 and B-739 as primers.
**The highest matched sequences in GenBank (release 68.0) next to the jun genes.

TABLE 26

Human-rodent common c-jun specific probes.

| | Name in GenBank | C-2101 (5'-3') GAGGAAAAAGTGAAAACCTTGAAAGC | Seq. ID No: | C-2219 (5'-3') GCCAACTCATGCTAACGCAG | Seq. ID No: | Size (bp) |
|---|---|---|---|---|---|---|
| Mouse | | | | | | |
| jun-B | MUSJUNBA | -----C--G-----G--AC-C--G-- | 614 | ----GT-GC-----GG-GTC | 329 | |
| c-JUN | MUSCJUN | -------------------------- | 615 | -------------------- | 330 | 138 |
| jun-D | MUSJUND | -----G-----C--G---C-C---AG | 616 | T----A-GCC--A-G----A | 331 | |
| Human | | | | | | |
| jun-B | HUMJUNCA | -----C--G-----G--GC-C--G-- | 617 | ----G-C-CC-AG-----GC | 332 | |
| C-jun | HUMJUNA | -------------------------- | 618 | -------------------- | 333 | 138 |
| jun-D | HUMJUNDR | --A--G--------G---C-C--GAG | 619 | T----G-GCC--A-G----A | 334 | |
| GenBank | | | | | | |
| | HUMGASTA | A-A------AA-----A---A----- | 620 | | | |
| | MUSOCT22 | | | C------------G---GGC | 335 | |

*Size of PCR products using C-2101 and C-2219 as primers.
**The highest matched sequences in GenBank (release 68.0) next to the jun genes.

TABLE 27

Human-rodent common jun-D specific probes.

| | Name in GenBank | D-916 (5'-3') GACGTGCCGAGCTTCGG | Seq. ID No: | D-1153 (5'-3') AAAGTCCTCAGCCACGTCAAC | Seq. ID No: | Size (bp) |
|---|---|---|---|---|---|---|
| Mouse | | | | | | |
| jun-B | MUSJUNBA | CTG-G-------ACT-- | 628 | --G---A-G-C---T----G- | 336 | |
| c-JUN | MUSCJUN | T-A-----AG---AGAC | 629 | ------A-G-A------T--- | 337 | 258 |
| jun-D | MUSJUND | ----------------- | 630 | --------------------- | 338 | |
| Human | | | | | | |
| jun-B | HUMJUNCA | C---C----CC-----C | 631 | --G---A-G-C--------G- | 339 | |
| C-jun | HUMJUNA | T-A---TT-----CG-- | 632 | ------A-G-A------T--- | 340 | |
| jun-D | HUMJUNDR | ----------------- | 633 | --------------------- | 341 | 258 |
| GenBank | | | | | | |
| | HUMTRKR | ------TG--------- | 634 | | | |
| | HUMBSSL | | | ---A-----------A--CTG | 342 | |

*Size of PCR products using D-916 and D-1153 as primers.
**The highest matched sequences in GenBank (release 68.0) next to the jun genes.

Identifying Probes and PCR Primers

Probes and PCR primers for use in the methods of the present invention can be identified in any way known to the art. Preferably, however, such probes and primers are identified by a computer. We have developed a novel computer system for identifying the sequences to be used in such probes and primers. This system is an automated system which allows the user to calculate and design extremely accurate oligonucleotide probes and PCR primers.

The software of the present invention runs under Microsoft Windows® on IBM® compatible personal computers (PC's). This invention allows a researcher to design oligonucleotide probes based on the GenBank database of DNA and mRNA sequences. The present invention further allows examination of probes for specificity or commonality with respect to a user-selected target gene sequences. Hybridization strength between a probe and a target subsequence of DNA or mRNA can be estimated through a hybridization strength model. Quantitatively, hybridization strength is given as the melting temperature (Tm).

Two models for estimating hybridization strength models are supported by this invention: 1) the Mismatch Model and 2) the H-Site Model. In either case, the user can select the following calculations for each probe, results of which are then made available for display and analysis: 1) Sequence, Melting Temperature (Tm) and Hairpin characteristics (a hairpin is a nucleoitide sequence that is homologous to itself and can "fold back" with one portion of the probe hybridizing to another portion of the same probe); 2) Hybridization to other species within the preparation mixture; and (3) Location and Tm for the strongest hybridizations. The results of the invention's calculations are then displayed on a Mitsuhashi Probe Selection Diagram (MPSD) which is a graphic display of all potential hybridizations between the target mRNA and the probe sequences in the preparation.

The Main OligoProbe Design Station dialog window controls all user-definable settings in the program. The user is offered a number of options at this window. The File option allows the user to print, print in color, save selected probes, and exit the program. The Preparation option allows the user to open and create preparation (PRP) files. The Models option allows the user to chose between the two hybridization models currently supported by the OligoProbe DesignStation: 1) the H-Site Model and 2) the Mismatch Model.

If the user selects the H-Site Model option, the melting temperature for each probe and the nucleation threshold parameters can be set. The nucleation threshold is the number of base pairs constituting a nucleation site (a subsequence with an exact match). If the user selects the Mismatch Model option, the probe length and mismatches (N) can be set.

Mismatch Model

The Mismatch Model is used for designing DNA and mRNA probes utilizing sequence database information from sources such as GenBank. In this Model, hybridization strength is related only to the number of base pair mismatches between a probe and its target. Generally, the more mismatches a user allows when setting parameters, the more probes will be identified. The Mismatch Model does not take into account the GC content of candidate probes so there is no calculation of the probe's binding strength.

The basic technologies employed by the Mismatch model are hashing and continuous seed filtration. Hashing involves the application of an algorithm to the records in a set of data to obtain a symmetric grouping of the records. When using an indexed set of data such as a database, hashing is the process of transforming a record key to an index value for storing and retrieving a record. The Mismatch Model is essentially a quick process for determining exact and inexact matching between DNA and mRNA sequences to support the Mitsuhashi Probe Selection Diagram (MPSD).

The algorithm used by the Mismatch Model is based on the Waterman-Pevzner Algorithm (WPALG), which is a computer-based probe selection process. Essentially, this is a combination of new and improved pattern matching processes. See Hume and Sunday (1991, Ref. 4), Landau et al (1986–1990, Refs. 6, 7, 8), Grossi and Luccio (1989, Ref. 3), and Ukkonen (1982, Ref. 14).

There are three principal programs that make up the Mismatch Model in this implementation of the invention. The first is designated by the inventors as "k_diff." WPALG uses k_diff to find all locations of matches of length greater than or equal to one (1) (length is user-specified) with less than or equal to k number of mismatches (k is also user-specified) between the two sequences. If a candidate oligonucleotide probe fails to match that well, it is considered unique. k_diff uses hashing and continuous seed filtration, and looks for homologs by searching GenBank and other databases with similar file formats. The technique of continuous seed filtration allows for much more efficient searching than previously implemented techniques.

A seed is defined in this invention to be a subsequence having a length equal to the longest exact match in the worst case scenario. For example, suppose the user selects a probe length (l) of 18, with 2 or fewer mismatches (k). If a match exists with 2 mismatches, then there must be a perfectly matching subsequence of length equal to 6. Once the seed length has been determined, the Mismatch Model looks at all substrings of that seed length (in this example, the seed length would be 6), finds the perfectly matched base pair subsequence of length equals 6, and then looks to see if this subsequence extends to a sequence of length equal to the user selected probe length (i.e., 18 in this example). If so, a candidate probe has been found that meets the user's criteria.

Where the seed size is large (i.e., a long string of unique nucleotides), the program allocates a relatively large amount of memory for the hash table. This invention has an option that allows memory allocation for GenBank entries just once at the beginning of the program, instead of reallocating memory for each GenBank entry. This reduces input time for GenBank entries by as much as a factor of two (2), but this method requires the user to know the maximum GenBank entry size in advance.

A probe is found to hybridize if it has k or fewer mismatches with a target sequence from the database or file searched. The hit extension time for all appropriate parameters of the Mismatch Model has been found by experimentation to be less than thirty-five (35) seconds, except in one case where the minimum probe length (l) was set to 24 and the maximum number of mismatches (k) was set to four (4). This situation would rarely be used in real gene localization experiments because the hybridization conditions are too weak.

H-Site Model

In this embodiment of the invention, the second hybridization strength model is termed the H-Site Model. One aspect of the H-Site Model uses a generalization of an experimental formula to analize nucleotide binding strength. The basic formula on which this aspect of the model is built is as follows:

$$Tm=81.5-16.6(\log[Na])-0.63\%(formamide)+0.41(\%(G+C))-600/N$$

In this formula, $\log[Na]$ is the log of the sodium concentration, $\%(G+C)$ is the fraction of matched base pairs which are G–C complementary, and N is the probe length. This formula relates the fact that melting temperature is a function of both probe length and percent GC content. This basic formula has been modified in this invention to account for the presence of mismatches. Each percent of mismatch reduces the melting temperature by an average of 1.25° (2° C. for an AT mismatch, and 4° C. for a GC mismatch). This formula is, however, an approximation. The actual melting temperature might potentially differ from this approximation, especially for short probes or probes with a relatively large number of mismatches.

Hybridization strength in the H-Site Modlel is related to each of the following factors: 1) "binding region"; 2) type of mismatch (GC or AT substitution); 3) length of the probe; 4) GC content of the binding region; and 5) existence of a "nucleation site" (a subsequence with an exact match). The type of mismatch and GC content of the binding region from each sequence contributes to a candidate probe's binding strength. The binding strength from each probe is thereby determined enabling the user to select an optimal probe.

The fundamental assumption of the H-Site Model is that binding strength is mostly determined by a paired subsequence of the probe and target, called the binding region. If the subsequence binding region contains more GC pairs than AT pairs, the binding strength will be higher due to the greater number of hydrogen bonds between G and C bases (three bonds) in comparison to A and T bases (two bonds). Thus, GC rich probes have a higher melting temperature and subsequently form stronger hybridizations.

In the H-Site Model the program determines optimal probes, ideally without any mismatches to the target gene. With this model, however, a candidate probe can have more AT mismatches if the sequence is GC rich. The amount of allowable AT mismatches in a specific sequence is determined in the present invention program by looking primarily at subsequence regions of the probe and target that match without penalizing the probe for areas that mismatch. If the mismatches are located at either or both of the ends of the binding region, there is little effect on the overall stability of the base-pairing. Centrally located mismatches in the binding region are much more deleterious, as this will significantly lower the binding strength of the probe.

The formula cited above for the melting temperature applies within the binding region. The length of the probe is used to calculate percentages, but all other parameters of the formula are applied to the binding region only. The H-Site Model further assumes the existence of a nucleation site. The length of this nucleation site may be set by the user. Typically, a value of 8 to 10 base pairs is used. To complete the H-Site Model, the binding region is chosen so as to maximize the melting temperature Tm among all regions containing a nucleation site, assuming one exists (otherwise, Tm=0).

The H-Site Model is more complex than the Mismatch Model discussed above in that hybridization strength is modeled as a sum of multiple subsequence contributions, with matches generally providing positive binding energy and mismatches generally providing negative binding energy. The exact binding energies to be used depend only on the matched or mismatched pair. These coefficients may be specified by the user, although in the current version of this invention these coefficients are not explicitly user-selectable, but rather are selected to best fit the hybridization strength formulas developed by Itakura et al (1984, Ref. 5), Bolton and McCarthy (1962, Ref. 2), Benner et al (1973, Ref. 1), and Southern (1975, Ref. 13).

A unique aspect of the H-Site Model is that hybridization strength is determined by the optimal binding region between the candidate probe and binding locus. This binding region is called the hybridization site, or h-site, and is selected so as to maximize overall hybridization strength, so that mismatches outside the binding region do not detract from the estimated hybridization strength. Several other unique features of the H-Site Model include the fact that it is more oriented toward RNA and especially cDNA sequences than DNA sequences, and the fact that the user has control over preparation and environmental variables.

The emphasis on RNA and cDNA sequences allows the user to concentrate on coding regions of genes, rather than necessitating sorting through all of a genomic sequence for the desired probe. The enhanced user control over environmental and preparation variables allows the user to more accurately simulate laboratory conditions that closely correspond with any experiments he or she is conducting. Further, this implementation of the invention does some preliminary preprocessing of the GenBank database to sort out and select the cDNA sequences. This is done by locating a keyword (in this case CDS) in each GenBank record, thereby eliminating any sequences containing introns.

Figure 28A:
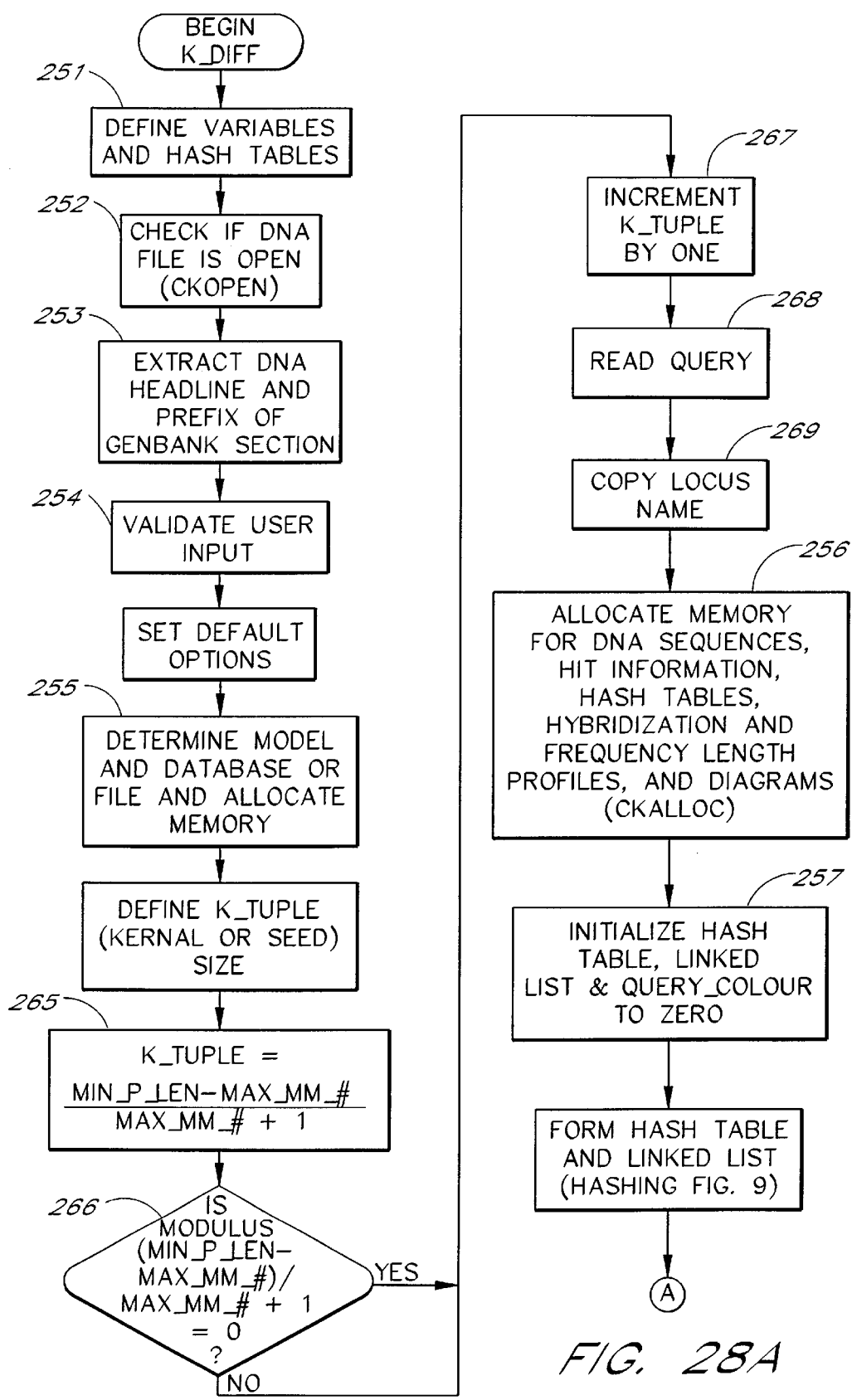
FIG. 28 is a flow chart of the k_diff module of this invention.
Figure 28B:
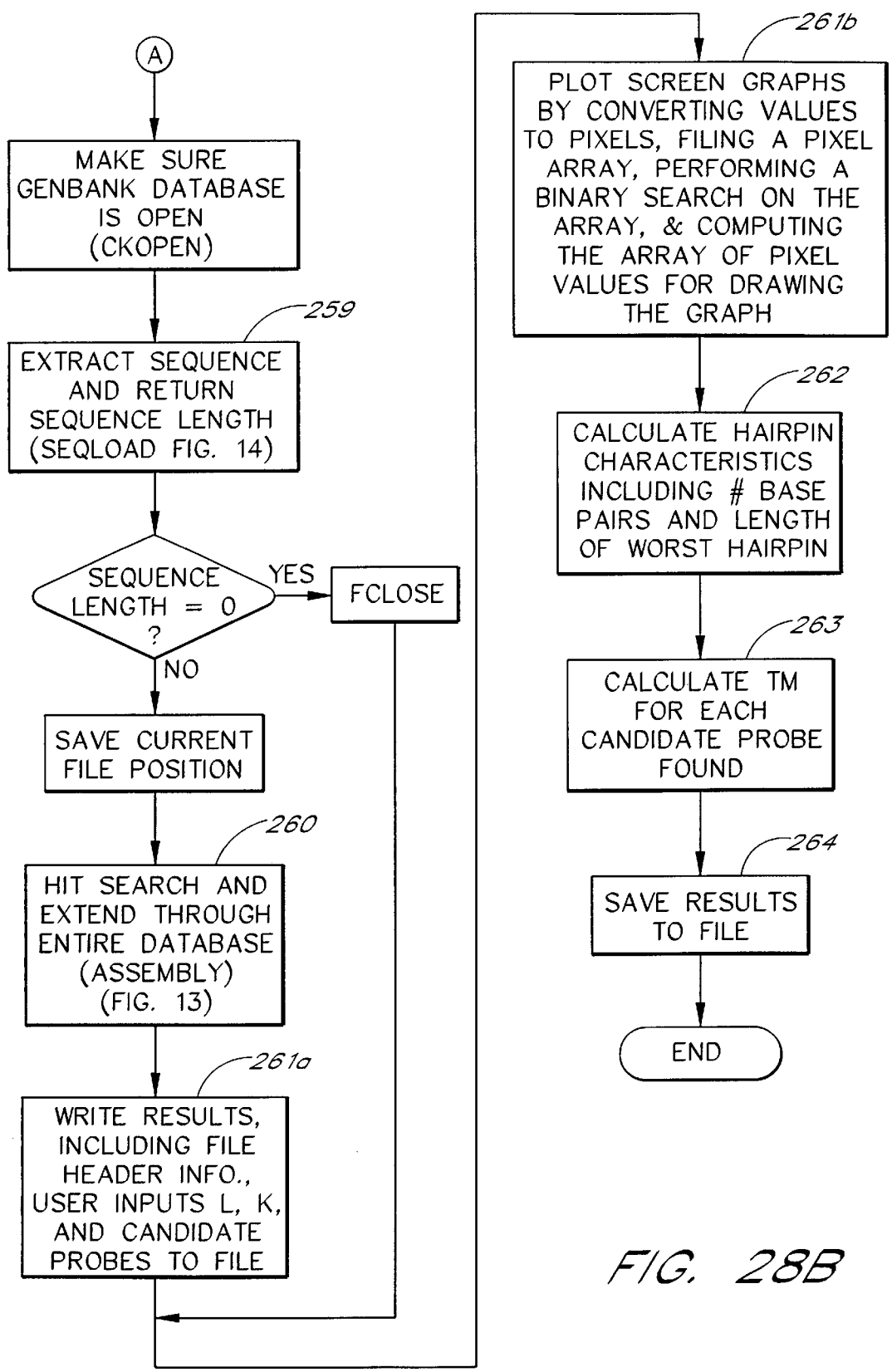

The Mitsuhashi Probe Selection Diagram (MPSD), FIG. 28, is a key feature of this invention, as it is a unique way of visualizing the results of the probe designed by the Mismatch and H-Site Models. It is a graphic display of all of the hybridizations of candidate oligonucleotide probes and the target with all sequences in the preparation. Given a gene sequence database and a target mRNA sequence, the MPSD graphically displays all of the candidate probes and their hybridization strengths with all sequences from the database. In the present implementation, each melting temperature is displayed as a different color, from red (highest Tm) to blue (lowest Tm). The MPSD allows the user to see visually the number of false hybridizations at various temperatures for all candidate probes, and the sources of these false hybridizations (with a loci and sequence comparison). A locus may be a specific site or place, or, in the genetic sense, a locus is any of the homologous parts of a pair of chromosomes that may be occupied by allelic genes.

These probes may then be used to test for the presence of precursors of specific proteins in living tissues. The oligonucleotide probes designed with this invention may be used for medical diagnostic kits, DNA identification, and potentially continuous monitoring of metabolic processes in human beings. The present implementation of this computerized design tool runs under Microsoft® Windows™ v. 3.1 (made by Microsoft Corporation; Redmond, Wash.) on IBM® compatible personal computers (PC's).

The H-Site Model of this invention is unique in that it offers a multitude of information on selected probes and original and distinctive means of visualizing, analyzing and selecting among candidate probes designed with the invention. Candidate probes are analyzed using the H-Site Model for their binding specificity relative to some known set of mRNA or DNA sequences, collected in a database such as the GenBank database. The first step involves selection of candidate probes at some or all the positions along a given target. Next, a melting temperature model is selected, and an accounting is made of how many false hybridizations each candidate probe will produce and what the melting temperature of each will be. Lastly, the results are presented to the researcher along with a unique set of tools for visualizing, analyzing and selecting among the candidate probes.

This invention is both much faster and much more accurate than the methods that are currently in use. It is unique because it is the only method that can find not only the most specific and unique sequence, but also the common sequences. Further, it allows the user to perform many types of analysis on the candidate probes, in addition to comparing those probes in various ways to the target sequences and to each other.

Therefore, it is the object of this invention to provide a practical and user-friendly system that allows a researcher to design both specific and common oligonucleotide probes, and to do this in less time and with much more accuracy than currently done.

Figure 20:
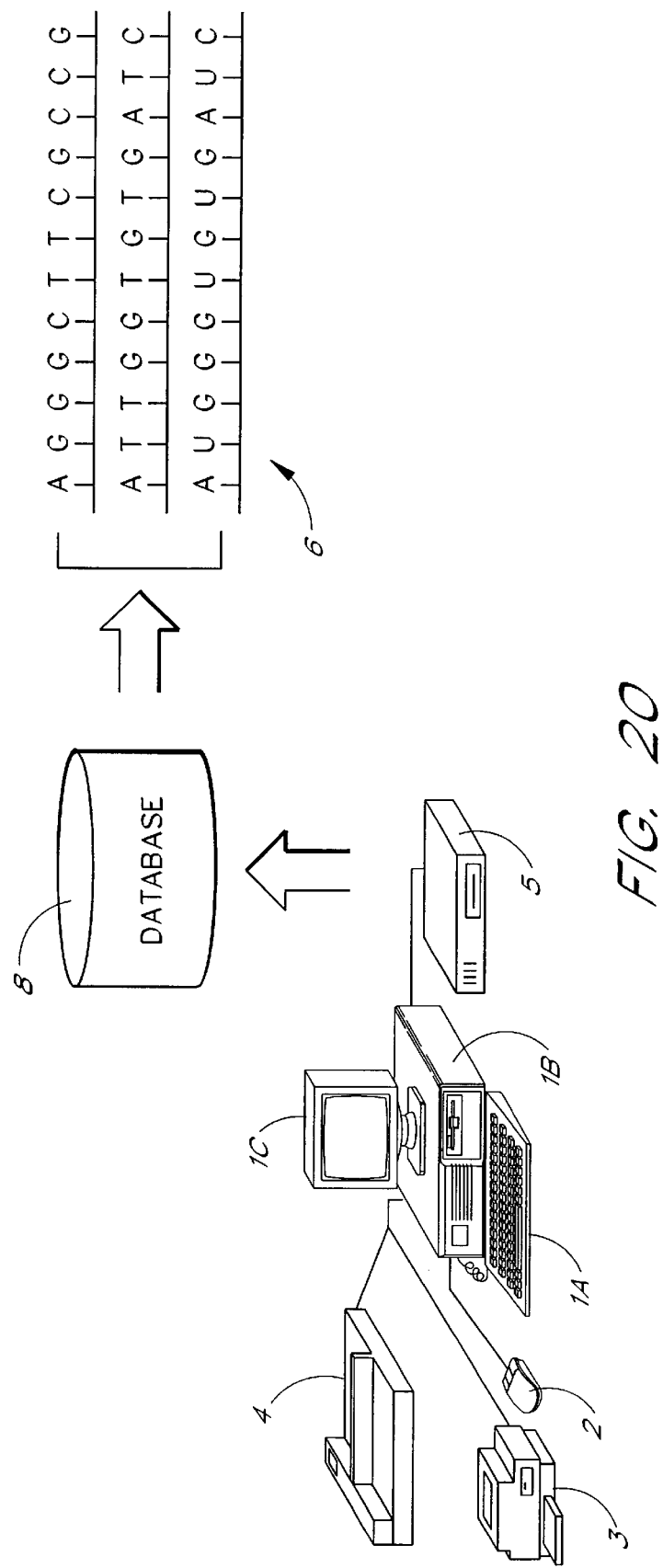
FIG. 20 is a simplified block diagram of a computer system illustrating the overall design of this invention.

This invention is employed in the form best seen in FIG. 20. There, the combination of this invention consists of an IBM® compatible personal computer (PC), running software specific to this invention, and having access to a distributed database with the file formats found in the GenBank database and other related databases.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

The preferred computer hardware capable of operating this invention involves of a system with at least the following specifications (FIG. 20): 1) an IBM® compatible PC, generally designated 1A, 1B, and 1C, with an 80486 coprocessor, running at 33 Mhz or faster; 2) 8 or more MB of RAM, 1A; 3) a hard disk 1B with at least 200 MB of storage space, but preferably 1 GB; 4) a VGA color monitor (1C) with graphics capabilities of a size sufficient to display the invention's output in readable format, preferably with a resolution of 1024×768; and 5) a 580 MB CD ROM drive 5 (1B of FIG. 20 generally refers to the internal storage systems included in this PC, clockwise from upper right, two floppy drives, and a hard disk). Because the software of this invention preferably has a Microsoft® Windows™ interface, the user will also need a mouse 2, or some other type of pointing device.

The preferred embodiment of this invention would also include a laser printer 3 and/or a color plotter 4. The invention may also require a modem (which can be internal or external) if the user does not have access to the CD ROM versions of the GenBank database 8 (containing a variable number of gene sequences 6). If a modem is used, information and instructions are transmitted via telephone lines to and from the GenBank database 8. If a CD ROM drive 5 is used, the GenBank database (or specific portions of it) is stored on a number of CDs.

The computer system should preferably have at least the Microsoft® DOS version 5.0 operating system running Microsoft® Windows™ version 3.1. All of the programs in the preferred embodiment of the invention were written in the Borland® C++ (Borland International, Inc.; Scotts Valley, Calif.) computer language. It should be noted that subsequently developed computers, storage systems, and languages may be adapted to utilize this invention and vice versa.

This inventive computer program is designed to enable the user to access DNA, mRNA and cDNA sequences stored either in the GenBank or in databases with similar file formats. GenBank is a distributed flat file database made up of records, each record containing a variable number of fields in ASCII file format. The stored database itself is distributed, and there is no one database management system (DBMS) common to even a majority of its users. One general format called the line type format, is used both for the distributed database and for all of GenBank's internal record keeping. All data and system files and indexes for GenBank are kept in text files in this line type format.

The primary GenBank database is currently distributed in a multitude of files or divisions, each of which represents the genome of a particular species (or at least as much of it as is currently known and sequenced and publicly available). The GenBank provides a collection of nucleotide sequences as well as relevant bibliographic and biological annotation. Release 72.0 (6/92) of the GenBank CD distribution contains over 71,000 loci with a total of over ninety-two (92) million nucleotides. GenBank is distributed by IntelliGenetics, of Mountain View, Calif., in cooperation with the National Center for Biotechnology Information, National Library of Medecinge, in Bethesda, Md.

1. Overall Description of the OligoProbe DesignStation a. General Theory

The intent of this invention is to provide one or more fast processes for performing exact and inexact matching between DNA sequences to support the Mitsuhashi Probe Selection Diagram (MPSD) discussed below, and other analysis with interactive graphical analysis tools. Hybridization strength between a candidate oligonucleotide probe and a target subsequence of DNA, mRNA or cDNA can be estimated through a hybridization strength model. Quantitatively, hybridization strength is given as the melting temperature (Tm). Currently, two hybridization strength models are supported by the invention: 1) the Mismatch Model and 2) the H-Site Model.

b. Inputs i. Main OligoProbe DesignStation Dialog Window

Figure 21A:
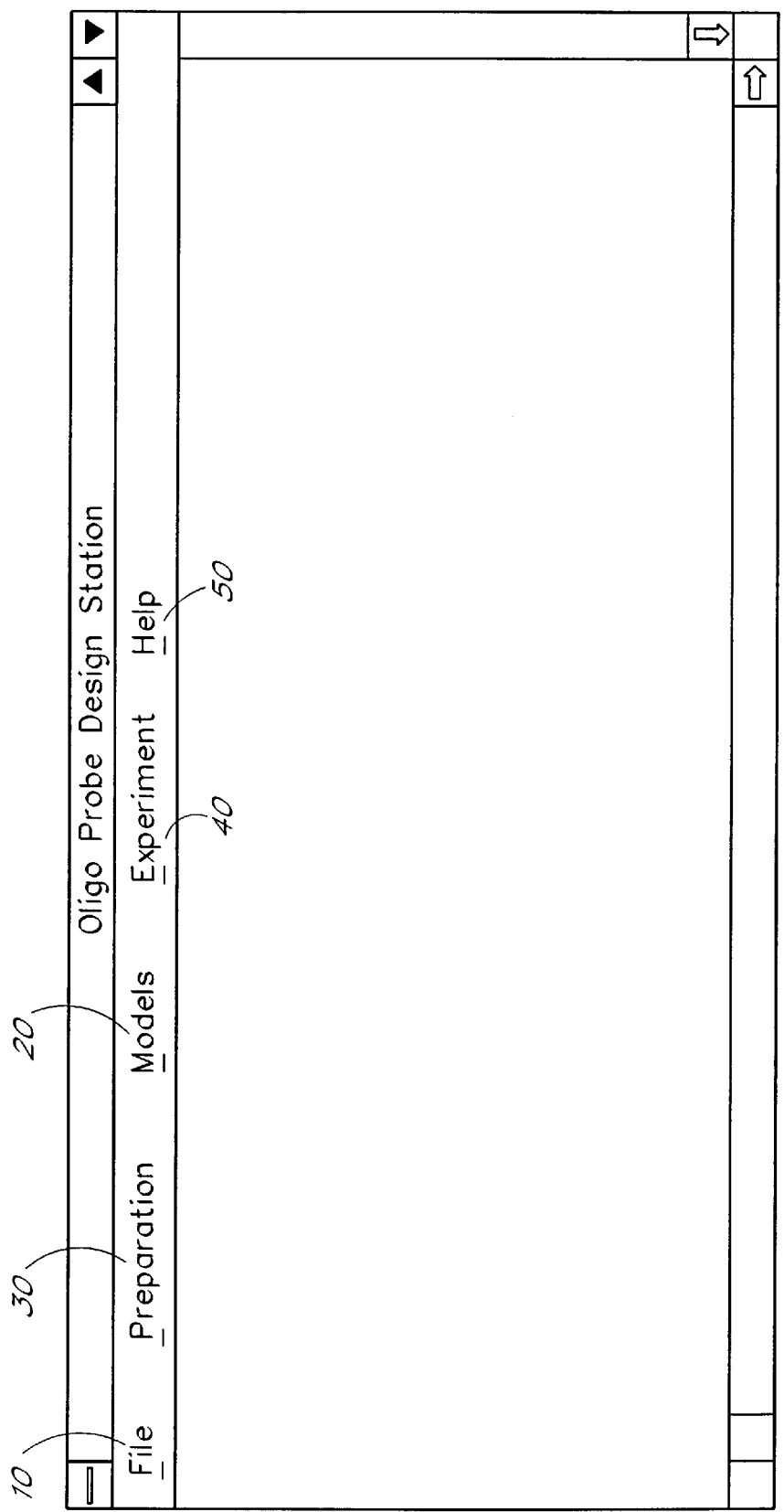
Figure 21B:
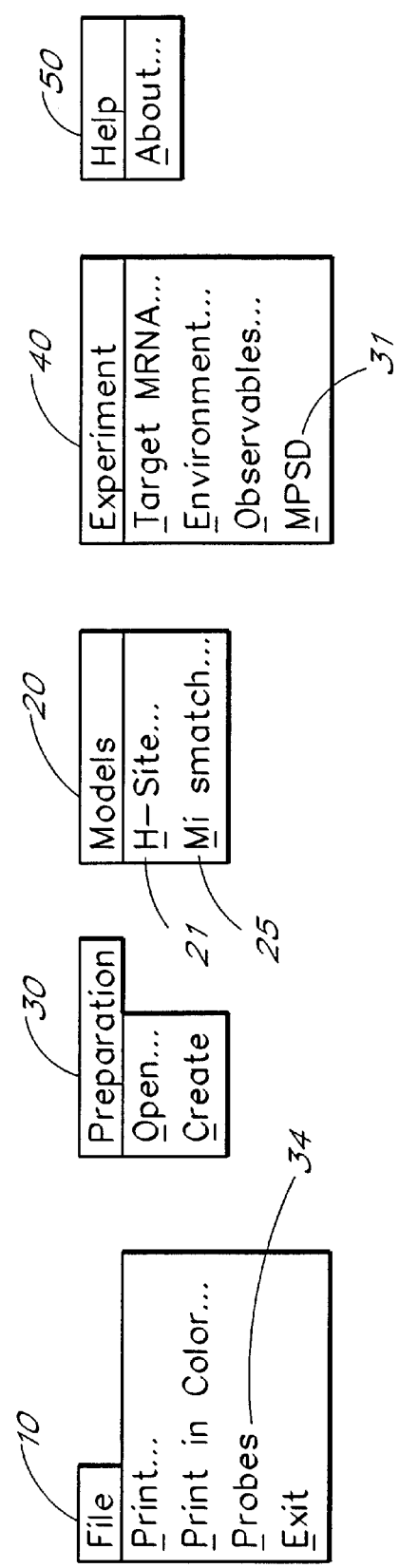

The Main OligoProbe DesignStation dialog window, FIG. 21, controls all user-definable settings. This window has a menu bar offering five options: 1) File 10; 2) Preparation 80; 3) Models 70; 4) Experiment 90; and 5) Help 50. The File 10 option allows the user to print, print in color, save selected probes, and exit the program. The Preparation 80 option allows the user to open and create preparation (PRP) files.

The Models 20 option allows the user to chose between the two hybridization models currently supported by the OligoProbe DesignStation: 1) the H-Site Model 21 and 2) the Mismatch Model 25. If the user selects the H-Site Model 21 option, the left hand menu of FIG. 21C is displayed and the user sets the following model parameters: 1) the melting temperature $T_m$ 22 for which probes are being designed (i.e., the melting temperature that corresponds to a particular experiment or condition the user desires to simulate); and 2) the nucleation threshold 23, which is the number of base pairs constituting a nucleation site. If the user selects the Mismatch Model 25 option, the right hand menu of FIG. 21C is displayed and the user sets the following model parameters: 1) probe length 26, which is the number of base pairs in probes to be considered; and 2) mismatch N 27, which is the maximum number of mismatches constituting a hybridization. Computation of the user's request takes longer with the H-Site Model if the threshold 23 setting is decreased, but longer with the Mismatch Model if the number of mismatches N 27 is increased.

In addition, for both Model options the user chooses the target species 11 DNA or mRNA for which probes are being designed and the preparation 12, a file of all sequences with which hybridizations are to be calculated. A sample of a target species file is shown in FIG. 47 (humbjunx.cds), while a sample of a preparation file is shown in FIG. 48 (junmix.seq). Each of these inputs is represented by a file name and extension in standard DOS format. In the target species and preparation fields, the file format follows the GenBank format with each of the fields having a default file extension. Pressing the "OK" button 41 (FIG. 21C) will initiate processing, while pressing the "Cancel" button 43 will stop the processing.

The Experiment 40 option and the Help 50 option are expansion options not yet available in the current implementation of the invention.

c. Processing

Figure 22A:
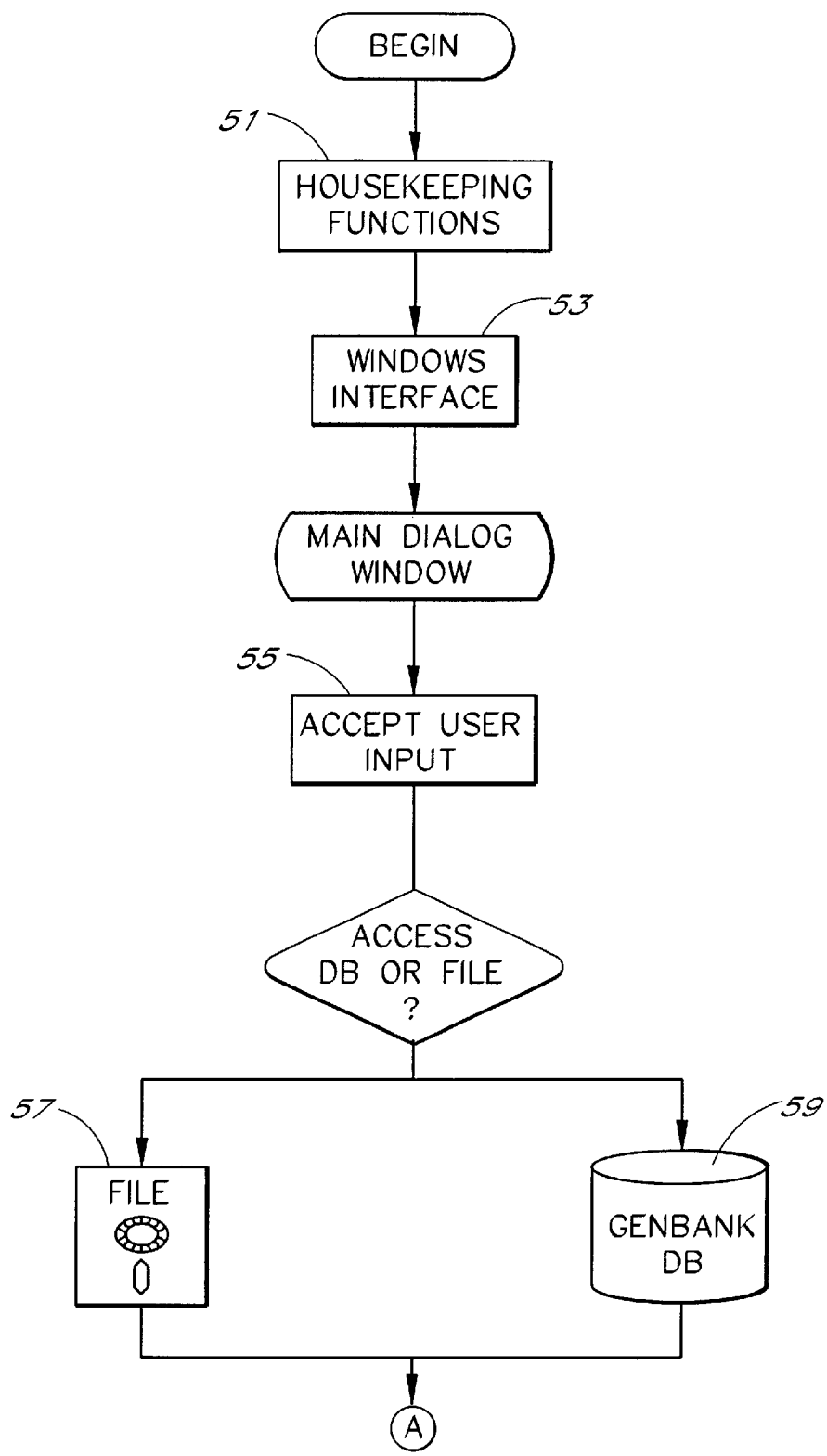
FIG. 22 is a flow chart of the overall invention illustrating the program and the invention's sequence and structure.
Figure 22B:
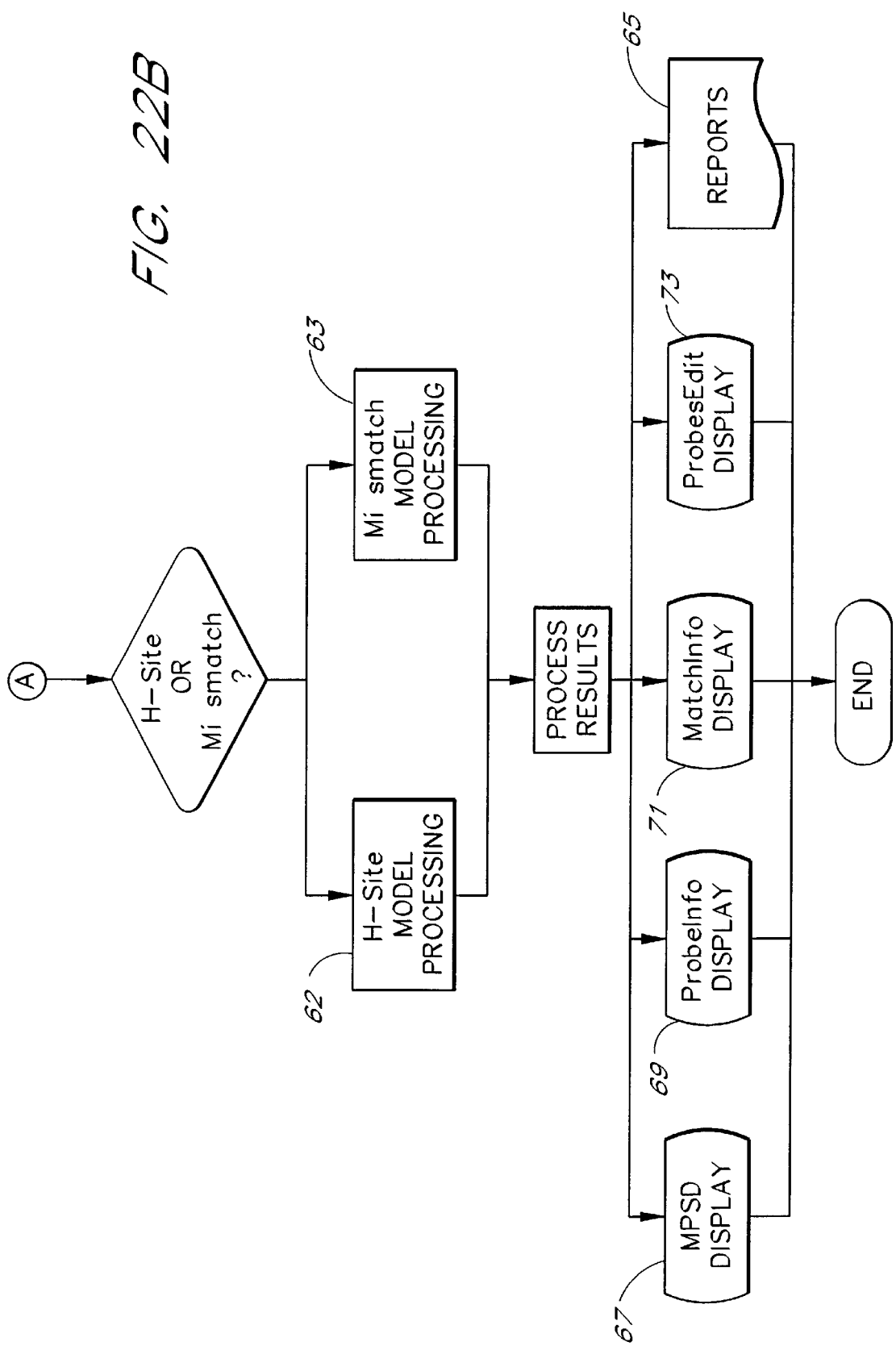

FIG. 22 is a flow chart of the overall OligoProbe Design-Station Program, illustrating its sequence and structure. Generally, the main or "control" program of the OligoProbe DesignStation performs overall maintenance and control functions. This program, as illustrated in FIG. 22, accomplishes the general housekeeping functions 51, such as defining global variables. The user-friendly interface 53, carries out the user-input procedures 55, the file 57 or database 59 access procedures, calling of the model program 62 or 63 selected by the user, and the user-selected report 65 or display 67, 69, 71 and 73 features. Each of these features is discussed in more detail in later sections, with the exception of the input procedures, which involves capturing the user's set-up and control inputs.

d. Outputs i. The Mitsuhashi Probe Selection Diagram Window

Figure 23:
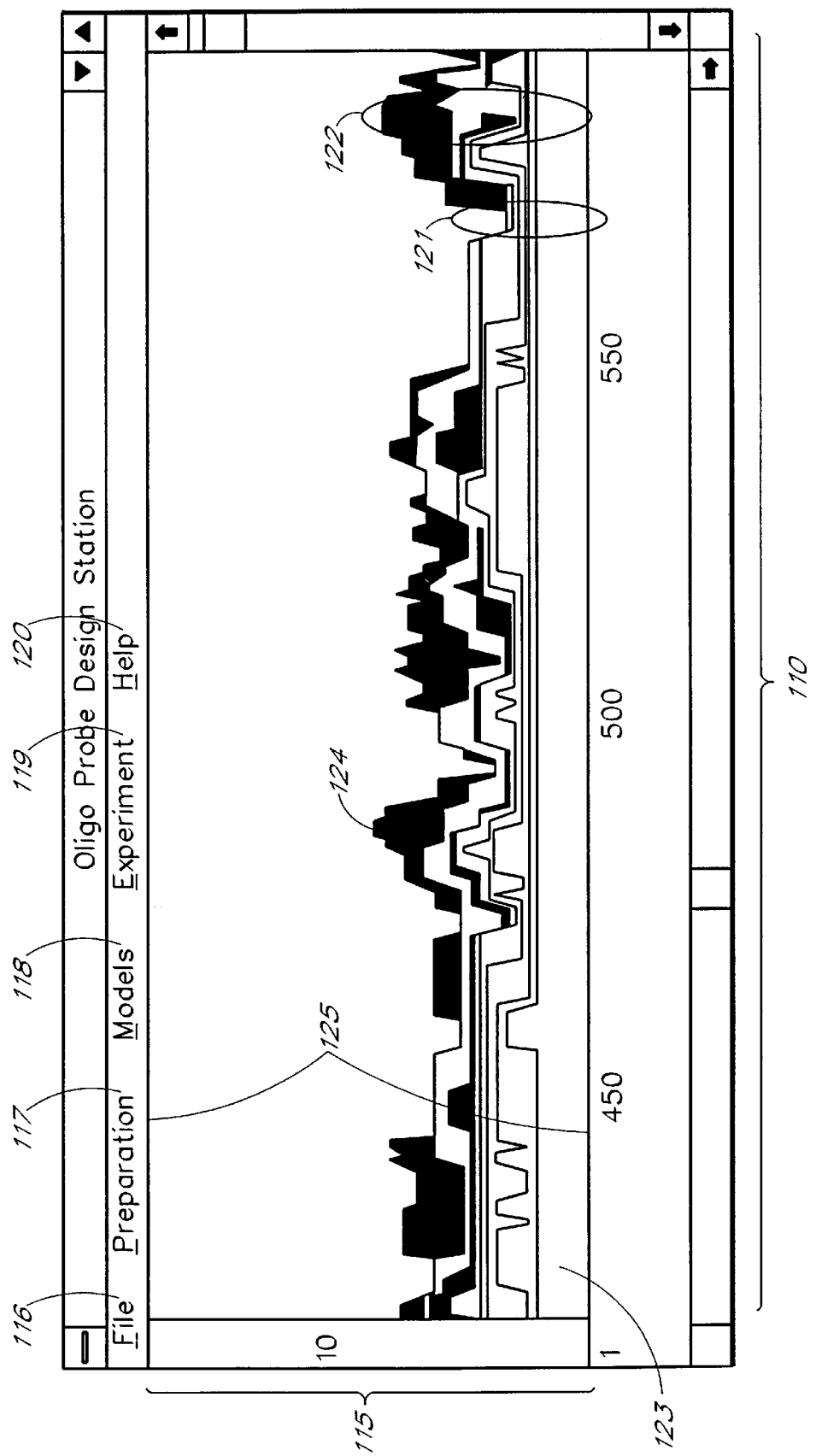
FIG. 23 is a display screen representation of the Mitsuhashi probe selection diagram.

The Mitsuhashi Probe Selection Diagram (MPSD), FIG. 23, is a key feature of the invention as it is a unique way of visualizing the results of the program's calculations. It is a graphic display of all of the hybridizations of probes with the target oligonucleotides in the preparation. Specifically, given a nucleotide sequence database and a target mRNA, the MPSD graphically displays all of the candidate probes and their hybridization strengths with all sequences from the nucleotide database. The MPSD allows the user to visualize the number of false hybridizations at various temperatures for all candidate probes, and the sources of these false hybridizations (with a loci and sequence comparison).

For each melting temperature selected, a graph showing the number of hybridizations for each probe is displayed. In the preferred embodiment, the graphs are color coded. In this implementation of the invention, the color red 123 identifies the highest melting temperature and the color blue 124 identifies the lowest melting temperature. Each mismatch results in a reduction in the Tm value. The melting temperature is also a function of probe length and percent GC content. Within the window, the cursor 125 shape is changed from a vertical line bisecting the screen to a small rectangle when the user selects a particular probe. The current probe is defined to be that probe under the cursor position (whether it be a line or a rectangle) in the MPSD window. More detailed information about the current probe is given in the ProbeInfo and MatchInfo windows, discussed below. Clicking the mouse button 2 once at the cursor 125 selects the current probe. Clicking the mouse button 2 a second time deselects the current probe. Moving the cursor across the screen causes the display to change and reflect the candidate probe under the current cursor position.

The x-axis 110 of the MPSD, FIG. 23, shows the candidate probes' starting positions along the given mRNA sequence. The user may "slide" the display to the left or right in order to display other probe starting positions. The y-axis 115 of the MPSD displays the probe specificity, which is calculated by the program.

The menu options 116, 117, 118, 119, and 120 available to the user while in the MPSD, FIG. 23, and are displayed along a menu bar at the top of the screen. The user can click the mouse 2 on the preferred option to briefly display the option choices, or can click and hold the mouse button on the option to allow an option to be selected. The user may also type a combination of keystrokes in order to display an option in accordance with well-known computer desk top interface operations. This combination usually involves holding down the ALT key while pressing the key representing the first letter of the desired option (i.e, F, P, M, E or H).

The File option 116 allows the user to specify input files and databases. The Preparation option 117 allows the user to create a preparation file summarizing the sequence database. The Models option 118 allows the user to specify the hybridization model (i.e., H-Site or Mismatch) and its parameters. The Experiment option 119 and the Help option 120 are not available in the current implementation of this invention. These options are part of the original Main OligoProbe DesignStation dialog window, FIG. 21.

Areas on the graphical display of the MPSD, FIG. 23, where the hybridizations for the optimal probes are displayed are lowest and most similar, such as shown at 121, indicate that the particular sequence displayed is common to all sequences. Areas on the graphical display of the MPSD where the hybridizations for the optimal probes are displayed are highest and most dissimilar, such as shown at 122, indicate that the particular sequence displayed is extremely specific to that particular gene fragment. The high points on the MPSD show many loci in the database, to which the candidate probe will hybridize (i.e., many false hybridizations). The low points show few hybridizations, at least relative to the given database. Specifically, the sequence shown at 121 would reflect a probe common to all of the gene fragments tested, such that this probe could be used to detect each of these genes. The sequence shown at 122 would reflect a probe specific to the particular gene fragment, such that this probe could be used to detect this particular gene and no others.

ii. The ProbeInfo and MatchInfo Window

Figure 24:
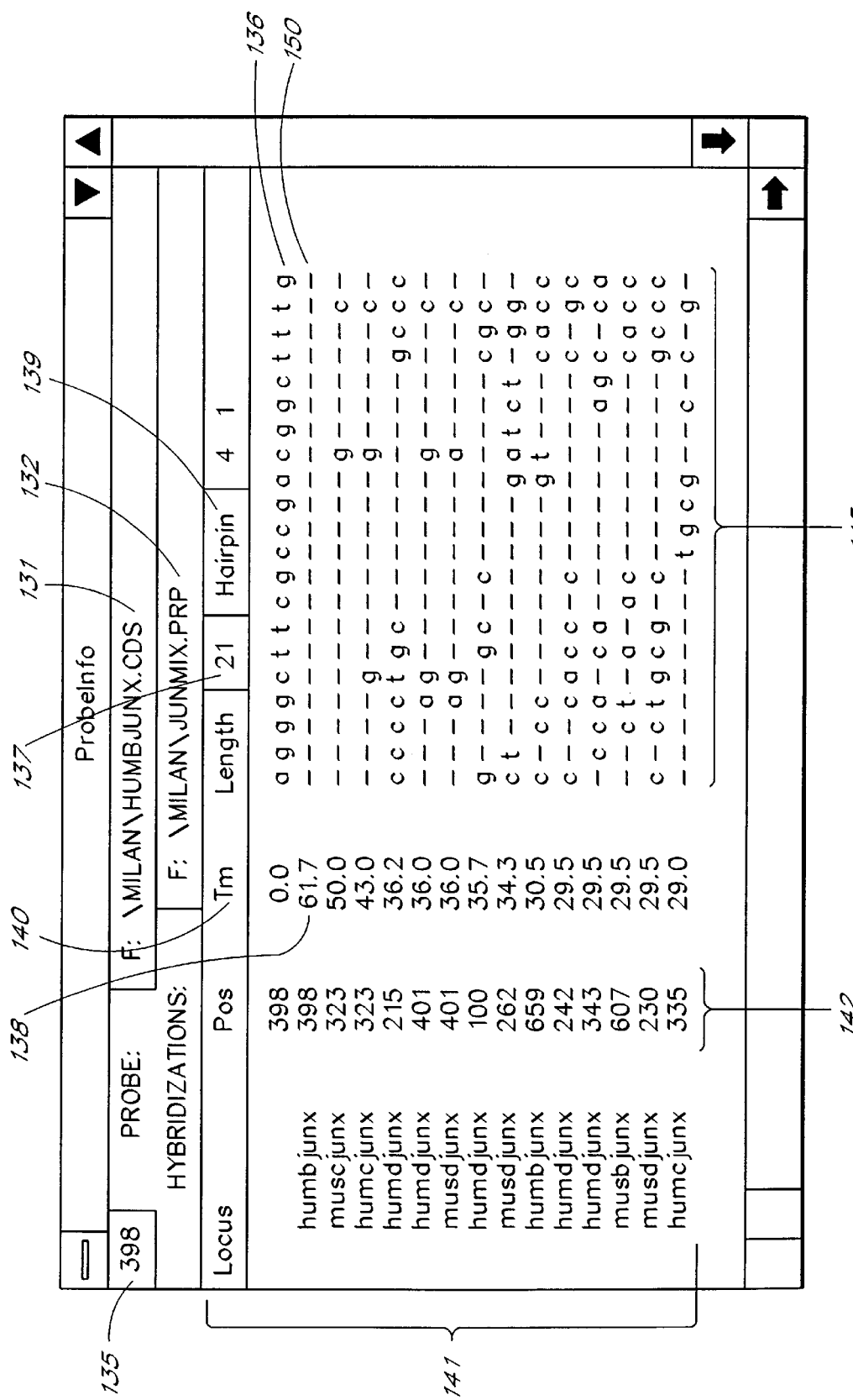
FIG. 24 is a display screen representation of the probeinfo and matchinfo window, wherein SEQ ID NO:343 is assigned to the first and second nucleotide sequences, and SEQ ID NOs:344 to 356 are assigned to the third nucleotide sequence to the last nucleotide sequence (from the top to the bottom), respectively.

The combined ProbeInfo and MatchInfo Window, FIG. 24, displays detailed information about the current candidate probe. The upper portion of the window is the ProbeInfo window, and the lower portion is the MatchInfo window. The ProbeInfo window portion displays the following types of information: the target locus (i.e., the mRNA, cDNA, or DNA from which the user is looking for probes) is displayed at 131, while the preparation used for hybridizations is displayed at 132. In the example shown in FIG. 24, the target locus 131 is the file named HUMBJUNX.CDS, which is shown as being located on drive F in the subdirectory MILAN. The preparation 132 is shown as being the file designated JUNMIX.PRP, which is also shown as being located on drive F in the subdirectory MILAN. The JUNMIX.PRP preparation in this example is a mixture of human and mouse jun loci.

The current and optimal probe's starting position is shown at 135. The current candidate oligonucleotide probe is defmed at 136, and is listed at 137 as having a length of 21 bases. The melting temperature for the probe 136 as hybridized with the targets is shown in column 140. The melting temperature for the optimal probe is given as 61.7 degrees C at 138. The ProbeInfo Window FIG. 24 also displays hairpin characteristics of the probe at 139. In the example shown, the ProbeInfo Window shows that there are four (4) base pairs involved in the worst hairpin, and that the worst hairpin has a length of one (1) (see FIG. 24, at 139).

The MatchInfo Window portion displays a list of hybridizations between the current probe and species within the preparation file, including hybridization loci and hybridization temperatures. The hybridizations are listed in descending order by melting temperature. The display shows the locus with which the hybridization occurs, the position within the locus, and the hybridization sequence.

In the MatchInfo window portion, the candidate probe 136 is shown at 150 as hybridizing completely with a high binding strength. This is because the target DNA is itself represented in the database in this case, so the candidate probe is seen at 150 to hybridize with itself (a perfect hybridization). The locus of each hybridization from the preparation 132 are displayed in column 141, while the starting position of each hybridization is given in column 142. The calculated hybridizations are shown at 145.

iii. The ProbesEdit Window

The ProbesEdit Window, FIG. 25, is a text editing window provided for convenient editing and annotation of OligoProbe DesignStation text file output. It is also used to accumulate probes selected from the MPSD, FIG. 23, by mouse button 2 clicks. Standard text editing capabilities are available within the ProbesEdit Window. The user may accumulate selected probes in this window (see 155 for an example) and then save them to a file (which will bear the name of the preparation sequence with the file extension of "prb" 156, or may be another file name selected by the user). A sample of this file is shown in FIG. 26A.

iv. Miscellaneous Output

The present embodiment of this invention also creates two output files, currently named "test.out" and "test1.out", depending upon which model the user has selected. The first file, "test.out", is created with both the Mismatch Model and the H-Site Model. This file is a textual representation of the Mitsuhashi Probe Selection Diagram (MPSD). It breaks the probe sequence down by position, length, delta Tm, screensN, and the actual probe sequence (i.e., nucleotides). An example of this file created by the Mismatch Model is shown in FIG. 40, and example created by the H-Site Model is shown in FIG. 44a. The second file, "test1.out", is created only by the H-Site Model. This file is a textual representation of the ProbeInfo and MatchInfo window that captures all hybridizations, along with their locus, starting position, melting temperature, and possible other hybridizations. A partial example of this file is shown in FIG. 44b (10 pages out of a total of 190 pages created by the H-Site Model).

2. Description of the Mismatch Model Program a. Overview

In this invention, one of the hybridization strength models is termed the Mismatch Model (see FIG. 21 for selection of this model). The basic operation of this model involves the techniques of hashing and continuous seed filtration, as defined earlier but described in more detail below. The essence of the Mismatch Model is a fast process for doing exact and inexact matching between nucleotide sequences to support the Mitsuhashi Probe Selection Diagram (MPSD). There are a number of modules in the present implementation of the Mismatch Model contained in this invention, the most significant of which are shown in the flow chart in FIG. 27 and in more detail in FIGS. 28 through 38. The main k_diff module shown in the flow chart in FIG. 28 is a structured program that provides overall control of the Mismatch Model, calling various submodules that perform different functions.

b. Inputs

The user-selected input variables for this model are minimum probe length 76 (which is generally from 18 to 30) and maximum number of mismatches 77 (which generally is from 1 to 5). These inputs are entered by the user in the Main OligoProbe DesignStation Dialog Window, FIG. 21C.

c. Processing i. k_diff Program

Some terms of art need to be defined before the processing performed by this module can be explained. A hash table basically is an array or table of data. A linked list is a classical data structure which is a chain of linked entries and involves pointers to other entry structures. Entries in a linked list do not have to be stored sequentially in memory, as is the case with elements contained in an array. Usually there is a pointer to the list associated with the list, which is often initially set to point to the start of the list. A pointer to a list is useful for sequencing through the entries in the list. A null pointer (i.e., a pointer with a value of zero) is used to mark the end of the list.

Figure 27:
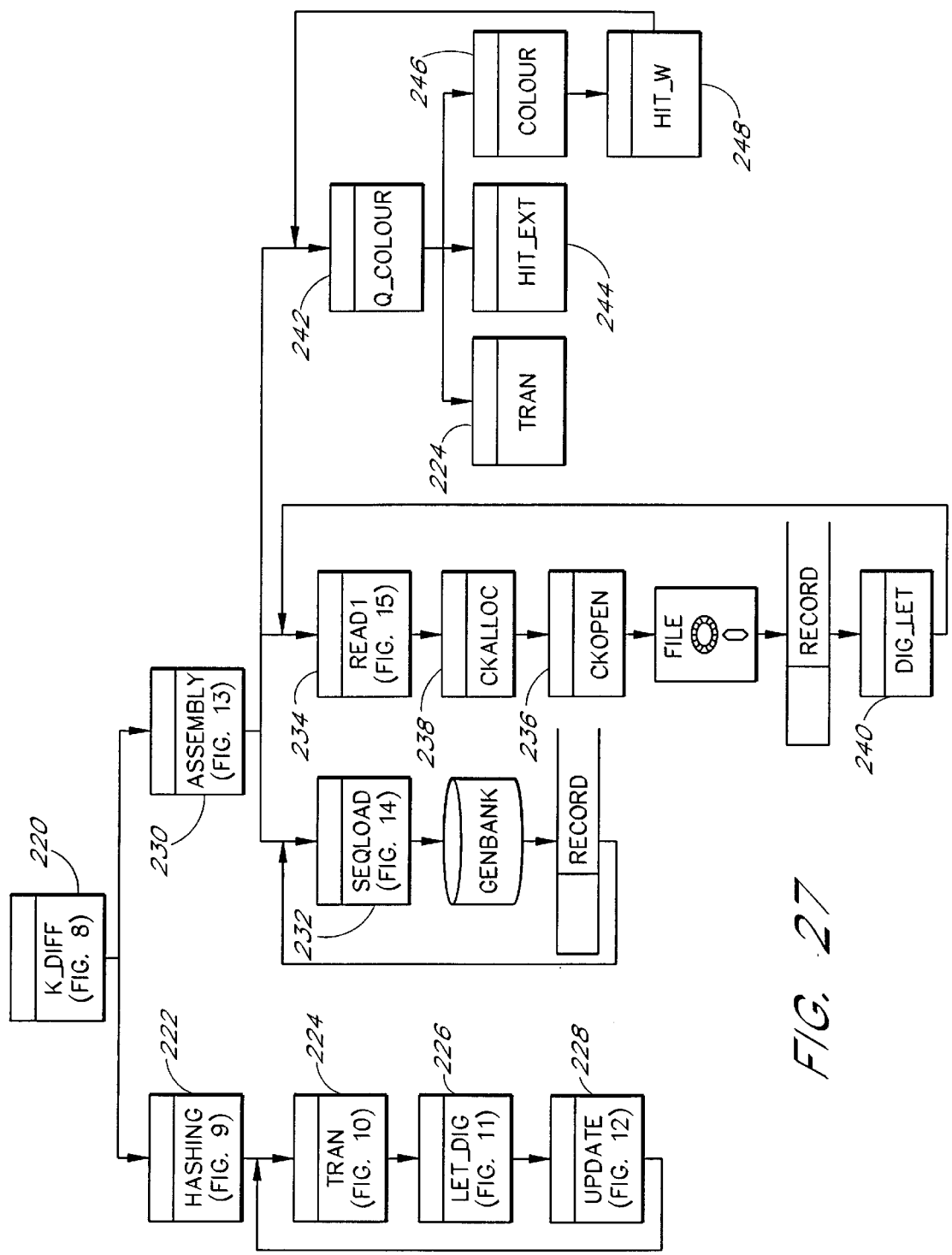
FIG. 27 is a flow chart of the overall k_diff program of the Mismatch Model of this invention, including its sequence and structure.

As the flow charts in FIGS. 27 and 28 illustrate, the general process steps and implemented functions of this model can be outlined as follows:

Step 1: First, create a hash table and linked list from the query (FIG. 27, hashing module 222).

Step 2: Next, while there are still GenBank entries available for searching (FIG. 27, assembly module 230):

Step 2a: Read the current GenBank entry (record) sequence of user-specified length (FIG. 27, seqload module 232), or read the current sequence (record) from the file selected by the user (FIG. 27, read1 module 234).

Step 2b: For the current sequence for each position of the sequence from the first position (or nucleotide) to the last position (or nucleotide) (incrementing the position number once each iteration of the loop) (FIG. 27, q_colour module 242), Step 2c: set the variable dna_hash equal to the hash of the current position of the current sequence (FIG. 27, q_colour module 242).

Step 2d: While not at the end of the linked list for dna_hash (FIG. 27, q_colour module 242), Step 2e: set the query_pos equal to the current position of dna_hash in the linked list (FIG. 27, q_colour module 242) and Step 2f: Extend the hit with the coordinates (query_pos, dna_pos) (FIG. 27, hit_ext module 244), Step 2g: If there exists a k_mismatch in the current extended hit (FIG. 27, colour module 246), then Step 2h: print the current hit (FIG. 27, q_colour module 242), and repeat from Step 2.

As this illustrates, there are three (3) basic looping or iteration processes with functions being performed based on variables such as whether the GenBank section end has been reached (the first "WHILE" loop, Step 2), whether the end of the current DNA entry has been reached (the "FOR" loop, Step 2b), and whether the end of the dna_hash linked list has been reached (the second "WHILE" loop, Step 2d). A "hit" will only be printed if there are k_mismatches in the current extended hit.

FIGS. 28 through 38 illustrate the functions of each of the modules of the present embodiment of this invention, all of which were generalized and summarized in the description above. FIG. 28, which outline the main "k_diff" module, shows that this module is primarily a program organization and direction module, in addition to performing routine "housekeeping" functions, such as defining the variables and hash tables 251, checking if the user-selected gene sequence file is open 252, extracting needed identification information from the GenBank 253, and ensuring valid user input 254. This module also performs a one-time allocation of memory for the gene sequences, and allocates memory for hit information, hashing, hybridization and frequency length profiles and output displays, 255 & 256. The "k_diff" module also initializes or "zeros out" the hashing table, the linked hashing list and the various other variables 257 in preparation for the hashing function. In addition, this module forms the hash tables 258 and extracts a sequence and finds the sequence length 259.

One of the most important functions performed by the "k_diff" module is to define the seed (or kernel or k_tuple) size. This is done by setting the variable k_tuple equal to (min_probe_length—max_mismatch_#)/(max_mismatch+#+1) FIG. 28 at 265. Next, if the remainder of the aforementioned process is not equal to zero 266, then the value of the variable k_tuple is incremented by one 267. The resulting value is the size of the seed. The module then reads the query 268 and copies the LOCUS name 269 for identification purposes (a definition of the term locus is given earlier in the specification).

The "k_diff" module FIG. 28 also calls the "assembly" module 260, writes the results to a file 261a, plots the results 261b (discussed below), calculates the hairpin characteristics 262 (i.e., the number of base pairs and the length of the worst hairpin) and the melting temperature (Tm) for each candidate probe 263, and saves the results to a file 264.

The screen graphs are plotted 261b by converting the result values to pixels, filing a pixel array and performing a binary search into the pixel array. Next, given the number of pixels per probe position and which function is of interest to the user (i.e., the three mismatch match numbers), the program interpolates the values at the value of (pixelsPerPositionN-1) and computes the array of pixel values for drawing the graph. These values are then plotted on the MPSD.

Figure 29:
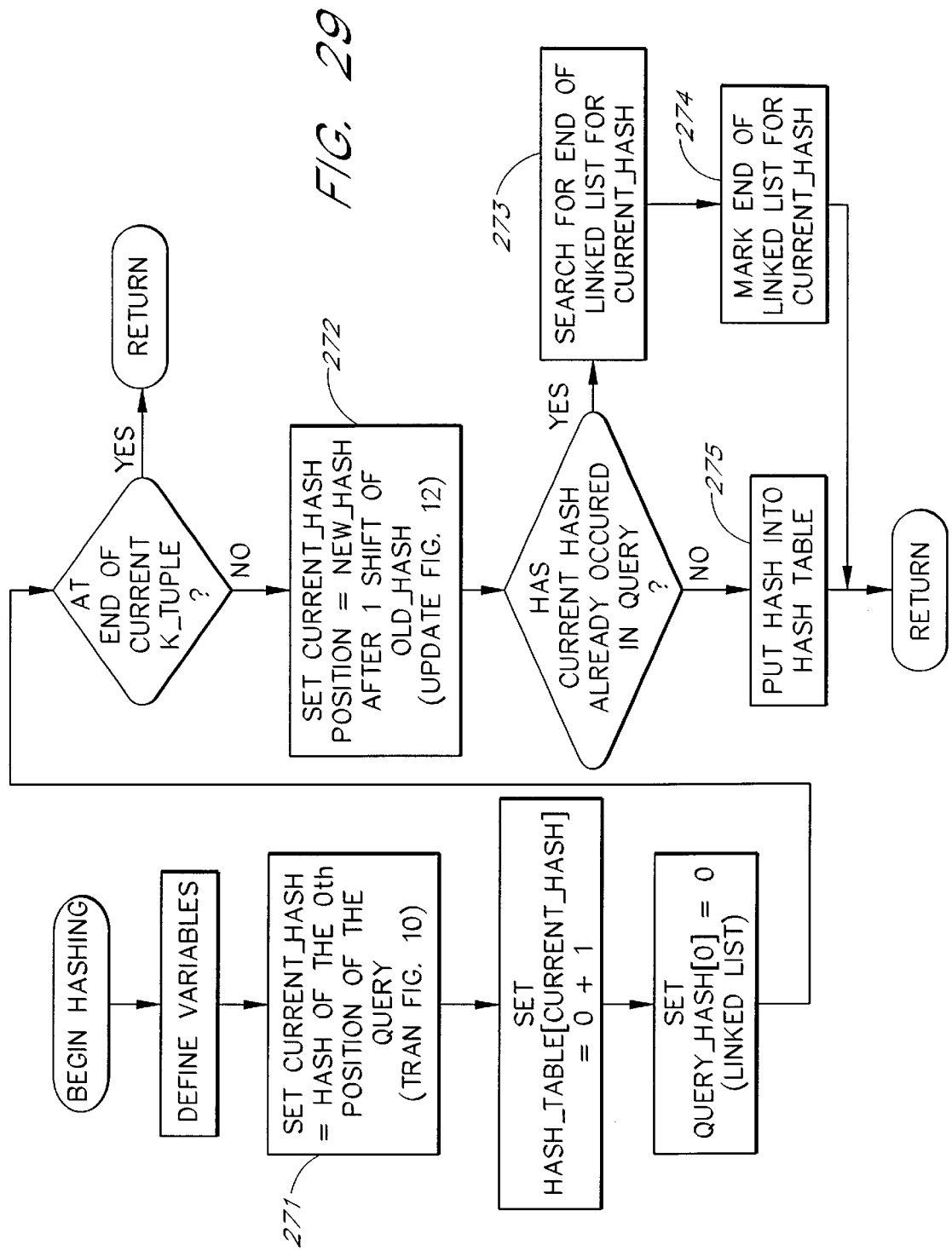
FIG. 29 is a flow chart of the hashing module of this invention.

The "hashing" module, FIG. 29, performs hashing of the query. In other words, it creates the hash table and linked list of query positions with the same hash. The variable has_table[i] equals the position of the first occurrence of hash i in the query. If i does not appear in the query, hash_table[i] is set to zero.

Figure 30:
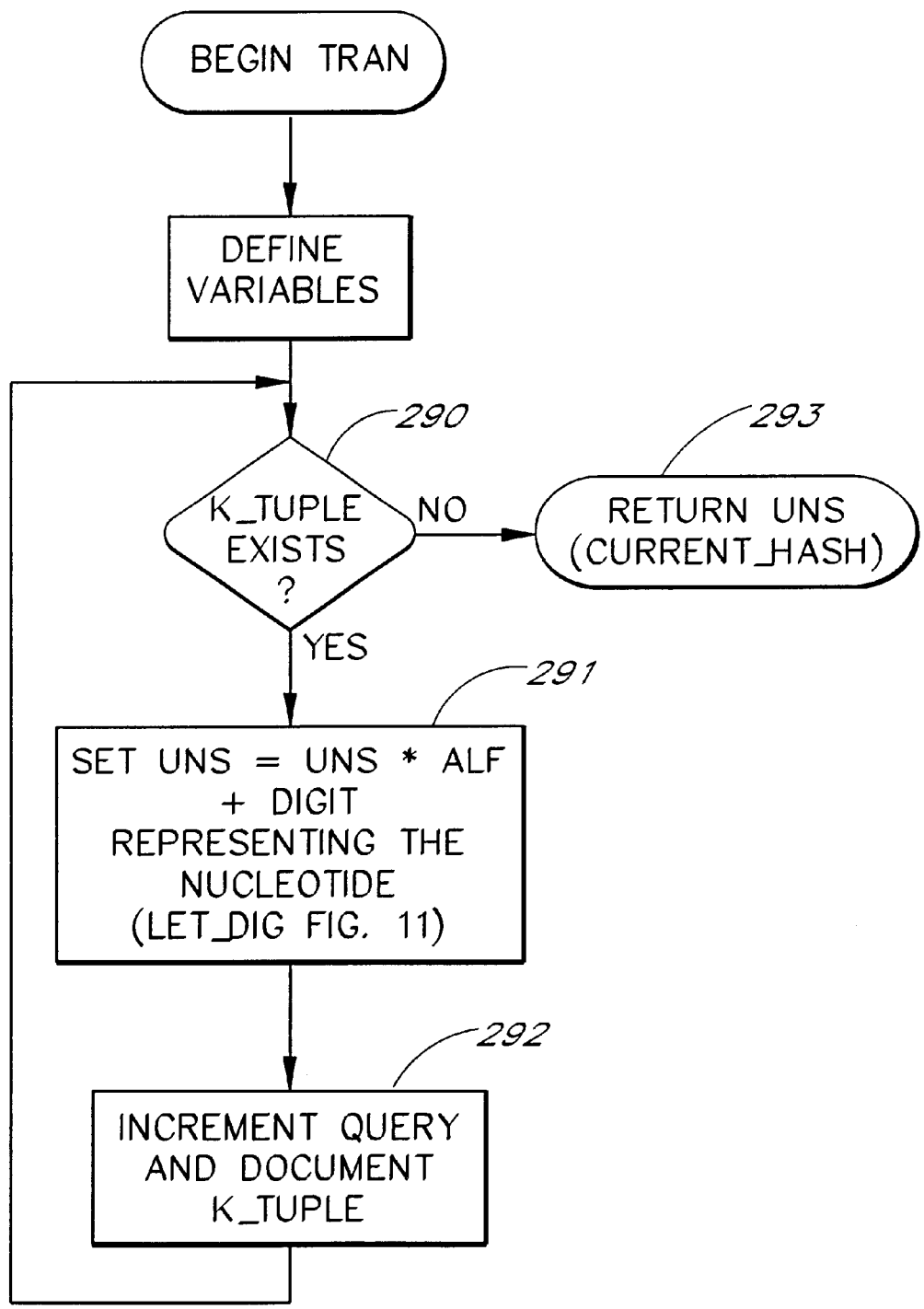
FIG. 30 is a flow chart of the tran module of this invention.

The "tran" module, FIG. 30, is called by the "hashing" module 271, and performs the hashing of the sequence of k_tuple (kernel or seed) size. If the k_tuple exists (i.e., its length is greater than zero), the variable uns is set equal to uns*ALF+p 291. The variable p represents the digit returned by the "let_dig" module FIG. 31 that represents the nucleotide being examined. ALF is a constant that is set by the program in this implementation to equal four. The query pointer is then incremented, while the size of k_tuple (the seed) is decremented 292. This process is repeated until the sequence of k_tuple has been entirely hashed. Then the "tran" module returns the variable current_hash 293 to the "hashing" module FIG. 29.

Figure 31:
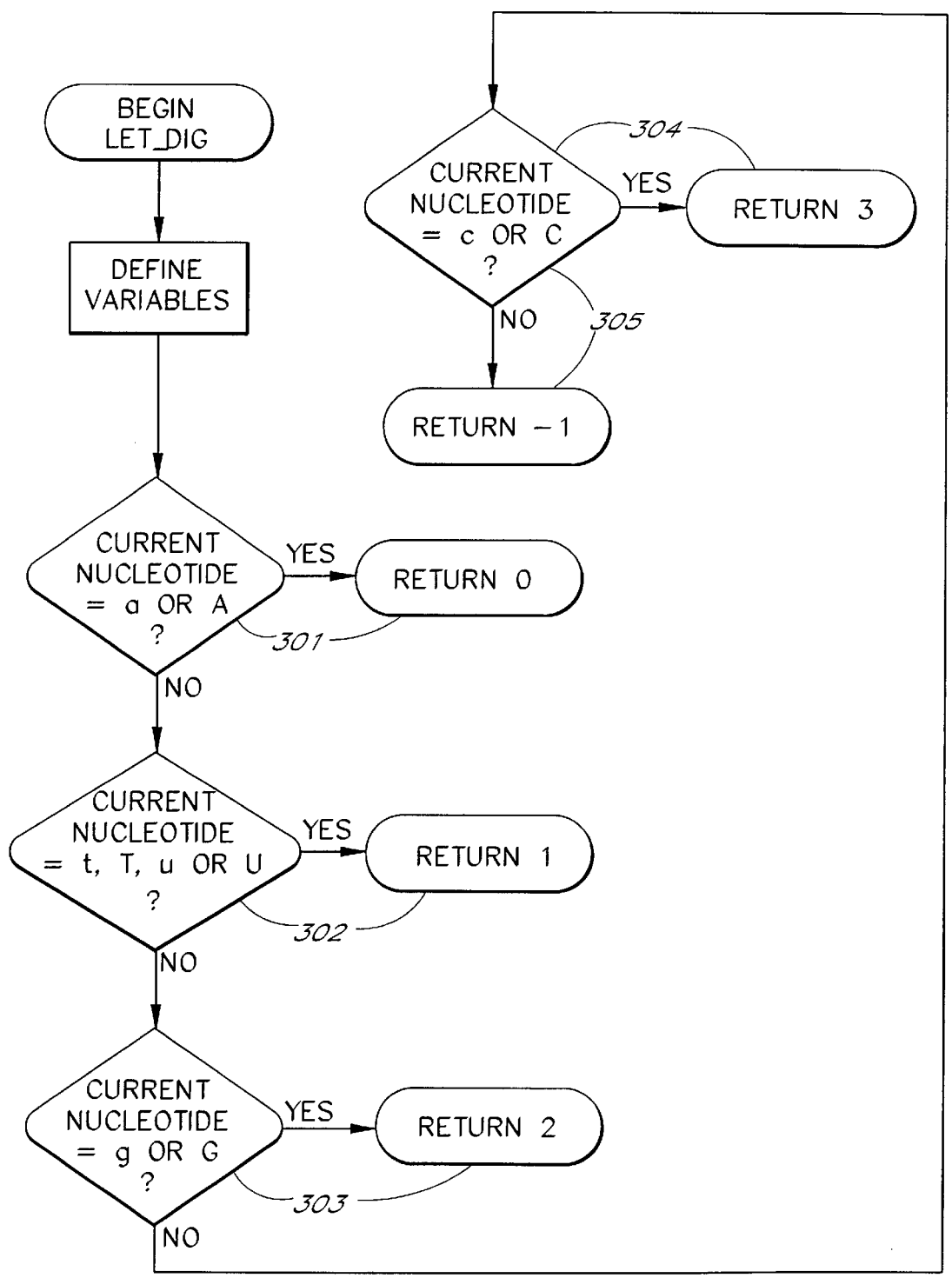
FIG. 31 is a flow chart of the let_dig module of this invention.
Figure 32:
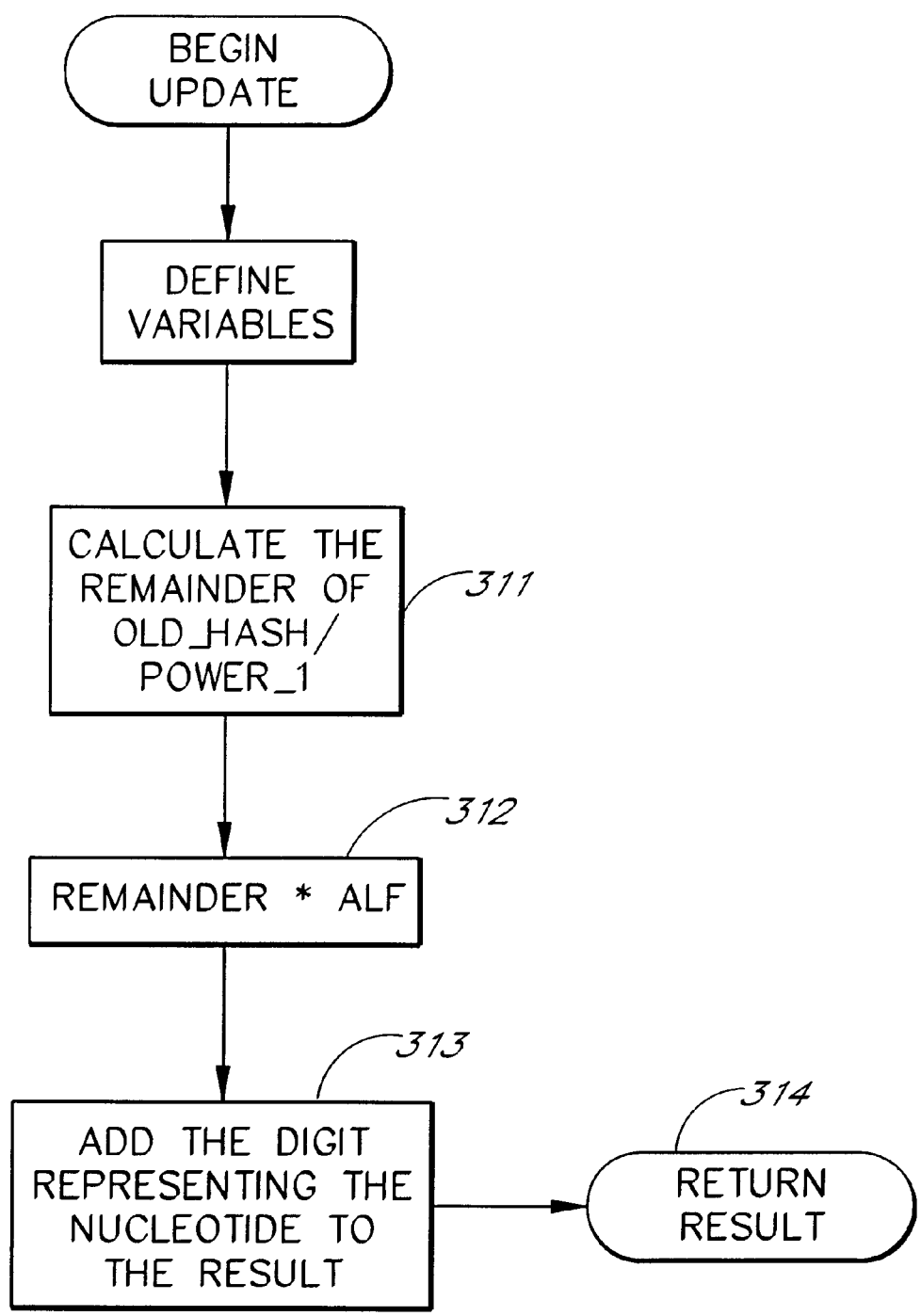
FIG. 32 is a flow chart of the update module of this invention.

The "let_dig" module, FIG. 31, is called by the "tran" module 291, and transforms the nucleotides represented as the characters "A", "T", "U", "G" and "C" in the GenBank and the user's query into numeric digits for easier processing by the program. This module transforms "a" and "A" into "0" 301, "t", "T", "u" and "U" into "1" 302, "g" and "G" into "2" 303, and "c" and "C" into "3" 305. If the character to be transformed does not match any one of those listed above, the module returns "−1" 305. The "hashing" module, FIG. 29, then calls the "update" module 272, FIG. 32, which updates the hash with a sliding window (i.e., it forms a new hash after shifting the old hash by "1"). The remainder of old_hash divided by power_1 is calculated 311 (a modulus operation), the remainder is multiplied by ALF 312 (i.e., four), and then the digit representing the nucleotide is added to the result 313. The "update" module then returns the result 314 to the "hashing" module FIG. 29.

If the current hash has already occurred in the query, the program searches for the end of the linked list for the current hash 273 and marks the end of the linked list for the current hash 274. If the current hash has not already occurred in the query, the program puts the hash into the hash table 275. The resulting hash table and linked list are then returned to the "k_diff" module, FIG. 28 at 258.

Figure 33A:
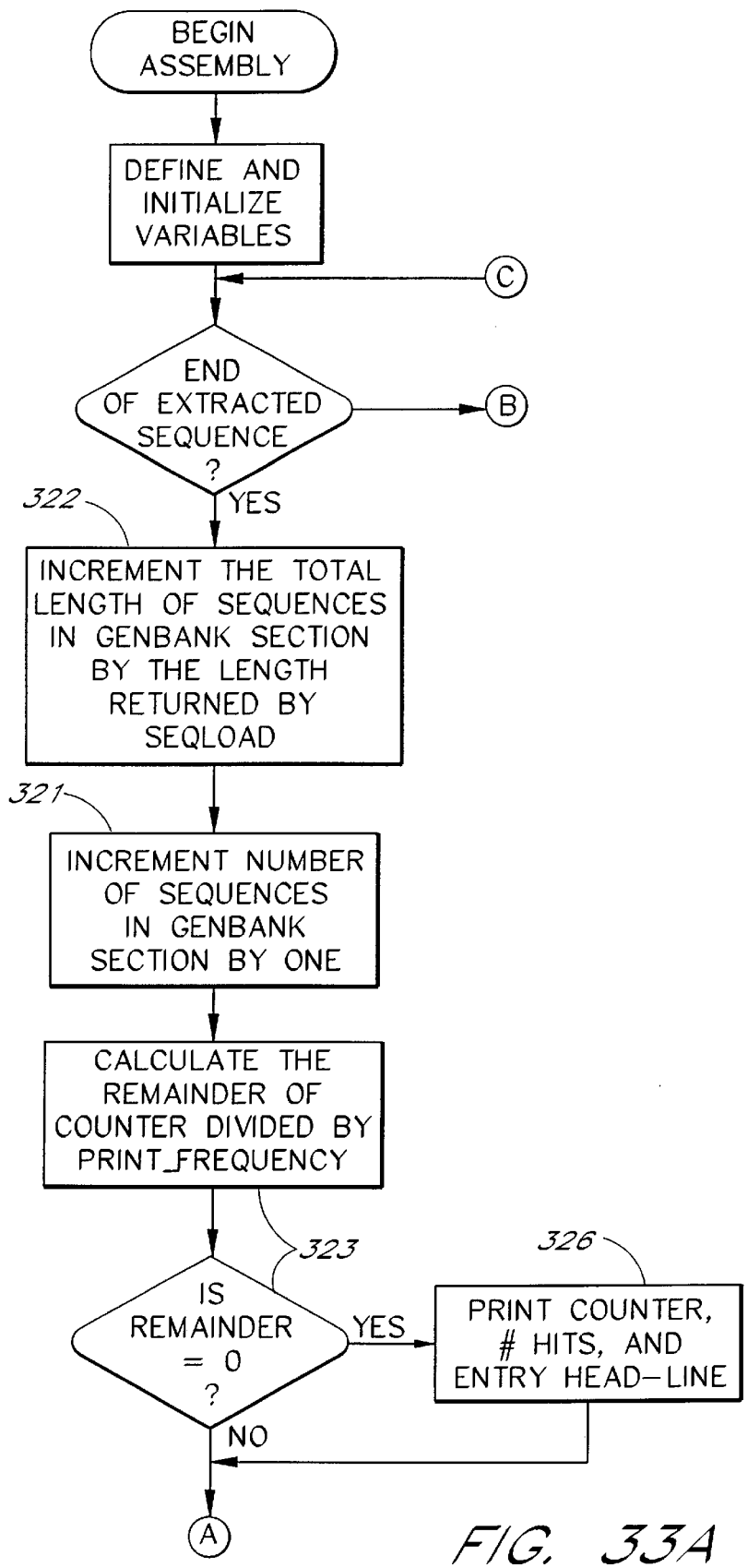
FIG. 33 is a flow chart of the assembly module of this invention.
Figure 33B:
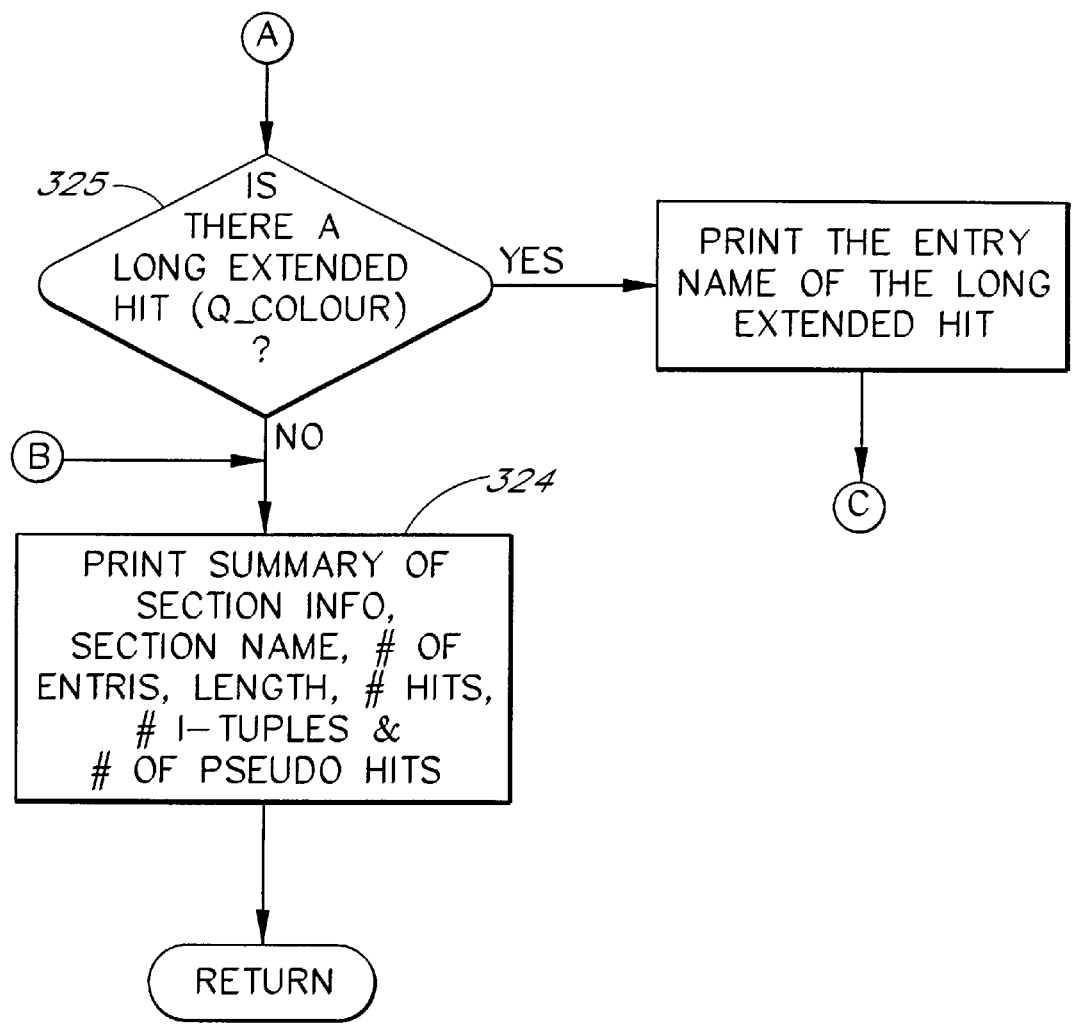

The "assembly" module, FIG. 33, extracts sequences from the GenBank and performs hit locating and extending functions. This module is called by the "k_diff" module FIG. 28 at 260 if the user has chosen to use the database to locate matches. The output from the "assembly" module (FIG. 33) tells the user that the section of the database searched contains E number of entries 321 of S summary length 322 with H number of hits 323. Further, the program tells the user that the number of considered 1-tuples equals T 324. The entry head line is also printed 326.

Figure 34A:
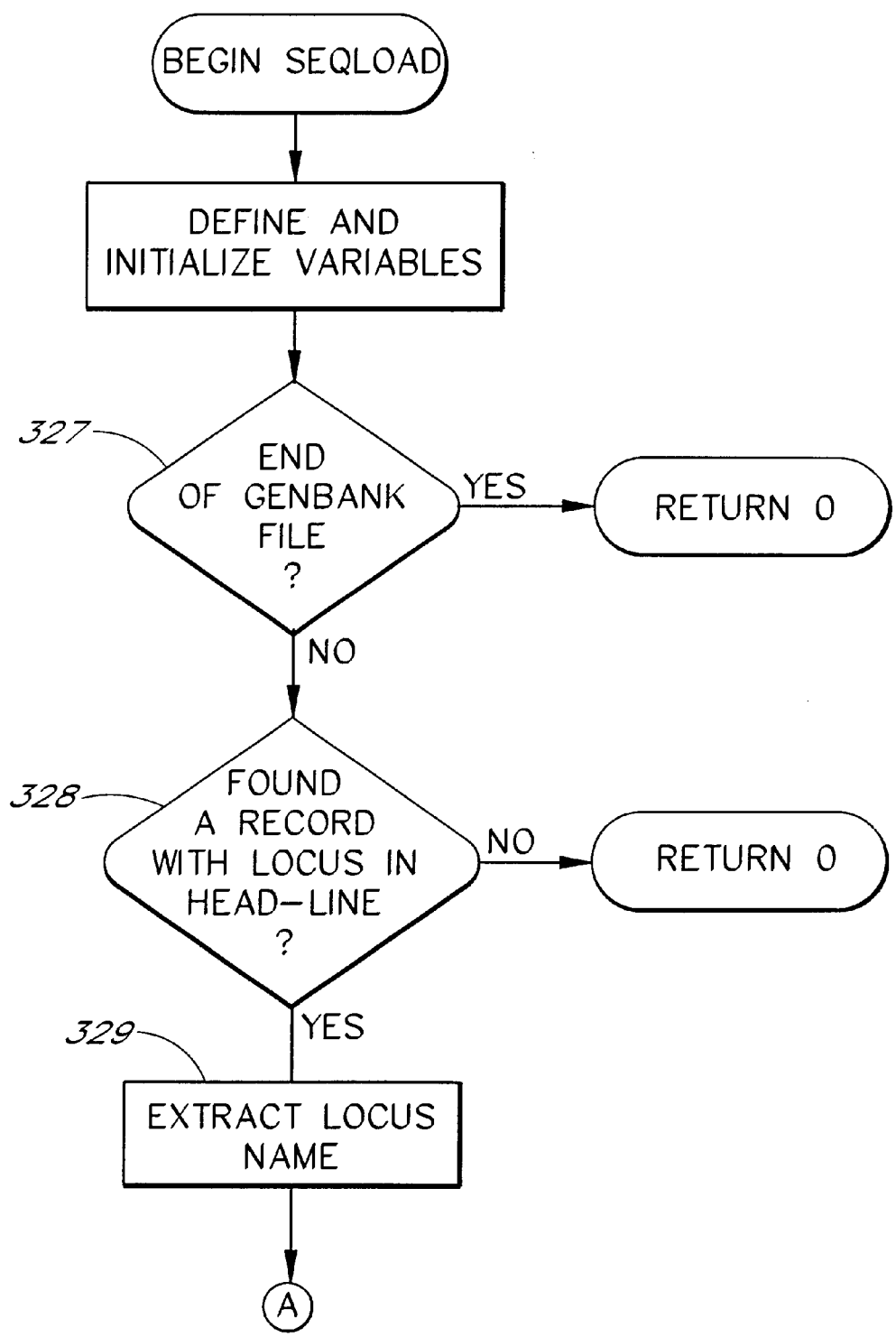
FIG. 34 is a flow chart of the seqload module of this invention.
Figure 34B:
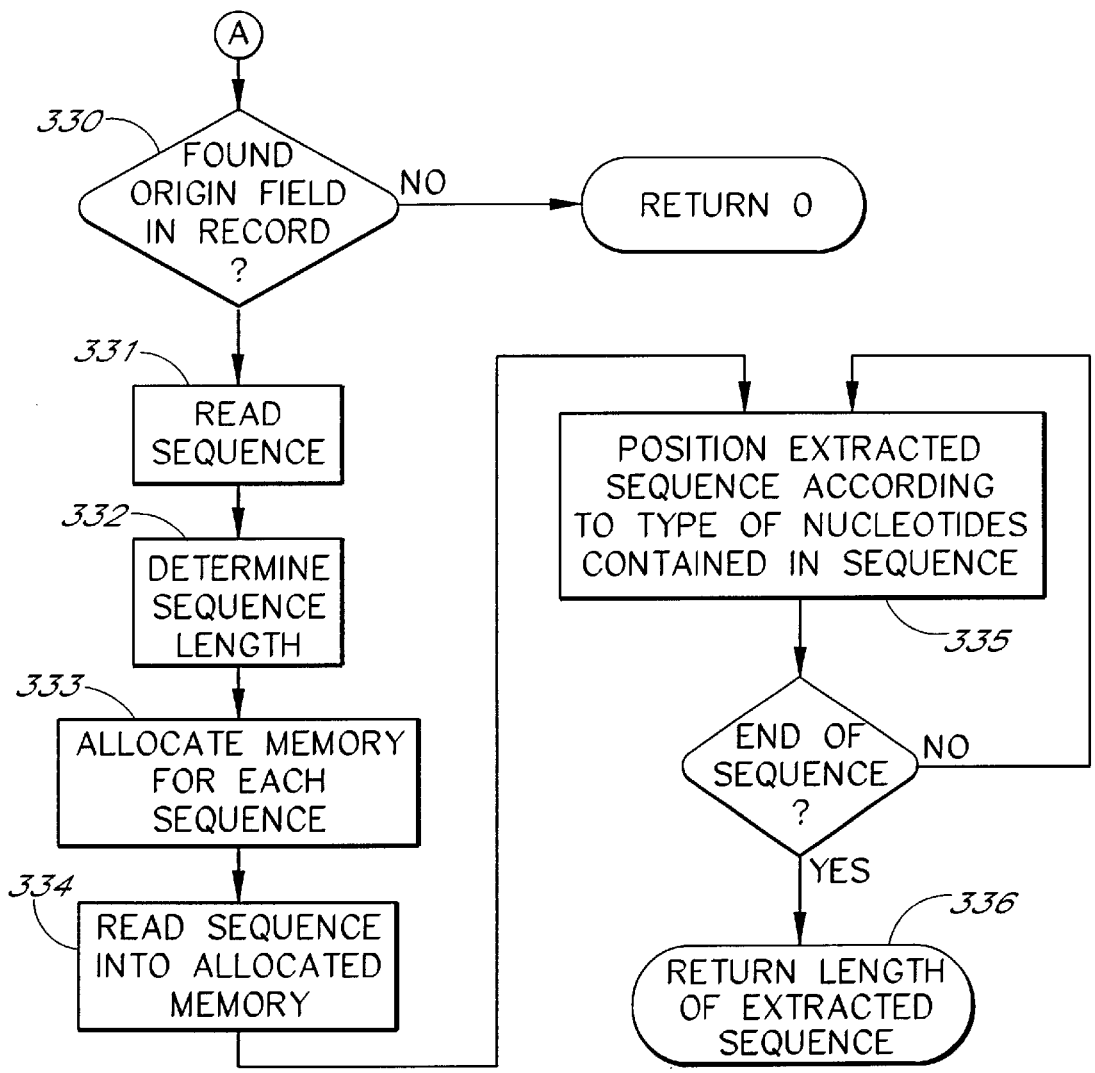

The "seqload" module, FIG. 34, is called by the "k_diff" module FIG. 28 at 259 once the query hash table and linked list have been formed by the "hashing" module FIG. 29. The "seqload" module FIG. 34 checks to see if the end of the GenBank file has been reached 327, and, if not, searches until a record is found with LOCUS in the head-line 328. Next, the LOCUS name is extracted 329 for identification purposes, and the program searches for the ORIGIN field in the record 330.

The program then extracts the current sequence 331 from the GenBank and performs two passes on each sequence. The first is to determine the sequence length 332 and allocate memory for each sequence 333, and the second pass is to read the sequence into the allocated memory 334. Since the sequences being extracted can contain either DNA nucleotides or protein nucleotides, the "seqload" module can recognize the characters "A", "T", "U", "G", and "C". The bases "A", "T", "G" and "C" are used in DNA sequences, while the bases "A", "U", "G" and "C" are used in RNA and mRNA sequences. The extracted sequence is then positioned according to the type of nucleotides contained in the sequence 335, and the process is repeated. Once the end of the sequence has been reached, the "seqload" module returns the sequence length 336 to the "k_diff" module FIG. 28.

Figure 35A:
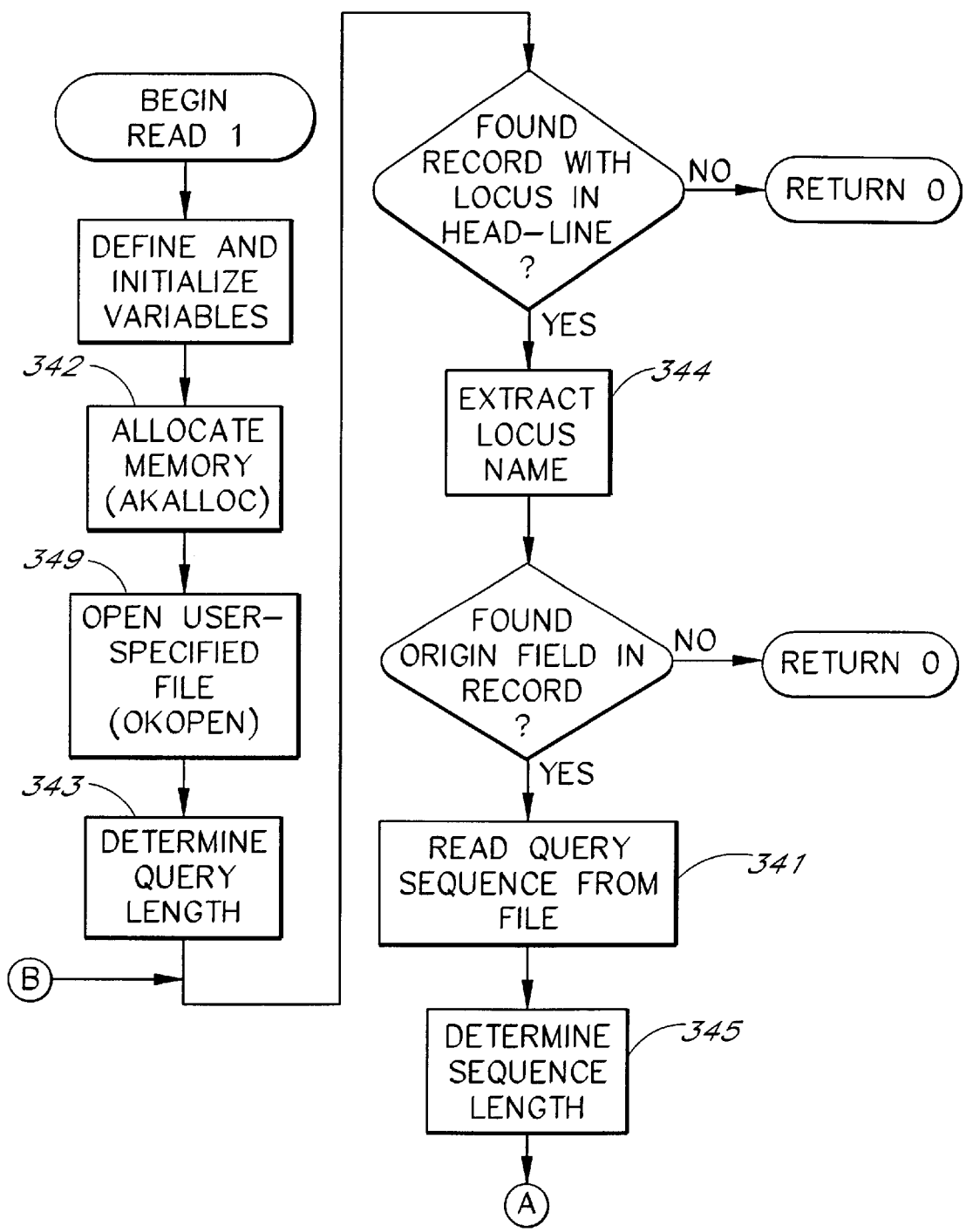
FIG. 35 is a flow chart of the read1 module of this invention.
Figure 35B:
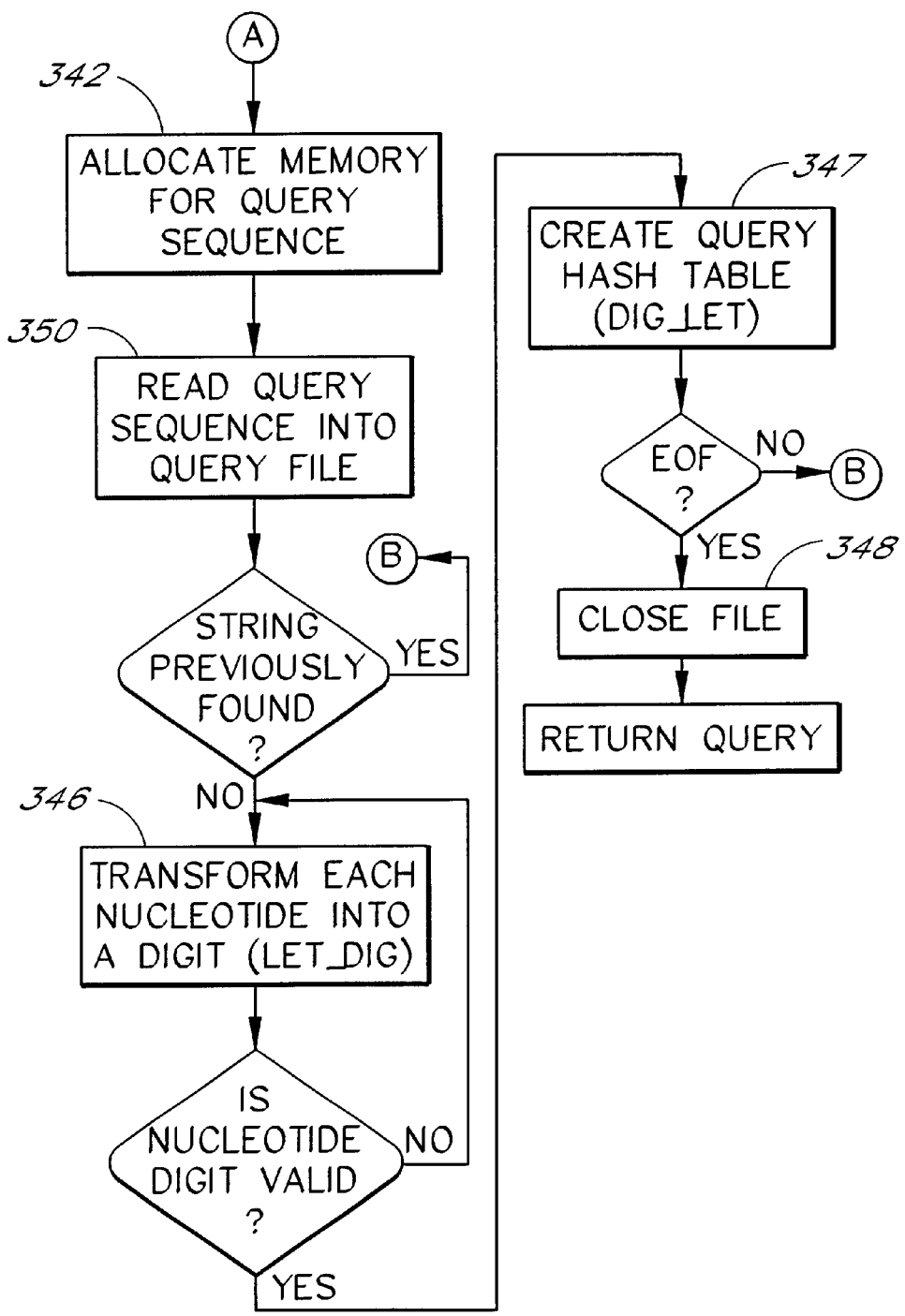

If the user has chosen to use one or more files to locate matches, rather than the database, the "read1" module, FIG. 35, rather than the "seqload" module FIG. 34, is called by the "k_diff" module FIG. 28. The "read1" module, FIG. 35, reads the sequence from the user specified query file 341 and allocates memory 342. This module also determines the query length 343, extracts sequence identification information 344, determines the sequence length 345, transforms each nucleotide into a digit 346 by calling the "let_dig" module FIG. 31, creates the query hash table 347 by calling the "dig_let: module FIG. 36, and closes the file 348 once everything has been read in.

First, the "read1" module FIG. 35 allocates space for the query 342. To do this, the "ckalloc" module, FIG. 35 at 342, is called. This module allocates space and checks whether this allocation is successful (i.e., is there enough memory or has the program run out of memory). After allocating space, the "read1" module FIG. 35 opens the user-specified file 349 (the "ckopen" module, FIG. 35 at 349, is called to ensure that the query file can be successfully opened 349), determines the query length 343, locates a record with LOCUS in the head-line and extracts the LOCUS name 344 for identification purposes, locates the ORIGIN field in the record and then reads the query sequence from the file 341. Next, the sequence length is determined 345, memory is allocated for the sequence 342, and the sequence is read into the query file 350. If the string has previously been found, processing is returned to 344. If not, then each character in the query file is read into memory 350.

Figure 36:
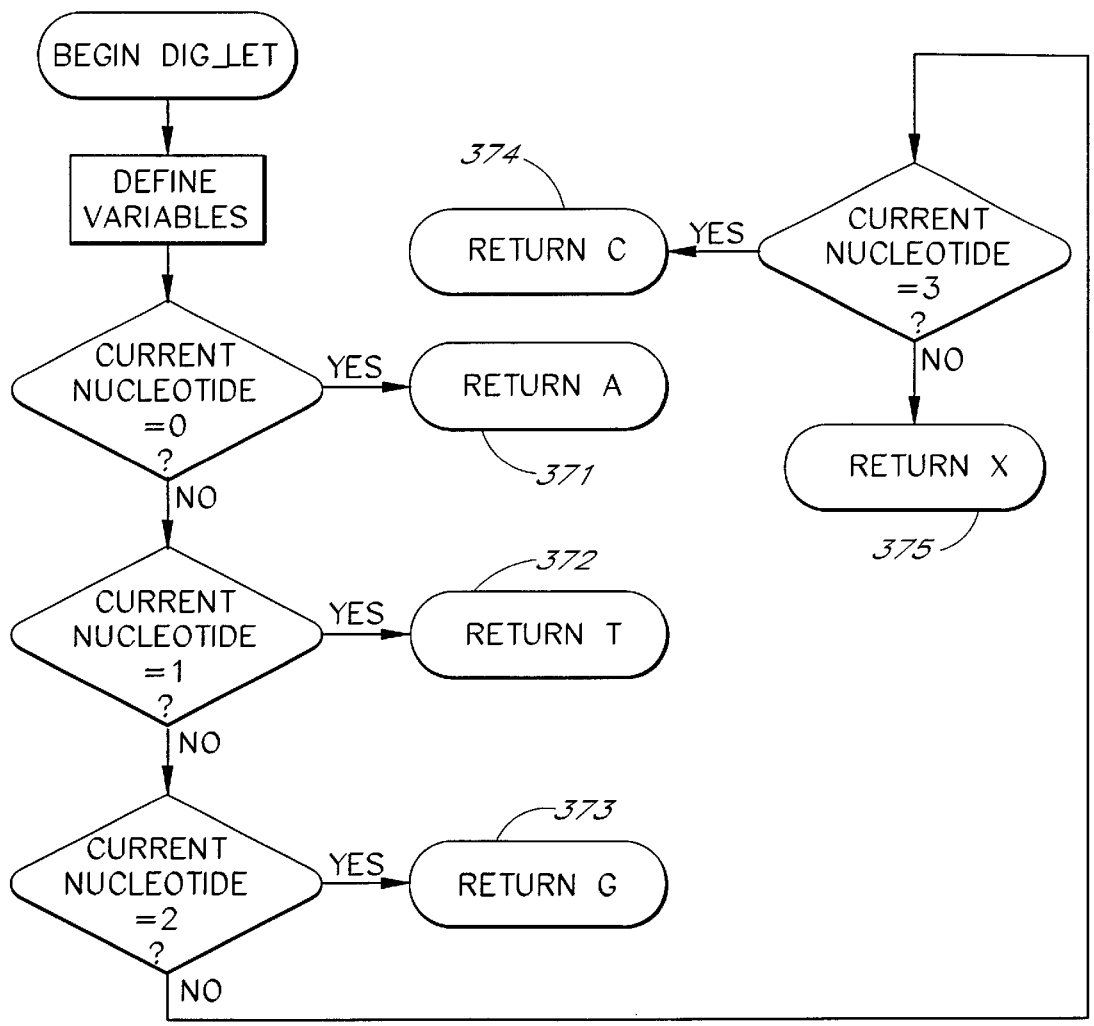
FIG. 36 is a flow chart of the dig_let module of this invention.

The characters are transformed into digits 346 using the "let_dig" module, FIG. 31, until a valid digit has been found, and then the hash table containing the query is set up 347 using the module "dig_let", FIG. 36, which transforms the digits into nucleotides represented by the characters "A" 371, "T" 371, "G" 373, "C" 374, and "X" 375 as a default. If the end of the file has not been reached, processing is returned to 344. If it has, the file is closed 348 and the query is then returned to the "read1" module FIG. 35 at 347.

The "q_colour" module, FIG. 27 (FIG. 33 at 325), is called by the "assembly" module FIG. 33 after the current sequence has been extracted from the GenBank. The "q_colour" module FIG. 37 performs the heart of the Mismatch Model process in that it performs the comparison between the query and the database or file sequences. If the module finds that there exists a long (i.e., greater than the min_hit_length) extended hit, it returns a "1" to the "assembly" module FIG. 34. Otherwise, the "q_colour" module, FIG. 37, returns a "0".

In the "q_colour" module, FIG. 37, all DNA positions are analyzed in the following manner. First, the entire DNA sequence is analyzed 391 to see whether each position is equal to zero 392 (i.e., whether it is empty or the sequence is finished). If it is not equal to zero 393, the "q_colour" module FIG. 40 calls the "tran" module, FIG. 30 described above, which performs the hashing of k_tuples. The "tran" module FIG. 30 calls other modules which transform the nucleotides represented by characters into digits for easier processing by the program and then updates the hash with a sliding window. If the position is equal to zero, the current_hash position is set to new_has after one shift of old_hash 390 by calling the "update" module FIG. 32.

If the nucleotide at the current hash position is equal to zero, processing is returned to 391. If not, the query position is set equal to (nucleotide at current hash position-1). Next, the "q_colour" module FIG. 37 looks for the current_hash in the hash table 394. If the current k_tuple does not match the query 395, then the next k_tuple is considered 395, and processing is returned to 391. If the current k_tuple does match the query, then the program checks the hit's (i.e., the match's) vicinity 396 by calling the "hit_ext" module, FIG. 38 to determine if the hit is weak. The inventors have found that if the code for the module "hit_ext" is included within the module "q_colour", rather than being a separate module utilizing the parameter transfer machinery, 25% of CPU time can be saved.

Figure 37A:
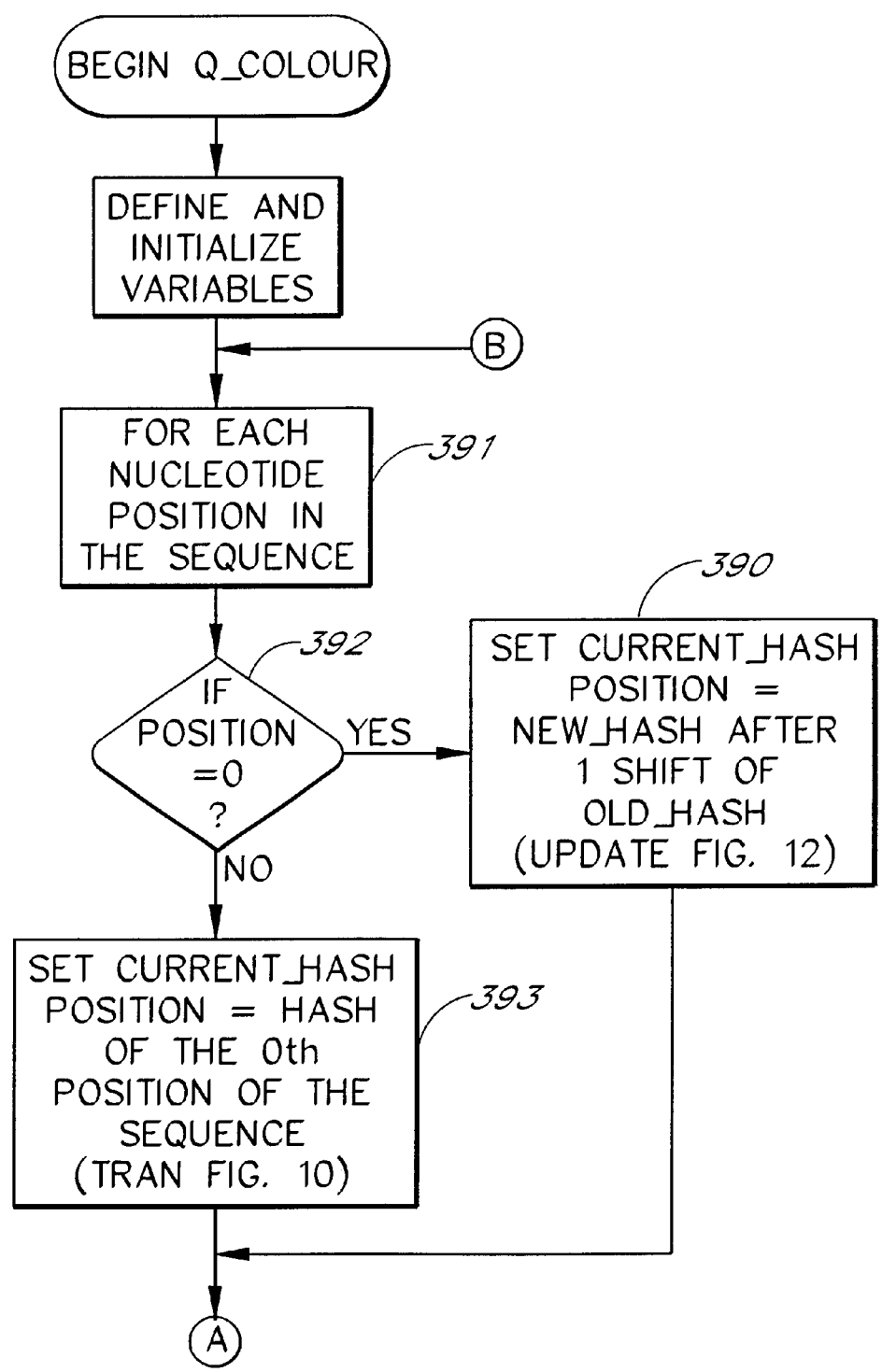
FIG. 37 is a flow chart of the q_colour module of this invention.
Figure 37B:
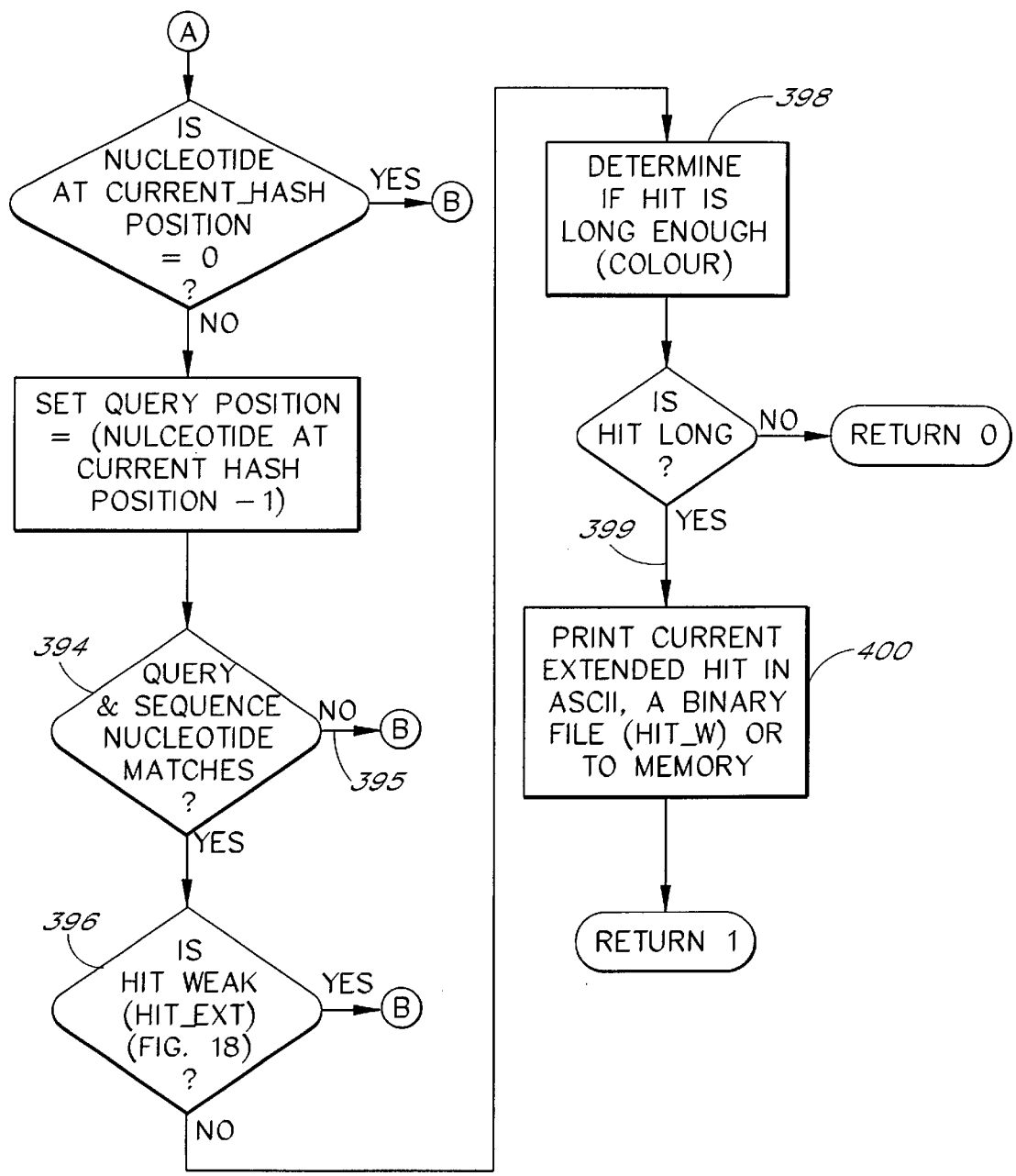
Figure 38:
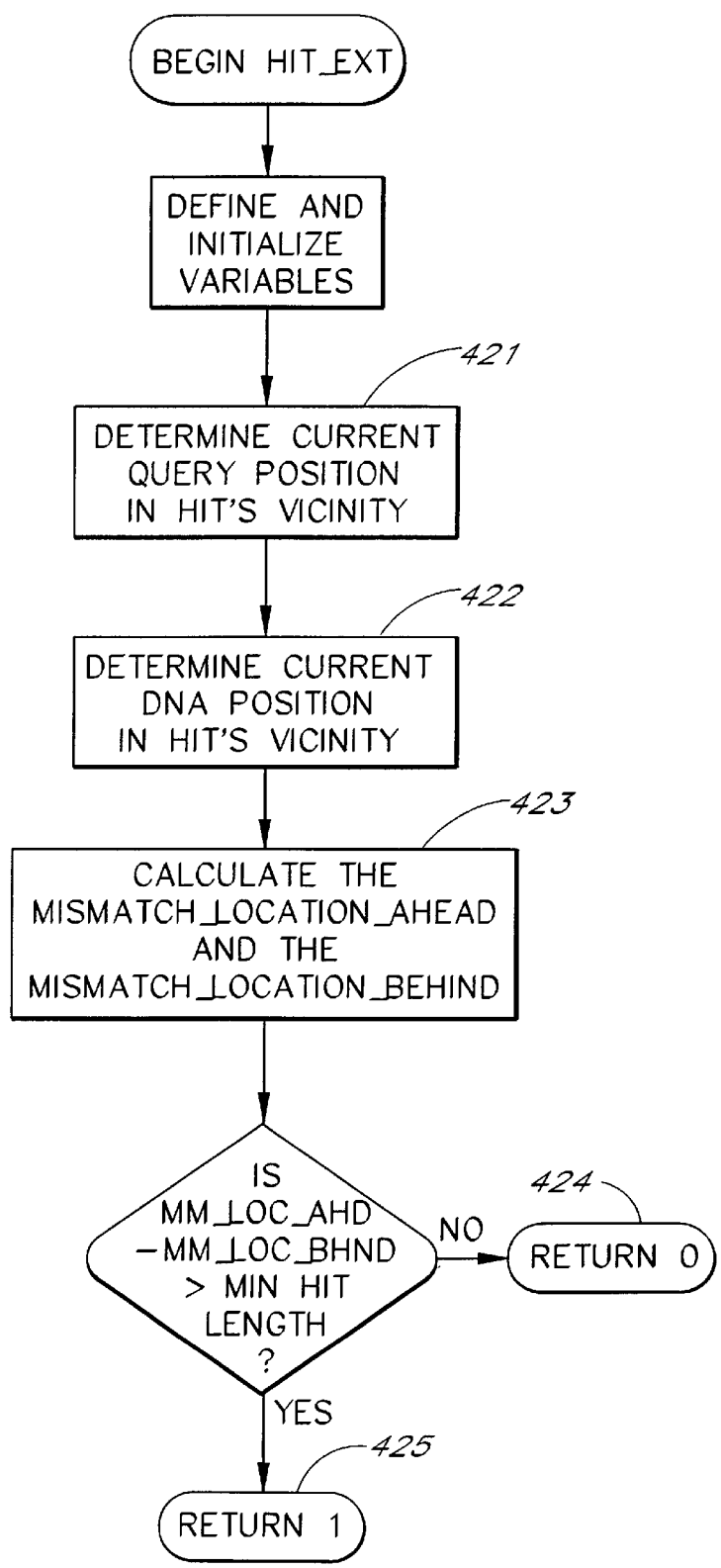
FIG. 38 is a flow chart of the hit_ext module of this invention.

The "hit_ext" module FIG. 38 determines the current query position in the hit's vicinity 421, determines the current DNA position in the hit's vicinity 422, and creates the list of mismatch positions (i.e., the mismatch_location_ahead 423, the mismatch_location_behind 423 and the kernel match location). If the hit is weak 424, the "hit_ext" module FIG. 38 returns "0" to the "q_colour" module FIG. 37. If the hit has a chance to contain 425, the module returns "1" to the "q_colour" module FIG. 37. A hit has a chance to contain, and is therefore not considered weak, if the mismatch_location_ahead—the mismatch_location_behind is greater than the min_hit_length. If not, it is a short hit and is too weak.

Figure 39:
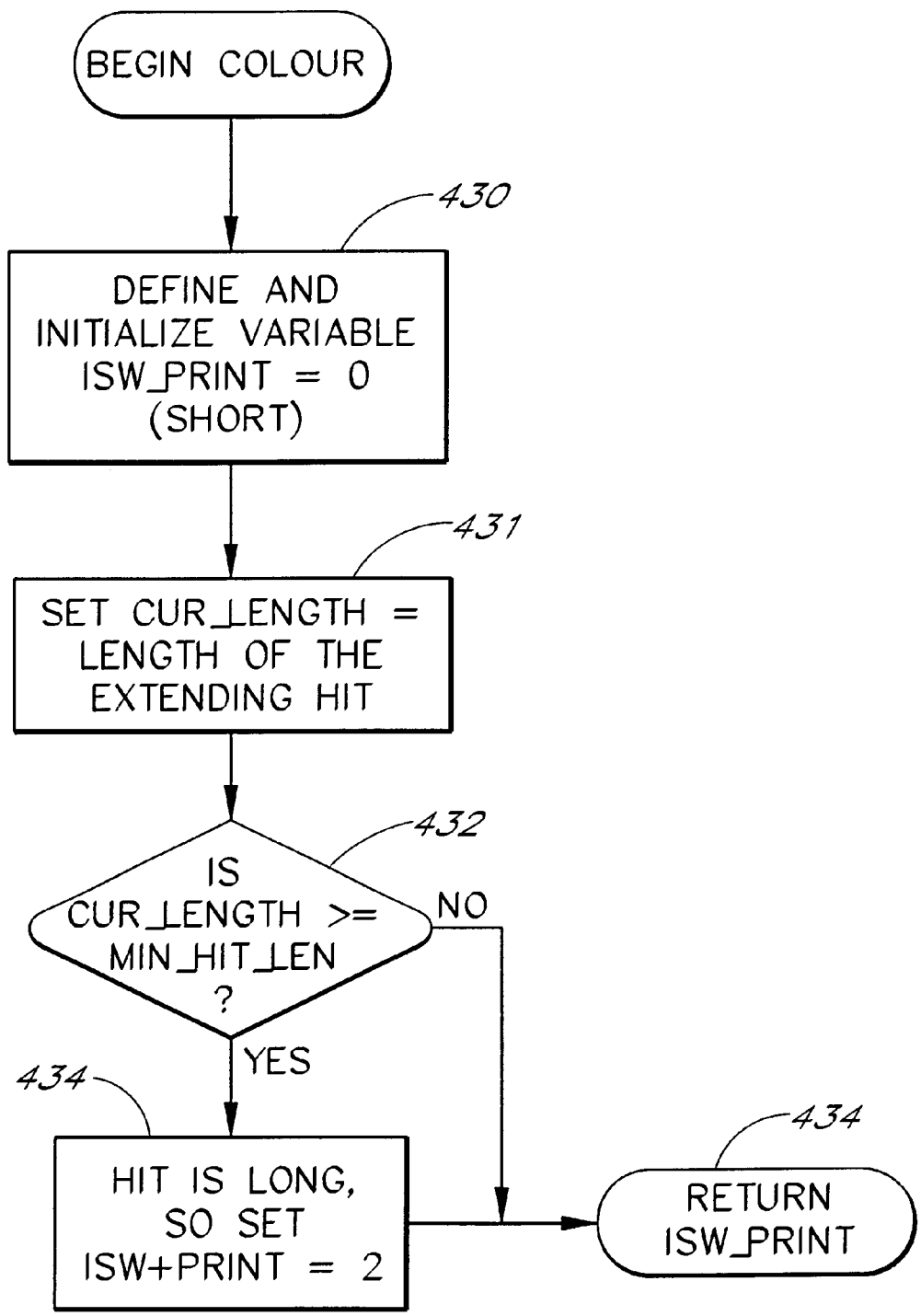
FIG. 39 is a flow chart of the colour module of this invention.

If the "hit_ext" module FIG. 38 tells the "q_colour" module FIG. 37 that the hit was not a weak one, then the "q_colour" module determines whether the current hit is long enough 398 by calling the "colour" module FIG. 39. The "colour" module FIG. 39 performs query_colour modification by the hit data, starting at pos_query and described by mismatch_location_ahead and mismatch_location_behind. After the variables to be used in this module are defined, variable isw_print (which is the switch indicating the hit length) is initialized to zero 430. The cur_length is then set equal to the length of the extending hit 431 (mismatch_location_behind[i]+mismatch_location_ahead[j]-1). Next, if cur_length is greater than or equal to the min_hit_length 432 (i.e., the minimum considered probe size), the hit is considered long and isw_print is set equal to two 433. The value of isw_print is then returned 434 to the "q_colour" module FIG. 37.

If the length of the extending hit is longer than the min_hit_length, the hit is considered long 399. Otherwise, the hit is considered short. If the hit is short, nothing more is done to the current hit and the module begins again. If, on the other hand, the hit is considered long 399, the "q_colour" module FIG. 37 prints the current extended hit 400. The current extended hit can be printed in ASCII, printed in a binary file, or printed to a memory file. The "q_colour" module FIG. 37 then repeats until the end of the linked list is reached.

d. Outputs

The output of the k_diff program may be either a binary file containing the number of extended hits and the k_mismatch hit locations (see FIG. 40), or the output may be kept in memory without writing it to a file. See Section 1(d)(iv) for more detail.

3. Description of the H-Site Model Program a. Overview

In this invention, the second hybridization strength model is termed the H-Site Model (see FIG. 21 for user selection of this model). The formula used in the H-Site Model is an expression of the fact that melting temperature Tm is a function of both probe length and percent of GC content. This basic formula has been modified in this invention to account for the presence of mismatches. Each percent of mismatch reduces the melting temperature Tm by an average of 1.25 degrees (2 degrees C for an AT mismatch, and 4 degrees C for a GC mismatch).

In addition, this implementation of the invention does some preliminary preprocessing of the GenBank database to sort out and select the cDNA sequences. This is done by locating a keyword (in this case CDS) in each GenBank record.

There are a number of modules in the present embodiment of the H-Site Model contained in this invention. Each step of the processing involved in the H-Site Model is more fully explained below, and is accompanied by detailed flow charts.

b. Inputs

There are two basic user-selected inputs for the H-Site Model (see FIG. 21C): 1) the melting temperature Tm 22 for which probes are being designed (i.e., the melting temperature that corresponds to a particular experiment or condition the user desires to simulate); and 2) the nucleation threshold 23, which is the number of base pairs constituting a nucleation site. The user is also required to select the 1) target species 11 gene sequence(s) (DNA, mRNA or cDNA) for which probes are being designed; 2) the preparation 12 of all sequences with which hybridizations are to be calculated; and 3) the probe output file 13. The preparation file is the most important, as discussed below.

c. Organization of the H-Site Model Program

The current implementation of the H-Site Model program of this invention is distributed between five files containing numerous modules. The main file is designated by the inventors as "ds.cpp" in its uncompiled version. This file provides overall control to the entire OligoProbe DesignStation invention. It is divided into six sections. Section 0 defines and manipulates global variables. Section 1 controls general variable definition and initialization (including the arrays and memory blocks). It also reads and writes buffers for user input selections, and constructs multi buffers.

Section 2 sets up and initializes various "snippet" variables (see section below for a complete definition of the term snippet), converts base pair characters to a representation that is 96 base pairs long and to ASCII base pair strings, and performs other sequence file manipulation such as comparing snippets. This section also reads the sequence format file, reads base pairs, checks for and extracts sequence identification information (such as ORIGIN and LOCUS) and filters out sequences beginning with numbers.

Section 3 involves preparation file manipulation. This section performs the preprocessing on the PRP file discussed above. It also merges and sorts the snippet files, creates a PRP file and sorts it, and outputs the sorted snippets. Next, this section streams through the PRP file.

Section 4 contains the essential code for H-Site Model processing (see FIGS. 41 through 43 for details, discussed below). Streams are set up, and then RIBI comparisons are performed for hybridizations (see file "ribi.cpp" for definitions of RIBI search techniques). Next, probes are generated, binding strength is converted to melting temperature, and hybridizations are calculated and stored (including hybridization strength). Lastly, other H-Site calculations are performed.

Section 5 is concerned with formatting and presenting diagnostic and user file (test.out, test1.out, and test2.out files) output. This section also handles the graphing functions (the MPSD diagram in particular). In addition, this section calculates the hairpin characteristics for the H-Site Model candidate probes.

The second H-Site Model file, designated as "ds.h" defines data variables and structures. Section 1 of this file concerns generic data structures (including memory blocks and arrays, and file inputs and outputs). Section 2 defines the variables and structures used with sequences, probes and hybridizations. Section 3 defines variables and structures concerned with protocols (i.e., function prototypes, graphing, etc.).

The third H-Site Model file, designated as "funcdoc.txt", contains very detailed documentation for this implementation of the H-Site Model program. Numerous variables and structures are also defined. The flow of the program is clearly shown in this file.

The fourth H-Site Model file, designated as "ribi.h" handles the sequence comparisons. The fifth and last H-Site Model file, designated as "ribi.cpp", performs internal B-Tree indexing. Definitions of Red-black Internal Binary Index (RIBI) searching are found in this file. Definitions are also included for the concepts keyed set, index, binary tree, internal binary index, paths, and red-black trees. Implementation notes are also included in this file.

d. Processing

Implementation of the H-Site Model in this invention is done in three stages. First, the invention creates the preparation (PRP) file, which contains all relevant information from the sequence database. This is the preprocessing stage discussed above. Next, the target is prepared by the program. Lastly, the invention calculates the MPSD data using the PRP file and target sequence to find probes.

i. Creation of the Preprocessed Preparation File

Figure 41:
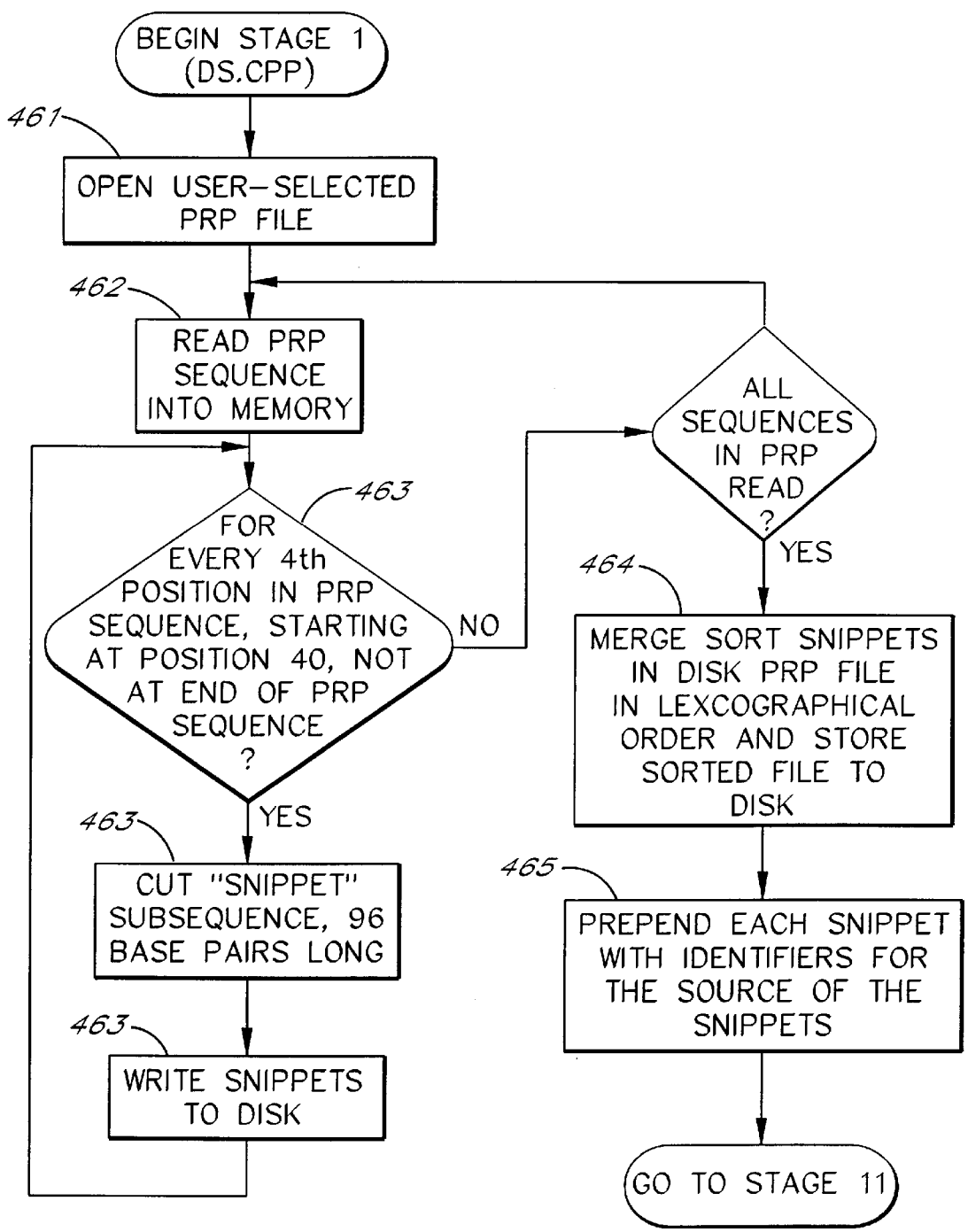
FIG. 41 is a flow chart of the H-Site Model, stage I, covering the creation of a preprocessed preparation file of this invention.

FIG. 41. Step 1: The program first opens the sequence database for reading into memory 461, 462. Step 2: Next, as sequence base pairs are read in 462, "snippets" are saved to disk 463, along with loci information. A snippet is a fixed-length subsequence of a preparation sequence. The purpose of snippets is to allow the user to examine a small portion of a preparation sequence together with its surrounding base pairs. Snippets in the implementation of this invention are 96 base pairs long (except for snippets near the end or beginning of a sequence, which may have fewer base pairs). The "origin" of the snippet is in position 40. For snippets taken near the beginning of a sequence, some of the initial 40 bases are undefined. For snippets near the end of a sequence, some of the final 55 bases are undefined. Snippets are arranged in the preparation file (PRP) in sorted order (lexicographical order beginning at position 40). In this invention, the term "lexicographical order" means a preselected order, such as alphabetical, numeric or alphanumeric. In order to conserve space, snippets are only taken at every 4th position of the preparation sequence.

Step 3: The snippets are merge sorted 464 to be able to search quickly for sequences which pass the "screen", discussed below. Step 4: The merged file is prepended with identifiers for the sources of the snippets 465. This is done to identify the loci from which hybridizations arise.

ii. Target Preparation

Figure 42:
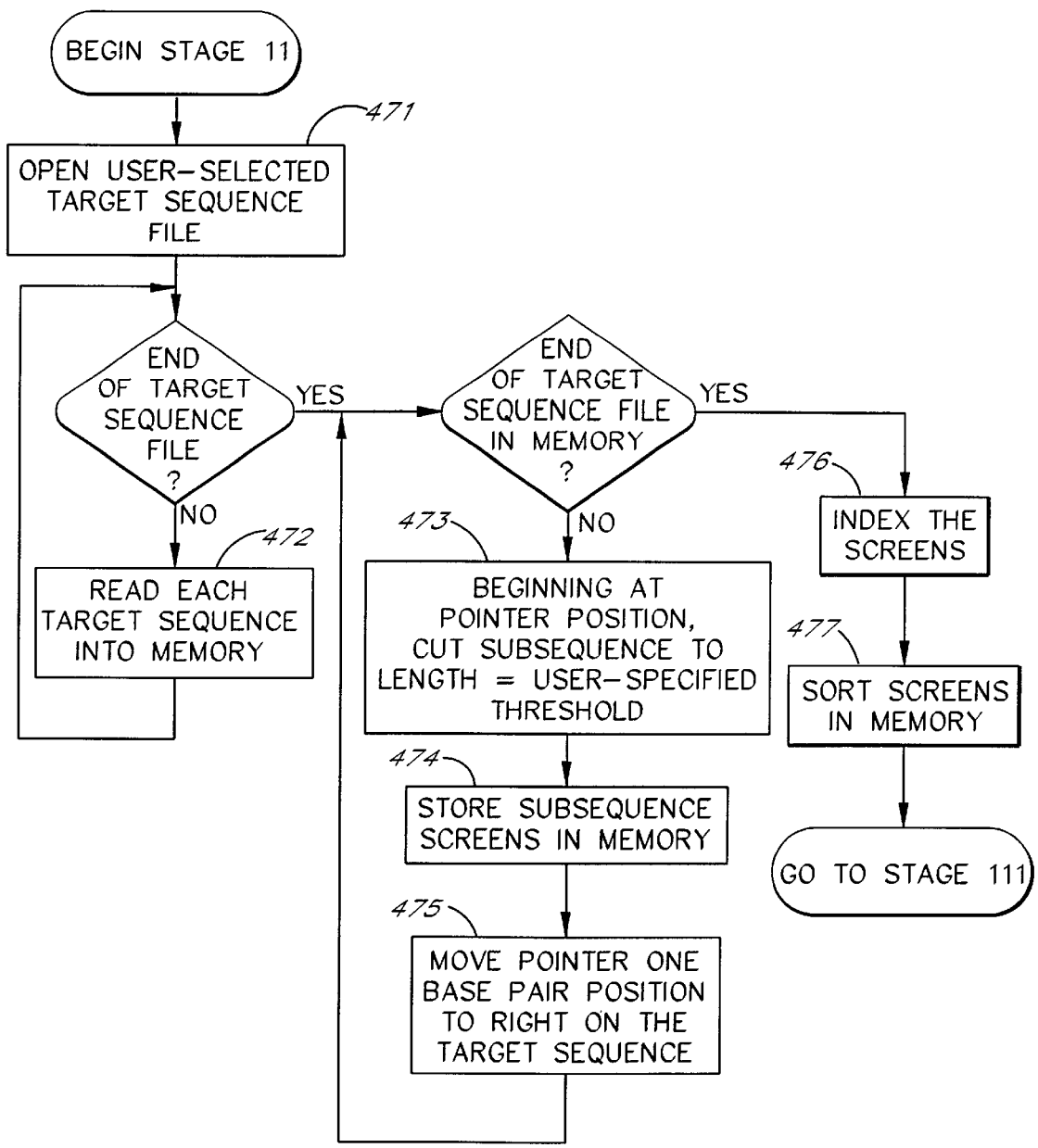
FIG. 42 is a flow chart of the H-Site Model, stage II, covering the preparation of the target sequence(s)
Figure 43A:
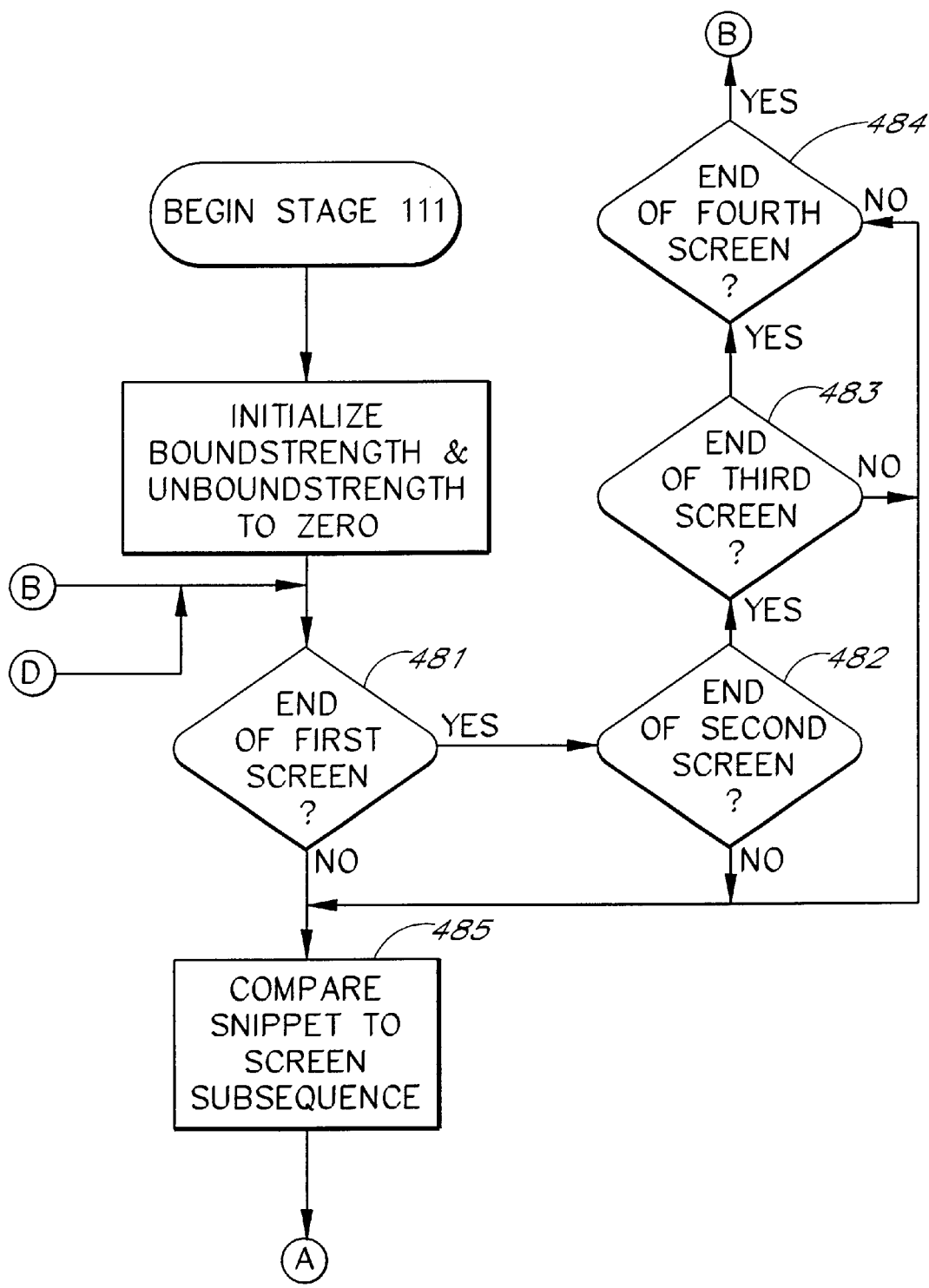
FIG. 43 is a flow chart of the H-Site Model stage III, covering the calculation of MPSD data.
Figure 43B:
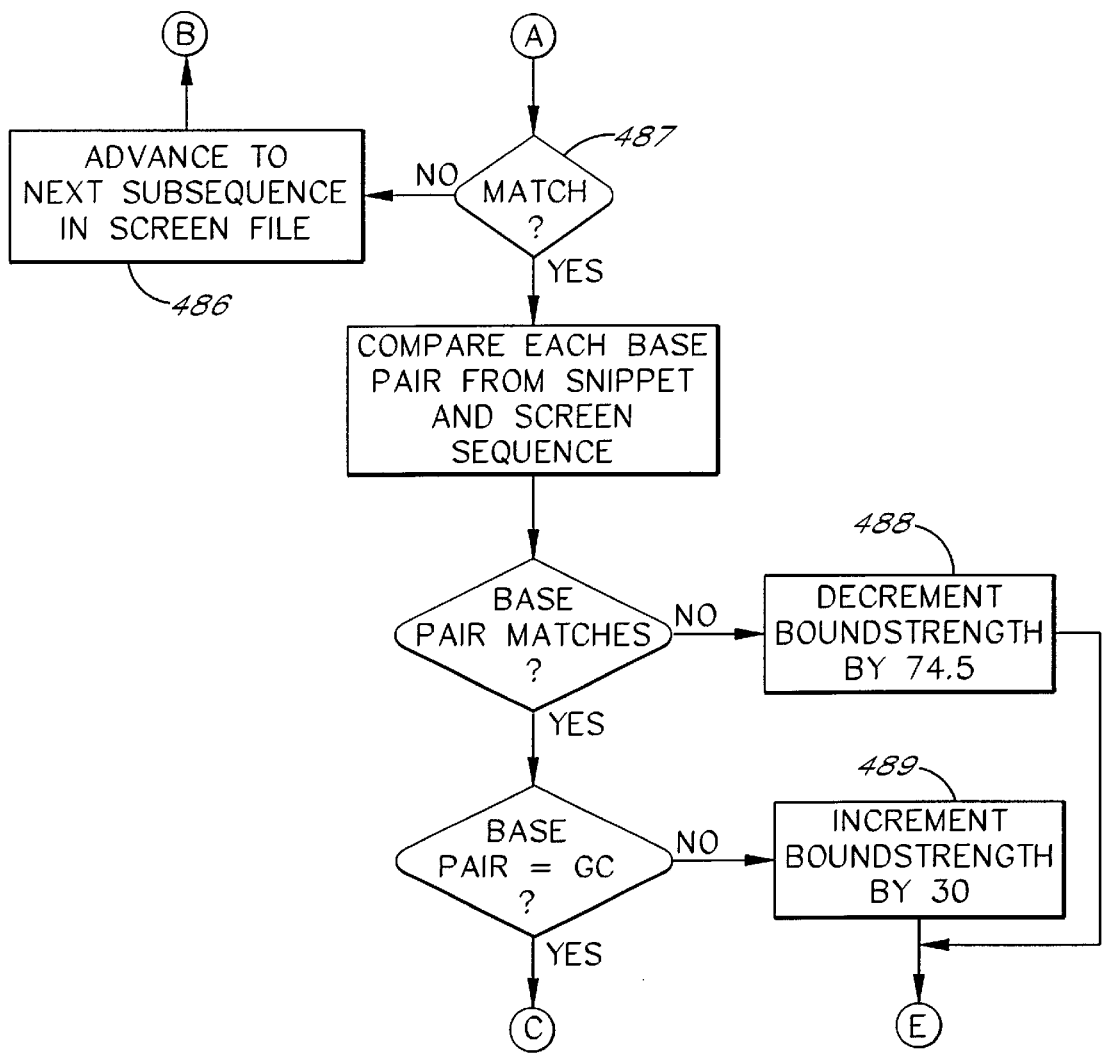
Figure 43C:
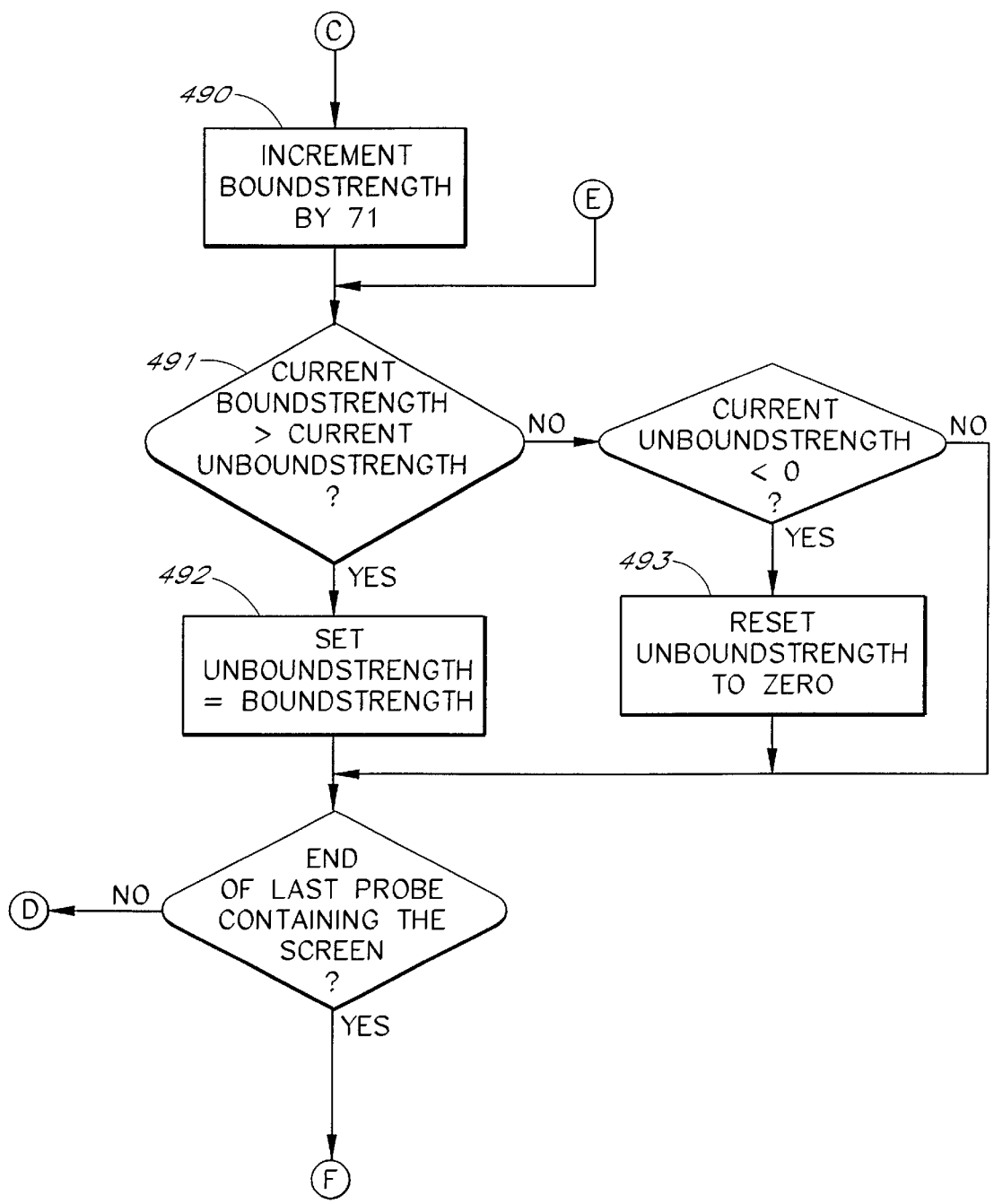
Figure 43D:
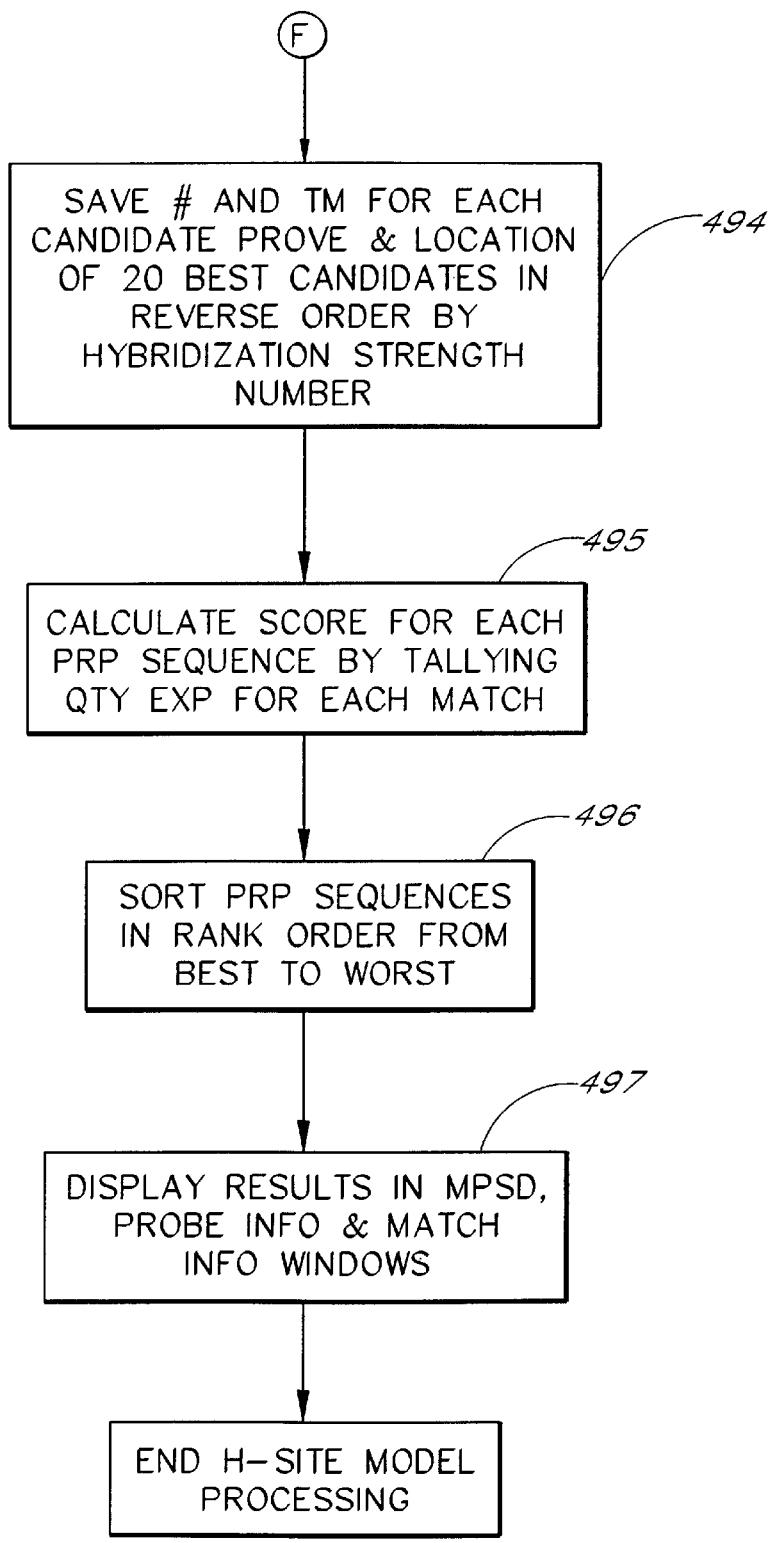

FIG. 42. Step 1: The target sequence file is opened 471 and read into memory 472. For each position in the target mRNA, the probe defined at that starting position is the shortest subsequence starting at that position whose hybridization strength is greater than the user specified melting temperature Tm. Typically, the probes are of length 18 to 50. Step 2: Four lists of "screens" are formed 473, 474, 475, each shifted by one base pair 475 to correspond to the fact that snippets are only taken at every four base pairs. A screen is a subsequence of the target mRNA of length equal to the screening threshold specified by the user. The screens are then indexed 476 and sorted in memory 477.

iii. Calculation of the MPSD Data

FIG. 43. Step 3: This step is the heart of the process. Step 3a: The program streams through the following five items in sync, examining them in sequential order: the snippet file and the four lists of screens 481–484. Step 3b: Each snippet is compared to a screen 485. Step 3c: If the snippet does not match, whichever stream is behind is advanced 486 and Step 3b is repeated. If the snippet does match, Step 4 is performed.

Step 4: If a snippet and a matching screen were found in Step 3b 487, the hybridization strength of the binding between the sequence containing the snippet and all of the probes containing the screen is calculated (see Step 5). Double counting is avoided by doing this only for the first matched screen containing the probe. Each pair of bases is examined and assigned a numerical binding strength. An AT pair would be assigned a lower binding strength than a GC pair because AT pairs have a lower melting temperature Tm. The process is explained more fully below at Step 5b.

Step 5: The hybridization strengths between sequence and all the probes containing it are calculated using a dynamic programming process. The process is as follows: Step 5a: Begin at the position of the first probe containing the given screen but not containing any other screens which start at an earlier position and also match the sequence. This is done to avoid double counting. Two running totals are maintained: a) boundStrength, which represents the hybridization strength contribution which would result if the sequence and probe were to match exactly for all base pairs to the right of the current position, and b) unboundStrength, which represents the strength of the maximally binding region. Step 5b: At each new base pair, the variable boundStrength is incremented by 71 if the sequence and probe match and the matched base pair is GC 489, incremented by 30 if the matched base pair is AT 490 (i.e., this number is about 42.25% of the first number 71), and decremented by 74.5 if there is not a match 488 (i.e., this number is about 5% larger than the first number 71). Step 5c: If the current boundStrength exceeds the current unboundStrength 491 (which was originally initialized to zero), a new binding region has been found, and unboundStrength is set equal to boundStrength 492. Step 5d: If the current boundStrength is negative, boundStrength is reset to zero 493. Step 5e: If the current position is at the end of a probe, the results (the hybridization strengths) are tallied for that probe. Step 5f: If the current position is at the end of the last probe containing the screen, the process stops.

Step 6: A tally is kept of the number and melting temperature of the matches for each candidate probe, and the location of the best 20 candidates, using a priority queue (reverse order by hybridization strength number) 494. Step 7: A numerical "score" is kept for each preparation sequence by tallying the quantity exp (which can be expressed as $\epsilon e^{-Tm}$) for each match 495, where Tm is the melting temperature for the "perfect" match, the probe itself. In other words, the probe hybridizes "perfectly" to its target.

Step 8: Hairpins are calculated by first calculating the complementary probe. In other words, the order of the bases in the candidate probe are reversed (CTATAG to GATATC), and complementary base pairs are substituted (A for T, T for A, G for C, and C for G, changing GATATC to CTATAG in the above example). Next, the variable representing the maximum hairpin length for a candidate probe is initialized to zero, as is the variable representing a hairpin's distance. For each offset, the original candidate probe and the complementary probe just created are then aligned with each other and compared. The longest match is then found. If any two matches have the same length, the one with the longest hairpin distance (i.e., the number of base pairs separating the match) is then saved.

Step 9: The preparation sequences are then sorted 496 and displayed in rank order, from best to worst 497. Step 10: The resulting MPSD, which includes all candidate probes, is then displayed on the screen. Step 11: The best 20 matches are also printed or displayed in rank order, as the user requests 497.

e. Outputs

The outputs of the H-Site Model are fully described in Section 1(d)(iv), above, and illustrated in FIGS. 23 through 25. Samples of the two output files created by the H-Site Model are shown in FIGS. 44A and 44B.

4. Description of the Mitsuhashi Probe Selection Diagram Processing

Figure 45:
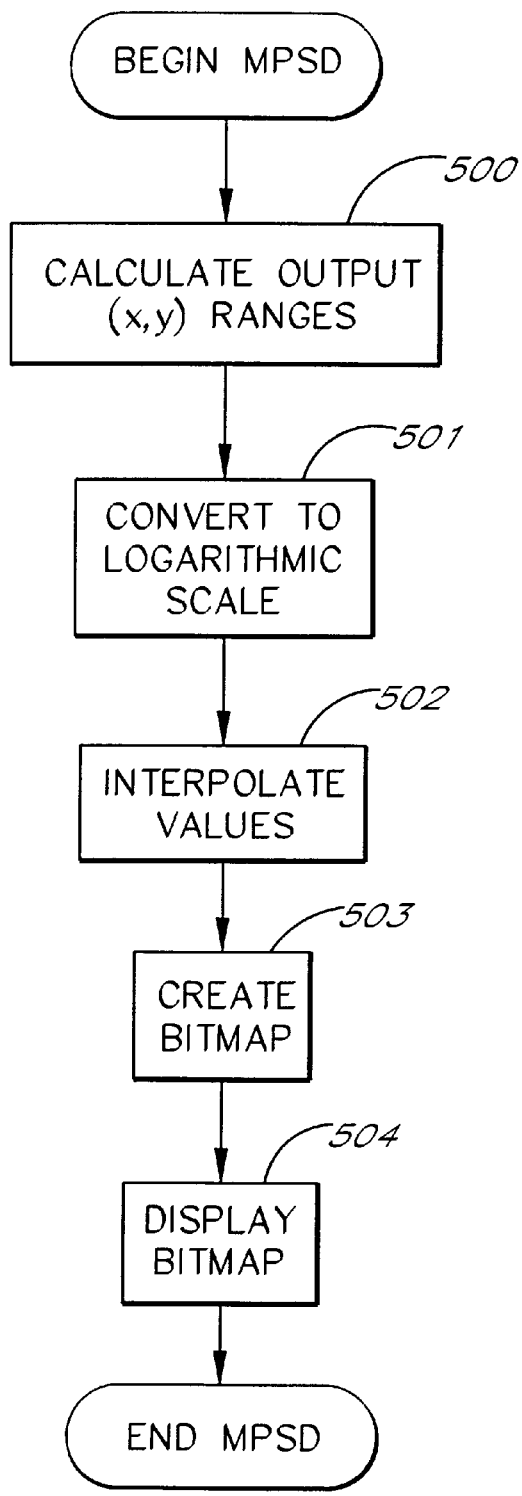
FIG. 45 is a flow chart of the processing used to create the Mitsuhashi probe selection diagram (MPSD)

Once the Mitsuhashi Probe Selection Diagram (MPSD) data has been calculated by the H-Site Model program (see stage three and FIG. 43, discussed above), it is necessary to convert this data to pixel format and plot a graph. An overview of this process is shown in FIG. 45. First, the program calculates the output (x,y) ranges 500. Next, these are converted to a logarithmic scale 501. The values are then interpolated 502, and a bitmap is created 503. Lastly, the bitmap is displayed on the screen 504 in MPSD format (discussed above in section 1(e)(i)). A sample MPSD is shown in FIG. 23.

5. Description of the MatchInfo Window Processing

Figure 46:
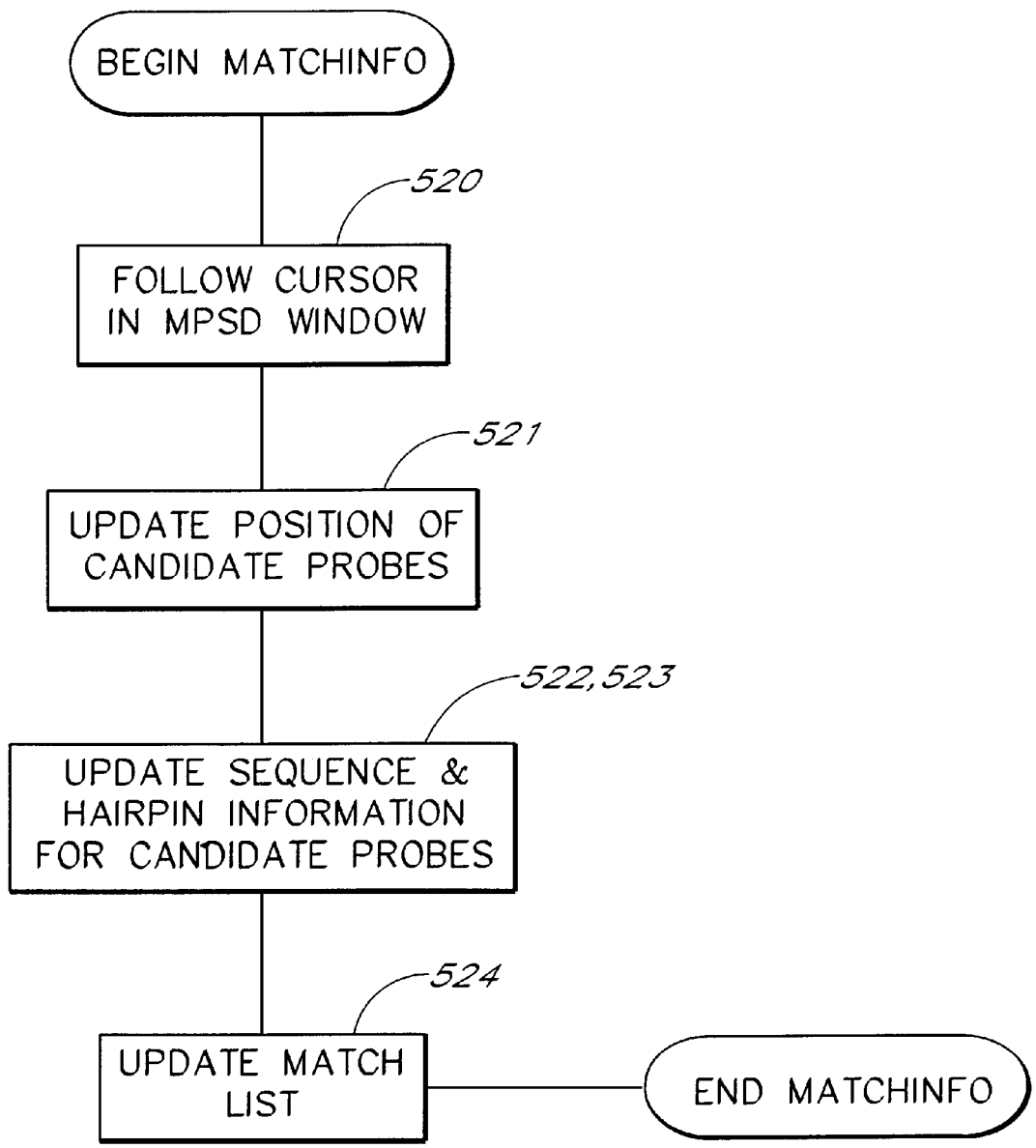
FIG. 46 is a flow chart of processing used to create the matchinfo window.

The ProbeInfo and MatchInfo windows are discussed in great detail in Section 1(e)(ii), and a sample of these windows is shown in FIG. 24. An overview of the processing involved in creating the MatchInfo portion of the window is given in the flow chart in FIG. 46. First, as the user moves the MPSD cursor 570 (seen as a vertical line bisecting the MPSD window), the program updates the position of the candidate probe shown under that cursor position 521. Next, based upon the candidate probe's position, the program updates the sequence 522 and hairpin information 523 for that probe. This updated information is then displayed in an updated match list 524, shown in the MatchInfo window.

Effect of the Invention

The invented method offers rapid characterization of mRNA in approximately 5 hours without the need for mRNA purification. Because conventional methods of mRNA quantification, for example Northern blots, require over 70 hours to complete, the method of the present invention significantly reduces the length of time needed for mRNA analysis. Furthermore, because various types of first nucleotide probes can be immobilized in each well of microtiter plate and identified using a single kind of labeled second nucleotide probe, the present invention advantageously can provide the simultaneous quantification of multiple varieties of mRNA.

As shown in the examples above, the meithods of the present invention provide high reliability and reproducibility. Therefore, these methods can be utilized for quantification and analysis of many mRNAs in addition to those exemplified here. Thus, this invention can be used as a rapid method of analyzing the pathogenesis of various diseases, as well as assisting in their diagnosis. Many such methods will suggest themselves to those with ordinary skill in the art upon a review of the present specification. Accordingly, the scope of the present invention is to be determined with reference to the appended claims, and is not to be limited to those methods specifically exemplified herein.

We claim:

1. A quantitative method for identifying probes and thereafter detecting and quantifying mRNA in a sample using said probes, without the need to purify mRNA from cells, said method comprising:
   (a) identifying an oligonucleotide sequence of no more than 40 nucleotides but no less than 17 nucleotides which is complementary to a sequence unique to said mRNA, which has a melting temperature ($T_m$) within a preselected range with said mRNA at a selected sodium and formamide concentration, said $T_m$ being determined by the formula;
   $T_m$=81.5−16.6(log[Na])−0.63%(formamide)+0.41(%(G+C))−600/N, wherein log[Na] is the log function of the sodium concentration, 0.63%(formamide) is the concentration of formamide, %(G+C) is the percentage of matched GC base pairs, and N is the probe length,
   said oligonucleotide sequence being identified by a method comprising:
      (i) retrieving a plurality of user-selected gene sequences including the gene sequence of said mRNA from a database and inputting said sequences into a computer system for calculating $T_m$;
      (ii) calculating the $T_m$s of a plurality of candidate oligonucleotide sequences extracted from the gene sequence of said mRNA, at the selected sodium and formamide concentration with said mRNA, using said computer system;
      (iii) calculating the $T_m$s of said plurality of candidate oligonucleotide sequences at the selected sodium and formamide concentration with each of said user-selected gene sequences other than that of said mRNA; and
      (iv) identifying said oligonucleotide sequence as the candidate sequence that has a $T_m$ within the preselected range with said mRNA and has the lowest $T_m$ overall with the other user-selected gene sequences;
   (b) immobilizing a specific probe having said oligonucleotide sequence to an insoluble support;
   (c) incubating said sample with said insoluble support under conditions wherein said nucleotide sequence unique to said mRNA will specifically hybridize with said specific probe, thereby immobilizing mRNA having said unique nucleotide sequence present in said sample to said insoluble support;
   (d) washing non-immobilized components of said sample from said insoluble support;
   (e) labeling mRNA on said support in a manner that the amount of label incorporated onto said support is related to the amount of mRNA on said support; and
   (f) measuring the amount of the label immobilized on said support.

2. The method of claim 1, wherein step (e) further comprises:
   i. incubating a labeled probe with said insoluble support under conditions wherein said labeled probe will hybridize with mRNA on said support, said labeled probe bearing a label and being complementary to a part of said mRNA other than a part of said mRNA complementary to said specific probe, thereby immobilizing to said insoluble support the label on said labeled probe which has hybridized with said mRNA; and
   ii. washing any non-immobilized labeled probe from said insoluble support.

3. The method of claim 1, wherein step (e) further comprises labeling oligonucleotides on said support with a nucleic acid stain.

4. The method of claim 1, wherein said specific probe hybridizes to said unique sequence of said mRNA and not to other polynucleotides present in said sample.

5. The method of claim 1, wherein said sample comprises a cell lysate.

6. The method of claim 1, wherein said candidate oligonucleotide sequences in step (a) are selected at positions along said mRNA, based on a nucleation threshold that places a minimum value on the number of base pairs at any nucleation site, selected by the user, in addition to said preselected $T_m$ range.

7. The method of claim 1, wherein said preselected $T_m$ range is specified by a lowest $T_m$ with said mRNA.

8. The method of claim 2, wherein said labeled probe comprises poly-d(T).

9. The method of claim 2, wherein said label comprises a radionuclide.

10. The method of claim 2, wherein said label comprises biotin.

11. The method of claim 2, wherein said label can be measured by light emitted therefrom, and wherein step (f) further comprises measuring the amount of light emitted by said label.

12. The method of claim 2, wherein said label comprises biotin and wherein step (f) additionally comprises adding streptavidin bound to alkaline phosphatase to said insoluble support, whereby the alkaline phosphatase bound to said insoluble support is measured.

13. The method of claim 2, wherein said labeled probe has an oligonucleotide sequence complementary to a part of said mRNA other than a part of said mRNA complementary to said specific probe and has a $T_m$ within a preselected range, the oligonucleotide sequence of which is identified by a method comprising the steps of:
   calculating the $T_m$s of a plurality of candidate oligonucleotide sequences at the selected sodium and formamide concentration with said mRNA at every possible hybridization point; and
   identifying as the candidate sequence said oligonucleotide sequence having a $T_m$ within the preselected range with the oligonucleotide sequence complementary to a part of said mRNA other than a part of said mRNA complementary to said specific probe and has the lowest $T_m$ with the oligonucleotide sequence complementary to said specific probe.

14. The method of claim 3, wherein said nucleic acid stain is selected from the group consisting of ethidium bromide, yoyo-1 and toto-1.

15. The method of claim 10, wherein step (f) further comprises:
incubation with enzyme-conjugated streptavidin; and
measurement of the amount of enzyme bound to said insoluble support.

16. The method of claim 11, wherein the step of measuring the amount of light comprises:
recording the amount of light on film; and
measuring the exposure of this film using a densitometer.

17. The method of claim 11, additionally comprising adding ATTOPHOS and measuring flourescense emitted therefrom.

18. The method of claim 17, wherein the step of measuring the amount of light comprises use of a fluorimeter.

19. The method of claim 13, wherein said candidate oligonucleotide sequences are selected at positions along said mRNA, based on a nucleation threshold that places a minimum value on the number of base pairs at any nucleation site, selected by the user, in addition to said preselected $T_m$ range.

20. The method of claim 13, wherein said preselected $T_m$ range is specified by a lowest $T_m$ with said mRNA.

21. A quantitative method for identifying probes and thereafter detecting and quantifying mRNA in a sample using said probes, without the need to purify mRNA from cells, said method comprising:
(a) identifying an oligonucleotide sequence of no more than 40 nucleotides but no less than 17 nucleotides that is complementary to a sequence unique to said mRNA, which has a melting temperature ($T_m$) within a preselected range with said mRNA at a selected sodium and formamide concentration, said $T_m$ being determined by the formula;
$T_m = 81.5 - 16.6(\log[Na]) - 0.63\%(\text{formamide}) + 0.41(\%(G+C)) - 600/N$, wherein $\log[Na]$ is the log function of the sodium concentration, $0.63\%(\text{formamide})$ is the concentration of formamide, $\%(G+C)$ is the percentage of matched GC base pairs, and N is the probe length, said oligonucleotide sequence being identified by a method comprising:
(i) retrieving a plurality of user-selected gene sequences including the gene sequence of said mRNA from a database and inputting said sequences into a computer system for calculating $T_m$;
(ii) calculating the $T_m$s of a plurality of candidate oligonucleotide sequences extracted from the gene sequence of said mRNA, at the selected sodium and formamide concentration with said mRNA, using said computer system;
(iii) calculating the $T_m$s of said plurality of candidate oligonucleotide sequences at the selected sodium and fornamide concentration with each of said user-selected gene sequences other than that of said mRNA; and
(iv) identifying said as the candidate sequence said oligonucleotide having a $T_m$ within the preselected range with said mRNA and has the lowest $T_m$ overall with the other user-selected gene sequences;

(b) immobilizing a specific probe having said oligonucleotide sequence to a microtiter plate said first oligonucleotide having a first sequence complementary to said sequence unique to said mRNA;

(c) incubating said sample with said microtiter plate under conditions wherein said nucleotide sequence unique to said mRNA will specifically hybridize with said specific probe, thereby immobilizing mRNA having said unique nucleotide sequence present in said sample to said microtiter plate;

(d) washing non-immobilized components of said sample from said microtiter plate;

(e) labeling mRNA on said support in a manner that the amount of label incorporated onto said support is related to the amount of mRNA on said support; and (f) measuring the amount of the label immobilized on said support.

* * * * *